US009394279B2

(12) United States Patent
Krueger et al.

(10) Patent No.: US 9,394,279 B2
(45) Date of Patent: Jul. 19, 2016

(54) ANTI-VIRAL COMPOUNDS

(75) Inventors: Allan C. Krueger, Gurnee, IL (US);
Warren M. Kati, Gurnee, IL (US);
William A. Carroll, Evanston, IL (US);
John K. Pratt, Kenosha, WI (US);
Douglas K. Hutchinson, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 681 days.

(21) Appl. No.: 13/328,848

(22) Filed: Dec. 16, 2011

(65) Prior Publication Data

US 2012/0172290 A1 Jul. 5, 2012

Related U.S. Application Data

(63) Continuation-in-part of application No. 12/964,027, filed on Dec. 9, 2010, now Pat. No. 8,921,514, which is a continuation-in-part of application No. 12/903,822, filed on Oct. 13, 2010, now abandoned, which is a continuation-in-part of application No. 12/813,301, filed on Jun. 10, 2010, now Pat. No. 8,691,938.

(60) Provisional application No. 61/423,906, filed on Dec. 16, 2010, provisional application No. 61/186,291, filed on Jun. 11, 2009, provisional application No. 61/242,836, filed on Sep. 16, 2009, provisional application No. 61/243,596, filed on Sep. 18, 2009, provisional application No. 61/446,800, filed on Feb. 25, 2011.

(51) Int. Cl.
*A61K 31/66* (2006.01)
*C07K 16/00* (2006.01)
*C07D 403/14* (2006.01)
*C07D 207/16* (2006.01)

(52) U.S. Cl.
CPC ............ *C07D 403/14* (2013.01); *C07D 207/16* (2013.01)

(58) Field of Classification Search
None
See application file for complete search history.

(56) References Cited

U.S. PATENT DOCUMENTS

| | | | |
|---|---|---|---|
| 5,830,867 A | 11/1998 | Bhatnagar et al. | |
| 5,935,982 A | 8/1999 | Dykstra et al. | |
| 6,235,493 B1 | 5/2001 | Bissell et al. | |
| 6,369,091 B1 | 4/2002 | Sircar et al. | |
| 6,703,403 B2 | 3/2004 | Norbeck et al. | |
| 6,919,366 B2 | 7/2005 | Sircar et al. | |
| 7,141,574 B2 | 11/2006 | Beaulieu et al. | |
| 7,659,270 B2 | 2/2010 | Bachand et al. | |
| 7,704,992 B2 | 4/2010 | Bachand et al. | |
| 7,728,027 B2 | 6/2010 | Pack et al. | |
| 7,741,347 B2 | 6/2010 | Bachand et al. | |
| 7,745,636 B2 | 6/2010 | Bachand et al. | |
| 7,759,495 B2 | 7/2010 | Bachand et al. | |
| 7,763,731 B2 | 7/2010 | Rockway et al. | |
| 7,906,655 B2 | 3/2011 | Belema et al. | |
| 8,101,643 B2 | 1/2012 | Qiu et al. | |
| 2003/0004203 A1 | 1/2003 | Sircar et al. | |
| 2003/0100582 A1 | 5/2003 | Sircar et al. | |
| 2004/0034189 A1* | 2/2004 | Cho et al. ...................... | 528/394 |
| 2005/0075343 A1 | 4/2005 | Sircar et al. | |
| 2005/0197375 A1 | 9/2005 | Sircar et al. | |
| 2006/0003942 A1 | 1/2006 | Tung et al. | |
| 2006/0058317 A1 | 3/2006 | Gravestock et al. | |
| 2006/0105997 A1 | 5/2006 | Arrington et al. | |
| 2007/0004741 A1 | 1/2007 | Apodaca et al. | |
| 2007/0015757 A1* | 1/2007 | Madsen et al. ................. | 514/241 |
| 2007/0142434 A1 | 6/2007 | Sandanayaka et al. | |
| 2007/0197558 A1 | 8/2007 | Betebenner et al. | |
| 2007/0232627 A1 | 10/2007 | Betebenner et al. | |
| 2007/0299068 A1 | 12/2007 | Karp et al. | |
| 2008/0044379 A1 | 2/2008 | Bachand et al. | |
| 2008/0044380 A1 | 2/2008 | Bachand et al. | |
| 2008/0050336 A1 | 2/2008 | Bachand et al. | |
| 2008/0075696 A1* | 3/2008 | Parsons et al. ............... | 424/85.6 |
| 2008/0221107 A1 | 9/2008 | Giordanetto et al. | |
| 2008/0299075 A1 | 12/2008 | Bachand et al. | |
| 2008/0311075 A1 | 12/2008 | Bachand et al. | |
| 2009/0004111 A1 | 1/2009 | Rice et al. | |
| 2009/0041716 A1 | 2/2009 | Kim et al. | |
| 2009/0043107 A1 | 2/2009 | Pack et al. | |
| 2009/0068140 A1 | 3/2009 | Bachand et al. | |
| 2009/0093456 A1 | 4/2009 | Arnold et al. | |
| 2009/0104151 A1 | 4/2009 | Hanson et al. | |
| 2009/0202478 A1 | 8/2009 | Bachand et al. | |
| 2009/0202483 A1 | 8/2009 | Bachand et al. | |

(Continued)

FOREIGN PATENT DOCUMENTS

BR    PI0401908 A    1/2006
DE    75755 C    6/1984

(Continued)

OTHER PUBLICATIONS

Adjabeng G., et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.
Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.
Aldous D.J., et al. , "A Simple Enantioselective Preparation of (2S,5S)-2,5-diphenylpyrrolidine and Related Diary Amines," Tetrahedron Asymmetry, 2000, vol. 11, pp. 2455-2462.
Alesso E.N., et al., "Synthesis of Diastereoisomeric 1,2,3-Triphenylindans," Australian Journal of Chemistry, 1997, vol. 50, pp. 149-152.

(Continued)

Primary Examiner — Jeanette Lieb
(74) Attorney, Agent, or Firm — Xu Zhang

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

7 Claims, No Drawings

(56) References Cited

U.S. PATENT DOCUMENTS

| | | |
|---|---|---|
| 2010/0055071 A1 | 3/2010 | Leivers et al. |
| 2010/0068176 A1 | 3/2010 | Belema et al. |
| 2010/0080772 A1 | 4/2010 | Belema et al. |
| 2010/0143499 A1 | 6/2010 | Condon |
| 2010/0158862 A1 | 6/2010 | Kim et al. |
| 2010/0160355 A1 | 6/2010 | DeGoey et al. |
| 2010/0168138 A1 | 7/2010 | Degoey et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0189129 A1 | 8/2011 | Qiu et al. |
| 2011/0195044 A1 | 8/2011 | Romine |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2012/0004196 A1 | 1/2012 | Degoey et al. |
| 2012/0028978 A1 | 2/2012 | Zhong et al. |
| 2012/0040977 A1 | 2/2012 | Li et al. |

FOREIGN PATENT DOCUMENTS

| | | |
|---|---|---|
| EP | 2242751 A1 | 10/2010 |
| JP | 2003282270 A | 10/2003 |
| JP | 2010126571 A | 6/2010 |
| WO | WO9427627 A1 | 12/1994 |
| WO | WO9961020 A1 | 12/1999 |
| WO | WO0012521 A1 | 3/2000 |
| WO | WO03082186 A2 | 10/2003 |
| WO | WO2004005283 A1 | 1/2004 |
| WO | WO2004014313 A2 | 2/2004 |
| WO | WO2004014852 A2 | 2/2004 |
| WO | WO2004014852 A3 | 4/2004 |
| WO | WO2004014313 A3 | 12/2005 |
| WO | WO2006020951 A1 | 2/2006 |
| WO | WO2006033703 A1 | 3/2006 |
| WO | WO2006133326 A1 | 12/2006 |
| WO | WO2007070556 A2 | 6/2007 |
| WO | WO2007070600 A2 | 6/2007 |
| WO | WO2007076034 A2 | 7/2007 |
| WO | WO2007076035 A2 | 7/2007 |
| WO | WO2007082554 A1 | 7/2007 |
| WO | WO2007070556 A3 | 8/2007 |
| WO | WO2007081517 A8 | 9/2007 |
| WO | WO2007070600 A3 | 11/2007 |
| WO | WO2007131366 A1 | 11/2007 |
| WO | WO2007136921 A2 | 11/2007 |
| WO | WO2007144174 A1 | 12/2007 |
| WO | WO2008014236 A1 | 1/2008 |
| WO | WO2008014238 A2 | 1/2008 |
| WO | WO2008021927 A2 | 2/2008 |
| WO | WO2008021928 A2 | 2/2008 |
| WO | WO2008021936 A2 | 2/2008 |
| WO | WO2008021928 A3 | 3/2008 |
| WO | WO2008021936 A3 | 4/2008 |
| WO | WO2008021927 A3 | 5/2008 |
| WO | WO2008064218 A2 | 5/2008 |
| WO | WO2008070447 A2 | 6/2008 |
| WO | WO2008074450 A2 | 6/2008 |
| WO | WO2008064218 A3 | 10/2008 |
| WO | WO2008128121 A1 | 10/2008 |
| WO | WO2008133753 A2 | 11/2008 |
| WO | WO2008144380 A1 | 11/2008 |
| WO | WO2009003009 A1 | 12/2008 |
| WO | WO2009020534 A2 | 2/2009 |
| WO | WO2009020825 A1 | 2/2009 |
| WO | WO2009020828 A1 | 2/2009 |
| WO | WO2008070447 A3 | 3/2009 |
| WO | WO2009093082 A1 | 7/2009 |
| WO | WO2009094224 A1 | 7/2009 |
| WO | WO2009102318 A1 | 8/2009 |
| WO | WO2009102325 A1 | 8/2009 |
| WO | WO2009102568 A1 | 8/2009 |
| WO | WO2009102633 A1 | 8/2009 |
| WO | WO2009102694 A1 | 8/2009 |
| WO | WO2009136290 A1 | 11/2009 |
| WO | WO2009143361 A1 | 11/2009 |
| WO | WO2009155709 A1 | 12/2009 |
| WO | WO2010015090 A1 | 2/2010 |
| WO | WO2010017401 A1 | 2/2010 |
| WO | WO2010039793 A1 | 4/2010 |
| WO | WO2010059858 A1 | 5/2010 |
| WO | WO2010062821 A1 | 6/2010 |
| WO | WO2010065668 A1 | 6/2010 |
| WO | WO2010065674 A1 | 6/2010 |
| WO | WO2010065681 A1 | 6/2010 |
| WO | WO2010075376 A2 | 7/2010 |
| WO | WO2010091413 A1 | 8/2010 |
| WO | WO2010096302 A1 | 8/2010 |
| WO | WO2010096462 A1 | 8/2010 |
| WO | WO2010096777 A1 | 8/2010 |
| WO | WO2010099527 A1 | 9/2010 |
| WO | WO2010111483 A1 | 9/2010 |
| WO | WO2010111534 A1 | 9/2010 |
| WO | WO2010111673 A1 | 9/2010 |
| WO | WO2010115767 A1 | 10/2010 |
| WO | WO2010117635 A1 | 10/2010 |
| WO | WO2010117704 A1 | 10/2010 |
| WO | WO2010117977 A1 | 10/2010 |
| WO | WO2010120621 A1 | 10/2010 |
| WO | WO2010120935 A1 | 10/2010 |
| WO | WO2010122162 A1 | 10/2010 |
| WO | WO2010132538 A1 | 11/2010 |
| WO | WO2010132601 A1 | 11/2010 |
| WO | WO2010138368 A1 | 12/2010 |
| WO | WO2010138488 A1 | 12/2010 |
| WO | WO2010138790 A1 | 12/2010 |
| WO | WO2010138791 A1 | 12/2010 |
| WO | WO2010144646 A2 | 12/2010 |
| WO | WO2010148006 A1 | 12/2010 |
| WO | WO2011004276 A1 | 1/2011 |
| WO | WO2011009084 A2 | 1/2011 |
| WO | WO2011015658 A1 | 2/2011 |
| WO | WO2011026920 A1 | 3/2011 |
| WO | WO2011028596 A1 | 3/2011 |
| WO | WO2011031904 A1 | 3/2011 |
| WO | WO2011031934 A1 | 3/2011 |
| WO | WO2011050146 A1 | 4/2011 |

(56) References Cited

FOREIGN PATENT DOCUMENTS

| WO | WO2011054834 A1 | 5/2011 |
|---|---|---|
| WO | WO2011059850 A1 | 5/2011 |
| WO | WO2011059887 A1 | 5/2011 |
| WO | WO2011060000 A1 | 5/2011 |
| WO | WO2011066241 A1 | 6/2011 |
| WO | WO2011068941 A2 | 6/2011 |
| WO | WO2011075439 A1 | 6/2011 |
| WO | WO2011075607 A1 | 6/2011 |
| WO | WO2011075615 A1 | 6/2011 |
| WO | WO2011079327 A1 | 6/2011 |
| WO | WO2011081918 A1 | 7/2011 |
| WO | WO2011082077 A1 | 7/2011 |
| WO | WO2011087740 A1 | 7/2011 |
| WO | WO2011091417 A1 | 7/2011 |
| WO | WO2011091446 A1 | 7/2011 |
| WO | WO2011091532 A1 | 8/2011 |
| WO | WO2011112429 A1 | 9/2011 |
| WO | WO2011119853 A1 | 9/2011 |
| WO | WO2011119858 A1 | 9/2011 |
| WO | WO2011119860 A1 | 9/2011 |
| WO | WO2011119870 A1 | 9/2011 |
| WO | WO2011127350 A1 | 10/2011 |
| WO | WO2011146401 A1 | 11/2011 |
| WO | WO2011150243 A1 | 12/2011 |
| WO | WO2011156543 A2 | 12/2011 |

OTHER PUBLICATIONS

Angiolini M., et al., "Synthesis of Azabicycloalkane Amino Acid Scaffolds as Reverse-Turn Inducer Dipeptide Mimics ," European Journal Organization Chemistry, 2000, pp. 2571-2581.

Boehm T., et al., "Uber Die Bildung Von Gamma-Piperidonderivaten Aus Azetessigester, Aromatischen Aldehyden und Aminen, Eine Modifikation Der Hantzschschen Pyridinsynthese," Pharmaceutical, 1943, vol. 281, pp. 62-77.

Brettle R., et al., "A Highly Efficient Enzymic Route to Novel Chiral Liquid Crystals based on 3-Aryl-2-cycloalken-1 -ones," Journal of the Chemical Society, Chemical Communications, 1994, pp. 2305-2306.

Bundgaard H., "Design of Pro Drugs," 1985, pp. 1-6.

Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51 (17), pp. 5243-5263.

Chong J.M., et al., "Asymmetric Synthesis of trans.2,5-Diphenylpyrrolidine: A C2-Symmetric Chirai Amine," Tetrahedron Asymmetry, 1995, vol. 6 (2), pp. 409-418.

Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.

Clarke P.A., et al., "Pot, Atom and Step Economic (Pase) Synthesis of Highly Functionalized Piperidines: A Five-Component Condensation," Tetrahedron Letters , 2007, vol. 48 , pp. 5209-5212.

Clarke P.A., et al., "Pot, Atom and Step Economic (PASE) Synthesis of Highly Substituted Piperidines:A Five-Component Condensation," Synthesis, 2008, No. 28, pp. 3530-3532.

Collado I., et al , "Stereoselective Addition of Grignard-Derived Organocopper Reagents to N-Acyliminium Ions: Synthesis of Enantiopure 5- and 4,5-Substituted Prolinates ," Journal of Organic Chemistry , 1995, vol. 60, pp. 5011-5015.

Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.

Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.

Effenberger F., et al., "Synthesis, Structure, and Spectral Behavior of Donor-Acceptor Substituted Biphenyls," The Journal of Organic Chemistry, 1983, vol. 48, pp. 4649-4658.

Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.

Gordon T.D., et al , "Synthetic Approaches to the Azole Peptide Mimetics," Tetrahedron Letters, 1993, vol. 34(12), pp. 1901-1904.

Greene T.W., et al., "Protection for the Amino group," Protective Groups in Organic Synthesis, 1999, Third Edition, pp. 494-653.

Hartwig J.F., et al., "III.3.2 Palladium-Catalyzed Amination of Aryl Halides and Related Reactions," Handbook of Organopalladium Chemistry for Organic Synthesis, 2002, pp. 1051-1096.

Hoover J.E, Remington's Pharmaceutical Sciences, 15th Edition, 1975, Table of Contents.

International Preliminary Report on Patentability and Written Opinion for the Application No. PCT/US2010/031102, mailed on Oct. 18, 2011, 7 pages.

International Search Report and Written Opinion for Application No. PCT/US2009/038077, mailed on Jan. 21, 2011, 16 pages.

International Search Report and Written Opinion for Application No. PCT/US2009/069177, mailed on Aug. 10, 2010, 17 pages.

International Search Report for Application No. PCT/US2009/069188, mailed on Jun. 8, 2010, 4 pages.

International Search Report for the Application No. PCT/US2010/031102, mailed on Sep. 1, 2010, 4 pages.

Jacques et al., "Enantiomers, Racemates, and Resolutions," J. Wiley & Sons, Chapter 3, pp. 197-213, 1981.

Jeffrey J.L., et al., "Concise Synthesis of Pauciflorol F Using a Larock Annulation," Organic Letters, 2009, vol. 11 (23), pp. 5450-5453.

Jing Q., et al., "Bulky Achiral Triarylphosphines Mimic Binap in Ru(II)—Catalyzed Asymmetric Hydrogenation of Ketones," Advanced Synthesis & Catalysis, 2005, vol. 347, pp. 1193-1197.

Khan A.T., et al., "Effects of Substituents in the -Position of 1,3-Dicarbonyl Compounds in Bromodimethylsulfonium Bromide-Catalyzed Multicomponent Reactions: A Facile Access to Functionalized Piperidines," Journal of organic chemistry, 2008, vol. 73 , pp. 8398-8402.

Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67 (17), pp. 5993-6000.

Li Chuan-Ying., et al., "Olefination of Ketenes for the Enantioselective Synthesis of Allenes via an Ylide Route," Tetrahedron, 2007, vol. 63, pp. 8046-8053.

Lieberman L., et al., eds., Pharmaceutical Dosage Forms, vol. 1, Marcel Dekker, Inc., 1980, Table of Contents.

Louie J., et al., "Palladium-Catalyzed Amination of Aryl Triflates and Importance of Triflate Addition Rate," Journal of Organic Chemistry, 1997, vol. 62 (5), pp. 1268-1273.

L-selectride, Retrieved from the Internet:<URL:http://en.wikipedia.org/w/index.php?oldid=488453454>.

Lucas S., et al.,"In Vivo Active Aldosterone Synthase Inhibitors with Improved Aelectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.

Masters K., "Spray Drying Handbook" 4th Edition, John Wiley & Sons, 1985, Table of Contents.

Masui M., et al., "A Practical Method for Asymmetric Borane Reduction of Prochiral Ketones Using Chiral Amino Alcohols and Trimethyl Borate," Synlett, 1997, pp. 273-274.

Matzeit A., et al., "Radical Tandem Cyclizations by Anodic Decarboxylation of Carboxylic Acids," Synthesis, 1995, pp. 1432-1444.

Misra M., et al., "Organocatalyzed Highly Atom Economic One Pot Synthesis of Tetrahydropyridines as Antimalarials," Bioorganic & Medicinal Chemistry, 2009, vol. 17 , pp. 625-633.

(56) References Cited

OTHER PUBLICATIONS

Moinet C., et al., "Novel Non-Peptide Ligands for the Somatostatin sst3 Receptor," Bioorganic & Medicinal Chemistry Letters, 2001, vol. 11 (8), pp. 991-995.

Muci A.R., et al., "Practical Palladium Catalysts for C—N. And C—O Bond Formation," Topics in Current Chemistry, 2002, vol. 219, pp. 131-209.

Muri E.M.F., et al., "Pseudo-Peptides Derived From Isomannide as Potential Inhibitors of Serine Proteases," Amino Acids, 2005, vol. 28 (4), pp. 413-419.

Naylor E.M., et al., "3-Pyridylethanolamines: Potent and Selective Human 63 Adrenergic Receptor Agonists," Bioorganic & Medicinal Chemistry Letters, 1998, vol. 8 (21), pp. 3087-3092.

Nevar N.M., et al., "One Step Preparation of 1,4-Diketones from Methyl Ketones and a-Bromomethyl Ketones in the Presence of $ZnCl_2 \cdot t\text{-BuOH} \cdot Et_2NR$ as a Condensation Agent," Synthesis, 2000, vol. 9, pp. 1259-1262.

Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.

Peng T., et al., "Construction of a Library of Rhodol Fluorophores for Developing New Fluorescent Probes," Organic Letters, 2010, vol. 12 (3), pp. 496-499.

Penning T.D., et al., "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer," Bioorganic & Medicinal Chemistry, 2008, vol. 16(14), pp. 6965-6975.

Polymer Handbook, Brandrup J., et al., Eds., Interscience Publishers, 1975, Table of Contents.

Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.

Sato M., et al., "Efficient Preparation of Optically Pure C2-Symmetrical Cyclic Amines for Chiral Auxiliary," Synthesis, 2004, vol. 9, pp. 1434-1438.

Sawyer J.S., et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.

Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.

Smith D.C., et al., "Reissert Compound Chemistry. XXVI. The Syntheses of Bis-Benzylisoquinolines," Journal of Heterocyclic Chemistry, 1976, vol. 13, pp. 573-576.

Sperling L. H., "Introduction to Physical Polymer Science," 2nd Edition, John Wiley & Sons, Inc., 1992, Table of Contents.

Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.

Takagi S., et al., "Antimicrobial Agents From Bletilla Striata," Phyrochemisrry, 1983, vol. 22 (4), pp. 1011-1015.

Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.

Tellinghuisen T.L., et al., "Structure of the Zinc-Binding Domain of an Essential Component of the Hepatitis C Virus Replicase," Nature, 2005, vol. 435 (7040), pp. 374-379.

Vallee R.J., et al., "Photoannelation Reactions of 3-(Alk-1-ynyl)cyclohept-2-en-1-ones," Helvetica Chimica Acta, 2010, vol. 93 (1), pp. 17-24.

Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.

Willis M.C., et al., "Palladium-Catalyzed Tandem Alkenyl and Aryl C—N. Bond Formation: A Cascade N-Annulation Route to 1-Functionalized Indoles," Angewandte Chemie International Edition, 2005, vol. 44 (3), pp. 403-406.

Wolfe J.P., et al., "Palladium-Catalyzed Amination of Aryl Triflates," Journal of Organic Chemistry, 1997, vol. 62 (5), pp. 1264-1267.

Xiao D., et al., "A Practical Synthetic Pathway to Polysubstituted Tetrahydropyridines via Multicomponent Reactions Catalyzed by $BF_3 \cdot OEt_2$," Synlett, 2005, vol. 10, pp. 1531-1534.

Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Journal of the American Chemical Society, 2002, vol. 4(23), pp. 4029-4032.

\* cited by examiner

ANTI-VIRAL COMPOUNDS

The present application claims priority from U.S. Provisional Application Ser. No. 61/423,906, filed Dec. 16, 2010 and U.S. Provisional Application Ser. No. 61/446,800, filed Feb. 25, 2011; this application is also a continuation-in-part of U.S. patent application Ser. No. 12/964,027, filed Dec. 9, 2010, which is a continuation-in-part of U.S. patent application Ser. No. 12/903,822, filed Oct. 13, 2010, which is a continuation-in-part of U.S. patent application Ser. No. 12/813,301, filed Jun. 10, 2010, which claims the benefit from U.S. Provisional Application Ser. No. 61/186,291, filed Jun. 11, 2009, U.S. Provisional Application Ser. No. 61/242,836, filed Sep. 16, 2009, and U.S. Provisional Application Ser. No. 61/243,596, filed Sep. 18, 2009. All of these applications are incorporated herein by reference in their entireties.

FIELD

The present invention relates to compounds effective in inhibiting replication of Hepatitis C virus ("HCV"). The present invention also relates to compositions comprising these compounds and methods of using these compounds to treat HCV infection.

BACKGROUND

HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY

The present invention features compounds of Formulae I, $I_A$, $I_B$, $I_C$, $I_D$, $I_E$, $I_F$ or $I_G$, and pharmaceutically acceptable salts thereof. These compounds and salts can inhibit the replication of HCV and therefore are useful for treating HCV infection.

The present invention also features compositions comprising the compounds or salts of the present invention. The compositions can also include additional therapeutic agents, such as HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features compounds having Formula I, and pharmaceutically acceptable salts thereof,

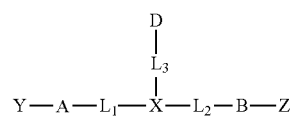

wherein:
X is $C_3$-$C_8$cycloalkyl or $C_5$-$C_8$cycloalkenyl, and is optionally substituted with one or more $R_A$ or $R_F$;

$L_1$ and $L_2$ are each independently selected from bond; or $C_1$-$C_6$alkylene, $C_2$-$C_6$alkenylene or $C_2$-$C_6$alkynylene, each of which is independently optionally substituted at each occurrence with one or more $R_L$;

$L_3$ is bond or -$L_S$-K-$L_S'$-, wherein K is selected from bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B'$)—, —N($R_B$)SO$_2$N($R_B'$)—, or —N($R_B$)S(O)N($R_B'$)—;

A and B are each independently $C_3$-$C_{12}$carbocycle or 3- to 12-membered heterocycle, and are each independently optionally substituted with one or more $R_A$;

D is $C_3$-$C_{12}$carbocycle or 3- to 12-membered heterocycle, and is optionally substituted with one or more $R_A$; or D is $C_3$-$C_{12}$carbocycle or 3- to 12-membered heterocycle which is substituted with J and optionally substituted with one or more $R_A$, where J is $C_3$-$C_{12}$carbocycle or 3- to 12-membered heterocycle and is optionally substituted with one or more $R_A$, or J is —SF$_5$; or D is hydrogen or $R_A$;

Y is selected from -T'-C($R_1R_2$)N($R_5$)-T-$R_D$, -T'-C($R_3R_4$)C($R_6R_7$)-T-$R_D$, -$L_K$-T-$R_D$, or -$L_K$-E;

$R_1$ and $R_2$ are each independently $R_C$, and $R_5$ is $R_B$; or $R_1$ is $R_C$, and $R_2$ and $R_5$, taken together with the atoms to which they are attached, form a 3- to 12-membered heterocycle which is optionally substituted with one or more $R_A$;

$R_3$, $R_4$, $R_6$, and $R_7$ are each independently $R_C$; or $R_3$ and $R_6$ are each independently $R_C$, and $R_4$ and $R_7$, taken together with the atoms to which they are attached, form a 3- to 12-membered carbocycle or heterocycle which is optionally substituted with one or more $R_A$;

Z is selected from -T'-C($R_8R_9$)N($R_{12}$)-T-$R_D$, -T'-C($R_{10}R_{11}$)C($R_{13}R_{14}$)-T-$R_D$, -$L_K$-T-$R_D$, or -$L_K$-E;

$R_8$ and $R_9$ are each independently $R_C$, and $R_{12}$ is $R_B$; or $R_8$ is $R_C$, and $R_9$ and $R_{12}$, taken together with the atoms to which they are attached, form a 3- to 12-membered heterocycle which is optionally substituted with one or more $R_A$;

$R_{10}$, $R_{11}$, $R_{13}$, and $R_{14}$ are each independently $R_C$; or $R_{10}$ and $R_{13}$ are each independently $R_C$, and $R_{11}$ and $R_{14}$, taken together with the atoms to which they are attached, form a 3- to 12-membered carbocycle or heterocycle which is optionally substituted with one or more $R_A$;

T and T' are each independently selected at each occurrence from bond, -$L_S$-, -$L_S$-M-$L_S$'-, or -$L_S$-M-$L_S$'-M'-$L_S$''-, wherein M and M' are each independently selected at each occurrence from bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_B$')—, —N($R_B$)SO$_2$N($R_B$')—, —N($R_B$)S(O)N($R_B$')—, $C_3$-$C_{12}$carbocycle or 3- to 12-membered heterocycle, and wherein said $C_3$-$C_{12}$carbocycle and 3- to 12-membered heterocycle are each independently optionally substituted at each occurrence with one or more $R_A$;

$L_K$ is independently selected at each occurrence from bond, -$L_S$-N($R_B$)C(O)-$L_S$'- or -$L_S$-C(O)N($R_B$)-$L_S$'-; or $C_1$-$C_6$alkylene, $C_2$-$C_6$alkenylene or $C_2$-$C_6$alkynylene, each of which is independently optionally substituted at each occurrence with one or more $R_L$; or $C_3$-$C_{12}$carbocycle or 3- to 12-membered heterocycle, each of which is independently optionally substituted at each occurrence with one or more $R_A$;

E is independently selected at each occurrence from $C_3$-$C_{12}$carbocycle or 3- to 12-membered heterocycle, and is independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or -$L_S$-$R_E$, wherein two adjacent $R_A$, taken together with the atoms to which they are attached and any atoms between the atoms to which they are attached, can optionally form carbocycle or heterocycle;

$R_B$ and $R_B$' are each independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_B$ or $R_B$' is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_C$ is independently selected at each occurrence from hydrogen, halogen, hydroxy, mercapto, amino, carboxy, nitro, oxo, phosphonoxy, phosphono, thioxo, formyl or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_C$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_E$ is independently selected at each occurrence from —O—$R_S$, —S—$R_S$, —C(O)$R_S$, —OC(O)$R_S$, —C(O)OR$_S$, —N($R_SR_S$'), —S(O)$R_S$, —SO$_2R_S$, —C(O)N($R_SR_S$'), —N($R_S$)C(O)$R_S$', —N($R_S$)C(O)N($R_S$'$R_S$''), —N($R_S$)SO$_2R_S$', —SO$_2$N($R_SR_S$'), —N($R_S$)SO$_2$N($R_S$'$R_S$''), —N($R_S$)S(O)N($R_S$'$R_S$''), —OS(O)—$R_S$, —OS(O)$_2$—$R_S$, —S(O)$_2$OR$_S$, —S(O)OR$_S$, —OC(O)OR$_S$, —N($R_S$)C(O)OR$_S$', —OC(O)N($R_SR_S$'), —N($R_S$)S(O)—$R_S$', —S(O)N($R_SR_S$'), —P(O)(OR$_S$)$_2$, or —C(O)N($R_S$)C(O)—$R_S$'; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$, or —N($R_SR_S$');

$R_F$ is independently selected at each occurrence from $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is independently optionally substituted with one or more $R_L$; or —($R_X$—$R_Y$)$_Q$—($R_X$—$R_Y$'), wherein Q is 0, 1, 2, 3 or 4, and each $R_X$ is independently O, S or N($R_B$), wherein each $R_Y$ is independently $C_1$-$C_6$alkylene, $C_2$-$C_6$alkenylene or $C_2$-$C_6$alkynylene each of which is independently optionally substituted with one or more substituents selected from halogen, hydroxy, mercapto, amino, carboxy, nitro, oxo, phosphonoxy, phosphono, thioxo, formyl or cyano, and wherein each $R_Y$' is independently $C_1$-$C_6$alkyl, $C_2$-$C_6$alkenyl or $C_2$-$C_6$alkynyl each of which is independently optionally substituted with one or more substituents selected from halogen, hydroxy, mercapto, amino, carboxy, nitro, oxo, phosphonoxy, phosphono, thioxo, formyl or cyano;

$R_L$ is independently selected at each occurrence from halogen, nitro, oxo, phosphonoxy, phosphono, thioxo, cyano, —O—$R_S$, —S—$R_S$, —C(O)$R_S$, —OC(O)$R_S$, —C(O)OR$_S$, —N(R$_S$R$_S$'), —S(O)R$_S$, —SO$_2$R$_S$, —C(O)N(R$_S$R$_S$') or —N(R$_S$)C(O)R$_S$'; or C$_3$-C$_6$carbocycle 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl; wherein two adjacent R$_L$, taken together with the atoms to which they are attached and any atoms between the atoms to which they are attached, can optionally form carbocycle or heterocycle;

L$_S$, L$_S$' and L$_S$" are each independently selected at each occurrence from bond; or C$_1$-C$_6$alkylene, C$_2$-C$_6$alkenylene or C$_2$-C$_6$alkynylene, each of which is independently optionally substituted at each occurrence with one or more R$_L$; and R$_S$, R$_S$' and R$_S$" are each independently selected at each occurrence from hydrogen; C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —O—C$_1$-C$_6$alkyl, —O—C$_1$-C$_6$alkylene-O—C$_1$-C$_6$alkyl, or 3- to 6-membered carbocycle or heterocycle; or 3- to 6-membered carbocycle or heterocycle; wherein each 3- to 6-membered carbocycle or heterocycle in R$_S$, R$_S$' or R$_S$" is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

A and B preferably are independently selected from C$_5$-C$_6$carbocycle (e.g., phenyl), 5- to 6-membered heterocycle (e.g., pyridinyl or thiazolyl), or 8- to 12-membered bicycles such as

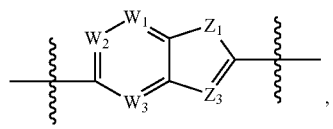,

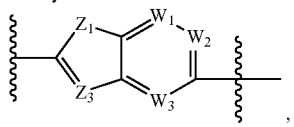,

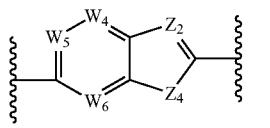, or

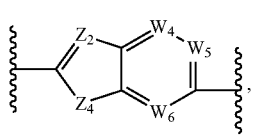

where Z$_1$ is independently selected at each occurrence from O, S, NH or CH$_2$, Z$_2$ is independently selected at each occurrence from N or CH, Z$_3$ is independently selected at each occurrence from N or CH, Z$_4$ is independently selected at each occurrence from O, S, NH or CH$_2$, and W$_1$, W$_2$, W$_3$, W$_4$, W$_5$ and W$_6$ are each independently selected at each occurrence from CH or N. A and B are each independently optionally substituted with one or more R$_4$.

More preferably, A is selected from C$_5$-C$_6$carbocycle, 5- to 6-membered heterocycle,

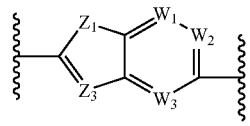

or

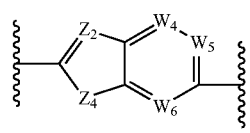, and is optionally substituted with one or more R$_4$; B is selected from C$_5$-C$_6$carbocycle, 5- to 6-membered heterocycle,

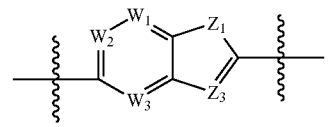

or

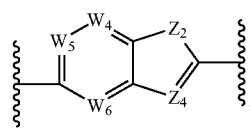, and is optionally substituted with one or more R$_4$; where Z$_1$, Z$_2$, Z$_3$, Z$_4$, W$_1$, W$_2$, W$_3$, W$_4$, W$_5$, W$_6$ are as defined above. Preferably, Z$_3$ is N and Z$_4$ is NH. For instance, A can be selected from phenyl (e.g.,

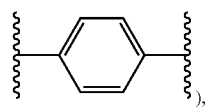), pyridinyl (e.g.,

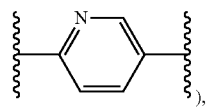), thiazolyl (e.g.,
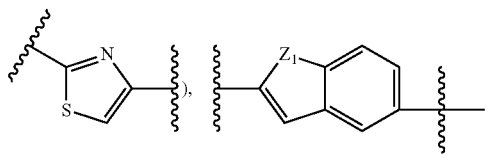
(e.g.,
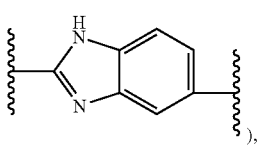 [SMILES: *c1ccc2[nH]c(*)nc2c1]
or
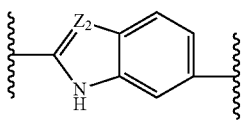
(e.g.,
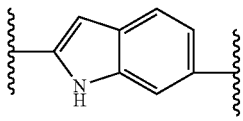
or
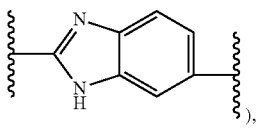 [SMILES: *c1ccc2nc(*)[nH]c2c1]
and is optionally substituted with one or more $R_A$; and B can be selected from phenyl (e.g.,
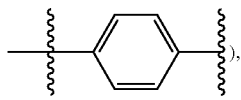
pyridinyl (e.g.,
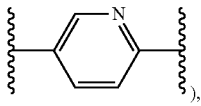
thiazolyl (e.g.,
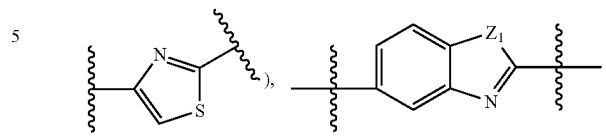
(e.g.,
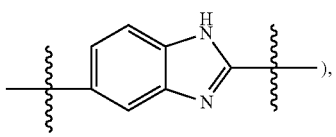 [SMILES: *c1ccc2[nH]c(*)nc2c1]
or
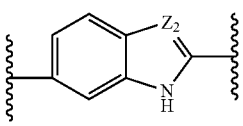
(e.g.,
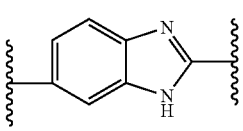
or
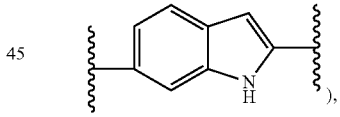
and is optionally substituted with one or more $R_A$. Highly preferably, both A and B are phenyl (e.g., both A and B are
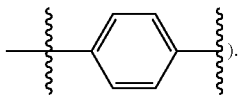
Also highly preferably, A is
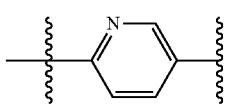 [SMILES: *c1ccc(*)nc1]

and B is

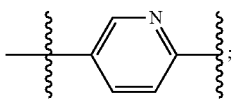

or A is

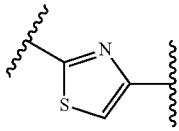 [SMILES: *c1csc(*)n1]

and B is

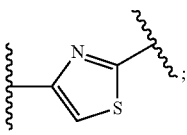 [SMILES: *c1csc(*)n1]

or A is

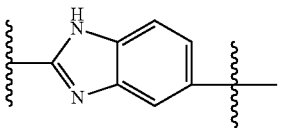 [SMILES: *c1ccc2[nH]c(*)nc2c1]

and B is

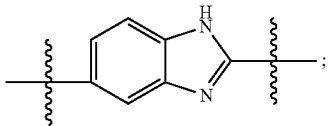 [SMILES: *c1ccc2[nH]c(*)nc2c1]

or A is

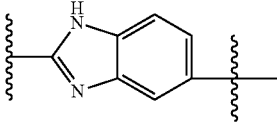 [SMILES: *c1ccc2[nH]c(*)nc2c1]

and B is

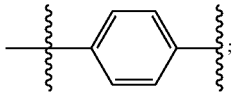

or A is

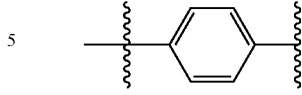

and B is

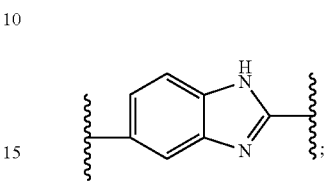

wherein each A and B is independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle (e.g., phenyl), 5- to 6-membered heterocycle (e.g., pyridinyl, pyrimidinyl, thiazolyl), or 6- to 12-membered bicycles (e.g., indanyl, 4,5,6,7-tetrahydrobenzo[d]thiazolyl, benzo[d]thiazolyl, indazolyl, benzo[d][1,3]dioxol-5-yl), and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

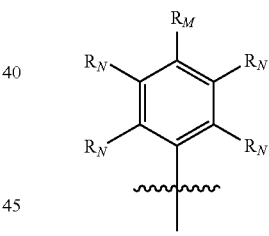

or

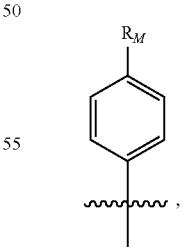

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

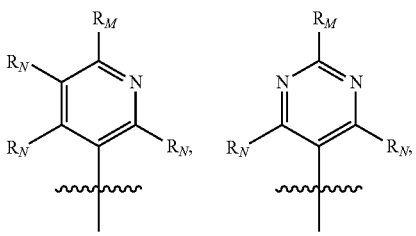

or

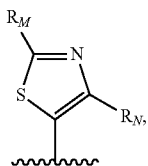

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

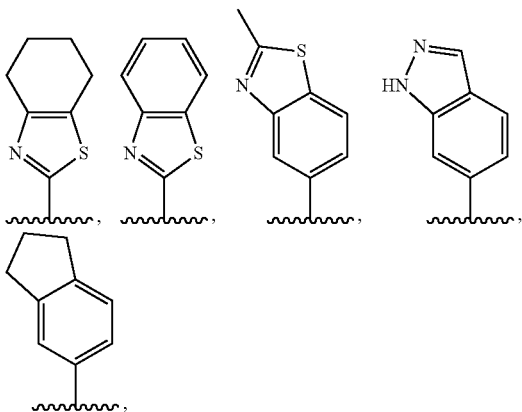

or

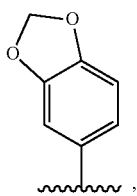

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C($CF_3$)$_2$—OH, —C($CH_3$)$_2$—CN, —C($CH_3$)$_2$—$CH_2$OH, or —C($CH_3$)$_2$—$CH_2 NH_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$-alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)O$C_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$ (e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —C$_1$-C$_6$alkylene-P(O)(OR$_S$)$_2$ (e.g., —CH$_2$—P(O)(OEt)$_2$). Also more preferably R$_M$ is C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, —C(O)OR$_S$, or —N(R$_S$R$_S$'). For example R$_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, R$_M$ is C$_1$-C$_6$alkyl which is optionally substituted with one or more substituents selected from halogen, hydroxy, mercapto, amino or carboxy (e.g., tert-butyl, CF$_3$).

More preferably, D is C$_5$-C$_6$carbocycle, 5- to 6-membered heterocycle or 6- to 12-membered bicycle and is substituted with J and optionally substituted with one or more R$_4$, wherein J is C$_3$-C$_6$carbocycle, 3- to 6-membered heterocycle or 6- to 12-membered bicycle and is optionally substituted with one or more R$_4$. Preferably, J is substituted with a C$_3$-C$_6$carbocycle or 3- to 6-membered heterocycle, wherein said C$_3$-C$_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'), and J can also be optionally substituted with one or more R$_4$. Also preferably, D is C$_5$-C$_6$carbocycle or 5- to 6-membered heterocycle and is substituted with J and optionally substituted with one or more R$_4$, and J is C$_3$-C$_6$carbocycle or 3- to 6-membered heterocycle and is optionally substituted with one or more R$_4$, and preferably, J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Also preferably, D is C$_5$-C$_6$carbocycle or 5- to 6-membered heterocycle and is substituted with J and optionally substituted with one or more R$_4$, and J is 6- to 12-membered bicycle (e.g., a 7- to 12-membered fused, bridged or spiro bicycle comprising a nitrogen ring atom through which J is covalently attached to D) and is optionally substituted with one or more R$_4$. More preferably, D is phenyl and is substituted with J and optionally substituted with one or more R$_4$, and J is C$_3$-C$_6$carbocycle, 3- to 6-membered heterocycle or 6- to 12-membered bicycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Highly preferably, D is

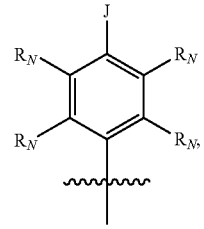

wherein each R$_N$ is independently selected from R$_D$ and preferably is hydrogen or halogen, and J is C$_3$-C$_6$carbocycle, 3- to 6-membered heterocycle or 6- to 12-membered bicycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'). Also preferably, D is

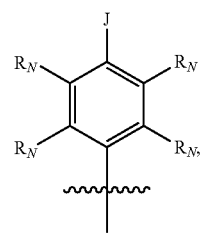

wherein each R$_N$ is independently selected from R$_D$ and preferably is hydrogen or halogen, and J is C$_3$-C$_6$carbocycle or 3- to 6-membered heterocycle and is substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$'), and J can also be optionally substituted with one or more R$_4$. Also preferably, D is

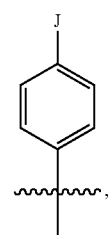

and J is C$_3$-C$_6$carbocycle or 3- to 6-membered heterocycle and is optionally substituted with one or more R$_4$, and preferably J is at least substituted with a C$_3$-C$_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C(O)OR$_S$ or —N(R$_S$R$_S$').

X preferably is $C_3$-$C_8$cycloalkyl or $C_5$-$C_8$cycloalkenyl and is optionally substituted with one or more $R_A$. X can also be $C_3$-$C_8$cycloalkyl or $C_5$-$C_8$cycloalkenyl which is optionally substituted with one or more $R_A$, wherein two adjacent $R_A$ on X, taken together with the ring atoms to which they are attached, optionally form a 5- to 6-membered carbocycle or heterocycle. More preferably, X is cyclopropyl, cyclopentyl or cyclopentenyl, and is optionally substituted with one or more $R_A$ or $R_F$, wherein two adjacent $R_A$ on X, taken together with the ring atoms to which they are attached, optionally form a 5- to 6-membered carbocycle or heterocycle.

Non-limiting examples of preferred X include the following cyclopropyl rings, each of which is optionally substituted with one or more $R_A$ or $R_F$:

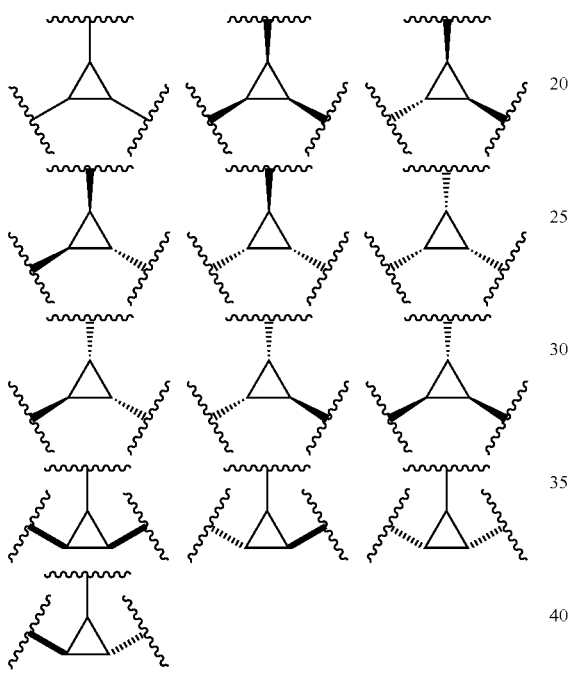

As shown, the relative stereochemistry at the any of the positions of the above cyclopropyl ring may be either cis or trans. The stereochemistries of optional substituents $R_A$ or $R_F$ at any of the positions of the cyclopropyl may vary relative to any substituent at any other position on the cyclopropyl ring. Depending on the particular substituents attached to the cyclopropyl, the stereochemistry at any carbon may be either (R) or (S).

Non-limiting examples of preferred X include the following cyclopentyl or cyclopentenyl rings, each of which is optionally substituted with one or more $R_A$ or $R_F$:

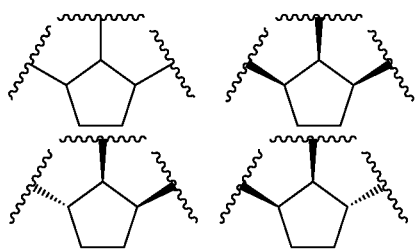

-continued

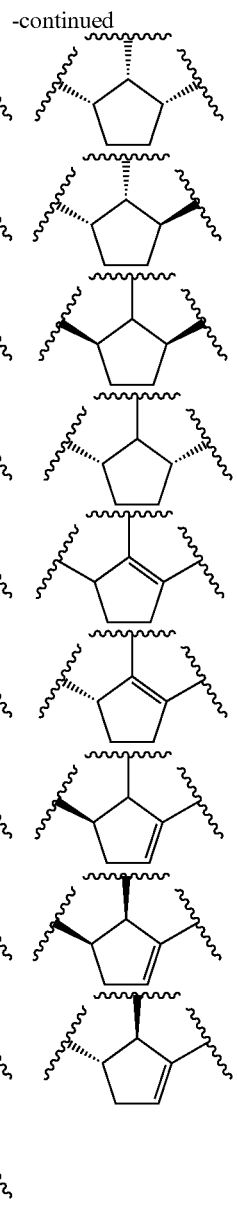

As shown, the relative stereochemistry at the any of the positions of the above cyclopentyl ring may be either cis or trans. The stereochemistries of optional substituents $R_A$ or $R_F$ at any of the positions of the cyclopentyl or cyclopentenyl may vary relative to any substituent at any other position on the cyclopropyl ring. Depending on the particular substituents attached to the cyclopentyl or cyclopentenyl, the stereochemistry at any carbon may be either (R) or (S).

Preferably, $R_F$ is $C_1$-$C_{10}$alkyl, $C_2$-$C_{10}$alkenyl or $C_2$-$C_{10}$alkynyl, each of which contains 0, 1, 2, 3, 4 or 5 heteroatoms selected from O, S or N and is independently optionally substituted with one or more substituents selected from halogen, hydroxy, mercapto, amino, carboxy, nitro, oxo, phosphonoxy, phosphono, thioxo, formyl or cyano. Also preferably, $R_F$ is $C_1$-$C_{10}$alkyl, $C_2$-$C_{10}$alkenyl or $C_2$-$C_{10}$alkynyl, each of which contains 0, 1, 2, 3, 4 or 5 O and is independently optionally substituted with one or more $R_L$. Also preferably, $R_F$ is —$(R_X$—$R_Y)_Q$—$(R_X$—$R_Y')$, wherein Q is 0, 1, 2, 3 or 4; each $R_X$ is independently O, S or N($R_B$); each $R_Y$ is independently $C_1$-$C_6$alkylene, $C_2$-$C_6$alkenylene or $C_2$-$C_6$alkynylene each of which is independently optionally substituted with one or more substituents selected from halogen, hydroxy, mercapto, amino, carboxy, nitro, oxo, phosphonoxy, phosphono, thioxo, formyl or cyano; and each $R_Y{}^1$ is independently $C_1$-$C_6$alkyl, $C_2$-$C_6$alkenyl or $C_2$-$C_6$alkynyl each of which is independently optionally substituted with one or more substituents selected from halogen, hydroxy, mercapto, amino, carboxy, nitro, oxo, phosphonoxy, phosphono, thioxo, formyl or cyano. Preferably, each $R_X$ is O. More preferably, X is optionally substituted with one or more $R_A$ or $R_F$, each $R_F$ is independently selected from $C_1$-$C_{10}$alkyl, $C_2$-$C_{10}$alkenyl or $C_2$-$C_{10}$alkynyl, each of which contains 0, 1, 2 or 3 O and is independently optionally substituted with one or more substituents selected from halogen, hydroxy, mercapto, amino, carboxy, nitro, oxo, phosphonoxy, phosphono, thioxo, formyl or cyano. Also preferably, X is optionally substituted with one or more $R_A$ or $R_F$, each $R_F$ is independently selected from —(O—$C_1$-$C_6$alkylene)$_Q$-(O—$C_1$-$C_6$alkyl), wherein Q preferably is 0, 1, 2 or 3.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently a bond or $C_1$-$C_6$alkylene (e.g., —CH$_2$— or —CH$_2$CH$_2$—), and are each independently optionally substituted with one or more $R_L$. Highly preferably, $L_1$, $L_2$ and $L_3$ are each a bond.

Y is preferably selected from -$L_S$-C($R_1R_2$)N($R_5$)-T-$R_D$, -$L_S$-C($R_3R_4$)C($R_6R_7$)-T-$R_D$, -G-C($R_1R_2$)N($R_5$)-T-$R_D$, -G-C($R_3R_4$)C($R_6R_7$)-T-$R_D$, —N($R_B$)C(O)C($R_1R_2$)N($R_5$)-T-$R_D$, —N($R_B$)C(O)C($R_3R_4$)C($R_6R_7$)-T-$R_D$, —C(O)N($R_B$)C($R_1R_2$)N($R_5$)-T-$R_D$, —C(O)N($R_B$)C($R_3R_4$)C($R_6R_7$)-T-$R_D$, —N($R_B$)C(O)-$L_S$-E, or —C(O)N($R_B$)-$L_S$-E. G is $C_5$-$C_6$carbocycle or 5- to 6-membered heterocycle, such as

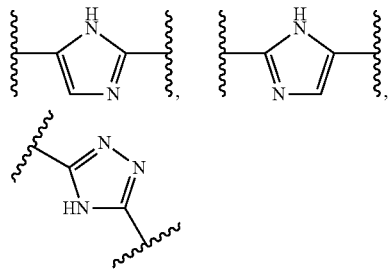

or

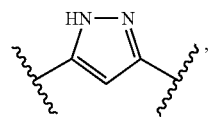

and is optionally substituted with one or more $R_A$ (e.g., one or more chloro or bromo). E preferably is a 7- to 12-membered bicycle (such as

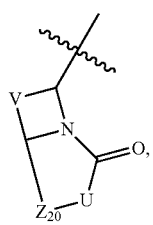

wherein U is independently selected at each occurrence from —(CH$_2$)— or —(NH)—; V and $Z_{20}$ are each independently selected from $C_1$-$C_4$alkylene, $C_2$-$C_4$alkenylene or $C_2$-$C_4$alkynylene, in which at least one carbon atom can be independently optionally replaced with O, S or N), and is optionally substituted with one or more $R_A$. More preferably, $R_1$ is $R_C$, and $R_2$ and $R_5$, taken together with the atoms to which they are attached, form a 5- to 6-membered heterocycle or 6- to 12-membered bicycle (e.g.,

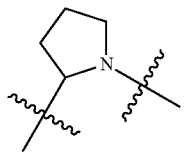 [SMILES: *C1CCCN1*]

or

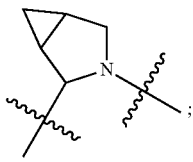 [SMILES: *C1C2CC2CN1*]

or

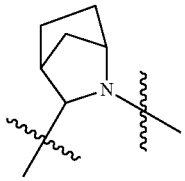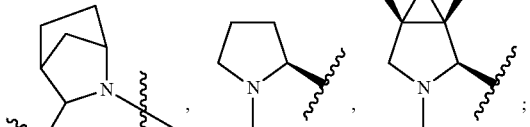

or

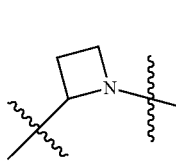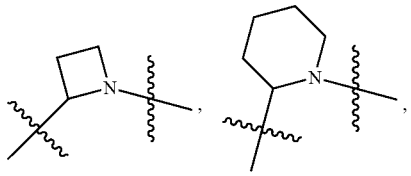

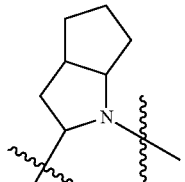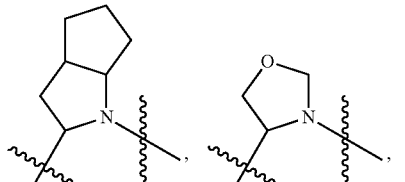

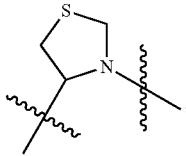

or

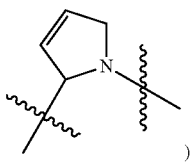 [SMILES: *C1C=CCN1*]

)

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)); and $R_3$ and $R_6$ are each independently $R_C$, and $R_4$ and $R_7$, taken together with the atoms to which they are attached, form a 5- to 6-membered carbocycle/heterocycle or 6- to 12-membered bicycle (e.g.,

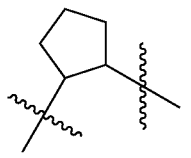 [SMILES: *C1CCCC1*]

or

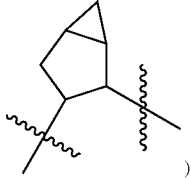 [SMILES: *C1CC2CC2C1*]

)

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Y can also be selected from -M-C($R_1R_2$)N($R_5$)—C(O)-$L_Y$'-M'—$R_D$, -M-C($R_1R_2$)N($R_5$)-$L_Y$'-M'—$R_D$, -$L_S$-C($R_1R_2$)N($R_5$)—C(O)-$L_Y$'-M'—$R_D$, -$L_S$-C($R_1R_2$)N($R_5$)-$L_Y$'-M'—$R_D$, -M-C($R_3R_4$)C($R_6R_7$)—C(O)-$L_Y$'-M'—$R_D$, -M-C($R_3R_4$)C($R_6R_7$)-$L_Y$'-M'—$R_D$, -$L_S$-C($R_3R_4$)C($R_6R_7$)—C(O)-$L_Y$'-M'-$R_D$, or -$L_S$-C($R_3R_4$)C($R_6R_7$)-$L_Y$'-M'-$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$')—, —N($R_B$)S(O)— or —N($R_B$)S(O)$_2$—, and $L_Y$' preferably is $C_1$-$C_6$alkylene which is optionally substituted with one or more $R_L$. $L_Y$' is $L_S$'. $L_Y$', for example, is a $C_1$-$C_6$alkylene such as, but not limited to,

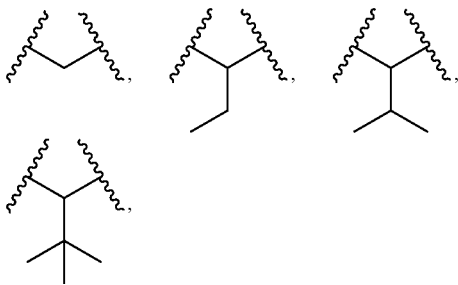

or

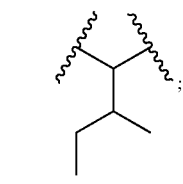 [SMILES: *C(*)C(C)CC]

;

and the optional $R_L$ is a substituent such as, but not limited to phenyl, —SMe, or methoxy. Any stereochemistry at a carbon within the group $L_Y$' can be either (R) or (S). More preferably, $R_1$ is $R_C$, and $R_2$ and $R_5$, taken together with the atoms to which they are attached, form a 5- to 6-membered heterocycle or 6- to 12-membered bicycle (e.g.,

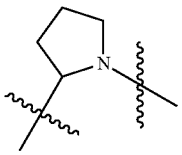

or

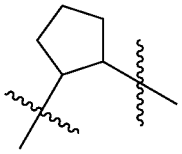 [SMILES: *C1CCCC1*]

)

which is optionally substituted with one or more $R_A$ (e.g., one or more hydroxy); and $R_3$ and $R_6$ are each independently $R_C$, and $R_4$ and $R_7$, taken together with the atoms to which they are attached, form a 5- to 6-membered carbocycle/heterocycle or 6- to 12-membered bicycle (e.g.,

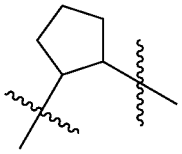 [SMILES: *C1CCCC1*]

or

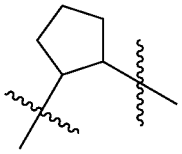 [SMILES: *C1CCCC1*]

)

which is optionally substituted with one or more $R_A$.

Also preferably, Y is selected from —N($R_B$)CO—C($R_1R_2$)N($R_5$)—C(O)-$L_Y$'-N($R_B$)C(O)O—$R_D$, —N($R_B$)CO—C($R_1R_2$)N($R_5$)—C(O)-$L_Y$'-N($R_B$)C(O)—$R_D$, —N($R_B$)CO—C($R_1R_2$)N($R_5$)—C(O)-$L_Y$'-N($R_B$)S(O)$_2$—$R_D$, —N($R_B$)CO—C($R_1R_2$)N($R_5$)—C(O)-$L_Y$'-N($R_BR_B$')—$R_D$, —N($R_B$)CO—C $(R_1R_2)N(R_5)$—C(O)-$L_Y'$-O—$R_D$, —N($R_B$)CO—C($R_1R_2$)N($R_5$)—C(O)-$L_Y'$-$R_D$, —N($R_B$)CO—C($R_1R_2$)N($R_5$)—$R_D$, -$L_S$-C($R_1R_2$)N($R_5$)—C(O)-$L_Y'$-N($R_B$)C(O)O—$R_D$, -$L_S$-C($R_1R_2$)N($R_5$)—C(O)-$L_Y'$-N($R_B$)C(O)—$R_D$, -$L_S$-C($R_1R_2$)N($R_5$)—C(O)-$L_Y'$-N($R_B$)S(O)$_2$—$R_D$, -$L_S$-C($R_1R_2$)N($R_5$)—C(O)-$L_Y'$-N($R_BR_B'$)—$R_D$, -$L_S$-C($R_1R_2$)N($R_5$)—C(O)-$L_Y'$-O—$R_D$, -$L_S$-C($R_1R_2$)N($R_5$)—C(O)-$L_Y'$-$R_D$, -$L_S$-C($R_1R_2$)N($R_5$)—$R_D$, —N($R_B$)CO—C($R_3R_4$)C($R_6R_7$)—C(O)-$L_Y'$-N($R_B$)C(O)O—$R_D$, —N($R_B$)CO—C($R_3R_4$)C($R_6R_7$)—C(O)-$L_Y'$-N($R_B$)C(O)—$R_D$, —N($R_B$)CO—C($R_3R_4$)C($R_6R_7$)—C(O)-$L_Y'$-N($R_B$)S(O)$_2$—$R_D$, —N($R_B$)CO—C($R_3R_4$)C($R_6R_7$)—C(O)-$L_Y'$-N($R_BR_B'$)—$R_D$, —N($R_B$)CO—C($R_3R_4$)C($R_6R_7$)—C(O)-$L_Y'$-O—$R_D$, —N($R_B$)CO—C($R_3R_4$)C($R_6R_7$)—C(O)-$L_Y'$-$R_D$, —N($R_B$)CO—C($R_3R_4$)C($R_6R_7$)—$R_D$, -$L_S$-C($R_3R_4$)C($R_6R_7$)—C(O)-$L_Y'$-N($R_B$)C(O)O—$R_D$, -$L_S$-C($R_3R_4$)C($R_6R_7$)—(O)— $L_Y'$-N($R_B$)C(O)—$R_D$, -$L_S$-C($R_3R_4$)C($R_6R_7$)—C(O)-$L_Y'$-N($R_B$)S(O)$_2$—$R_D$, -$L_S$-C($R_3R_4$)C($R_6R_7$)—C(O)-$L_Y'$-N($R_BR_B'$)—$R_D$, -$L_S$-C($R_3R_4$)C($R_6R_7$)—C(O)-$L_Y'$-O—$R_D$, -$L_S$-C($R_3R_4$)C($R_6R_7$)—C(O)-$L_Y'$-$R_D$, or -$L_S$-C($R_3R_4$)C($R_6R_7$)—$R_D$, wherein $L_Y'$ preferably is $C_1$-$C_6$alkylene which is optionally substituted with one or more $R_L$. $R_1$ may be $R_C$, and $R_2$ and $R_5$, taken together with the atoms to which they are attached, may form a 5- to 6-membered heterocycle or 6- to 12-membered bicycle (e.g.,

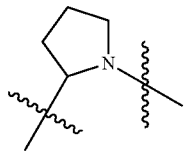 [SMILES: *C1CCCN1*]

or

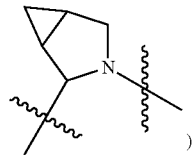 [SMILES: *C1C2CC2CN1*]

)

which is optionally substituted with one or more $R_A$; and $R_3$ and $R_6$ may be each independently $R_C$, and $R_4$ and $R_7$, taken together with the atoms to which they are attached, may form a 5- to 6-membered carbocycle/heterocycle or 6- to 12-membered bicycle (e.g.,

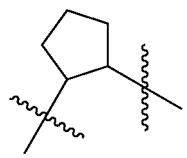 [SMILES: *C1CCCC1*]

or

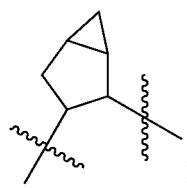

)

which is optionally substituted with one or more $R_A$.

Highly preferably, Y is selected from —N($R_B''$)CO—C($R_1R_2$)N($R_5$)—C(O)-$L_Y$-N($R_B''$)C(O)-$L_S$-$R_E$ or —C($R_1R_2$)N($R_5$)—C(O)-$L_Y$-N($R_B''$)C(O)-$L_S$-$R_E$, or Y is -G-C($R_1R_2$)N($R_5$)—C(O)-$L_Y$-N($R_B''$)C(O)-$L_S$-$R_E$, wherein $L_Y$ is $C_1$-$C_6$alkylene optionally substituted with one or more $R_L$, and $R_B''$ is each independently $R_B$. $R_B''$ and $R_1$ are each preferably hydrogen or $C_1$-$C_6$alkyl, and $R_2$ and $R_5$, taken together with the atoms to which they are attached, preferably form a 5- to 6-membered heterocycle or 6- to 12-membered bicycle (e.g.,

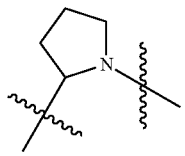 [SMILES: *C1CCCN1*]

or

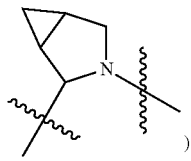 [SMILES: *C1C2CC2CN1*]

)

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)). $L_Y$ is each independently $L_S$. Preferably, $L_Y$ is $C_1$-$C_6$alkylene substituted with one or more $R_L$ such as a $C_3$-$C_6$carbocycle 3- to 6-membered heterocycle which is optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. Highly preferably, $L_Y$ is a $C_1$-$C_6$alkylene such as, but not limited to,

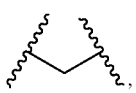 , 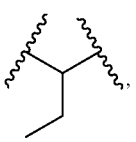 , 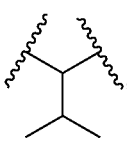 ,

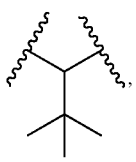 , or

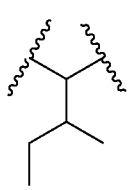

(stereochemistry at a carbon within the group $L_Y$ can be either (R) or (S)), $L_Y$ is optionally substituted with one or more $R_L$ (e.g., one or more phenyl or methoxy), G preferably is
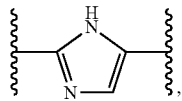
$R_B''$ is hydrogen; —$C(R_1R_2)N(R_5)$— is
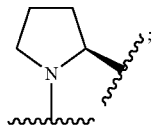 [SMILES: *[C@@H]1CCCN1*]
$L_S$ is a bond; and $R_E$ is methoxy.
Non-limiting examples of preferred Y include:
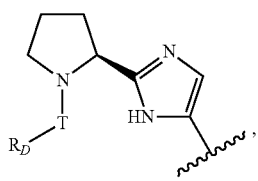
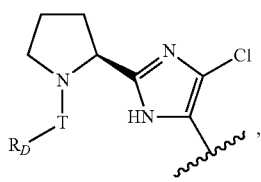
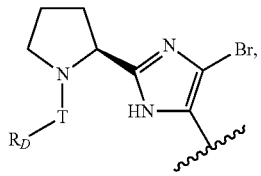
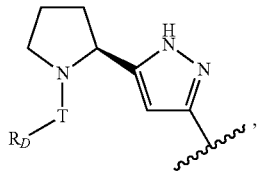
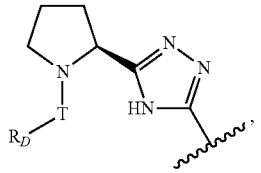
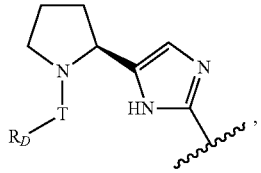
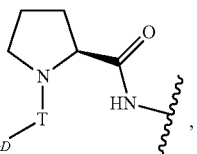
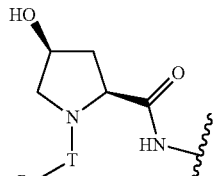
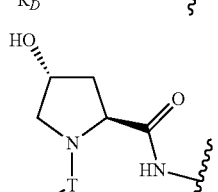
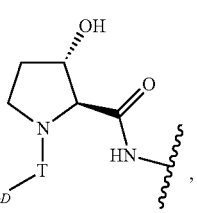
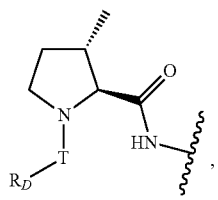
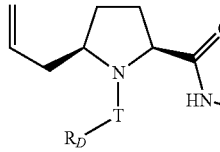
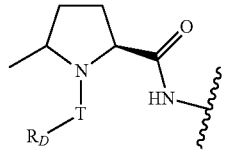
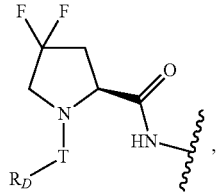
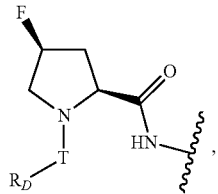

-continued

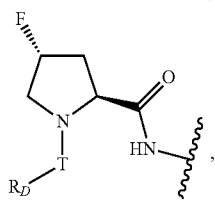,

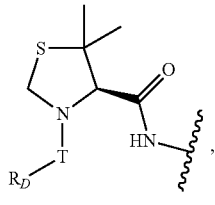,

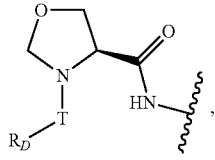,

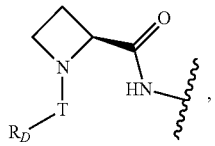,

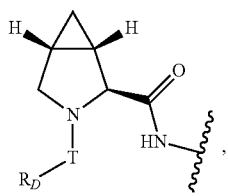, or

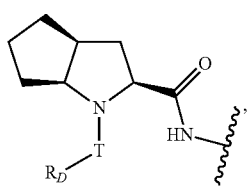, wherein T and $R_D$ are as defined herein. T, for example, can be -$L_S$-M-$L_S'$-M'-$L_S''$- where $L_S$ is a bond; M is C(O); $L_S'$ is $C_1$-$C_6$alkylene such as, but not limited to,

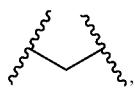


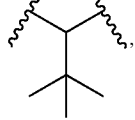

or

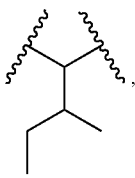, where $L_S'$ is optionally substituted with one or more $R_L$; $R_L$ is a substituent such as, but not limited to phenyl or methoxy; M' is —NHC(O)— or —NMeC(O)—; and $L_S''$ is a bond. Any stereochemistry at a carbon within the group $L_S'$ can be either (R) or (S). $R_D$, for example is methoxy. T-$R_D$ includes, but is not limited to:

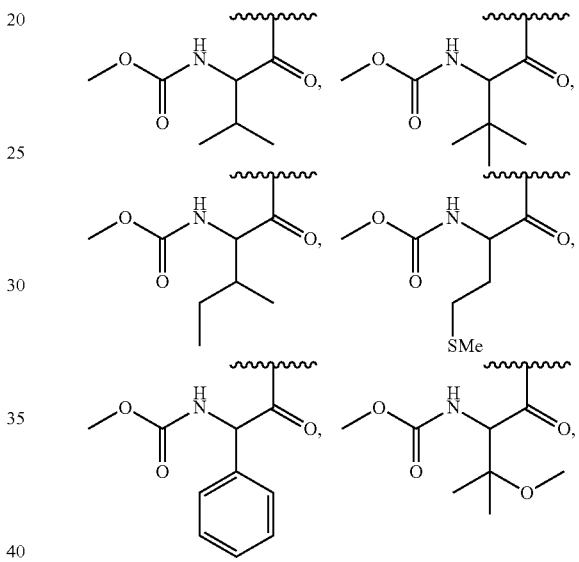

or

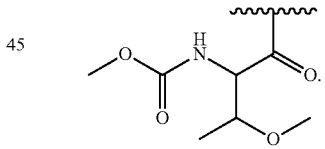

T-$R_D$ may also include certain stereochemical configurations; thus T-$R_D$ includes, but is not limited to:

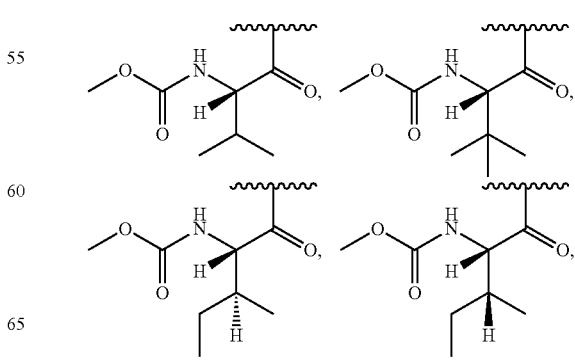

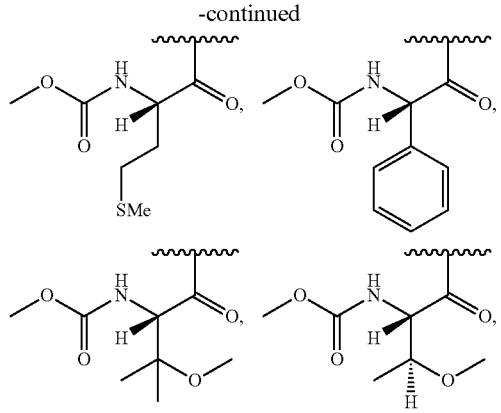
and
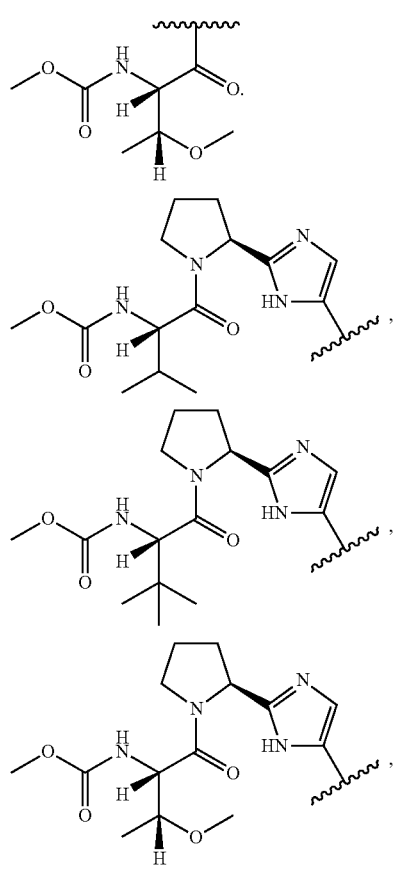
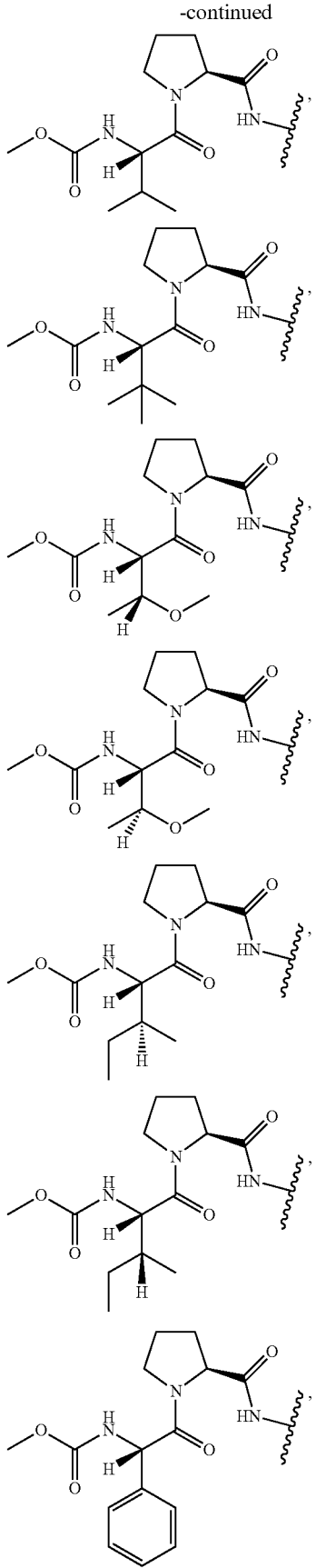
Non-limiting examples of preferred Y also include: or
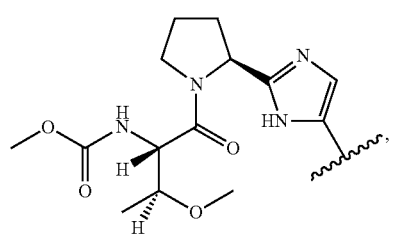

or

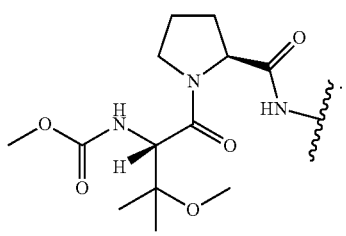 [SMILES: *NC(=O)[C@@H]1CCCN1C(=O)[C@@H](NC(=O)OC)C(C)(C)OC]

Z is preferably selected from -L_S-C(R_8R_9)N(R_{12})-T-R_D, -L_S-C(R_{10}R_{11})C(R_{13}R_{14})-T-R_D, -G-C(R_8R_9)N(R_{12})-T-R_D, -G-C(R_{10}R_{11})C(R_{13}R_{14})-T-R_D, —N(R_B)C(O)C(R_8R_9)N(R_{12})-T-R_D, —N(R_B)C(O)C(R_{10}R_{11})C(R_{13}R_{14})-T-R_D, —C(O)N(R_B)C(R_8R_9)N(R_{12})-T-R_D, —C(O)N(R_B)C(R_{10}R_{11})C(R_{13}R_{14})-T-R_D, —N(R_B)C(O)-L_S-E, or —C(O)N(R_B)-L_S-E. G is $C_5$-$C_6$carbocycle or 5- to 6-membered heterocycle, such as

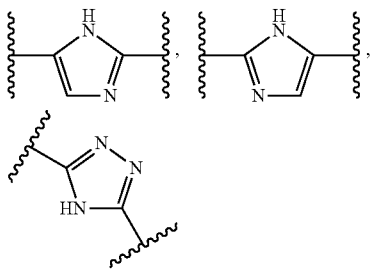

or

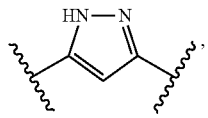

and is optionally substituted with one or more $R_A$ (e.g., one or more chloro or bromo). E preferably is a 8- to 12-membered bicycle (such as

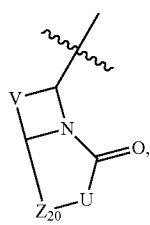

wherein U is independently selected at each occurrence from —(CH_2)— or —(NH)—; and V and $Z_{20}$ are each independently selected from $C_1$-$C_4$alkylene, $C_2$-$C_4$alkenylene or $C_2$-$C_4$alkynylene, in which at least one carbon atom is independently optionally replaced with O, S or N), and is optionally substituted with one or more $R_A$.

More preferably, $R_8$ is $R_C$, and $R_9$ and $R_{12}$, taken together with the atoms to which they are attached, form a 5- to 6-membered heterocycle or 6- to 12-membered bicycle (e.g.,

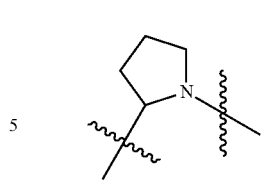

or

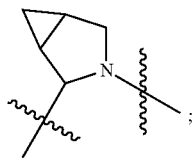 [SMILES: *C1C2CC2CN1*]

or

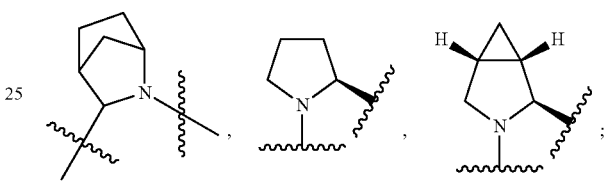

or

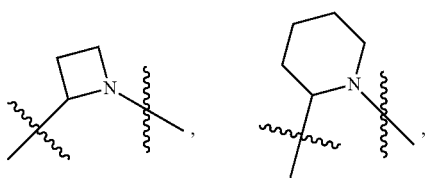

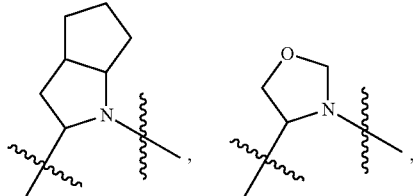

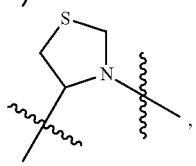

or

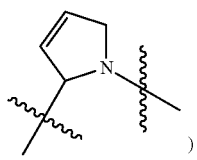 [SMILES: *C1C=CCN1*]

)

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle (e.g.,

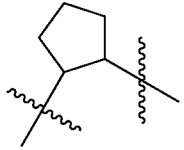 [SMILES: *C1CCCC1*]

or

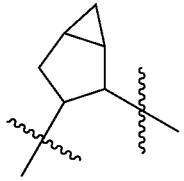

)

which is optionally substituted with one or more $R_A$ (such as, but not limited to hydroxy, halo (e.g., fluoro), $C_1$-$C_6$alkyl (e.g., methyl), or $C_2$-$C_6$alkenyl (e.g., allyl)).

Z can also be selected from -M-C($R_8R_9$)N($R_{12}$)—C(O)-$L_Y$'-M'—$R_D$, -M-C($R_8R_9$)N($R_{12}$)-$L_Y$'-M'—$R_D$, -$L_S$-C($R_8R_9$)N($R_{12}$)—C(O)-$L_Y$'-M'—$R_D$, -$L_S$-C($R_8R_9$)N($R_{12}$)-$L_Y$'-M'—$R_D$, -M-C($R_{10}R_{11}$)C($R_{13}R_{14}$)—C(O)-$L_Y$'-M'—$R_D$, -M-C($R_{10}R_{11}$)C($R_{13}R_{14}$)-$L_Y$'-M'-$R_D$, -$L_S$-C($R_{10}R_{11}$C($R_{13}R_{14}$)—C(O)-$L_Y$'-M'—$R_D$, or -$L_S$-C($R_{10}R_{11}$)C($R_{13}R_{14}$)-$L_Y$'-M'—$R_D$, wherein M preferably is bond, —C(O)N($R_B$)— or —N($R_B$)C(O)—, M' preferably is bond, —C(O)N($R_B$)—, —N($R_B$)C(O)—, —N($R_B$)C(O)O—, N($R_B$)C(O)N($R_B$')—, —N($R_B$)S(O)— or —N($R_B$)S(O)$_2$—, and $L_Y$' preferably is $C_1$-$C_6$alkylene which is optionally substituted with one or more $R_L$. $L_Y$' is each independently $L_S$. $L_Y$', for example, is a $C_1$-$C_6$alkylene such as, but not limited to,

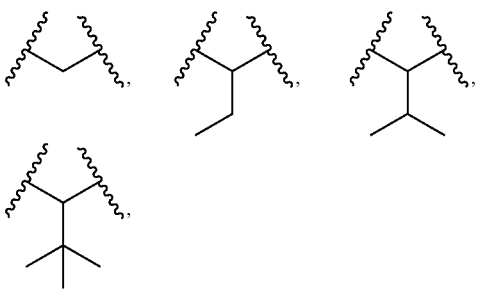

or

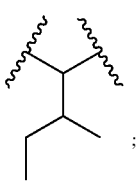 [SMILES: *C(*)C(C)CC]

;

and the optional $R_L$ is a substituent such as, but not limited to phenyl, —SMe, or methoxy. Any stereochemistry at a carbon within the group $L_Y$' can be either (R) or (S). More preferably, $R_8$ is $R_C$, and $R_9$ and $R_{12}$, taken together with the atoms to which they are attached, form a 5- to 6-membered heterocycle or 6- to 12-membered bicycle (e.g.,

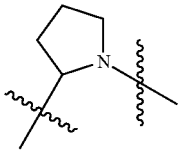 [SMILES: *C1CCCN1*]

or

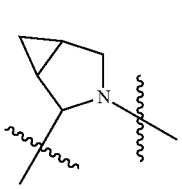

)

which is optionally substituted with one or more $R_A$ (e.g., one or more hydroxy); and $R_{10}$ and $R_{13}$ are each independently $R_C$, and $R_{11}$ and $R_{14}$, taken together with the atoms to which they are attached, form a 5- to 6-membered carbocycle/heterocycle or 6- to 12-membered bicycle (e.g.,

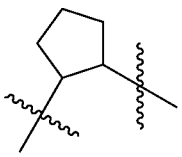 [SMILES: *C1CCCC1*]

or

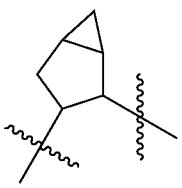

)

which is optionally substituted with one or more $R_A$.

Also preferably, Z is selected from —N($R_B$)CO—C($R_8R_9$)N($R_{12}$)—C(O)-$L_Y$'-N($R_B$)C(O)O—$R_D$, —N($R_B$)CO—C($R_8R_9$)N($R_{12}$)—C(O)-$L_Y$'-N($R_B$)C(O)—$R_D$, —N($R_B$)CO—C($R_8R_9$)N($R_{12}$)—C(O)-$L_Y$'-N($R_B$)S(O)$_2$—$R_D$, —N($R_B$)CO—C($R_8R_9$)N($R_{12}$)—C(O)-$L_Y$'-N($R_BR_B$')—$R_D$, —N($R_B$)CO—C($R_8R_9$)N($R_{12}$)—C(O)-$L_Y$'-O—$R_D$, —N($R_B$)CO—C($R_8R_9$)N($R_{12}$)—C(O)-$L_Y$'-$R_D$, —N($R_B$)CO—C($R_8R_9$)N($R_{12}$)—$R_D$, -$L_S$-C($R_8R_9$)N($R_{12}$)—C(O)-$L_Y$'-N($R_B$)C(O)O—$R_D$, -$L_S$-C($R_8R_9$)N($R_{12}$)—C(O)-$L_Y$'-N($R_B$)C(O)—$R_D$, -$L_S$-C($R_8R_9$)N($R_{12}$)—C(O)-$L_Y$'-N($R_B$)S(O)$_2$—$R_D$, -$L_S$-C($R_8R_9$)N($R_{12}$)—C(O)-$L_Y$'-N($R_BR_B$')—$R_D$, -$L_S$-C($R_8R_9$)N($R_{12}$)—C(O)-$L_Y$'-O—$R_D$, -$L_S$-C($R_8R_9$)N($R_{12}$)—C(O)-$L_Y$'-$R_D$, -$L_S$-C($R_8R_9$)N($R_{12}$)—$R_D$, —N($R_B$)CO—C($R_{10}R_{11}$)C($R_{13}R_{14}$)—C(O)-$L_Y$'-N($R_B$)C(O)O—$R_D$, —N($R_B$)CO—C($R_{10}R_{11}$)C($R_{13}R_{14}$)—C(O)-$L_Y$'-N($R_B$)C(O)—$R_D$, —N($R_B$)CO—C($R_{10}R_{11}$)C($R_{13}R_{14}$)—C(O)-$L_Y$'-N($R_B$)S(O)$_2$—$R_D$, —N($R_B$)CO—C($R_{10}R_{11}$)C($R_{13}R_{14}$)—C(O)-$L_Y$'-N($R_BR_B$')—$R_D$, —N(R$_B$)CO—C(R$_{10}$R$_{11}$)C(R$_{13}$R$_{14}$)—C(O)-L$_Y$'-O—R$_D$, —N(R$_B$)CO—C(R$_{10}$R$_{11}$)C(R$_{13}$R$_{14}$)—C(O)-L$_Y$'-R$_D$, —N(R$_B$)CO—C(R$_{10}$R$_{11}$)C(R$_{13}$R$_{14}$)—R$_D$, -L$_S$-C(R$_{10}$R$_{11}$)C(R$_{13}$R$_{14}$)—C(O)-L$_Y$'-N(R$_B$)C(O)O—R$_D$, -L$_S$-C(R$_{10}$R$_{11}$)C(R$_{13}$R$_{14}$)—C(O)-L$_Y$'-N(R$_B$)C(O)—R$_D$, -L$_S$-C(R$_{10}$R$_{11}$)C(R$_{13}$R$_{14}$)—C(O)-L$_Y$'-N(R$_B$)S(O)$_2$—R$_D$, -L$_S$-C(R$_{10}$R$_{11}$)C(R$_{13}$R$_{14}$)—C(O)-L$_Y$'-N(R$_B$R$_B$')—R$_D$, -L$_S$-C(R$_{10}$R$_{11}$)C(R$_{13}$R$_{14}$)—C(O)-L$_Y$'-O—R$_D$, -L$_S$-C(R$_{10}$R$_{11}$)C(R$_{13}$R$_{14}$)—C(O)-L$_Y$'-R$_D$, or -L$_S$-C(R$_{10}$R$_{11}$)C(R$_{13}$R$_{14}$)—R$_D$, wherein L$_Y$' preferably is C$_1$-C$_6$alkylene which is optionally substituted with one or more R$_L$. R$_8$ may be R$_C$, and R$_9$ and R$_{12}$, taken together with the atoms to which they are attached, may form a 5- to 6-membered heterocycle or 6- to 12-membered bicycle (e.g.,

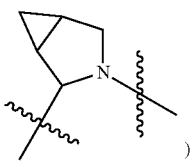 [SMILES: *C1C2CC2CN1*]

or

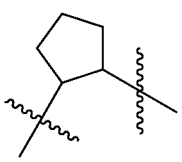 [SMILES: *C1CCCC1*]

)

which is optionally substituted with one or more R$_A$; and R$_{10}$ and R$_{13}$ may be each independently R$_C$, and R$_{11}$ and R$_{14}$, taken together with the atoms to which they are attached, may form a 5- to 6-membered carbocycle/heterocycle or 6- to 12-membered bicycle (e.g.,

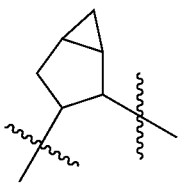

or

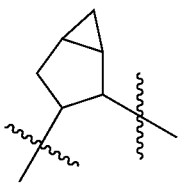

)

which is optionally substituted with one or more R$_A$.

Highly preferably, Z is selected from —N(R$_B$")CO—C(R$_8$R$_9$)N(R$_{12}$)—C(O)-L$_Y$-N(R$_B$")C(O)-L$_S$-R$_E$ or —C(R$_8$R$_9$)N(R$_{12}$)—C(O)-L$_Y$-N(R$_B$")C(O)-L$_S$-R$_E$, or Z is -G-C(R$_8$R$_9$)N(R$_{12}$)—C(O)-L$_Y$-N(R$_B$")C(O)-L$_S$-R$_E$, wherein L$_Y$ is C$_1$-C$_6$alkylene optionally substituted with one or more R$_L$, and R$_B$" is each independently R$_B$. R$_B$" and R$_8$ are each preferably hydrogen or C$_1$-C$_6$alkyl, and R$_9$ and R$_{12}$, taken together with the atoms to which they are attached, preferably form a 5- to 6-membered heterocycle or 6- to 12-membered bicycle (e.g.,

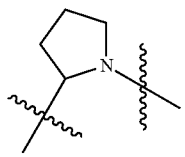 [SMILES: *C1CCCN1*]

or

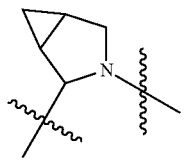

)

which is optionally substituted with one or more R$_A$ (such as, but not limited to hydroxy, halo (e.g., fluoro), C$_1$-C$_6$alkyl (e.g., methyl), or C$_2$-C$_6$alkenyl (e.g., allyl)). L$_Y$ is each independently L$_S$. Preferably, L$_Y$ is C$_1$-C$_6$alkylene substituted with one or more R$_L$ such as a C$_3$-C$_6$carbocycle 3- to 6-membered heterocycle which is optionally substituted with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl. Highly preferably, L$_Y$ is a C$_1$-C$_6$alkylene such as, but not limited to,

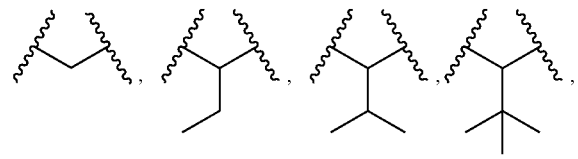

or

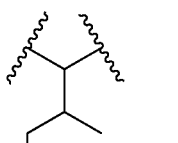

(stereochemistry at a carbon within the group L$_Y$ can be either (R) or (S)); L$_Y$ is optionally substituted with one or more R$_L$ (e.g., one or more phenyl or methoxy); G preferably is

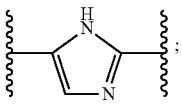 [SMILES: *c1cnc(*)[nH]1]

$R_B''$ is hydrogen; —C($R_8R_9$)N($R_{12}$)— is
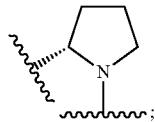
$L_S$ is a bond; and $R_E$ is methoxy.
Non-limiting examples of preferred Z include
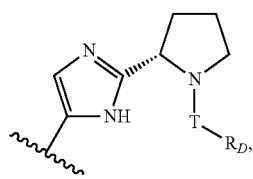
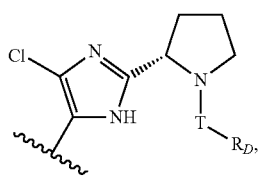
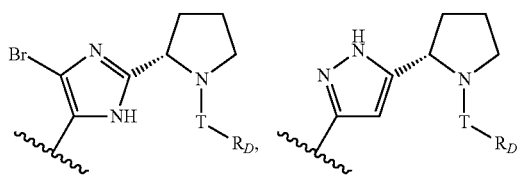
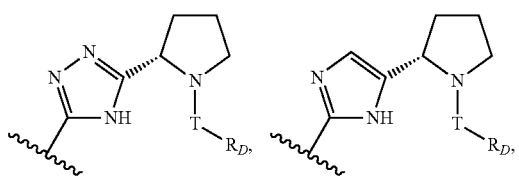
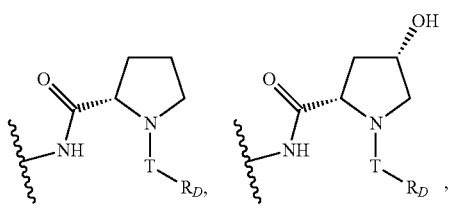
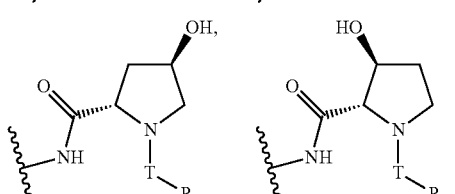
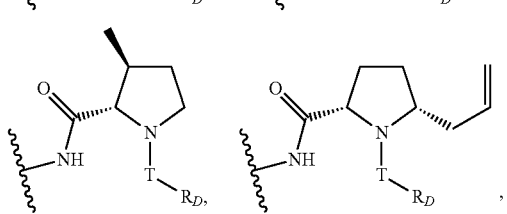
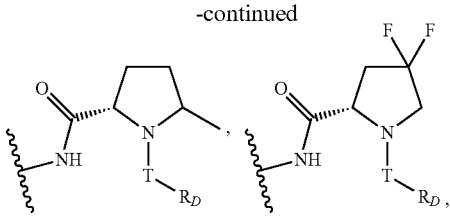
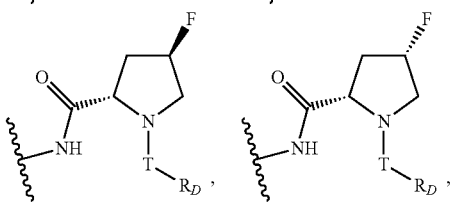
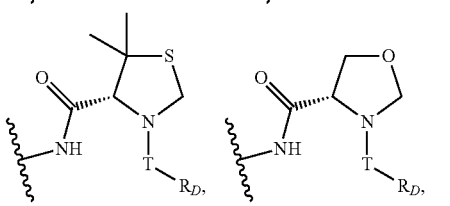
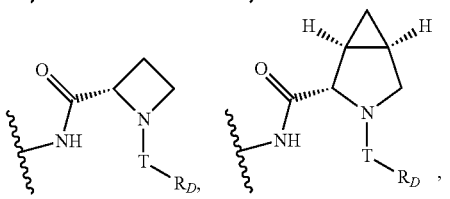
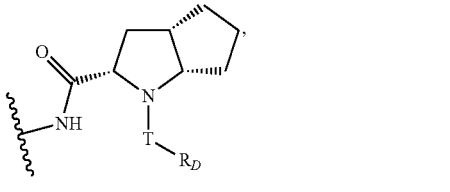
wherein T and $R_D$ are as defined herein. T, for example, can be -$L_S$-M-$L_S'$-M'-$L_S''$- where $L_S$ is a bind; M is C(O); $L_S'$ is $C_1$-$C_6$alkylene such as, but not limited to,
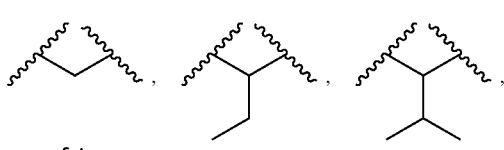
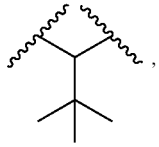
or
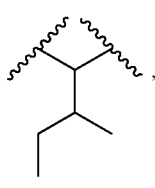

where $L_S'$ is optionally substituted with one or more $R_L$; the optional $R_L$ is a substituent such as, but not limited to phenyl or methoxy; M' is —NHC(O)— or —NMeC(O)—; and $L_S''$ is a bond. Any stereochemistry at a carbon within the group $L_S'$ can be either (R) or (S). $R_D$, for example is methoxy. T-$R_D$ includes, but is not limited to,

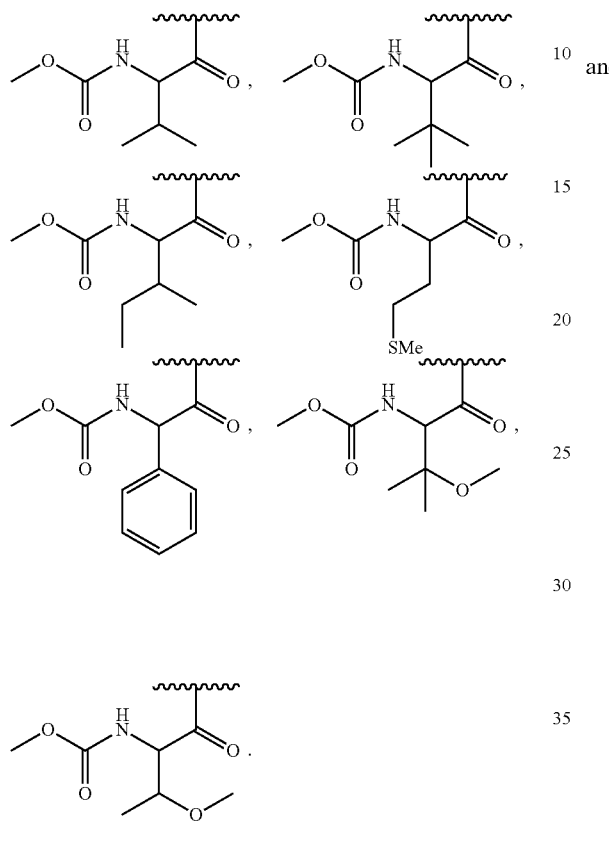

or

T-$R_D$ may also include certain stereochemical configurations; thus T-$R_D$ includes, but is not limited to:

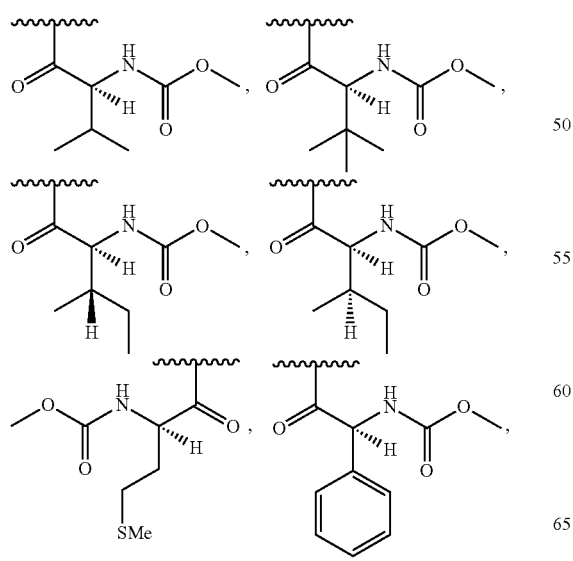

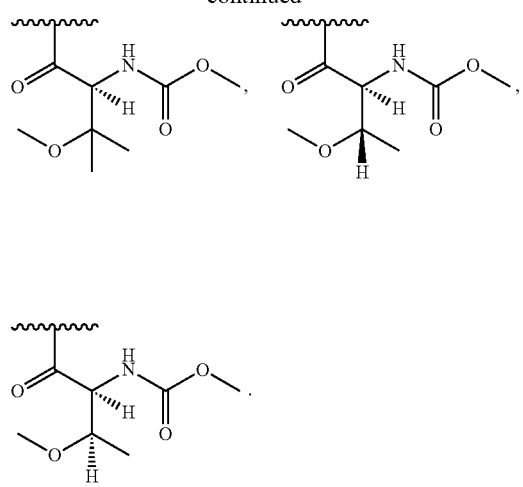

and

Non-limiting examples of preferred Z also include:

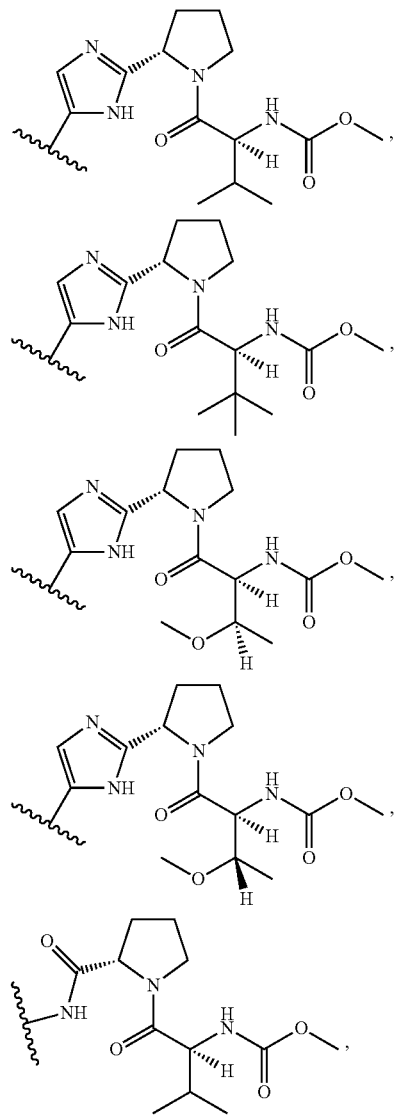

-continued

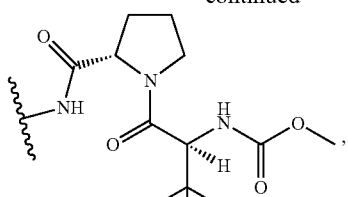

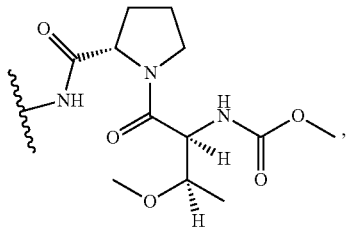

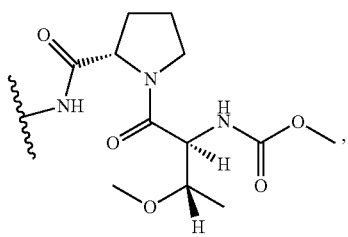

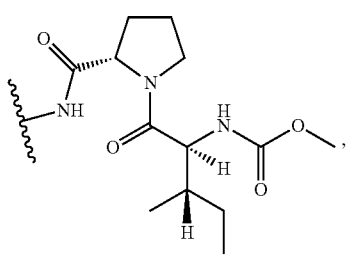

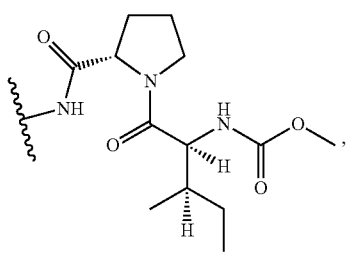

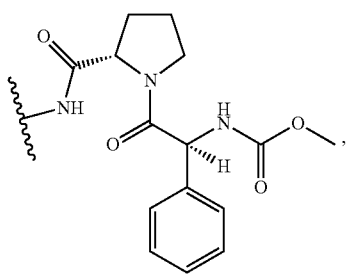

or

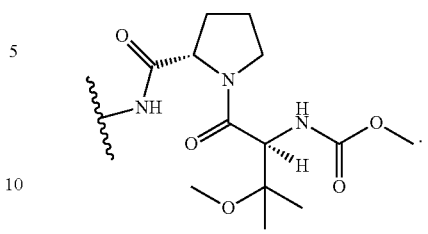

T can be without limitation, independently selected at each occurrence from —C(O)-$L_S$'-, —C(O)O-$L_S$'-, —C(O)-$L_S$'-N($R_B$)C(O)-$L_S$"-, —C(O)-$L_S$'-N($R_B$)C(O)O-$L_S$"-, —N($R_B$)C(O)-$L_S$'-N($R_B$)C(O)-$L_S$"-, —N($R_B$)C(O)-$L_S$'-N($R_B$)C(O)O-$L_S$"-, or —N($R_B$)C(O)-$L_S$'-N($R_B$)-$L_S$"-. Preferably, T is independently selected at each occurrence from —C(O)-$L_S$'-M'-$L_S$"- or —N($R_B$)C(O)-$L_S$'-M'-$L_S$"-. More preferably, T is independently selected at each occurrence from —C(O)-$L_S$'-N($R_B$)C(O)-$L_S$"- or —C(O)-$L_S$'-N($R_B$)C(O)O-$L_S$"-.

T can also be, for example, -$L_S$-M-$L_S$'-M'-$L_S$"- where $L_S$ is a bond; M is C(O); $L_S$' is $C_1$-$C_6$alkylene (e.g.,

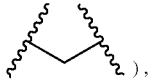), where $L_S$' is optionally substituted with $R_T$; the optional $R_T$ is a substituent selected from —$C_1$-$C_6$alkyl, —$C_2$-$C_6$alkenyl, —$C_1$-$C_6$alkyl-OH, —$C_1$-$C_6$alkyl-O—$C_1$-$C_6$alkyl, 3- to 6-membered heterocycle (e.g., tetrahydrofuranyl), or $C_3$-$C_6$carbocyclyl (e.g., phenyl, cyclohexyl); M' is —NHC(O)—, —N(Et)C(O)— or —N(Me)C(O)—; and $L_S$" is a bond. $R_D$ preferably is hydrogen, —$C_1$-$C_6$alkyl (e.g., methyl), —O—$C_1$-$C_6$alkyl (e.g., methoxy, tert-butoxy), methoxymethyl, or —N($C_1$-$C_6$alkyl)$_2$ (e.g., —NMe$_2$).

T-$R_D$ can be, without limitation,

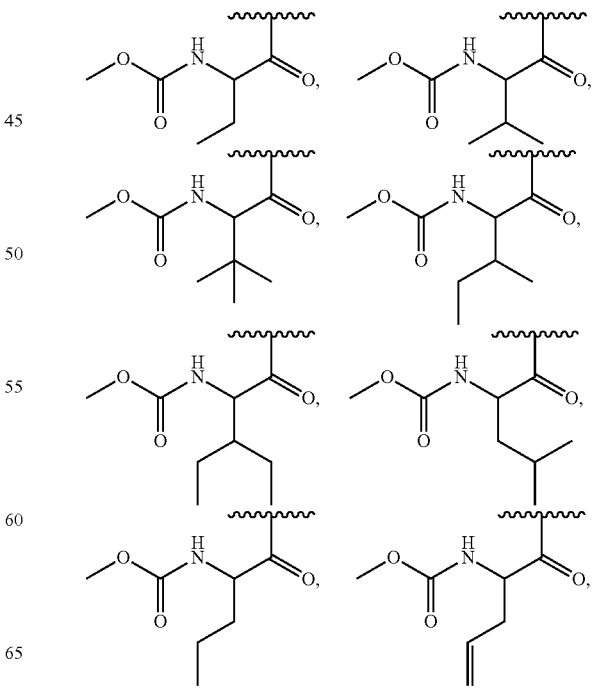

-continued

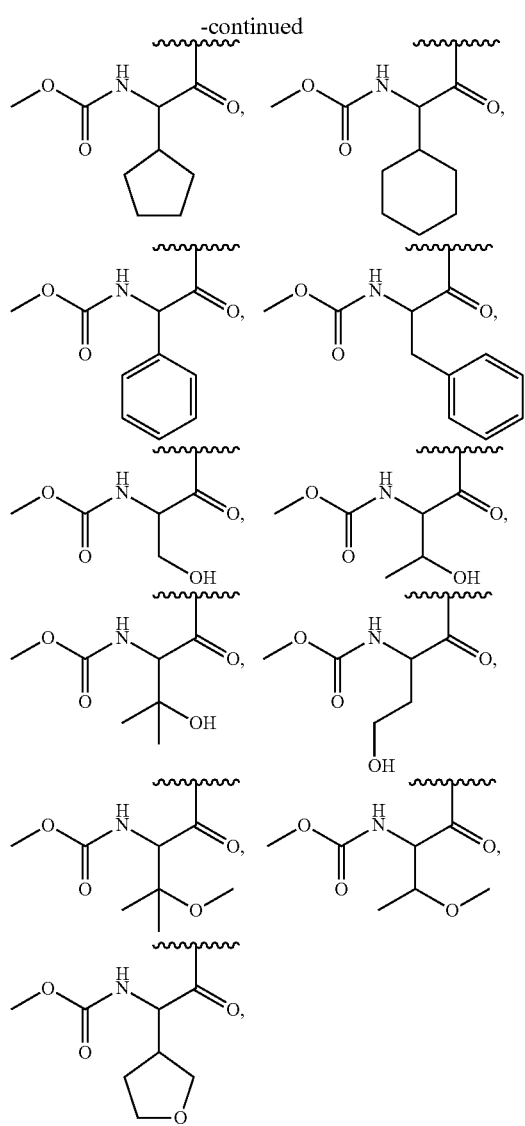

or

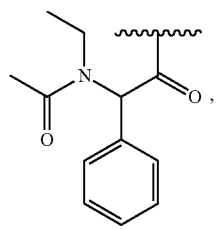 [SMILES: *C(=O)C(c1ccccc1)N(CC)C(C)=O]

wherein the stereochemistry at a carbon within the group T-R_D can be either (R) or (S).

T can also be, without limitation, -L_S-M-L_S'- where L_S is a bond; M is C(O); L_S' is $C_1$-$C_6$alkylene (e.g.,

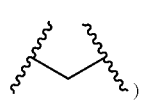)

where L_S' is optionally substituted with R_T; the optional R_T is a substituent selected from —$C_1$-$C_6$alkyl, —$C_1$-$C_6$alkyl-OH, —$C_1$-$C_6$alkyl-O—$C_1$-$C_6$alkyl, or a $C_3$-$C_6$carbocyclyl (e.g., phenyl, cyclohexyl). R_D, for example is —OH; —OC(O)Me; —NH($C_1$-$C_6$alkyl) (e.g., —NHMe, —NHEt); —N($C_1$-$C_6$alkyl)$_2$ (e.g., —NMe$_2$, —NEt$_2$); a 3- to 10-membered heterocyclyl (e.g., pyrrolidinyl, imidazolidinyl, hexahydropyrimidinyl, morpholinyl, piperidinyl) optionally substituted with one or more halogen, oxo; $C_3$-$C_{10}$-carbocycle (e.g., cyclopentyl) optionally substituted with —OH; —$C_1$-$C_6$alkyl (e.g., isopropyl, 3-pentyl) optionally substituted with —OH; or NHR_T where R_T is a 3- to 6-membered heterocyclyl (e.g., thiazolyl, pyrimidinyl). T-R_D includes, but is not limited to:

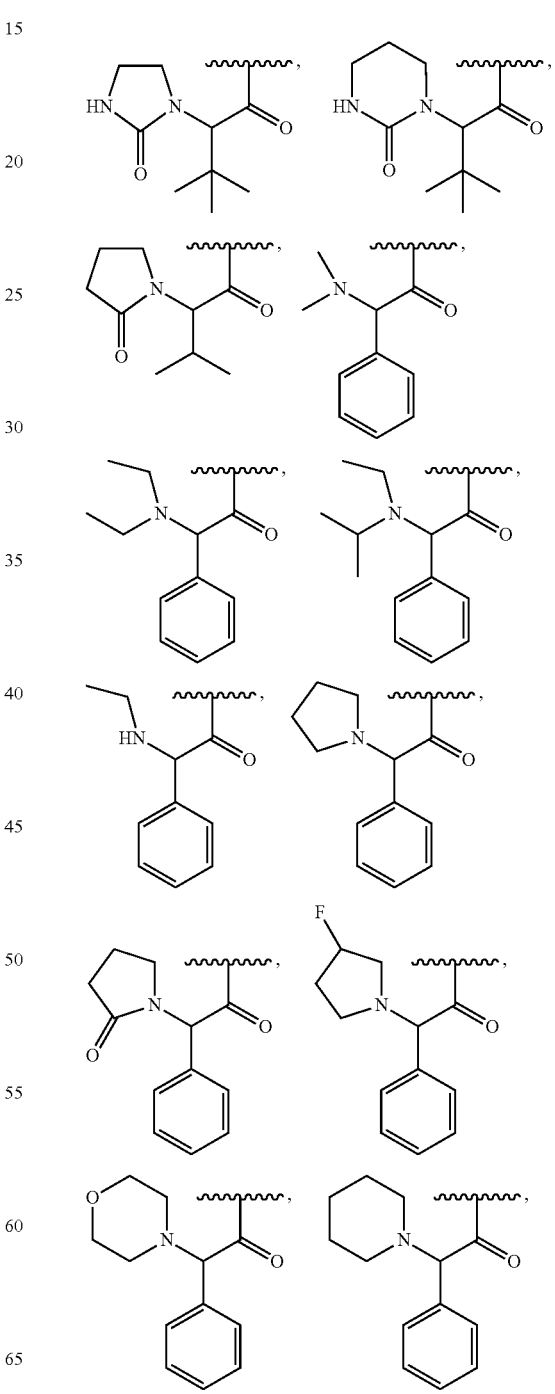

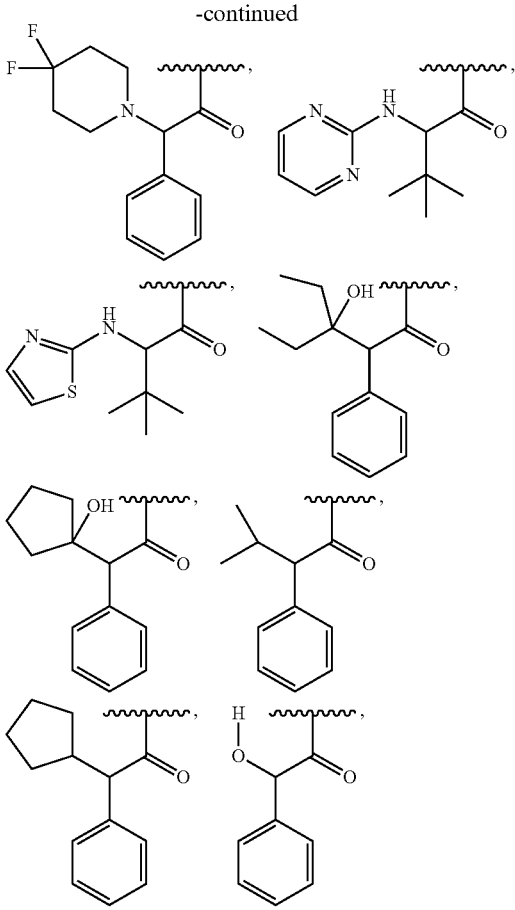

or

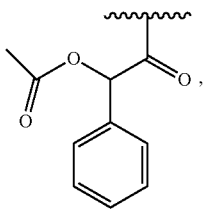 [SMILES: *C(=O)C(OC(C)=O)c1ccccc1]

wherein the stereochemistry at a carbon within the group T-R$_D$ can be either (R) or (S).

For each compound of Formula I, L$_K$ can also be independently selected at each occurrence from a bond; -L$_S$'-N(R$_B$)C(O)-L$_S$-; -L$_S$'-C(O)N(R$_B$)-L$_S$-; or C$_1$-C$_6$alkylene, C$_2$-C$_6$alkenylene, C$_2$-C$_6$alkynylene, C$_3$-C$_{10}$carbocycle or 3- to 10-membered heterocycle, each of which is independently optionally substituted at each occurrence with one or more substituents selected from halogen, R$_T$, —O—R$_S$, —S—R$_S$, —N(R$_S$R$_S$'), —OC(O)R$_S$, —C(O)OR$_S$, nitro, oxo, phosphonoxy, phosphono, thioxo, formyl or cyano, wherein L$_S$ and L$_S$' are as defined above.

For Formula I as well as Formulae I$_A$, I$_C$, I$_D$, I$_E$, I$_F$ or I$_G$ described below, including each and every embodiment described thereunder, R$_A$ preferably is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl C$_2$-C$_6$haloalkynyl, C(O)OR$_S$ or R$_F$; or -L$_A$-O—R$_S$, -L$_A$-S—R$_S$, -L$_A$-C(O)R$_S$, -L$_A$-OC(O)R$_S$, -L$_A$-C(O)OR$_S$, -L$_A$-N(R$_S$R$_S$'), -L$_A$-S(O)R$_S$, -L$_A$-SO$_2$R$_S$, -L$_A$-C(O)N(R$_S$R$_S$'), -L$_A$-N(R$_S$)C(O)R$_S$', -L$_A$-N(R$_S$)C(O)N(R$_S$'R$_S$''), -L$_A$-N(R$_S$)SO$_2$R$_S$', -L$_A$-SO$_2$N(R$_S$R$_S$'), -L$_A$-N(R$_S$)SO$_2$N(R$_S$'R$_S$''), -L$_A$-N(R$_S$)S(O)N(R$_S$'R$_S$''), -L$_A$-OS(O)—R$_S$, -L$_A$-OS(O)$_2$—R$_S$, -L$_A$-S(O)$_2$OR$_S$, -L$_A$-S(O)OR$_S$, -L$_A$-OC(O)OR$_S$, -L$_A$-N(R$_S$)C(O)OR$_S$', -L$_A$-OC(O)N(R$_S$R$_S$'), -L$_A$-N(R$_S$)S(O)—R$_S$', -L$_A$-S(O)N(R$_S$R$_S$') or -L$_A$-C(O)N(R$_S$)C(O)—R$_S$', wherein L$_A$ is bond, C$_1$-C$_6$alkylene, C$_2$-C$_6$alkenylene or C$_2$-C$_6$alkynylene.

More preferably, R$_A$ is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or C$_3$-C$_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl C$_2$-C$_6$haloalkynyl, C(O)OR$_S$ or R$_F$.

Highly preferably, R$_A$ is halogen, hydroxy, mercapto, amino, carboxy, nitro, oxo, phosphonoxy, phosphono, thioxo, cyano; or C$_1$-C$_6$alkyl, C$_2$-C$_6$alkenyl or C$_2$-C$_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

L$_S$, L$_S$' and L$_S$'' preferably are each independently selected at each occurrence from bond; or C$_1$-C$_6$alkylene, C$_2$-C$_6$alkenylene or C$_2$-C$_6$alkynylene.

A and B can be the same or different. Likewise, L$_1$ and L$_2$, or Y and Z, or Y-A- and Z—B—, or -A-L$_1$- and —B-L$_2$-, can be the same or different. In some instances, Y-A-L$_1$- is identical to Z—B-L$_2$-. In some other instances, Y-A-L$_1$- is different from Z—B-L$_2$-.

In one embodiment, A and B are each independently 5- or 6-membered carbocycle or heterocycle (e.g., phenyl such as

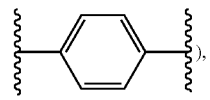

and are each independently optionally substituted with one or more R$_A$. X is C$_3$-C$_8$cycloalkyl or C$_5$-C$_8$cycloalkenyl and is optionally substituted with one or more R$_A$. Specific examples of X are described hereinabove. Preferably, X is cyclopropyl, cyclopentyl or cyclopentenyl, and is optionally substituted with one or more R$_A$ or R$_F$. More preferably, X is cyclopropyl is and is optionally substituted with one or more R$_A$ or R$_F$. D is C$_5$-C$_6$carbocycle or 5- to 6-membered heterocycle (e.g., phenyl), and is optionally substituted with one or more R$_A$, or is substituted with J and optionally substituted with one or more $R_4$, wherein J is $C_3$-$C_6$carbocycle, 3- to 6-membered heterocycle or 6- to 12-membered bicycle and is optionally substituted with one or more $R_4$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_S R_S')$, and J can also be optionally substituted with one or more $R_4$. Preferably, D is

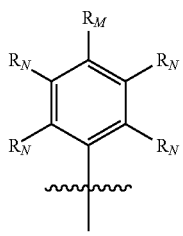

or

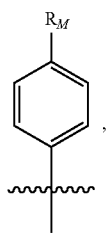

wherein $R_M$ and $R_N$ are as defined above. Also preferably, D is

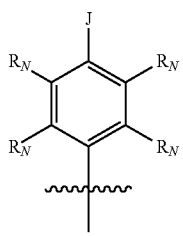

or

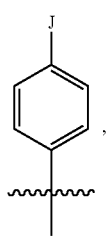

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1 R_2$)N($R_5$)-T-$R_D$, or —N($R_B$)C(O)C($R_3 R_4$)C($R_6 R_7$)-T-$R_D$, and Z is —N($R_B$)C(O)C($R_8 R_9$)N($R_{12}$)-T-$R_D$, or —N($R_B$)C(O)C($R_{10} R_{11}$)C($R_{13} R_{14}$)-T-$R_D$. $R_1$ is $R_C$, and $R_2$ and $R_5$, taken together with the atoms to which they are attached, form a 5- to 6-membered heterocyclic ring (e.g.,

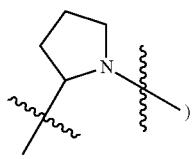

which is optionally substituted with one or more $R_4$; $R_3$ and $R_6$ are each independently $R_C$, and $R_4$ and $R_7$, taken together with the atoms to which they are attached, form a 5- to 6-membered carbocyclic or heterocyclic ring (e.g.,

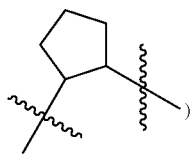

which is optionally substituted with one or more $R_4$. $R_8$ is $R_C$, and $R_9$ and $R_{12}$, taken together with the atoms to which they are attached, form a 5- to 6-membered heterocyclic ring (e.g.,

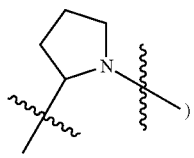

which is optionally substituted with one or more $R_4$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

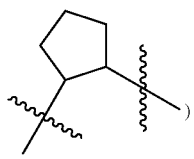

which is optionally substituted with one or more $R_4$. T is preferably independently selected at each occurrence from —C(O)-$L_Y$'-N($R_B$)C(O)-$L_S$''- or —C(O)-$L_Y$'-N($R_B$)C(O)O-$L_S$''-. $L_Y$' is each independently $L_S$' and, preferably, is each independently $C_1$-$C_6$alkylene (e.g., —$CH_2$—) and optionally substituted with one or more substituents selected from $R_L$. T can also be, without limitation, selected from —C(O)-$L_Y$'-$L_S$''-, —C(O)-$L_Y$'—O-$L_S$''-, —C(O)-$L_Y$'-N($R_B$)-$L_S$''-, or —C(O)-$L_Y$'-N($R_B$)S(O)$_2$-$L_S$''-. In some cases, at least one of Y and Z is, or both Y and Z are independently,

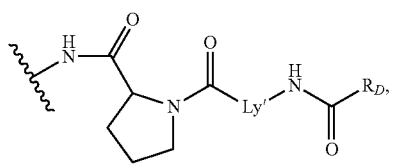

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_y'$ include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another embodiment, A is

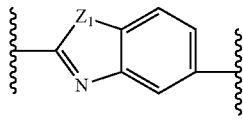

or

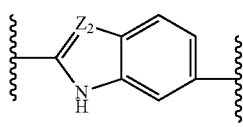

and is optionally substituted with one or more $R_A$; B is

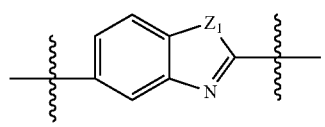

or

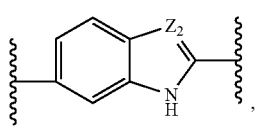

and is optionally substituted with one or more $R_A$. $Z_1$ is independently selected at each occurrence from O, S, NH or $CH_2$; and $Z_2$ is independently selected at each occurrence from N or CH. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$, and J can also be optionally substituted with one or more $R_A$. Preferably, D is

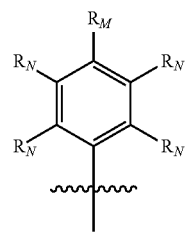

or

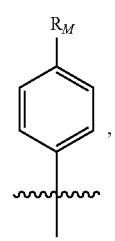

wherein $R_M$ and $R_N$ are as defined above. Also preferably, D is

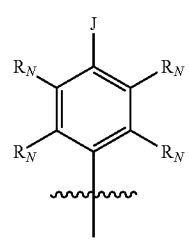

or

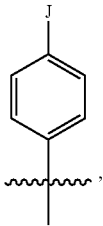

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -$L_S$-C($R_1R_2$)N($R_5$)-T-$R_D$ or -$L_S$-C($R_3R_4$)C($R_6R_7$)-T-$R_D$, and Z is -$L_S$-C($R_8R_9$)N($R_{12}$)-T-$R_D$ or -$L_S$-C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g.,

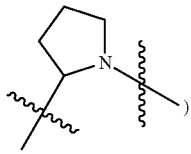

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

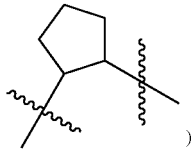 [SMILES: *C1CCCC1*]

which is optionally substituted with one or more $R_A$. $R_8$ is $R_C$, and $R_9$ and $R_{12}$, taken together with the atoms to which they are attached, form a 5- to 6-membered heterocyclic ring (e.g.,

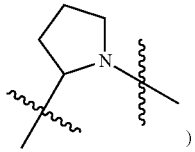 [SMILES: *C1CCCN1*]

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

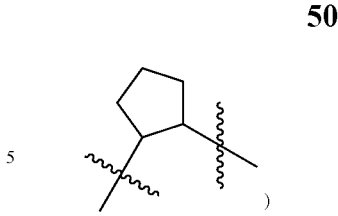

which is optionally substituted with one or more $R_A$. T is preferably independently selected at each occurrence from —C(O)-$L_Y$'-N($R_B$)C(O)-$L_S$''- or —C(O)-$L_Y$'-N($R_B$)C(O)O-$L_S$''-, $L_Y$' is each independently $L_S$' and, preferably, is independently $C_1$-$C_6$alkylene (e.g., —CH$_2$—) and optionally substituted with one or more substituents selected from $R_L$. T can also be, without limitation, selected from —C(O)-$L_Y$'-$L_S$''-, —C(O)-$L_Y$'—O-$L_S$''-, —C(O)-$L_Y$'-N($R_B$)-$L_S$''-, or —C(O)-$L_Y$'-N($R_B$)S(O)$_2$-$L_S$''-. In some cases, at least one of Y and Z is, or both Y and Z are independently,

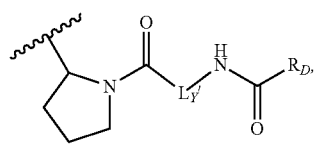

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In still yet another embodiment, A and B are each independently 5- or 6-membered carbocycle or heterocycle (e.g., A and B are each independently phenyl, such as

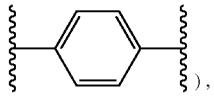 [SMILES: *c1ccc(*)cc1]

and are each independently optionally substituted with one or more $R_A$. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D can be, for example, $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)$OR_S$ or —N($R_SR_S'$), and J can also be optionally substituted with one or more $R_A$. Preferably, D is

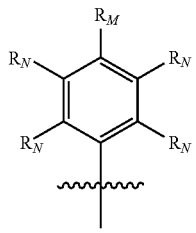

or

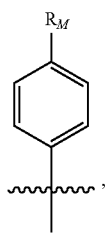

wherein $R_M$ and $R_N$ are as defined above. Also preferably, D is

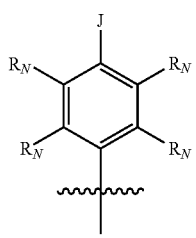

or

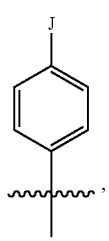

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -G-C($R_1R_2$)N($R_5$)-T-$R_D$ or -G-C($R_3R_4$)C($R_6R_7$)-T-$R_D$, and Z is -G-C($R_8R_9$)N($R_{12}$)-T-$R_D$ or -G-C($R_{10}R_{11}$)C($R_{13}R_{14}$)-T-$R_D$. G is independently $C_5$-$C_6$carbocycle or 5- to 6-membered heterocycle, such as

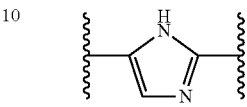

or

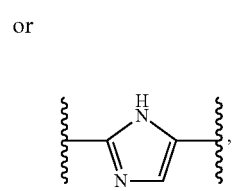

and is independently optionally substituted with one or more $R_A$. $R_1$ is $R_C$, and $R_2$ and $R_5$, taken together with the atoms to which they are attached, form a 5- to 6-membered heterocyclic ring (e.g.,

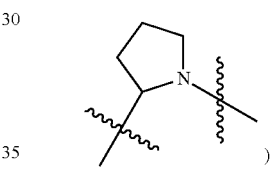

)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

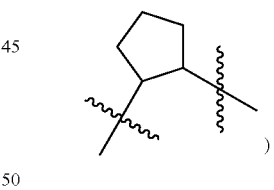

)

which is optionally substituted with one or more $R_A$. $R_8$ is $R_C$, and $R_9$ and $R_{12}$, taken together with the atoms to which they are attached, form a 5- to 6-membered heterocyclic ring (e.g.,

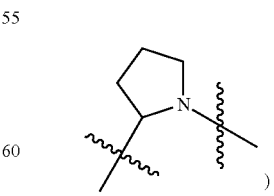

)

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

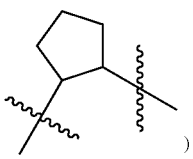 [SMILES: *C1CCCC1*])

which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$"-$L_S$"-, —C(O)-$L_Y$'—O-$L_S$"-, —C(O)-$L_Y$'-N($R_B$)-$L_S$"-, or —C(O)-$L_Y$'-N($R_B$)S(O)$_2$-$L_S$"-. In some cases, at least one of Y and Z is, or both Y and Z are independently,

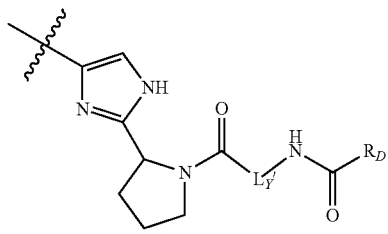

or

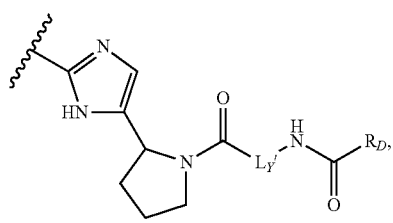

wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In yet another embodiment, A and B are each independently 5- or 6-membered carbocycle or heterocycle (e.g., A and B are each independently phenyl, such as

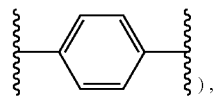), and are each independently optionally substituted with one or more $R_A$. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D can be, for example, $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N($R_S R_S$'), and J can also be optionally substituted with one or more $R_A$. Preferably, D is

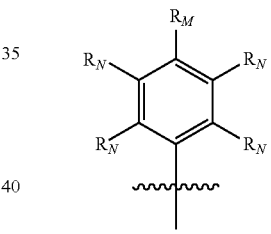

or

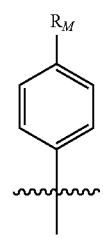

wherein $R_M$ and $R_N$ are as defined above. Also preferably, D is

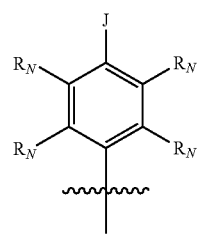

or

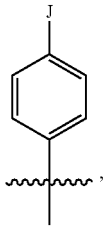, wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1R_2$)N($R_5$)-T-$R_D$ or —N($R_B$)C(O)C($R_3R_4$)C($R_6R_7$)-T-$R_D$, and Z is -G-C($R_8R_9$)N($R_{12}$)-T-$R_D$ or -G-C($R_{10}R_{11}$)C($R_{13}R_{14}$)-T-$R_D$; or Y is -G-C($R_1R_2$)N($R_5$)-T-$R_D$ or -G-C($R_3R_4$)C($R_6R_7$)-T-$R_D$, and Z is —N($R_B$)C(O)C($R_8R_9$)N($R_{12}$)-T-$R_D$ or —N($R_B$)C(O)C($R_{10}R_{11}$)C($R_{13}R_{14}$)-T-$R_D$. $R_1$ is $R_C$, and $R_2$ and $R_5$, taken together with the atoms to which they are attached, form a 5- to 6-membered heterocyclic ring (e.g.,

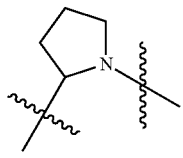)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

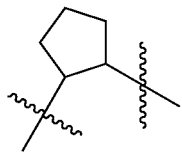)

which is optionally substituted with one or more $R_A$. $R_8$ is $R_C$, and $R_9$ and $R_{12}$, taken together with the atoms to which they are attached, form a 5- to 6-membered heterocyclic ring (e.g.,

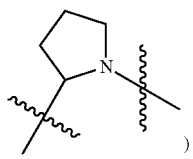 [SMILES: *C1CCCN1*])

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

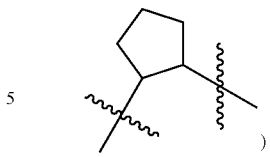)

which is optionally substituted with one or more $R_A$. G is independently $C_5$-$C_6$carbocycle or 5- to 6-membered heterocycle, such as

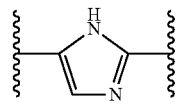 [SMILES: *c1cnc(*)[nH]1]

or

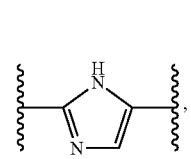, and is independently optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —CH$_2$—) and optionally substituted with one or more substituents selected from $R_L$. T can also be, without limitation, selected from —C(O)-$L_Y'$-$L_S''$-, —C(O)-$L_Y'$—O-$L_S''$-, —C(O)-$L_Y'$-N($R_B$)-$L_S''$-, or —C(O)-$L_Y'$-N($R_B$)S(O)$_2$-$L_S''$-. In some cases, Y is

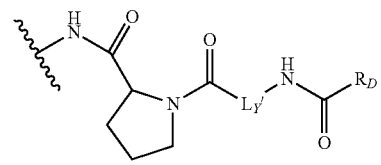

as described above, and Z is

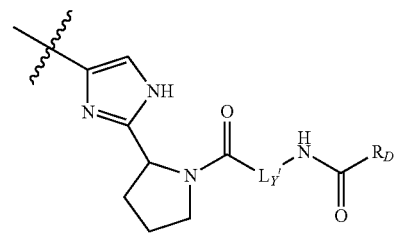

or

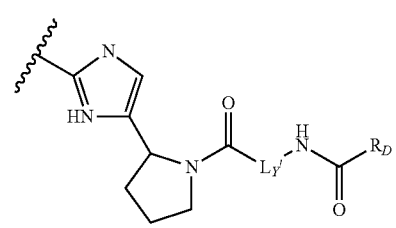

as described above. In some other cases, Y is
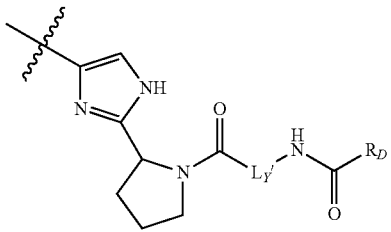
or
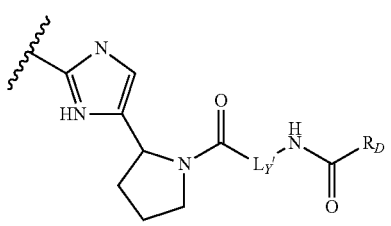
as described above, and Z is
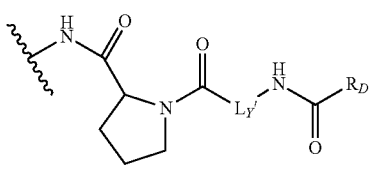
as described above.
In still another embodiment, A is 5- or 6-membered carbocycle or heterocycle (e.g., phenyl such as
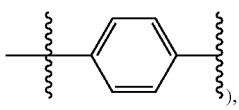
and B is
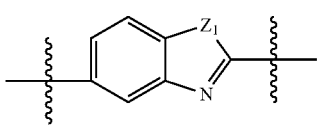
or
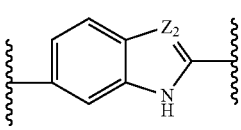
(e.g.,
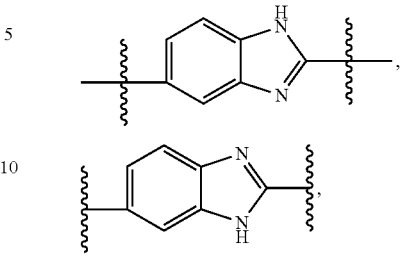
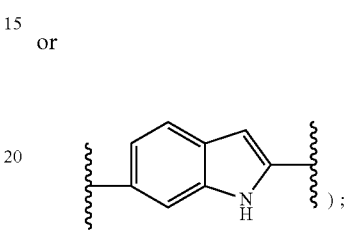
or
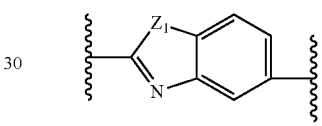
or A is
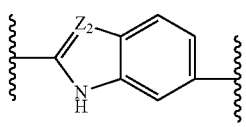
or
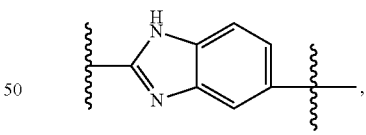
(e.g.,
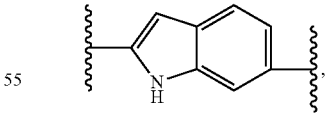
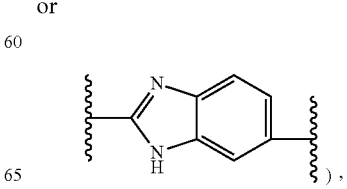
or and B is 5- or 6-membered carbocycle or heterocycle (e.g., phenyl such as

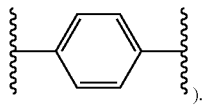).

A and B are each independently optionally substituted with one or more $R_A$. $Z_1$ is independently selected at each occurrence from O, S, NH or $CH_2$; and $Z_2$ is independently selected at each occurrence from N or CH. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more $R_A$. Preferably, D is

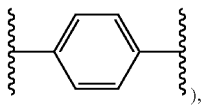

or

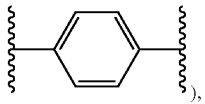

wherein $R_M$ and $R_N$ are as defined above. Also preferably, D is

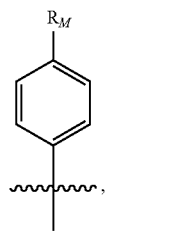

or

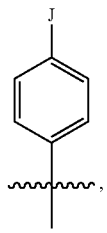

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. When A is 5- or 6-membered carbocycle or heterocycle (e.g., phenyl such as

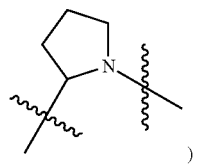),

Y is —N(R$_B$)C(O)C(R$_1$R$_2$)N(R$_5$)-T-R$_D$, —N(R$_B$)C(O)C(R$_3$R$_4$)C(R$_6$R$_7$)-T-R$_D$, -G-C(R$_1$R$_2$)N(R$_5$)-T-R$_D$ or -G-C(R$_3$R$_4$)C(R$_6$R$_7$)-T-R$_D$, and Z is -L$_S$-C(R$_8$R$_9$)N(R$_{12}$)-T-R$_D$ or -L$_S$-C(R$_{10}$R$_{11}$)C(R$_{13}$R$_{14}$)-T-R$_D$. When B is 5- or 6-membered carbocycle or heterocycle (e.g., phenyl such as

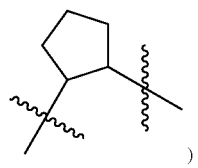),

Y is -L$_S$-C(R$_1$R$_2$)N(R$_5$)-T-R$_D$ or -L$_S$-C(R$_3$R$_4$)C(R$_6$R$_7$)-T-R$_D$, and Z is —N(R$_B$)C(O)C(R$_8$R$_9$)N(R$_{12}$)-T-R$_D$, —N(R$_B$)C(O)C(R$_{10}$R$_{11}$)C(R$_{13}$R$_{14}$)-T-R$_D$, -G-C(R$_8$R$_9$)N(R$_{12}$)-T-R$_D$ or -G-C(R$_{10}$R$_{11}$)C(R$_{13}$R$_{14}$)-T-R$_D$. $R_1$ is $R_C$, and $R_2$ and $R_5$, taken together with the atoms to which they are attached, form a 5- to 6-membered heterocyclic ring (e.g.,

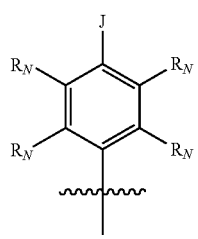)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

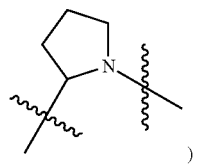)

which is optionally substituted with one or more $R_A$. $R_8$ is $R_C$, and $R_9$ and $R_{12}$, taken together with the atoms to which they are attached, form a 5- to 6-membered heterocyclic ring (e.g.,

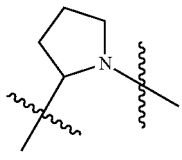
)

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

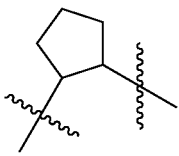
)

which is optionally substituted with one or more $R_A$. G is independently $C_5$-$C_6$carbocycle or 5- to 6-membered heterocycle, such as

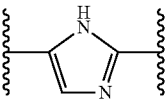 [SMILES: *c1cnc(*)[nH]1]

or

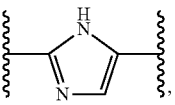

and is independently optionally substituted with one or more $R_A$. T is preferably independently selected at each occurrence from —C(O)-$L_Y'$-N($R_B$)C(O)-$L_S''$- or —C(O)-$L_Y'$-N($R_B$)C(O)O-$L_S''$-. $L_Y'$ is each independently $L_S'$ and, preferably, is each independently $C_1$-$C_6$alkylene (e.g., —CH$_2$—) and optionally substituted with one or more substituents selected from $R_L$. T can also be, without limitation, selected from —C(O)-$L_Y'$-$L_S''$-, —C(O)-$L_Y'$—O-$L_S''$-, —C(O)-$L_Y'$-N($R_B$)-$L_S''$-, or —C(O)-$L_Y'$-N($R_B$)S(O)$_2$-$L_S''$-. In some cases when A is 5- or 6-membered carbocycle or heterocycle (e.g., phenyl such as

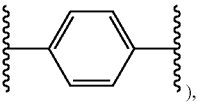

Y is

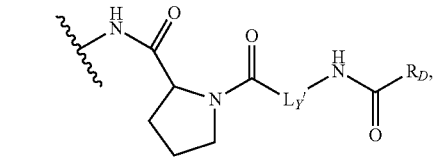

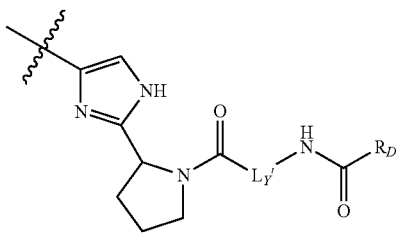

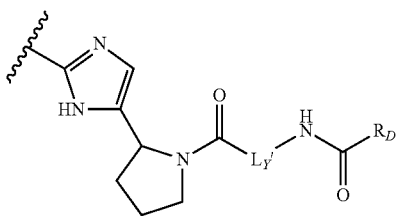

or

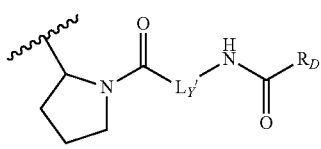

as described above, and Z is

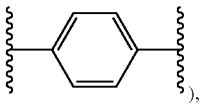

as described above. In some other cases when B is 5- or 6-membered carbocycle or heterocycle (e.g., phenyl such as

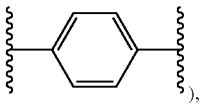

Y is

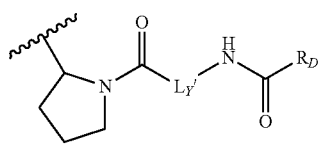

as described above, and Z is

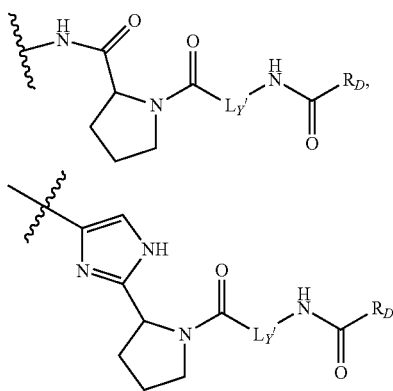

or

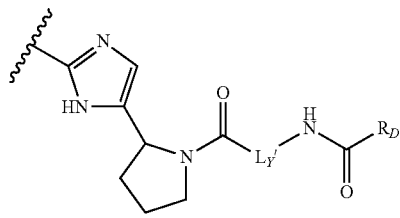

as described above.

The present invention also features compounds of Formulae I, $I_A$, $I_B$, $I_C$ and $I_D$ as described herein (including each embodiment described hereunder) and pharmaceutically acceptable salts thereof, wherein:

D is $C_3$-$C_{12}$carbocycle or 3- to 12-membered heterocycle, and is optionally substituted with one or more $R_A$; or D is $C_3$-$C_{12}$carbocycle or 3- to 12-membered heterocycle which is substituted with J and optionally substituted with one or more $R_A$, where J is $C_3$-$C_{15}$carbocycle or 3- to 15-membered heterocycle (e.g., a 3- to 6-membered monocycle, a 6- to 12-membered fused, bridged or spiro bicycle, a 10- to 15-membered tricycle containing fused, bridged or spiro rings, or a 13- to 15-membered carbocycle or heterocycle) and is optionally substituted with one or more $R_A$, or J is —$SF_5$; or D is hydrogen or $R_A$;

$R_E$ is independently selected at each occurrence from —O—$R_S$, —S—$R_S$, —C(O)$R_S$, —OC(O)$R_S$, —C(O)OR$_S$, —N($R_S R_S'$), —S(O)$R_S$, —SO$_2 R_S$, —C(O)N($R_S R_S'$), —N($R_S$)C(O)$R_S'$, —N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$OR$_S$, —S(O)OR$_S$, —OC(O)OR$_S$, —N($R_S$)C(O)OR$_S'$, —OC(O)N($R_S R_S'$), —N($R_S$)S(O)—$R_S'$, —S(O)N($R_S R_S'$), —P(O)(OR$_S$)$_2$, =C($R_S R_S'$), or —C(O)N($R_S$)C(O)—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle (e.g., 7- to 12-membered carbocycle or heterocycle), each of which is independently optionally substituted at each occurrence with one or more substituents selected from halogen, hydroxy, mercapto, amino, carboxy, nitro, oxo, phosphonoxy, phosphono, thioxo, formyl, cyano, trimethylsilyl, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —O—$R_S$, —S—$R_S$, —C(O)$R_S$, —C(O)OR$_S$, or —N($R_S R_S'$).

In one embodiment, A and B are each independently 5- or 6-membered carbocycle or heterocycle (preferably, A and B are each independently phenyl such as

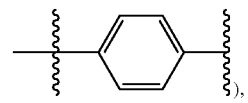

and are each independently optionally substituted with one or more $R_A$ (preferably, A and B are each independently substituted with at least one halo such as F). X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is a $C_5$-$C_6$carbocycle or 5- to 6-membered heterocycle (e.g., phenyl), and is substituted with J and optionally substituted with one or more $R_A$. J is $C_3$-$C_6$carbocycle, 3- to 6-membered heterocycle, 6- to 12-membered bicycle, 10- to 15-membered tricycle, or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$, or (2) trimethylsilyl, —O—$R_S$, —S—$R_S$, —C(O)$R_S$; and J can also be optionally substituted with one or more $R_A$. Preferably, D is

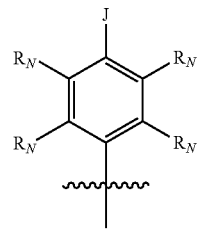

or

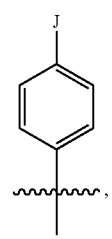

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is —N($R_B$)C(O)C($R_1R_2$)N($R_5$)-T-$R_D$, —N($R_B$)C(O)C($R_3R_4$)C($R_6R_7$)-T-$R_D$, -G-C($R_1R_2$)N($R_5$)-T-$R_D$ or -G-C($R_3R_4$)C($R_6R_7$)-T-$R_D$. Z is —N($R_B$)C(O)C($R_8R_9$)N($R_{12}$)-T-$R_D$, —N($R_B$)C(O)C($R_{10}R_{11}$)C($R_{13}R_{14}$)-T-$R_D$, -G-C($R_8R_9$)N($R_{12}$)-T-$R_D$ or -G-C($R_{10}R_{11}$)C($R_{13}R_{14}$)-T-$R_D$. $R_1$ is $R_C$; and $R_2$ and $R_5$, taken together with the atoms to which they are attached, form a 5- to 6-membered heterocyclic ring (e.g.,

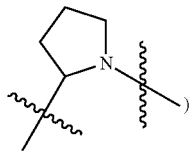 [SMILES: *C1CCCN1*]

or 6- to 12-membered bicycle (e.g.,

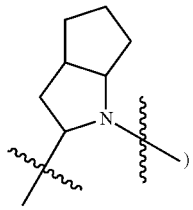 [SMILES: *C1CC2CCCC2N1*]

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

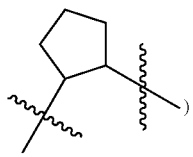 [SMILES: *C1CCCC1*]

or 6- to 12-membered bicycle which is optionally substituted with one or more $R_A$. $R_8$ is $R_C$; and $R_9$ and $R_{12}$, taken together with the atoms to which they are attached, form a 5- to 6-membered heterocyclic ring (e.g.,

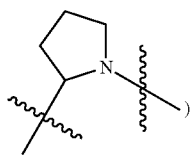

or 6- to 12-membered bicycle (e.g.,

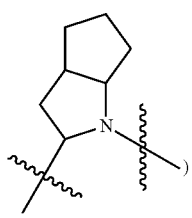 [SMILES: *C1CC2CCCC2N1*]

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

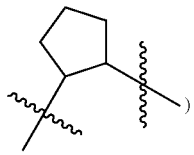 [SMILES: *C1CCCC1*]

or 6- to 12-membered bicycle which is optionally substituted with one or more $R_A$. G is independently $C_5$-$C_6$carbocycle or 5- to 6-membered heterocycle, such as

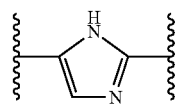 [SMILES: *c1cnc(*)[nH]1]

or

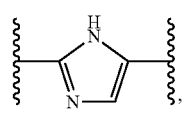

and is independently optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, Y is

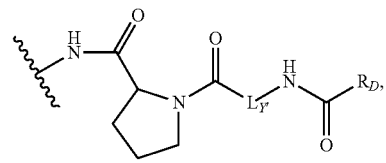

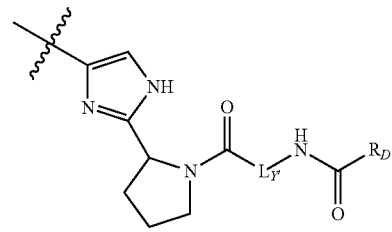

or

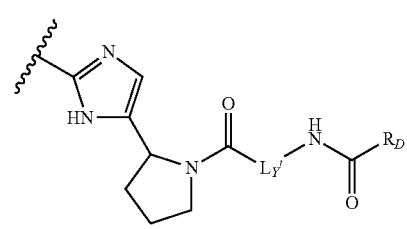

as described above, and Z is

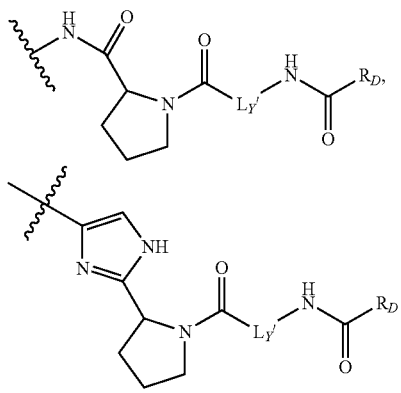

or

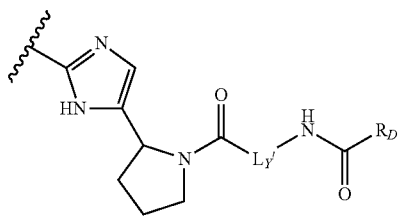

as described above.

In another embodiment, A is

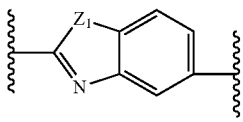

or

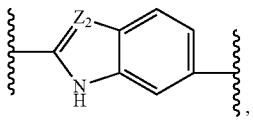, and is optionally substituted with one or more $R_A$; B is

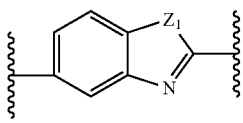

or

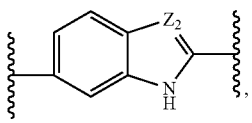, and is optionally substituted with one or more $R_A$. $Z_1$ is independently selected at each occurrence from O, S, NH or $CH_2$; and $Z_2$ is independently selected at each occurrence from N or CH. Preferably, A and B are each independently substituted with at least one halo such as F. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is a $C_5$-$C_6$carbocycle or 5- to 6-membered heterocycle (e.g., phenyl), and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$, or —C(O)R$_S$; and J can also be optionally substituted with one or more $R_A$. Preferably, D is

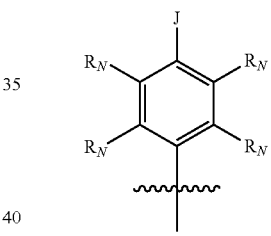

or

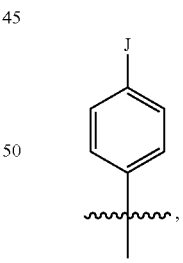, wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. Y is -$L_S$-C(R$_1$R$_2$)N(R$_5$)-T-R$_D$ or -$L_S$-C(R$_3$R$_4$)C(R$_6$R$_7$)-T-R$_D$. Z is -$L_S$-C(R$_8$R$_9$)N(R$_{12}$)-T-R$_D$ or -$L_S$-C(R$_{10}$R$_{11}$)C(R$_{13}$R$_{14}$)-T-R$_D$. $R_1$ is $R_C$; and $R_2$ and $R_5$, taken together with the atoms to which they are attached, form a 5- to 6-membered heterocyclic ring (e.g., or 6- to 12-membered bicycle (e.g.,

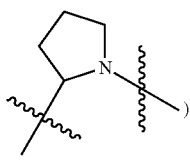
)

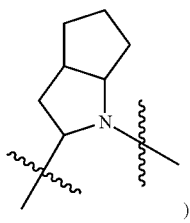
)

which is optionally substituted with one or more $R_A$; $R_3$ and $R_6$ are each independently $R_C$, and $R_4$ and $R_7$, taken together with the atoms to which they are attached, form a 5- to 6-membered carbocyclic or heterocyclic ring (e.g.,

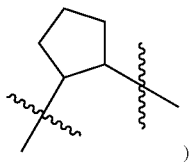
)

or 6- to 12-membered bicycle which is optionally substituted with one or more $R_A$. $R_8$ is $R_C$; and $R_9$ and $R_{12}$, taken together with the atoms to which they are attached, form a 5- to 6-membered heterocyclic ring (e.g.,

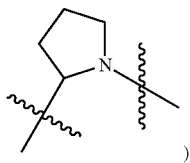
)

or 6- to 12-membered bicycle (e.g.,

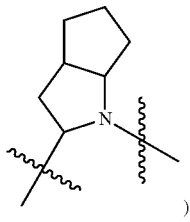
)

which is optionally substituted with one or more $R_A$; and $R_{10}$ and $R_{13}$ are each independently $R_C$, and $R_{11}$ and $R_{14}$, taken together with the atoms to which they are attached, form a 5- to 6-membered carbocyclic or heterocyclic ring (e.g.,

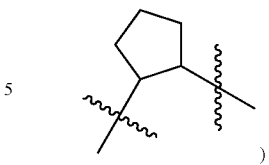
)

or 6- to 12-membered bicycle which is optionally substituted with one or more $R_A$. T is preferably independently selected at each occurrence from —C(O)-$L_Y$'-N($R_B$)C(O)-$L_S$"- or —C(O)-$L_Y$'-N($R_B$)C(O)O-$L_S$"-. $L_Y$' is each independently $L_S$' and, preferably, is each independently $C_1$-$C_6$alkylene (e.g., —CH$_2$—) and optionally substituted with one or more substituents selected from $R_L$. T can also be, without limitation, selected from —C(O)-$L_Y$'-$L_S$"-, —C(O)-$L_Y$'-O-$L_S$"-, —C(O)-$L_Y$'-N($R_B$)-$L_S$"-, or —C(O)-$L_Y$'-N($R_B$)S(O)$_2$-$L_S$"-. In some cases, Y and Z are independently

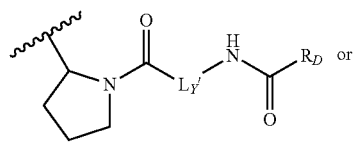 or

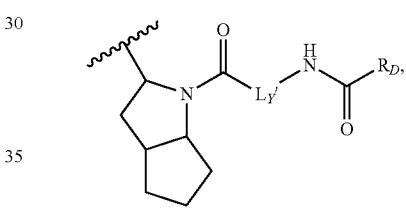, wherein non-limiting examples of $R_D$ include (1) —O—$C_1$-$C_6$alkyl, —O—$C_2$-$C_6$alkenyl, —O—$C_2$-$C_6$alkynyl, $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or (2) $C_3$-$C_6$carbocycle or 3- to 6-membered heterocycle each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; and non-limiting examples of $L_Y$' include $C_1$-$C_6$alkylene optionally substituted with halogen, hydroxy, mercapto, amino, carboxy, phosphonoxy, —O—$C_1$-$C_6$alkyl, —O—$C_2$-$C_6$alkenyl, —O—$C_2$-$C_6$alkynyl, or 3- to 6-membered carbocycle or heterocycle, said 3- to 6-membered carbocycle or heterocycle being optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

In another aspect, the present invention features compounds of Formula $I_A$ and pharmaceutically acceptable salts thereof.

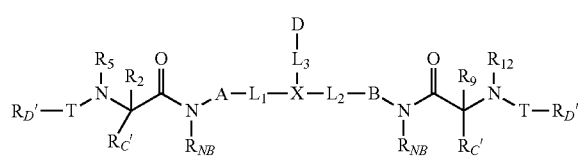

wherein:

$R_{NB}$ is each independently selected from $R_B$;

$R_C'$ is each independently selected from $R_C$;

$R_D'$ is each independently selected from $R_D$;

$R_2$ and $R_5$, taken together with the atoms to which they are attached, form a 3- to 12-membered heterocycle which is optionally substituted with one or more $R_A$;

$R_9$ and $R_{12}$, taken together with the atoms to which they are attached, form a 3- to 12-membered heterocycle which is optionally substituted with one or more $R_A$;

A, B, D, X, $L_1$, $L_2$, $L_3$, T, $R_A$, $R_B$, $R_C$, and $R_D$ are as described above in Formula I.

In this aspect, A and B preferably are independently selected from $C_5$-$C_6$carbocycle or 5- to 6-membered heterocycle, and are each independently optionally substituted with one or more $R_A$. More preferably, at least one of A and B is phenyl (e.g.,

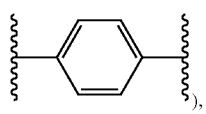

and is optionally substituted with one or more $R_A$. Highly preferably, both A and B are each independently phenyl (e.g.,

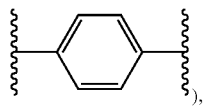

and are each independently optionally substituted with one or more $R_A$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

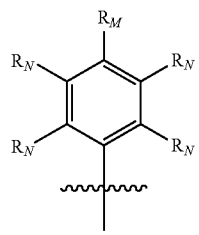

or

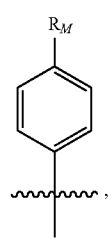

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

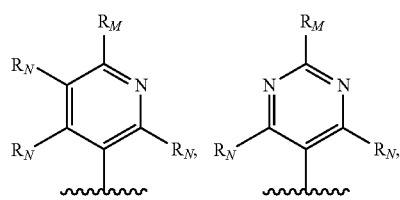

or

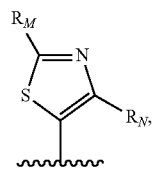

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

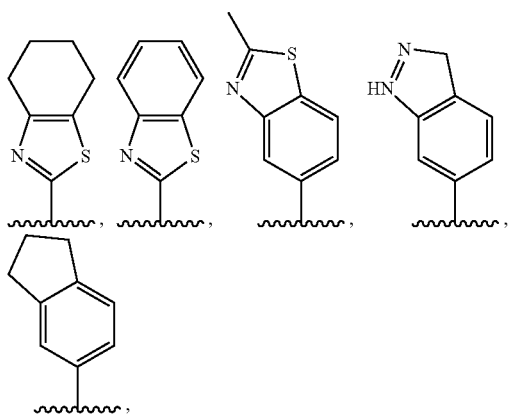

or

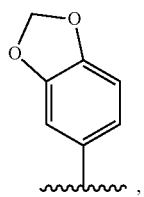

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is independently optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)O$C_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$(e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is independently optionally substituted with one or more substituents selected from halogen, hydroxy, mercapto, amino or carboxy (e.g., tert-butyl, CF$_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more R$_A$. Also preferably, D is $C_5$-$C_6$carbocycle or 5- to 6-membered heterocycle and is substituted with J and optionally substituted with one or more R$_A$, and J is $C_3$-$C_6$carbocycle or 3- to 6-membered heterocycle and is optionally substituted with one or more R$_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'). Also preferably, D is $C_5$-$C_6$carbocycle or 5- to 6-membered heterocycle and is substituted with J and optionally substituted with one or more R$_A$, and J is 6- to 12-membered bicycle (e.g., a 7- to 12-membered fused, bridged or spiro bicycle comprising a nitrogen ring atom through which J is covalently attached to D) and is optionally substituted with one or more R$_A$. More preferably, D is phenyl and is substituted with J and optionally substituted with one or more R$_A$, and J is $C_3$-$C_6$carbocycle, 3- to 6-membered heterocycle or 6- to 12-membered bicycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'). Highly preferably, D is

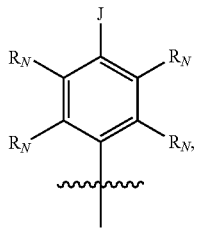

wherein each R$_N$ is independently selected from R$_D$ and preferably is hydrogen or halogen, and J is $C_3$-$C_6$carbocycle, 3- to 6-membered heterocycle or 6- to 12-membered bicycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'). Also preferably, D is

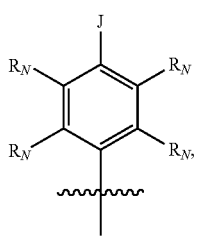

wherein each R$_N$ is independently selected from R$_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more R$_A$. Also preferably, D is

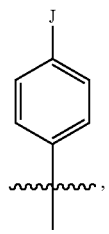

and J is $C_3$-$C_6$carbocycle or 3- to 6-membered heterocycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$').

X preferably is $C_3$-$C_8$cycloalkyl or $C_5$-$C_8$cycloalkenyl and is optionally substituted with one or more R$_A$. More preferably, X is cyclopropyl, cyclopentyl or cyclopentenyl and is optionally substituted with one or more R$_A$ or R$_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more R$_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more R$_L$. Highly preferably, $L_1$, $L_2$ and $L_3$ are each a bond.

$R_2$ and $R_5$, taken together with the atoms to which they are attached, preferably form a 5- to 6-membered heterocycle or 6- to 12-membered bicycle (e.g.,

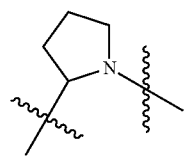 [SMILES: *C1CCCN1*]

or

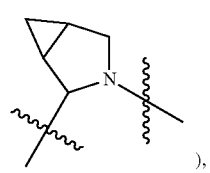 [SMILES: *C1C2CC2CN1*]

which is optionally substituted with one or more R$_A$.

$R_9$ and $R_{12}$, taken together with the atoms to which they are attached preferably form a 5- to 6-membered heterocycle or 6- to 12-membered bicycle (e.g.,

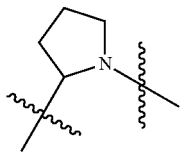 [SMILES: *C1CCCN1*]

or

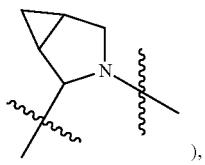 [SMILES: *C1C2CC2CN1*]

), which is optionally substituted with one or more $R_A$.

-T-$R_D$' can be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$'-$R_D$', wherein $L_Y$' is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_{NB}$ and $R_C$' are preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, -$L_A$-SO$_2 R_S$, -$L_A$-C(O)N($R_S R_S$'), -$L_A$-N($R_S$)C(O)$R_S$', -$L_A$-N($R_S$)C(O)N($R_S$'$R_S$"), -$L_A$-N($R_S$)SO$_2 R_S$', -$L_A$-SO$_2$N($R_S R_S$'), -$L_A$-N($R_S$)SO$_2$N($R_S$'$R_S$"), -$L_A$-N($R_S$)S(O)N($R_S$'$R_S$"), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$'), -$L_A$-C(O)N($R_S$)C(O)—$R_S$', or -$L_A$-P(O)(O$R_S$)$_2$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A and B are each independently phenyl, and are each independently optionally substituted with one or more $R_A$; D is phenyl, and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S$'), and J can also be optionally substituted with one or more $R_A$. Preferably, D is

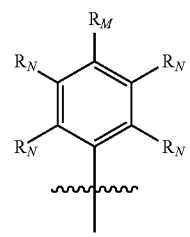

or

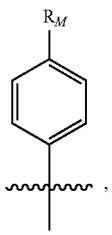

wherein $R_M$ and $R_N$ are as defined above. Also preferably, D is

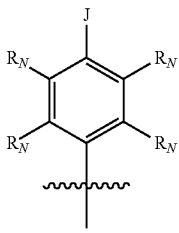

or

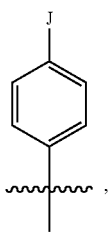

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'—O-$L_S$"-$R_D$', —C(O)-$L_Y$'-N($R_B$)-$L_S$"-$R_D$', or —C(O)-$L_Y$'-N($R_B$)S(O)$_2$-$L_S$"-$R_D$'. Preferably, $R_2$ and $R_5$, taken together with the atoms to which they are attached, form

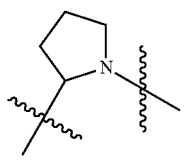 [SMILES: *C1CCCN1*]

which is optionally substituted with one or more $R_A$; $R_9$ and $R_{12}$, taken together with the atoms to which they are attached, form

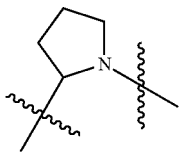 [SMILES: *C1CCCN1*]

which is optionally substituted with one or more $R_A$. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$.

In another embodiment of this aspect, A and B are each independently phenyl (e.g.,

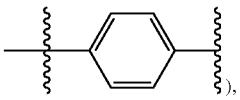 [SMILES: *c1ccc(*)cc1]

and are each independently optionally substituted with one or more $R_A$ (preferably, A and B are each independently substituted with at least one halo such as F). X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$ or —N($R_S R_S$'), or (2) trimethylsilyl, —O—$R_S$, —S—$R_S$ or —C(O)$R_S$; and J can also be optionally substituted with one or more $R_A$. Preferably, D is

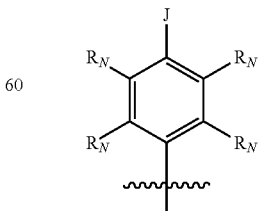

or

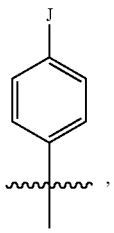

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'—O-$L_S$"-$R_D$', —C(O)-$L_Y$'-N($R_B$)-$L_S$"—$R_D$', or —C(O)-$L_Y$'-N($R_B$)S(O)$_2$-$L_S$"—$R_D$'. $R_2$ and $R_5$, taken together with the atoms to which they are attached, form a 5- to 6-membered heterocyclic ring (e.g.,

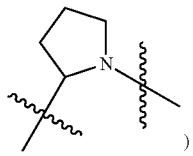 [SMILES: *C1CCCN1*]

or 6- to 12-membered bicycle (e.g.,

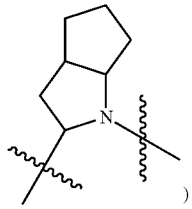 [SMILES: *C1CC2CCCC2N1*]

which is optionally substituted with one or more $R_4$; and $R_9$ and $R_{12}$, taken together with the atoms to which they are attached, form a 5- to 6-membered heterocyclic ring (e.g.,

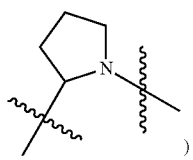 [SMILES: *C1CCCN1*]

or 6- to 12-membered bicycle (e.g.,

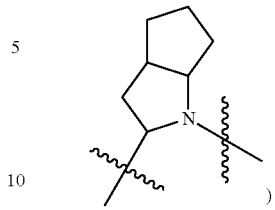

which is optionally substituted with one or more $R_4$.

In still another aspect, the present invention features compounds of Formula $I_B$ and pharmaceutically acceptable salts thereof:

$I_B$

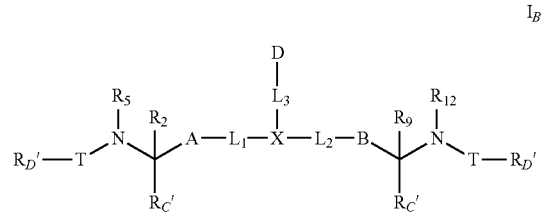

wherein:
$R_C$' is each independently selected from $R_C$;
$R_D$' is each independently selected from $R_D$;
$R_2$ and $R_5$, taken together with the atoms to which they are attached, form a 3- to 12-membered heterocycle which is optionally substituted with one or more $R_4$;
$R_9$ and $R_{12}$, taken together with the atoms to which they are attached, form a 3- to 12-membered heterocycle which is optionally substituted with one or more $R_4$;
A, B, D, X, $L_1$, $L_2$, $L_3$, T, $R_4$, $R_C$, and $R_D$ are as described above in Formula I.

In this aspect, A and B preferably are independently selected from 8- to 12-membered bicycles such as

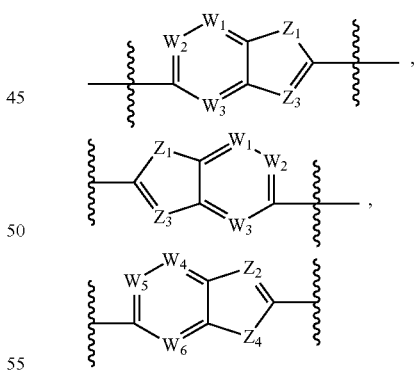

or

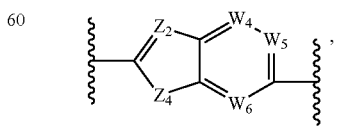

where $Z_1$ is independently selected at each occurrence from O, S, NH or CH$_2$, $Z_2$ is independently selected at each occurrence from N or CH, $Z_3$ is independently selected at each occurrence from N or CH, $Z_4$ is independently selected at each occurrence from O, S, NH or $CH_2$, and $W_1$, $W_2$, $W_3$, $W_4$, $W_5$ and $W_6$ are each independently selected at each occurrence from CH or N. A and B are each independently optionally substituted with one or more $R_A$.

More preferably, A is selected from

[structure with $Z_1$, $Z_3$, $W_1$, $W_2$, $W_3$]

or

[structure with $Z_2$, $Z_4$, $W_4$, $W_5$, $W_6$], and is optionally substituted with one or more $R_A$; B is selected from

[structure with $W_1$, $W_2$, $W_3$, $Z_1$, $Z_3$]

or

[structure with $W_4$, $W_5$, $W_6$, $Z_2$, $Z_4$], and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, A can be selected from

[benzimidazole structure with $Z_1$]

(e.g.,

[benzimidazole structure with NH]

)

or

[benzimidazole structure with $Z_2$, NH]

(e.g.,

[indole structure with NH]

or

[benzimidazole structure with N, NH]

), and is optionally substituted with one or more $R_A$; and B can be selected from

[benzimidazole structure with $Z_1$, N]

(e.g.,

[benzimidazole structure with NH, N]

)

or

[benzimidazole structure with $Z_2$, NH]

(e.g.,

[benzimidazole structure with N, NH]

or

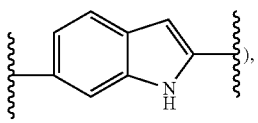 [SMILES: *c1ccc2cc(*)[nH]c2c1]

and is optionally substituted with one or more $R_A$.

Also preferably, A is

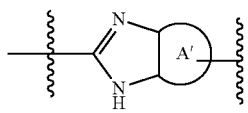

(e.g.,

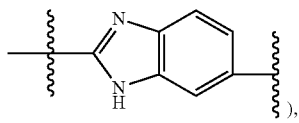 [SMILES: *c1ccc2nc(*)[nH]c2c1]

and B is

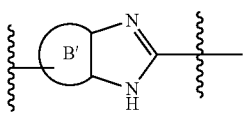

(e.g.,

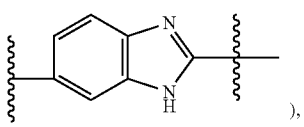

wherein A' and B' are independently selected from $C_5$-$C_6$carbocycle or 5- to 6-membered heterocycle, and A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

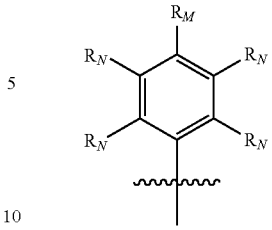

or

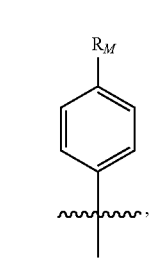

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

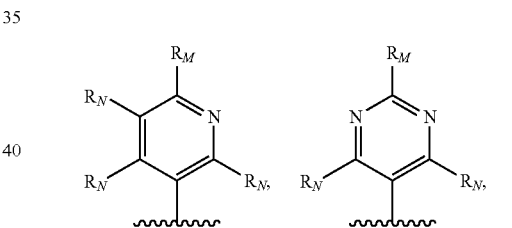

or

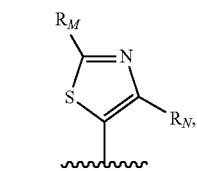

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

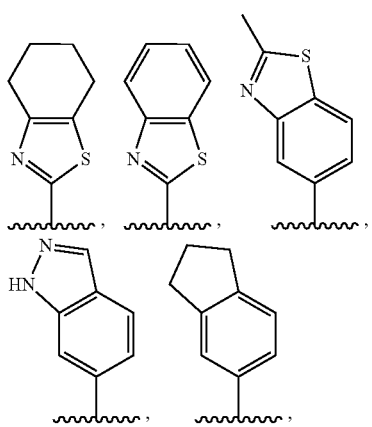

or

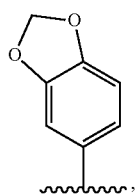

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is $CF_3$, —C($CF_3$)$_2$—OH, —C($CH_3$)$_2$—CN, —C($CH_3$)$_2$—$CH_2$OH, or —C($CH_3$)$_2$—$CH_2 NH_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N($CH_2 CH_2$OMe)$_2$); —N($C_1$-$C_6$alkyl)($C_1$-$C_6$alkylene-O—$C_1$-$C_6$alkyl) (e.g. —N($CH_3$)($CH_2 CH_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2 CF_3$); —O—$C_1$-$C_6$alkylene-piperidine (e.g., —O—$CH_2 CH_2$-1-piperidyl); —N($C_1$-$C_6$alkyl)C(O)OC$_1$-$C_6$alkyl (e.g., —N($CH_3$)C(O)O—$CH_2 CH$($CH_3$)$_2$), —N($C_1$-$C_6$alkyl)SO$_2 C_1$-$C_6$alkyl (e.g., —N($CH_3$)SO$_2 CH_3$); —SO$_2 C_1$-$C_6$alkyl (e.g., —SO$_2$Me); —SO$_2 C_1$-$C_6$haloalkyl (e.g., —SO$_2 CF_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C($CH_3$)$_2$—, —C($CH_3$)$_2$—$CH_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C($CH_3$)$_2$—$CH_2$—OMe); —$C_1$-$C_6$alkylene-C(O)O$R_S$(e.g., —C($CH_3$)$_2$—C(O)OMe); —$C_1$-$C_6$alkylene-N($R_S$)C(O)O$R_S'$ (e.g., —C($CH_3$)$_2$—$CH_2$—NHC(O)OCH$_3$); or —$C_1$-$C_6$alkylene-P(O)(O$R_S$)$_2$ (e.g., —$CH_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, $CF_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$, and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$. Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$. Highly preferably, D is

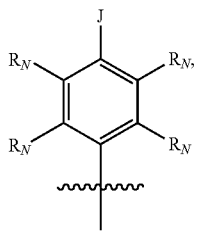

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$. Also preferably, D is

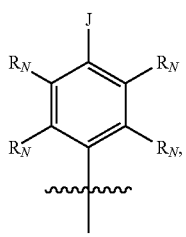

wherein each $R_N$ is independently selected from $R_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$, and J can also be optionally substituted with one or more $R_A$. Also preferably, D is

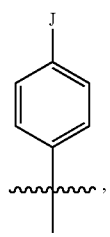

and J is $C_3$-$C_6$carbocycle or 3- to 6-membered heterocycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$.

X preferably is $C_3$-$C_8$cycloalkyl or $C_5$-$C_8$cycloalkenyl and is optionally substituted with one or more $R_A$. More preferably, X is cyclopropyl, cyclopentyl or cyclopentenyl and is optionally substituted with one or more $R_A$ or $R_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more $R_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more $R_L$. Highly preferably, $L_1$, $L_2$ and $L_3$ are each a bond.

$R_2$ and $R_5$, taken together with the atoms to which they are attached, preferably form a 5- to 6-membered heterocycle or 6- to 12-membered bicycle (e.g.,

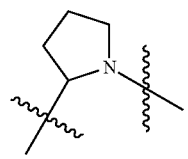 [SMILES: *C1CCCN1*]

or

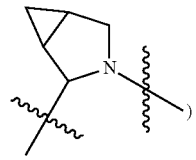 [SMILES: *C1C2CC2CN1*]
)

which is optionally substituted with one or more $R_A$. $R_9$ and $R_{12}$, taken together with the atoms to which they are attached, preferably form a 5- to 6-membered heterocycle or 6- to 12-membered bicycle (e.g.,

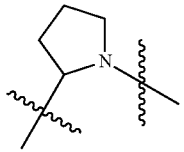 [SMILES: *C1CCCN1*]

or

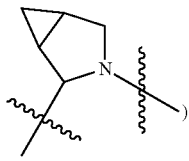 [SMILES: *C1C2CC2CN1*]

)

which is optionally substituted with one or more $R_A$.

-T-$R_D$' can be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'N($R_B$)C(O)-$L_S$'-$R_D$', —N($R_B$)C(O)-$L_Y$'-N($R_B$)C(O)O-$L_S$"-$R_D$', or —N($R_B$)C(O)-$L_Y$'-N($R_B$)-$L_S$"-$R_D$', wherein $L_Y$' is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_C$' is preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S$$R_S$'), -$L_A$-S(O)$R_S$, -$L_A$-SO$_2$$R_S$, -$L_A$-C(O)N($R_S$$R_S$'), -$L_A$-N($R_S$)C(O)$R_S$', -$L_A$-N($R_S$)C(O)N($R_S$'$R_S$"), -$L_A$-N($R_S$)SO$_2$$R_S$', -$L_A$-SO$_2$N($R_S$$R_S$'), -$L_A$-N($R_S$)SO$_2$N($R_S$'$R_S$"), -$L_A$-N($R_S$)S(O)N($R_S$'$R_S$"), -$L_A$-OS(O)—$R_S$, -$L_A$-OS(O)$_2$—$R_S$, -$L_A$-S(O)$_2$O$R_S$, -$L_A$-S(O)O$R_S$, -$L_A$-OC(O)O$R_S$, -$L_A$-N($R_S$)C(O)O$R_S$', -$L_A$-OC(O)N($R_S$$R_S$'), -$L_A$-N($R_S$)S(O)—$R_S$', -$L_A$-S(O)N($R_S$$R_S$'), -$L_A$-C(O)N($R_S$)C(O)—$R_S$', or -$L_A$-P(O)(O$R_S$)$_2$ wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A is

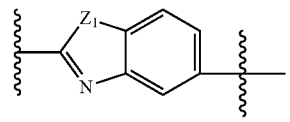

or

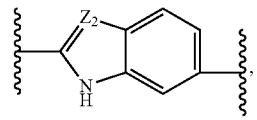

, and is optionally substituted with one or more $R_A$; B is

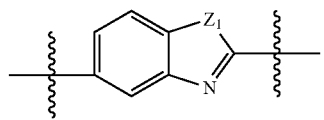

or

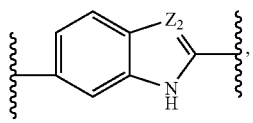

and is optionally substituted with one or more $R_A$; and D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more $R_A$. Preferably, D is

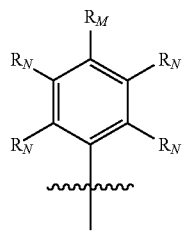

or

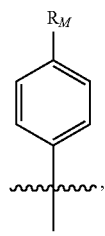

wherein $R_M$ and $R_N$ are as defined above. Also preferably, D is

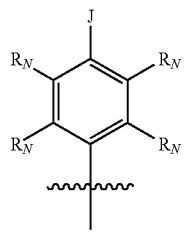

or

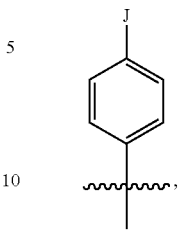

wherein J and $R_N$ are as defined above. $Z_1$ is independently selected at each occurrence from O, S, NH or CH$_2$; and $Z_2$ is independently selected at each occurrence from N or CH. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$.

Preferably, $L_1$, $L_2$, and $L_3$ are bond. -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_Y$' is $C_1$-$C_6$alkylene (e.g., —CH$_2$—) and optionally substituted with one or more substituents selected from $R_L$, and L$_S$" preferably is bond. -T-R$_D$' can also be, without limitation, selected from —C(O)-L$_Y$'-L$_S$"-R$_D$', —C(O)-L$_Y$'-O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$.

In another embodiment of this aspect, A is

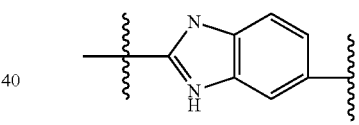

and optionally substituted with one or more $R_A$ (e.g., halogen); B is

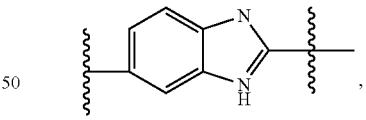

and is optionally substituted with one or more $R_A$ (e.g., halogen); and D is $C_5$-$C_6$carbocycle or 5- to 6-membered heterocycle (e.g., phenyl), and is optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more $R_A$. Preferably, D is

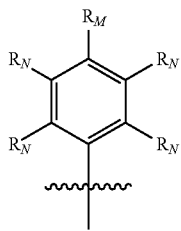

or

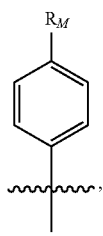

wherein $R_M$ and $R_N$ are as defined above. Also preferably, D is

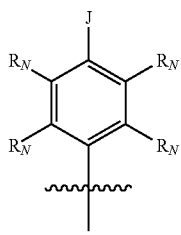

or

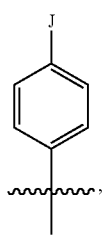

wherein J and $R_N$ are as defined above. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$', wherein $L_Y$' is $C_1$-$C_6$alkylene (e.g., —CH$_2$—) and optionally substituted with one or more substituents selected from $R_L$, and $L_S$" preferably is bond. -T-$R_D$' can also be, without limitation, selected from —C(O)-$L_Y$'-$L_S$"-$R_D$', —C(O)-$L_Y$'-O-$L_S$"-$R_D$', —C(O)-$L_Y$'-N($R_B$)-$L_S$'-$R_D$', or —C(O)-$L_Y$'-N($R_B$)S(O)$_2$-$L_S$"-$R_D$'. $R_2$ and $R_5$, taken together with the atoms to which they are attached, preferably form a 5- to 6-membered heterocycle or 6- to 12-membered bicycle (e.g.,

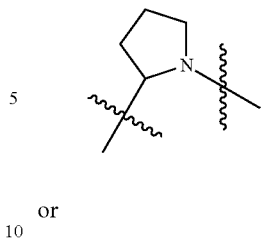

or

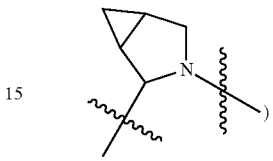

)

which is optionally substituted with one or more $R_4$. $R_9$ and $R_{12}$, taken together with the atoms to which they are attached, preferably form a 5- to 6-membered heterocycle or 6- to 12-membered bicycle (e.g.,

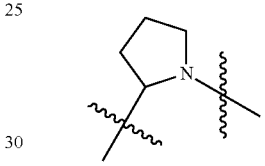

or

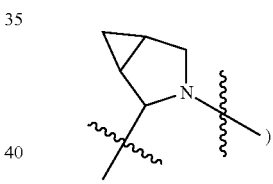

)

which is optionally substituted with one or more $R_4$. More preferably, $R_2$ and $R_5$, taken together with the atoms to which they are attached, form

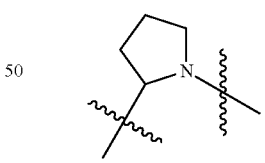

which is optionally substituted with one or more $R_4$; $R_9$ and $R_{12}$, taken together with the atoms to which they are attached, form

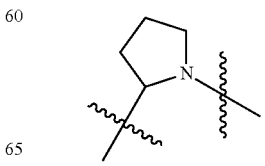

which is optionally substituted with one or more $R_A$. X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$.

In still another embodiment of this aspect, A is

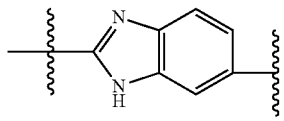 [SMILES: *c1ccc2nc(*)[nH]c2c1]

and optionally substituted with one or more $R_A$ (preferably, A is substituted with at least one halogen such as F); B is

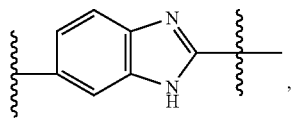 [SMILES: *c1ccc2nc(*)[nH]c2c1 ; ","]

and is optionally substituted with one or more $R_A$ (preferably, B is substituted with at least one halogen such as F). X is $C_3$-$C_8$cycloalkyl or $C_5$-$C_8$cycloalkenyl and is optionally substituted with one or more $R_A$. Specific examples of X are described hereinabove. Preferably, X is cyclopropyl, cyclopentyl or cyclopentenyl, and is optionally substituted with one or more $R_A$ or $R_F$. More preferably, X is cyclopropyl is and is optionally substituted with one or more $R_A$ or $R_F$. D is phenyl, and is substituted with J and optionally substituted with one or more $R_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more $R_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$ or —C(O)R$_S$; and J can also be optionally substituted with one or more $R_A$. Preferably, D is

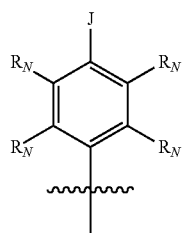

or

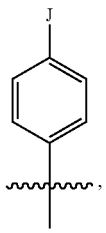

wherein J is as defined above, and each $R_N$ is independently selected from $R_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more $R_L$. Preferably, $L_1$, $L_2$, and $L_3$ are bond. -T-$R_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_Y$' is $C_1$-$C_6$alkylene (e.g., —CH$_2$—) and optionally substituted with one or more substituents selected from $R_L$, and L$_S$" preferably is bond. -T-$R_D$' can also be, without limitation, selected from —C(O)-L$_Y$'-L$_S$"-R$_D$', —C(O)-L$_Y$'—O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. $R_2$ and $R_5$, taken together with the atoms to which they are attached, preferably form a 5- to 6-membered heterocycle or 6- to 12-membered bicycle (e.g.,

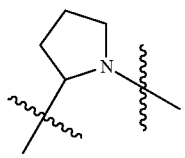 [SMILES: *C1CCCN1*]

or

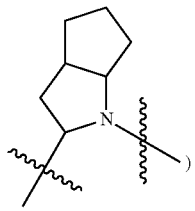

which is optionally substituted with one or more $R_A$. $R_9$ and $R_{12}$, taken together with the atoms to which they are attached, preferably form a 5- to 6-membered heterocycle or 6- to 12-membered bicycle (e.g.

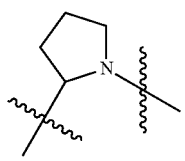

or

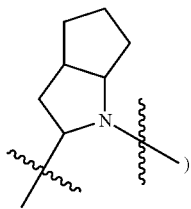

which is optionally substituted with one or more $R_A$. More preferably, $R_2$ and $R_5$, taken together with the atoms to which they are attached, form

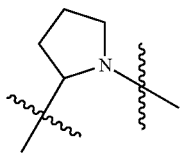 [SMILES: *C1CCCN1*]

which is optionally substituted with one or more $R_A$; $R_9$ and $R_{12}$, taken together with the atoms to which they are attached, form

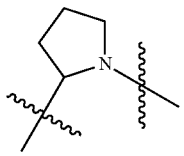 [SMILES: *C1CCCN1*]

which is optionally substituted with one or more $R_A$.

In yet another aspect, the present invention further features compounds of Formula $I_C$ and pharmaceutically acceptable salts thereof.

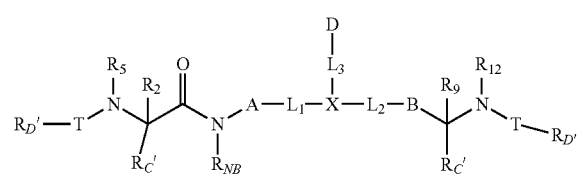

$I_C$ wherein:
  $R_{NB}$ is $R_B$;
  $R_C'$ is each independently selected from $R_C$;
  $R_D'$ is each independently selected from $R_D$;
  $R_2$ and $R_5$, taken together with the atoms to which they are attached, form a 3- to 12-membered heterocycle which is optionally substituted with one or more $R_A$;
  $R_9$ and $R_{12}$, taken together with the atoms to which they are attached, form a 3- to 12-membered heterocycle which is optionally substituted with one or more $R_A$;
  A, B, D, X, $L_1$, $L_2$, $L_3$, T, $R_A$, $R_B$, $R_C$, and $R_D$ are as described above in Formula I.

In this aspect, A preferably is $C_5$-$C_6$-carbocycle or 5- to 6-membered heterocycle, and is optionally substituted with one or more $R_A$; and B preferably is 8- to 12-membered bicycle (such as

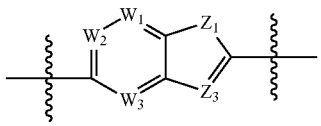

or

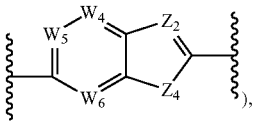

and is optionally substituted with one or more $R_A$. $Z_1$ is O, S, NH or $CH_2$; $Z_2$ is N or CH; $Z_3$ is N or CH; $Z_4$ is O, S, NH or $CH_2$; and $W_1$, $W_2$, $W_3$, $W_4$, $W_5$ and $W_6$ are each independently selected from CH or N.

More preferably, A is phenyl (e.g.,

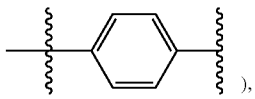

and is optionally substituted with one or more $R_A$; and B is

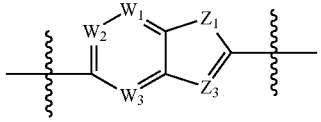

or

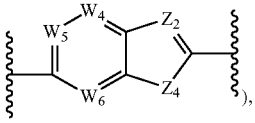

and is optionally substituted with one or more $R_A$, where $Z_1$, $Z_2$, $Z_3$, $Z_4$, $W_1$, $W_2$, $W_3$, $W_4$, $W_5$, $W_6$ are as defined above. Preferably, $Z_3$ is N and $Z_4$ is NH. For instance, B can be

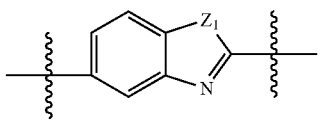

(e.g.,

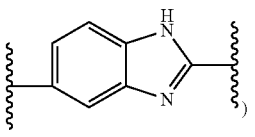
)

or

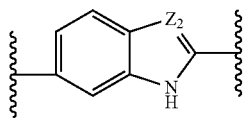

(e.g.

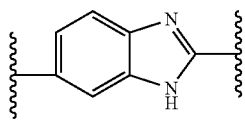 [SMILES: *c1ccc2nc(*)[nH]c2c1]

or

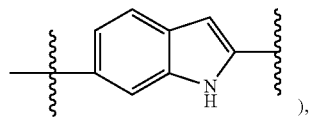 [SMILES: *c1ccc2cc(*)[nH]c2c1]), and is optionally substituted with one or more $R_A$.

Also preferably, A is $C_5$-$C_6$carbocycle (e.g., phenyl such as

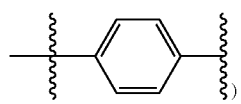)

or 5- to 6-membered heterocycle; and B is

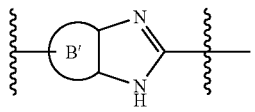

(e.g.,

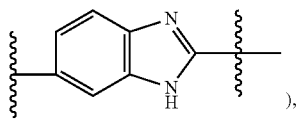 [SMILES: *c1ccc2nc(*)[nH]c2c1]), wherein B' is selected from $C_5$-$C_6$carbocycle or 5- to 6-membered heterocycle. A and B are independently optionally substituted with one or more $R_A$.

D preferably is selected from $C_5$-$C_6$carbocycle, 5- to 6-membered heterocycle, or 6- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more substituents selected from $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$.

More preferably, D is phenyl, and is substituted with one or more $R_M$, wherein $R_M$ is as defined above. Highly preferably, D is

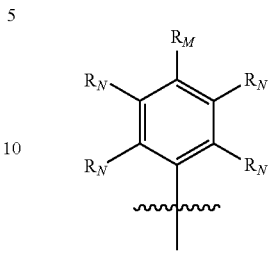

or

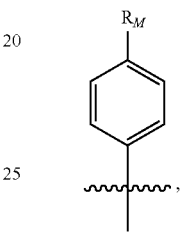, wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

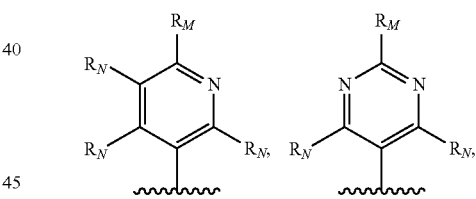

or

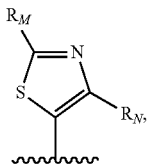

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

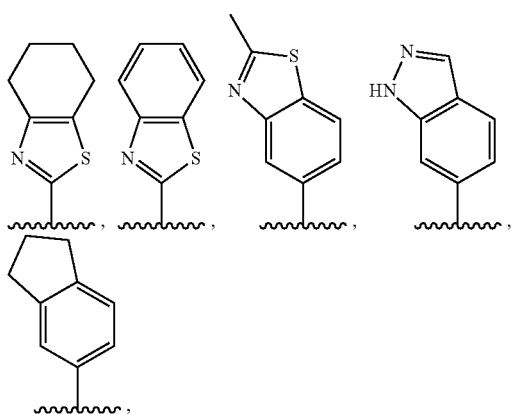

or

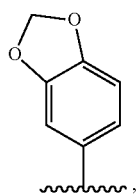

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2$$R_S'$, —SO$_2$$R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2$$R_S'$, —SO$_2$$R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)OC$_1$-$C_6$alkyl (e.g., —N(CH$_3$)C(O)O—CH$_2$CH(CH$_3$)$_2$), —N($C_1$-$C_6$alkyl)SO$_2$$C_1$-$C_6$alkyl (e.g., —N(CH$_3$)SO$_2$CH$_3$); —SO$_2$$C_1$-$C_6$alkyl (e.g., —SO$_2$Me); —SO$_2$$C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$(e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, CF$_3$).

More preferably, D is $C_5$-$C_6$carbocycle, 5- to 6-membered heterocycle or 6- to 12-membered bicycle and is substituted with J and optionally substituted with one or more $R_4$, wherein J is $C_3$-$C_6$carbocycle, 3- to 6-membered heterocycle or 6- to 12-membered bicycle and is optionally substituted with one or more $R_4$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$), and J can also be optionally substituted with one or more R$_A$. Also preferably, D is $C_5$-$C_6$carbocycle or 5- to 6-membered heterocycle and is substituted with J and optionally substituted with one or more R$_A$, and J is $C_3$-$C_6$carbocycle or 3- to 6-membered heterocycle and is optionally substituted with one or more R$_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$). Also preferably, D is $C_5$-$C_6$carbocycle or 5- to 6-membered heterocycle and is substituted with J and optionally substituted with one or more R$_A$, and J is 6- to 12-membered bicycle (e.g., a 7- to 12-membered fused, bridged or spiro bicycle comprising a nitrogen ring atom through which J is covalently attached to D) and is optionally substituted with one or more R$_A$. More preferably, D is phenyl and is substituted with J and optionally substituted with one or more R$_A$, and J is $C_3$-$C_6$carbocycle, 3- to 6-membered heterocycle or 6- to 12-membered bicycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$). Highly preferably, D is

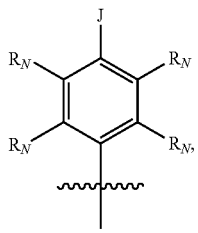

wherein each R$_N$ is independently selected from R$_D$ and preferably is hydrogen or halogen, and J is $C_3$-$C_6$carbocycle, 3- to 6-membered heterocycle or 6- to 12-membered bicycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$). Also preferably, D is

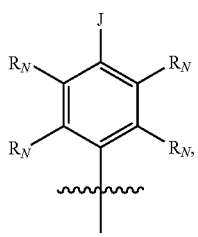

wherein each R$_N$ is independently selected from R$_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$), and J can also be optionally substituted with one or more R$_A$. Also preferably, D is

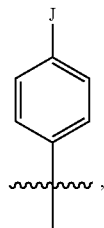

and J is $C_3$-$C_6$carbocycle or 3- to 6-membered heterocycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S'$).

X preferably is $C_3$-$C_8$cycloalkyl or $C_5$-$C_8$cycloalkenyl and is optionally substituted with one or more R$_A$. More preferably, X is cyclopropyl, cyclopentyl or cyclopentenyl and is optionally substituted with one or more R$_A$ or R$_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more R$_L$. More preferably, $L_1$, $L_2$ and $L_3$ are each independently a bond or $C_1$-$C_6$alkylene (e.g., —CH$_2$— or —CH$_2$CH$_2$—), and are each independently optionally substituted with one or more R$_L$. Highly preferably, $L_1$, $L_2$ and $L_3$ are each a bond. $L_1$ and $L_2$ can be the same or different.

R$_2$ and R$_5$, taken together with the atoms to which they are attached, preferably form a 5- to 6-membered heterocycle or 6- to 12-membered bicycle (e.g.,

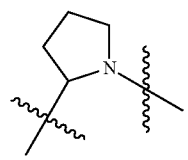 [SMILES: *C1CCCN1*]

or

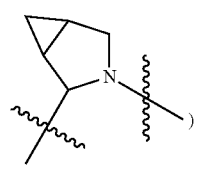)

which is optionally substituted with one or more $R_4$. $R_9$ and $R_{12}$, taken together with the atoms to which they are attached, preferably form a 5- to 6-membered heterocycle or 6- to 12-membered bicycle (e.g.,

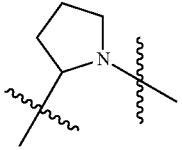 [SMILES: *C1CCCN1*]

or

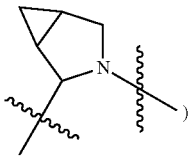

)

which is optionally substituted with one or more $R_4$.

-T-$R_D$' can be, without limitation, independently selected at each occurrence from —C(O)-$L_Y$'-$R_D$', —C(O)O-$L_Y$'-$R_D$', —C(O)-$L_Y$'-N($R_B$)C(O)-$L_S$"-$R_D$', —C(O)-$L_Y$'-N($R_B$)C(O)O-$L_S$"-$R_D$', —N($R_B$)C(O)-$L_Y$'-N($R_B$)C(O)-$L_S$"-$R_D$', —N($R_B$)C(O)-$L_Y$'-N($R_B$)C(O)O-$L_S$"-$R_D$', or —N($R_B$)C(O)-$L_Y$'-N($R_B$)-$L_S$'-$R_D$', wherein $L_1$ is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$"-$R_D$' or —N($R_B$)C(O)-$L_Y$'-M'-$L_S$"-$R_D$'. More preferably, -T-$R_D$' is independently selected at each occurrence from —C(O)-$L_Y$'-N($R_B$)C(O)-$L_S$"-$R_D$' or —C(O)-$L_Y$'-N($R_B$)C(O)O-$L_S$"-$R_D$'. Highly preferably, -T-$R_D$' is independently selected at each occurrence from —C(O)-$L_Y$'-N($R_B$)C(O)—$R_D$' or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_{NB}$ and $R_C$' are preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_4$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_4$-O—$R_S$, -$L_4$-S—$R_S$, -$L_4$-C(O)$R_S$, -$L_4$-OC(O)$R_S$, -$L_4$-C(O)O$R_S$, -$L_4$-N($R_S R_S$'), -$L_4$-S(O)$R_S$, -$L_4$-SO$_2 R_S$, -$L_4$-C(O)N($R_S R_S$'), -$L_4$-N($R_S$)C(O)$R_S$'-$L_4$-N($R_S$)C(O)N($R_S$'$R_S$"), -$L_4$-N($R_S$)SO$_2 R_S$', -$L_4$-SO$_2$N($R_S R_S$'), -$L_4$-N($R_S$)SO$_2$N($R_S$'$R_S$"), -$L_4$-N($R_S$)S(O)N($R_S$'$R_S$"), -$L_4$-OS(O)—$R_S$, -$L_4$-OS(O)$_2$—$R_S$, -$L_4$-S(O)$_2$O$R_S$, -$L_4$-S(O)O$R_S$, -$L_4$-OC(O)O$R_S$, -$L_4$-N($R_S$)C(O)O$R_S$', -$L_4$-OC(O)N($R_S R_S$'), -$L_4$-N($R_S$)S(O)—$R_S$', -$L_4$-S(O)N($R_S R_S$'), -$L_4$-C(O)N($R_S$)C(O)—$R_S$', or -$L_4$-P(O)(O$R_S$)$_2$, wherein $L_4$ is bond, $C_1$-$C_6$alkylene, $C_2$-$C_6$alkenylene or $C_2$-$C_6$alkynylene.

More preferably, $R_4$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_4$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$" preferably are each independently selected at each occurrence from bond; or $C_1$-$C_6$alkylene, $C_2$-$C_6$alkenylene or $C_2$-$C_6$alkynylene.

In one embodiment of this aspect, A is phenyl, and is optionally substituted with one or more $R_4$; and B is

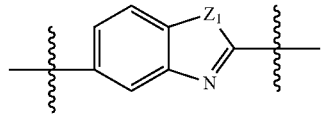

or

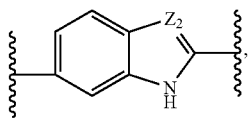

and is optionally substituted with one or more $R_4$, wherein $Z_1$ is O, S, NH or CH$_2$; and $Z_2$ is N or CH. D is $C_5$-$C_6$carbocycle or 5- to 6-membered heterocycle (e.g., phenyl), and is optionally substituted with one or more $R_4$, or is substituted with J and optionally substituted with one or more $R_4$, wherein J is $C_3$-$C_6$carbocycle, 3- to 6-membered heterocycle or 6- to 12-membered bicycle and is optionally substituted with one or more $R_4$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more R$_A$. Preferably, D is

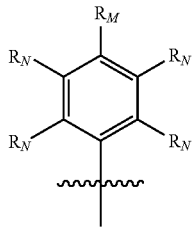

or

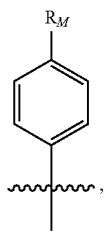

wherein R$_M$ and R$_N$ are as defined above. Also preferably, D is

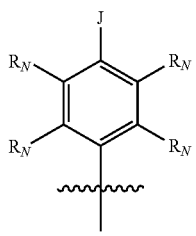

or

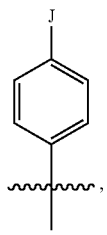

wherein J and R$_N$ are as defined above. L$_1$ and L$_2$ are each independently bond or $C_1$-$C_6$alkylene, and L$_3$ is bond, $C_1$-$C_6$alkylene or —C(O)—, and L$_1$, L$_2$, and L$_3$ are each independently optionally substituted with one or more R$_L$. Preferably, L$_1$, L$_2$, and L$_3$ are bond. -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_Y$' is $C_1$-$C_6$alkylene (e.g., —CH$_2$—) and optionally substituted with one or more substituents selected from R$_L$, and L$_S$" preferably is bond. -T-R$_D$' can also be, without limitation, selected from —C(O)-L$_Y$'-L$_S$"-R$_D$', —C(O)-L$_Y$'—O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. Preferably, R$_2$ and R$_5$, taken together with the atoms to which they are attached, form

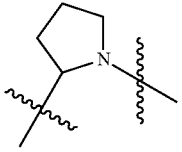 [SMILES: *C1CCCN1*]

which is optionally substituted with one or more R$_A$; R$_9$ and R$_{12}$, taken together with the atoms to which they are attached, form

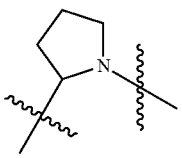 [SMILES: *C1CCCN1*]

which is optionally substituted with one or more R$_A$. X is $C_3$-$C_8$cycloalkyl or $C_5$-$C_8$cycloalkenyl and is optionally substituted with one or more R$_A$. Specific examples of X are described hereinabove. Preferably, X is cyclopropyl, cyclopentyl or cyclopentenyl, and is optionally substituted with one or more R$_A$ or R$_F$. More preferably, X is cyclopropyl is and is optionally substituted with one or more R$_A$ or R$_F$.

In another embodiment of this aspect, A is phenyl (e.g.,

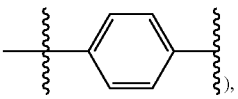), and is optionally substituted with one or more R$_A$ (preferably, A is substituted with at least one halogen such as F); and B is

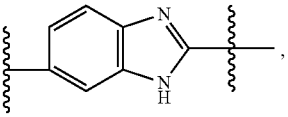 [SMILES: *c1ccc2nc(*)[nH]c2c1], and is optionally substituted with one or more R$_A$ (preferably, B is substituted with at least one halogen such as F). X is $C_3$-$C_8$cycloalkyl or $C_5$-$C_8$cycloalkenyl and is optionally substituted with one or more R$_A$. Specific examples of X are described hereinabove. Preferably, X is cyclopropyl, cyclopentyl or cyclopentenyl, and is optionally substituted with one or more R$_A$ or R$_F$. More preferably, X is cyclopropyl is and is optionally substituted with one or more R$_A$ or R$_F$. D is phenyl, and is substituted with J and optionally substituted with one or more R$_A$. J is $C_3$-$C_6$carbocycle, 3- to 6-membered heterocycle, 6- to 12-membered bicycle, 10- to 15-membered tricycle or 13- to 15-membered carbocycle/heterocycle, and J is optionally substituted with one or more R$_A$. Preferably, J is substituted with a $C_3$-$C_6$carbocycle, 3- to 6-membered heterocycle, 6- to 12-membered bicycle or 7- to 12-membered carbocycle/heterocycle, which is independently optionally substituted with one or more substituents selected from (1)

halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$ or —C(O)R$_S$; and J can also be optionally substituted with one or more R$_A$. Preferably, D is

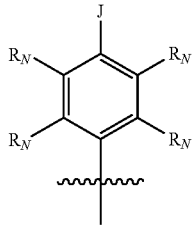

or

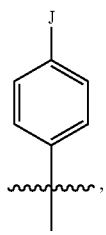

wherein J is as defined above, and each R$_N$ is independently selected from R$_D$ and preferably is hydrogen or halo such as F. $L_1$ and $L_2$ are each independently bond or $C_1$-$C_6$alkylene, and $L_3$ is bond, $C_1$-$C_6$alkylene or —C(O)—, and $L_1$, $L_2$, and $L_3$ are each independently optionally substituted with one or more R$_L$. Preferably, $L_1$, $L_2$, and $L_3$ are bond. -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_Y$' is $C_1$-$C_6$alkylene (e.g., —CH$_2$—) and optionally substituted with one or more substituents selected from R$_L$, and L$_S$" preferably is bond. -T-R$_D$' can also be, without limitation, selected from —C(O)-L$_Y$'-L$_S$"-R$_D$', —C(O)-L$_Y$'-O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. Preferably, $R_2$ and $R_5$, taken together with the atoms to which they are attached, form a 5- to 6-membered heterocyclic ring (e.g.,

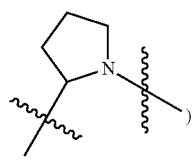 [SMILES: *C1CCCN1*]

or 6- to 12-membered bicycle (e.g.,

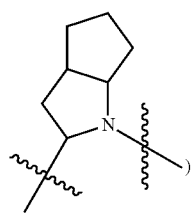 [SMILES: *C1CC2CCCC2N1*]

which is optionally substituted with one or more R$_A$; $R_9$ and $R_{12}$, taken together with the atoms to which they are attached, form a 5- to 6-membered heterocyclic ring (e.g.,

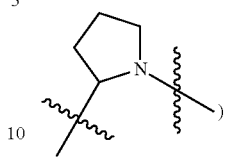

or 6- to 12-membered bicycle (e.g.,

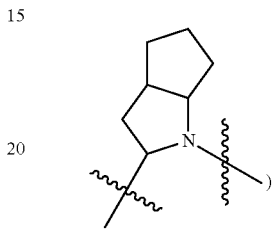

which is optionally substituted with one or more R$_A$.

In yet another aspect, the present invention features compounds of Formula $I_D$ and pharmaceutically acceptable salts thereof.

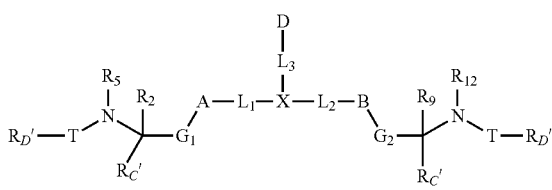

$I_D$ wherein:
$G_1$ and $G_2$ are each independently selected from $C_5$-$C_6$carbocycle or 5- to 6-membered heterocycle, and are each independently optionally substituted with one or more R$_A$;
$R_C$' is each independently selected from R$_C$;
$R_D$' is each independently selected from R$_D$;
$R_2$ and $R_5$, taken together with the atoms to which they are attached, form a 3- to 12-membered heterocycle which is optionally substituted with one or more R$_A$;
$R_9$ and $R_{12}$, taken together with the atoms to which they are attached, form a 3- to 12-membered heterocycle which is optionally substituted with one or more R$_A$;
A, B, D, X, $L_1$, $L_2$, $L_3$, T, R$_A$, R$_C$, and R$_D$ are as described above in Formula I.

In this aspect, A and B preferably are independently selected from $C_5$-$C_6$carbocycle or 5- to 6-membered heterocycle, and are each independently optionally substituted with one or more R$_A$. More preferably, at least one of A and B is phenyl (e.g.,

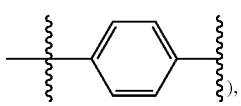), and is optionally substituted with one or more $R_A$. Highly preferably, both A and B are each independently phenyl (e.g.,

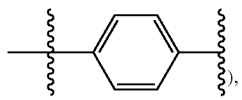

and are each independently optionally substituted with one or more $R_A$.

D preferably is selected from $C_5$-$C_6$carbocycle, 5- to 6-membered heterocycle, or 8- to 12-membered bicycles, and is optionally substituted with one or more $R_A$. D can also be preferably selected from $C_1$-$C_6$alkyl, $C_2$-$C_6$alkenyl or $C_2$-$C_6$alkynyl, and is optionally substituted with one or more $R_L$. More preferably, D is $C_5$-$C_6$carbocycle, 5- to 6-membered heterocycle, or 6- to 12-membered bicycles, and is substituted with one or more $R_M$, where $R_M$ is halogen, nitro, oxo, phosphonoxy, phosphono, thioxo, cyano, or -$L_S$-$R_E$. Also preferably, D is phenyl, and is optionally substituted with one or more $R_A$. More preferably, D is phenyl, and is substituted with one or more $R_M$, wherein $R_M$ is as defined above. Highly preferably, D is

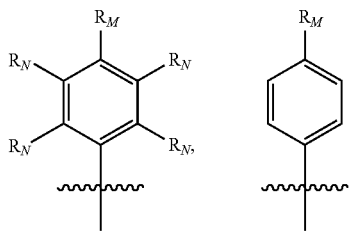

or

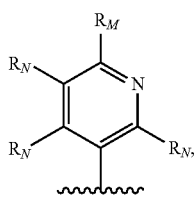

wherein $R_M$ is as defined above, and each $R_N$ is independently selected from $R_D$ and preferably is hydrogen. One or more $R_N$ can also preferably be halo such as F.

D is also preferably pyridinyl, pyrimidinyl, or thiazolyl, optionally substituted with one or more $R_A$. More preferably D is pyridinyl, pyrimidinyl, or thiazolyl, and is substituted with one or more $R_M$. Highly preferably, D is

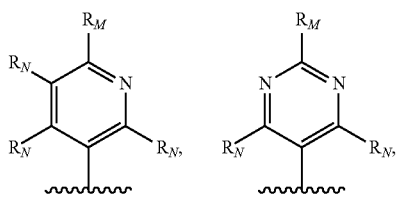

or

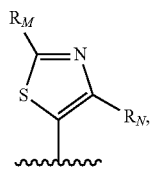

wherein $R_M$ is as defined above, and each $R_N$ is independently selected from $R_D$ and preferably is hydrogen. One or more $R_N$ can also preferably be halo such as F. D is also preferably indanyl, 4,5,6,7-tetrahydrobenzo[d]thiazolyl, benzo[d]thiazolyl, or indazolyl, and is optionally substituted with one or more $R_A$. More preferably D is indanyl, 4,5,6,7-tetrahydrobenzo[d]thiazolyl, benzo[d]thiazolyl, indazolyl, or benzo[d][1,3]dioxol-5-yl, and is substituted with one or more $R_M$. Highly preferably, D is

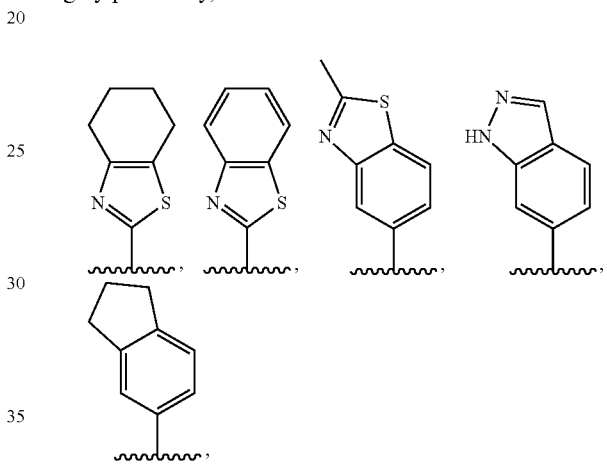

or

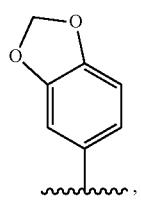

and is optionally substituted with one or more $R_M$.

Preferably, $R_M$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl. More preferably, $R_M$ is halogen, hydroxy, mercapto, amino, carboxy; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino or carboxy. Highly preferably, $R_M$ is $C_1$-$C_6$alkyl which is optionally substituted with one or more substituents selected from halogen, hydroxy, mercapto, amino or carboxy.

Also preferably, $R_M$ is halogen, hydroxy, mercapto, amino, carboxy, nitro, oxo, phosphonoxy, phosphono, thioxo, or cyano; or $R_M$ is -$L_S$-$R_E$, wherein $L_S$ is a bond or $C_1$-$C_6$alkylene, and $R_E$ is —N($R_S R_S'$), —O—$R_S$, —C(O)$R_S$, —C(O)O$R_S$, —C(O)N($R_S R_S'$), —N($R_S$)C(O)$R_S'$, —N($R_S$)C(O)O$R_S'$, —N($R_S$)SO$_2 R_S'$, —SO$_2 R_S$, —S$R_S$, or —P(O)(O$R_S$)$_2$, wherein $R_S$ and $R_S'$ can be, for example, each independently selected at each occurrence from (1) hydrogen or (2) $C_1$-$C_6$alkyl optionally substituted at each occurrence with one or more halogen, hydroxy, —O—$C_1$-$C_6$alkyl or 3- to 6-membered heterocycle; or $R_M$ is $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). More preferably, $R_M$ is halogen (e.g., fluoro, chloro, bromo, iodo), hydroxy, mercapto, amino, carboxy, or $C_1$-$C_6$alkyl (e.g., methyl, isopropyl, tert-butyl), $C_2$-$C_6$alkenyl or $C_2$-$C_6$alkynyl, each of which is independently optionally substituted at each occurrence with one or more substituents selected from halogen, hydroxy, mercapto, amino, cyano, or carboxy. For example $R_M$ is CF$_3$, —C(CF$_3$)$_2$—OH, —C(CH$_3$)$_2$—CN, —C(CH$_3$)$_2$—CH$_2$OH, or —C(CH$_3$)$_2$—CH$_2$NH$_2$. Also preferably $R_M$ is -$L_S$-$R_E$ where $L_S$ is a bond and $R_E$ is —N($R_S R_S'$), —O—$R_S$, —N($R_S$)C(O)O$R_S'$, —N($R_S$)SO$_2 R_S'$, —SO$_2 R_S$, or —S$R_S$. For example where $L_S$ is a bond, $R_E$ is —N($C_1$-$C_6$alkyl)$_2$ (e.g., —NMe$_2$); —N($C_1$-$C_6$alkylene-O—$C_1$-$C_6$alkyl)$_2$ (e.g. —N(CH$_2$CH$_2$OMe)$_2$); —N($C_1$-$C_6$alkyl)($C_1$-$C_6$alkylene-O—$C_1$-$C_6$alkyl) (e.g. —N(CH$_3$)(CH$_2$CH$_2$OMe)); —O—$C_1$-$C_6$alkyl (e.g., —O-Me, —O-Et, —O-isopropyl, —O-tert-butyl, —O-n-hexyl); —O—$C_1$-$C_6$haloalkyl (e.g., —OCF$_3$, —OCH$_2$CF$_3$); —O—$C_1$-$C_6$alkylene-piperidine (e.g., —O—CH$_2$CH$_2$-1-piperidyl); —N($C_1$-$C_6$alkyl)C(O)O$C_1$-$C_6$alkyl (e.g., —N(CH$_3$)C(O)O—CH$_2$CH(CH$_3$)$_2$), —N($C_1$-$C_6$alkyl)SO$_2 C_1$-$C_6$alkyl (e.g., —N(CH$_3$)SO$_2$CH$_3$); —SO$_2 C_1$-$C_6$alkyl (e.g., —SO$_2$Me); —SO$_2 C_1$-$C_6$haloalkyl (e.g., —SO$_2$CF$_3$); or —S—$C_1$-$C_6$haloalkyl (e.g., SCF$_3$). Also preferably $R_M$ is -$L_S$-$R_E$ where $L_S$ is $C_1$-$C_6$alkylene (e.g., —CH$_2$—, —C(CH$_3$)$_2$—, —C(CH$_3$)$_2$—CH$_2$—) and $R_E$ is —O—$R_S$, —C(O)O$R_S$, —N($R_S$)C(O)O$R_S'$, or —P(O)(O$R_S$)$_2$. For example $R_M$ is —$C_1$-$C_6$alkylene-O—$R_S$ (e.g., —C(CH$_3$)$_2$—CH$_2$—OMe); —$C_1$-$C_6$alkylene-C(O)O$R_S$(e.g., —C(CH$_3$)$_2$—C(O)OMe); —$C_1$-$C_6$alkylene-N($R_S$)C(O)O$R_S'$ (e.g., —C(CH$_3$)$_2$—CH$_2$—NHC(O)OCH$_3$); or —$C_1$-$C_6$alkylene-P(O)(O$R_S$)$_2$ (e.g., —CH$_2$—P(O)(OEt)$_2$). Also more preferably $R_M$ is $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)O$R_S$, or —N($R_S R_S'$). For example $R_M$ is cycloalkyl (e.g., cyclopropyl, 2,2-dichloro-1-methylcycloprop-1-yl, cyclohexyl), phenyl, heterocyclyl (e.g., morpholin-4-yl, 1,1-dioxidothiomorpholin-4-yl, 4-methylpiperazin-1-yl, 4-methoxycarbonylpiperazin-1-yl, pyrrolidin-1-yl, piperidin-1-yl, 4-methylpiperidin-1-yl, 3,5-dimethylpiperidin-1-yl, 4,4-difluoropiperidin-1-yl, tetrahydropyran-4-yl, pyridinyl, pyridin-3-yl, 6-(dimethylamino)pyridin-3-yl). Highly preferably, $R_M$ is $C_1$-$C_6$alkyl which is optionally substituted with one or more substituents selected from halogen, hydroxy, mercapto, amino or carboxy (e.g., tert-butyl, CF$_3$).

More preferably, D is $C_5$-$C_6$carbocycle, 5- to 6-membered heterocycle or 6- to 12-membered bicycle and is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle, wherein said $C_3$-$C_6$carbocycle or 3- to 6-membered heterocycle is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$), and J can also be optionally substituted with one or more $R_A$. Also preferably, D is $C_5$-$C_6$carbocycle or 5- to 6-membered heterocycle and is substituted with J and optionally substituted with one or more $R_A$, and J is $C_3$-$C_6$carbocycle or 3- to 6-membered heterocycle and is optionally substituted with one or more $R_A$, and preferably, J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$). Also preferably, D is $C_5$-$C_6$carbocycle or 5- to 6-membered heterocycle and is substituted with J and optionally substituted with one or more $R_A$, and J is 6- to 12-membered bicycle (e.g., a 7- to 12-membered fused, bridged or spiro bicycle comprising a nitrogen ring atom through which J is covalently attached to D) and is optionally substituted with one or more $R_A$. More preferably, D is phenyl and is substituted with J and optionally substituted with one or more $R_A$, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)O$R_S$ or —N($R_S R_S'$). Highly preferably, D is

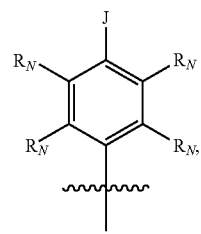

wherein each $R_N$ is independently selected from $R_D$ and preferably is hydrogen or halogen, and J is $C_3$-$C_6$carbocycle, 3- to 6-membered heterocycle or 6- to 12-membered bicycle and is optionally substituted with one or more $R_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'). Also preferably, D is

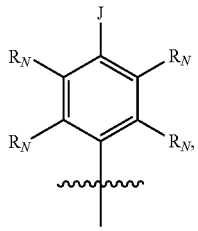

wherein each R$_N$ is independently selected from R$_D$ and preferably is hydrogen or halogen, and J is $C_3$-$C_6$carbocycle or 3- to 6-membered heterocycle and is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$'), and J can also be optionally substituted with one or more R$_A$. Also preferably, D is

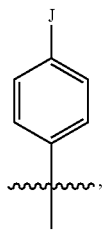

and J is $C_3$-$C_6$carbocycle or 3- to 6-membered heterocycle and is optionally substituted with one or more R$_A$, and preferably J is at least substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, C(O)OR$_S$ or —N(R$_S$R$_S$').

X preferably is $C_3$-$C_8$cycloalkyl or $C_5$-$C_8$cycloalkenyl and is optionally substituted with one or more R$_A$. More preferably, X is cyclopropyl, cyclopentyl or cyclopentenyl and is optionally substituted with one or more R$_A$ or R$_F$. Non-limiting examples of X are described hereinabove.

$L_1$ and $L_2$ are preferably independently bond or $C_1$-$C_6$alkylene, $L_3$ is preferably selected from bond, $C_1$-$C_6$alkylene or —C(O)—, and $L_1$, $L_2$, and $L_3$ are each independently optionally substituted with one or more R$_L$. More preferably, $L_1$, $L_2$ and $L_3$ are each independently bond or $C_1$-$C_6$alkylene (e.g., —CH$_2$— or —CH$_2$CH$_2$—), and are each independently optionally substituted with one or more R$_L$. Highly preferably, $L_1$, $L_2$ and $L_3$ are bond.

$R_2$ and $R_5$, taken together with the atoms to which they are attached, preferably form a 5- to 6-membered heterocycle or 6- to 12-membered bicycle (e.g.,

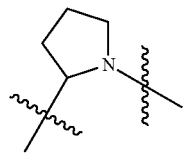 [SMILES: *C1CCCN1*]

or

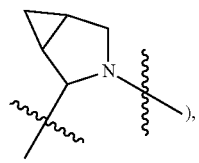 [SMILES: *C1C2CC2CN1*]

), which is optionally substituted with one or more R$_A$.

$R_9$ and $R_{12}$, taken together with the atoms to which they are attached, preferably form a 5- to 6-membered heterocycle or 6- to 12-membered bicycle (e.g.,

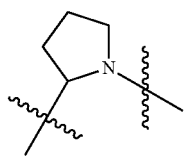 [SMILES: *C1CCCN1*]

or

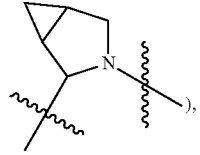 [SMILES: *C1C2CC2CN1*]

), which is optionally substituted with one or more R$_A$.

$G_1$ and $G_2$ preferably are each independently selected from

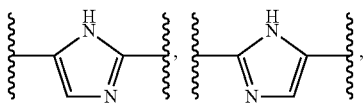

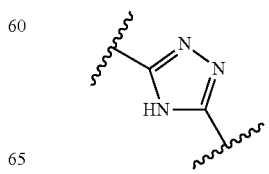

or

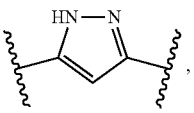

and are each independently optionally substituted with one or more $R_A$ (e.g., one or more chloro or bromo). More preferably, $G_1$ is

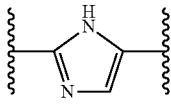 [SMILES: *c1cnc(*)[nH]1]

(including any tautomer thereof), and $G_2$ is

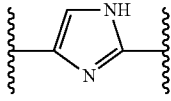

(including any tautomer thereof), and each $G_1$ and $G_2$ is independently optionally substituted with one or more $R_A$ (e.g., one or more chloro or bromo).

-T-$R_D$' can be, without limitation, independently selected at each occurrence from —C(O)-$L_Y$'-, —C(O)O-$L_Y$'-$R_D$', —C(O)-$L_Y$'-N($R_B$)C(O)-$L_S$'-$R_D$', —C(O)-$L_Y$'-N($R_B$)C(O)O-$L_S$'-$R_D$', —N($R_B$)C(O)-$L_Y$' N($R_B$)C(O)-$L_S$'-$R_D$', —N($R_B$)C(O)-$L_Y$'-N($R_B$)C(O)O-$L_S$''-$R_D$', or —N($R_B$)C(O)-$L_Y$'-N($R_B$)-$L_S$''-$R_D$', wherein $L_Y$' is each independently $L_S$' and, preferably, is each independently $C_1$-$C_6$alkylene (e.g., —CH$_2$—) and optionally substituted with one or more substituents selected from $R_L$. Preferably, -T-$R_D$' is independently selected at each occurrence from —C(O)-$L_Y$'-M'-$L_S$''-$R_D$' or N($R_B$)C(O)-$L_Y$'-M'-$L_S$''-$R_D$'. More preferably, -T-$R_D$' is independently selected at each occurrence from —C(O)-$L_Y$'-N($R_B$)C(O)-$L_S$'-$R_D$' or —C(O)-$L_Y$'-N($R_B$)C(O)O-$L_S$''-$R_D$'. Highly preferably, -T-$R_D$' is independently selected at each occurrence from —C(O)-$L_Y$'-N($R_B$)C(O)—$R_D$', or —C(O)-$L_Y$'-N($R_B$)C(O)O—$R_D$', wherein $L_Y$' preferably is each independently $C_1$-$C_6$alkylene (e.g., —CH$_2$—) and optionally substituted with one or more substituents selected from $R_L$.

$R_C$' is preferably hydrogen, and $R_D$' preferably is independently selected at each occurrence from $R_E$. More preferably, $R_D$' is independently selected at each occurrence from $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, $C_3$-$C_6$carbocycle or 3- to 6-membered heterocycle; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

$R_A$ preferably is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl; or -$L_A$-O—$R_S$, -$L_A$-S—$R_S$, -$L_A$-C(O)$R_S$, -$L_A$-OC(O)$R_S$, -$L_A$-C(O)O$R_S$, -$L_A$-N($R_S R_S$'), -$L_A$-S(O)$R_S$, -$L_A$-SO$_2 R_S$, -$L_A$-C(O)N($R_S R_S$'), -$L_A$-N($R_S$)C(O)$R_S$', -$L_A$-N($R_S$)C(O)N($R_S$'$R_S$''), -$L_A$-N($R_S$)SO$_2 R_S$', -$L_A$-SO$_2$N($R_S R_S$'), -$L_A$-N($R_S$)SO$_2$N($R_S$'$R_S$''), -$L_A$-N($R_S$)S(O)N($R_S$'$R_S$''), -$L_A$-OS(O)—$R_S$, -$L_A$-OS(O)$_2$—$R_S$, -$L_A$-S(O)$_2$O—$R_S$, -$L_A$-S(O)O$R_S$, -$L_A$-OC(O)O$R_S$, -$L_A$-N($R_S$)C(O)O$R_S$', -$L_A$-OC(O)N($R_S R_S$'), -$L_A$-N($R_S$)S(O)—$R_S$', -$L_A$-S(O)N($R_S R_S$')-$L_A$-C(O)N($R_S$)C(O)—$R_S$', or -$L_A$-P(O)(O$R_S$)$_2$, wherein $L_A$ is bond, $C_1$-$C_6$alkylene, $C_2$-$C_6$alkenylene or $C_2$-$C_6$alkynylene.

More preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl.

Highly preferably, $R_A$ is halogen, hydroxy, mercapto, amino, carboxy, nitro, oxo, phosphonoxy, phosphono, thioxo, cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano.

$L_S$, $L_S$' and $L_S$'' preferably are each independently selected at each occurrence from bond; or $C_1$-$C_6$alkylene, $C_2$-$C_6$alkenylene or $C_2$-$C_6$alkynylene.

A and B can be the same or different. Likewise, $L_1$ and $L_2$ can be the same or different.

In one embodiment of this aspect, A and B are each independently phenyl, and are each independently optionally substituted with one or more $R_A$; D is phenyl, and is independently optionally substituted with one or more $R_A$, or is substituted with J and optionally substituted with one or more $R_A$, wherein J is $C_3$-$C_6$carbocycle, 3- to 6-membered heterocycle or 6- to 12-membered bicycle and is optionally substituted with one or more $R_A$. Preferably, J is substituted with a $C_3$-$C_6$carbocycle or 3- to 6-membered heterocycle which is independently optionally substituted with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl C(O)O$R_S$ or —N($R_S R_S$'), and J can also be optionally substituted with one or more $R_A$; and $G_1$ is

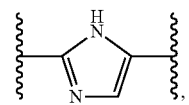 [SMILES: *c1cnc(*)[nH]1]

G$_2$ is

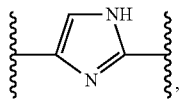

and each G$_1$ and G$_2$ is independently optionally substituted with one or more R$_A$ (e.g., one or more chloro or bromo).
Preferably, D is

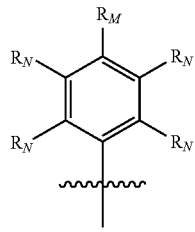

or

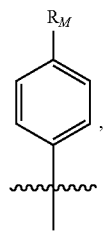

wherein R$_M$ and R$_N$ are as defined above. Also preferably, D is

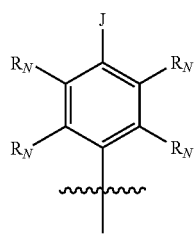

or

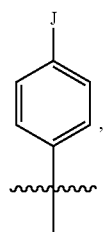

wherein J and R$_N$ are as defined above. L$_1$ and L$_2$ are each independently bond or C$_1$-C$_6$alkylene, and L$_3$ is bond, C$_1$-C$_6$alkylene or —C(O)—, and L$_1$, L$_2$, and L$_3$ are each independently optionally substituted with one or more R$_L$.

Preferably, L$_1$, L$_2$, and L$_3$ are bond. -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_1$ is C$_1$-C$_6$alkylene (e.g., —CH$_2$—) and optionally substituted with one or more substituents selected from R$_L$, and L$_S$" preferably is bond. -T-R$_D$' can also be, without limitation, selected from —C(O)-L$_Y$'-L$_S$"-R$_D$', —C(O)-L$_Y$'—O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. Preferably, R$_2$ and R$_5$, taken together with the atoms to which they are attached, form

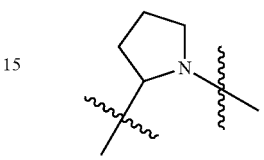

which is optionally substituted with one or more R$_A$; R$_9$ and R$_{12}$, taken together with the atoms to which they are attached, form

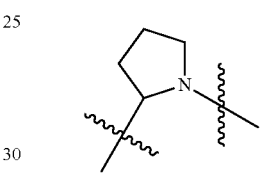

which is optionally substituted with one or more R$_A$. X is C$_3$-C$_8$cycloalkyl or C$_5$-C$_8$cycloalkenyl and is optionally substituted with one or more R$_A$. Specific examples of X are described hereinabove. Preferably, X is cyclopropyl, cyclopentyl or cyclopentenyl, and is optionally substituted with one or more R$_A$ or R$_F$. More preferably, X is cyclopropyl is and is optionally substituted with one or more R$_A$ or R$_F$.

In another embodiment of this aspect, A and B are each independently phenyl (e.g.,

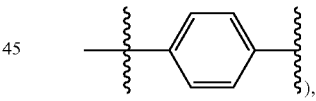

and are each independently optionally substituted with one or more R$_A$ (preferably, A and B are each independently substituted with at least one halogen such as F). X is C$_3$-C$_8$cycloalkyl or C$_5$-C$_8$cycloalkenyl and is optionally substituted with one or more R$_A$. Specific examples of X are described hereinabove. Preferably, X is cyclopropyl, cyclopentyl or cyclopentenyl, and is optionally substituted with one or more R$_A$ or R$_F$. More preferably, X is cyclopropyl is and is optionally substituted with one or more R$_A$ or R$_F$. D is phenyl, and is substituted with J and optionally substituted with one or more R$_A$. J is C$_3$-C$_6$carbocycle, 3- to 6-membered heterocycle, 6- to 12-membered bicycle, 10- to 15-membered tricycle or 13- to 15-membered carbocycle/heterocycle, and J is optionally substituted with one or more R$_A$. Preferably, J is substituted with a C$_3$-C$_6$carbocycle, 3- to 6-membered heterocycle, 6- to 12-membered bicycle or 7- to 12-membered carbocycle/heterocycle, which is independently optionally substituted with one or more substituents selected from (1) halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —C(O)OR$_S$ or —N(R$_S$R$_S$'), or (2) trimethylsilyl, —O—R$_S$, —S—R$_S$ or —C(O)R$_S$; and J can also be optionally substituted with one or more R$_A$. Preferably, D is

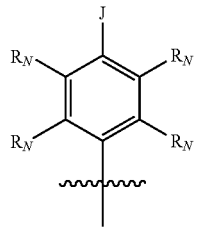

or

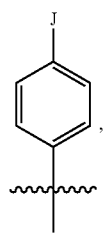

wherein J is as defined above, and each R$_N$ is independently selected from R$_D$ and preferably is hydrogen or halo such as F. G$_1$ is

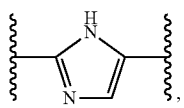

G$_2$ is

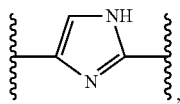 [SMILES: *c1c[nH]c(*)n1 ; ","]

and each G$_1$ and G$_2$ is independently optionally substituted with one or more R$_A$ (e.g., one or more chloro or bromo). L$_1$ and L$_2$ are each independently bond or $C_1$-$C_6$alkylene, and L$_3$ is bond, $C_1$-$C_6$alkylene or —C(O)—, and L$_1$, L$_2$, and L$_3$ are each independently optionally substituted with one or more R$_L$. Preferably, L$_1$, L$_2$, and L$_3$ are bond. -T-R$_D$' is independently selected at each occurrence from —C(O)-L$_Y$'-N(R$_B$)C(O)-L$_S$"-R$_D$' or —C(O)-L$_Y$'-N(R$_B$)C(O)O-L$_S$"-R$_D$', wherein L$_Y$' is $C_1$-$C_6$alkylene (e.g., —CH$_2$—) and optionally substituted with one or more substituents selected from R$_L$, and L$_S$" preferably is bond. -T-R$_D$' can also be, without limitation, selected from —C(O)-L$_Y$'-L$_S$"-R$_D$', —C(O)-L$_Y$'—O-L$_S$"-R$_D$', —C(O)-L$_Y$'-N(R$_B$)-L$_S$"-R$_D$', or —C(O)-L$_Y$'-N(R$_B$)S(O)$_2$-L$_S$"-R$_D$'. Preferably, R$_2$ and R$_5$, taken together with the atoms to which they are attached, form a 5- to 6-membered heterocyclic ring (e.g.,

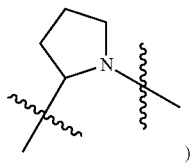

or 6- to 12-membered bicycle (e.g.,

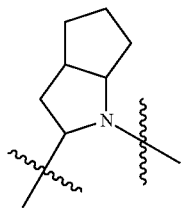

which is optionally substituted with one or more R$_A$; R$_9$ and R$_{12}$, taken together with the atoms to which they are attached, form a 5- to 6-membered heterocyclic ring (e.g.,

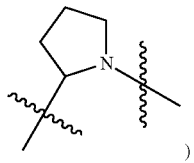

or 6- to 12-membered bicycle (e.g.,

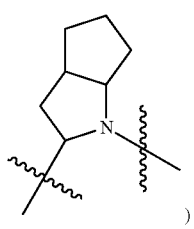

which is optionally substituted with one or more R$_A$.

In another aspect, the present invention features compounds having Formula I$_E$ and pharmaceutically acceptable salts thereof,

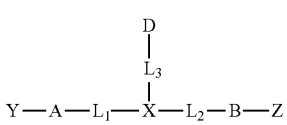

I$_E$ wherein:
X is $C_3$-$C_8$cycloalkyl or $C_5$-$C_8$cycloalkenyl, and is optionally substituted with one or more R$_A$;
L$_1$ and L$_2$ are each independently selected from bond or $C_1$-$C_6$alkylene which is independently optionally substituted at each occurrence with one or more halo, hydroxy, —O—$C_1$-$C_6$alkyl, or —O—$C_1$-$C_6$haloalkyl;
L$_3$ is bond or $C_1$-$C_6$alkylene;

A and B are each independently phenyl, pyridinyl, thiazolyl, or

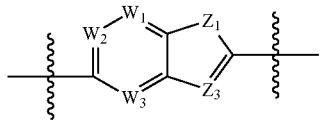

where $Z_1$ is independently selected at each occurrence from O, S, NH or $CH_2$, $Z_3$ is independently selected at each occurrence from N or CH, and $W_1$, $W_2$, and $W_3$ are each independently selected at each occurrence from CH or N; A and B are each independently optionally substituted with one or more $R_A$.

D is $C_6$-$C_{10}$-carbocycle or 5- to 12-membered heterocycle, each of which is optionally substituted with one or more $R_M$;

Y is -T'-C($R_1R_2$)N($R_5$)-T-$R_D$;

Z is -T'-C($R_8R_9$)N($R_{12}$)-T-$R_D$;

$R_1$ is hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl;

$R_2$ and $R_5$ are each independently hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl; or $R_2$ and $R_5$, taken together with the atoms to which they are attached, form a 3- to 12-membered heterocycle which is optionally substituted with one or more $R_A$ (e.g., 1, 2, 3, or 4 $R_A$);

$R_8$ is hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl;

$R_9$ and $R_{12}$ are each independently hydrogen, $C_1$-$C_6$alkyl, $C_1$-$C_6$haloalkyl, or 3- to 6-membered carbocycle or heterocycle, wherein each said 3- to 6-membered carbocycle or heterocycle is independently optionally substituted at each occurrence with one or more substituents selected from halogen, $C_1$-$C_6$alkyl, $C_1$-$C_6$haloalkyl, —O—$C_1$-$C_6$alkyl or —O—$C_1$-$C_6$haloalkyl; or $R_9$ and $R_{12}$, taken together with the atoms to which they are attached, form a 3- to 12-membered heterocycle which is optionally substituted with one or more $R_A$ (e.g., 1, 2, 3, or 4 $R_A$);

T is independently selected at each occurrence from bond or —C(O)-$L_S$'-;

T' is independently selected at each occurrence from bond, —C(O)N($R_B$)—, —N($R_B$)C(O)—, or 3- to 12-membered heterocycle, wherein said 3- to 12-membered heterocycle is independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or -$L_S$-$R_E$;

$R_B$ and $R_B$' are each independently selected at each occurrence from hydrogen; or $C_1$-$C_6$alkyl which is independently optionally substituted at each occurrence with one or more substituents selected from halogen or 3- to 6-membered carbocycle or heterocycle; or 3- to 6-membered carbocycle or heterocycle; wherein each 3- to 6-membered carbocycle or heterocycle in $R_B$ or $R_B$' is independently optionally substituted at each occurrence with one or more substituents selected from halogen, hydroxy, $C_1$-$C_6$alkyl, $C_1$-$C_6$haloalkyl, —O—$C_1$-$C_6$alkyl, or —O—$C_1$-$C_6$haloalkyl;

$R_E$ is independently selected at each occurrence from —O—$R_S$, —S—$R_S$, —C(O)$R_S$, —OC(O)$R_S$, —C(O)O$R_S$, —N($R_SR_S$'), —S(O)$R_S$, —SO$_2R_S$, —C(O)N($R_SR_S$'), —N($R_S$)C(O)$R_S$', —N($R_S$)C(O)N($R_S$'$R_S$''), —N($R_S$)SO$_2R_S$', —SO$_2$N($R_SR_S$'), —N($R_S$)SO$_2$N($R_S$'$R_S$''), —N($R_S$)S(O)N($R_S$'$R_S$''), —OS(O)—$R_S$, —OS(O)$_2$—$R_S$, —S(O)$_2$O$R_S$, —S(O)O$R_S$, —OC(O)O$R_S$, —N($R_S$)C(O)O$R_S$',—OC(O)N($R_SR_S$'), —N($R_S$)S(O)—$R_S$', —S(O)N($R_SR_S$'), —C(O)N($R_S$)C(O)—$R_S$', or =C($R_SR_S$'); or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_L$ is independently selected at each occurrence from halogen, nitro, oxo, phosphonoxy, phosphono, thioxo, cyano, —O—$R_S$, —S—$R_S$, —C(O)$R_S$, —OC(O)$R_S$, —C(O)O$R_S$, —N($R_SR_S$'), —S(O)$R_S$, —SO$_2R_S$, —C(O)N($R_SR_S$'), or —N($R_S$)C(O)$R_S$'; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$L_S$ is independently selected at each occurrence from bond; or $C_1$-$C_6$alkylene, $C_2$-$C_6$alkenylene or $C_2$-$C_6$alkynylene, each independently optionally substituted with halogen;

$L_S$' is independently selected at each occurrence from bond; or $C_1$-$C_6$alkylene, $C_2$-$C_6$alkenylene or $C_2$-$C_6$alkynylene, each of which is independently optionally substituted at each occurrence with one or more $R_L$;

$R_S$, $R_S$' and $R_S$'' are each independently selected at each occurrence from hydrogen; $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —O—$C_1$-$C_6$alkyl, —O—$C_1$-$C_6$haloalkyl, or 3- to 12-membered carbocycle or heterocycle; or 3- to 12-membered carbocycle or heterocycle; wherein each 3- to 12-membered carbocycle or heterocycle in $R_S$, $R_S'$ or $R_S''$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_M$ is independently selected at each occurrence from:
halogen, hydroxy, mercapto, amino, carboxy, nitro, oxo, phosphonoxy, phosphono, thioxo, cyano, $SF_5$, —$N(R_S R_S')$, —O—$R_S$, —$OC(O)R_S$, —$OC(O)OR_S$, —$OC(O)N(R_S R_S')$, —$C(O)R_S$, —$C(O)OR_S$, —$C(O)N(R_S R_S')$, —$N(R_S)C(O)R_S'$, —$N(R_S)C(O)OR_S'$, —$N(R_S)SO_2 R_S'$, —$S(O)R_S$, —$SO_2 R_S$, —$S(O)N(R_S R_S')$, —$SR_S$, —$Si(R_S)_3$, or —$P(O)(OR_S)_2$;

$C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano, —$N(R_S R_S')$, —O—$R_S$, —$OC(O)R_S$, —$OC(O)OR_S$, —$OC(O)N(R_S R_S')$, —$C(O)R_S$, —$C(O)OR_S$, —$C(O)N(R_S R_S')$, —$N(R_S)C(O)R_S'$, —$N(R_S)C(O)OR_S'$, —$N(R_S)SO_2 R_S'$, —$S(O)R_S$, —$SO_2 R_S$, —$S(O)N(R_S R_S')$, —$SR_S$, or —$P(O)(OR_S)_2$; or $G_2$, wherein $G_2$ is a $C_3$-$C_{12}$carbocycle or 3- to 12-membered heterocycle, each of which is independently optionally substituted at each occurrence with one or more $R_{G2}$, and each $R_{G2}$ is independently selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —O—$R_S$, —$C(O)OR_S$, —$C(O)R_S$, —$N(R_S R_S')$, or -$L_4$-$G_3$;

$L_4$ is a bond, $C_1$-$C_6$alkylene, $C_2$-$C_6$alkenylene, $C_2$-$C_6$alkynylene, —O—, —S—, —$N(R_B)$—, —$C(O)$—, —$S(O)_2$—, —$S(O)$—, —$C(O)O$—, —$OC(O)$—, —$OC(O)O$—, —$C(O)N(R_B)$—, —$N(R_B)C(O)$—, —$N(R_B)C(O)O$—, —$OC(O)N(R_B)$—, —$N(R_B)S(O)$—, —$N(R_B)S(O)_2$—, —$S(O)N(R_B)$—, —$S(O)_2 N(R_B)$—, —$N(R_B)C(O)N(R_B')$—, —$N(R_B)SO_2 N(R_B')$—, or —$N(R_B)S(O)N(R_B')$—;

$G_3$ is a $C_3$-$C_{12}$carbocycle or 3- to 12-membered heterocycle, and is optionally substituted with one or more $R_{G3}$; and $R_{G3}$ is each independently, at each occurrence, halogen, —$C_1$-$C_6$alkyl, —$C(O)C_1$-$C_6$alkyl, —$C_1$-$C_6$haloalkyl, —O—$C_1$-$C_6$alkyl, —O—$C_1$-$C_6$haloalkyl, $C_3$-$C_6$carbocycle, or 3- to 6-membered heterocycle.

As described hereinabove for compounds of Formula $I_E$ A and B are each phenyl, pyridinyl, thiazolyl, or

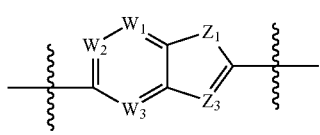

where $Z_1$ is independently selected at each occurrence from O, S, NH or $CH_2$, $Z_3$ is independently selected at each occurrence from N or CH, and $W_1$, $W_2$, and $W_3$ are each independently selected at each occurrence from CH or N; A and B are each independently optionally substituted with one or more $R_A$.

Preferably, A is selected from phenyl (e.g.,

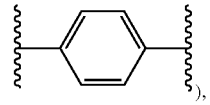), pyridinyl (e.g.,

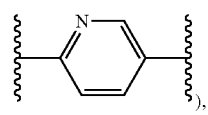), thiazolyl (e.g.,

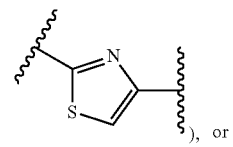), or (e.g.,

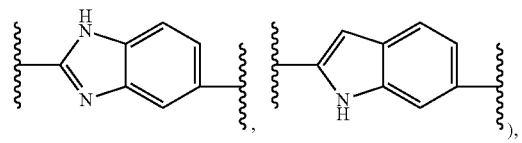), and is optionally substituted with one or more $R_A$.

Preferably, B is selected from phenyl (e.g.,

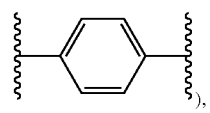), pyridinyl (e.g.,

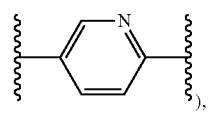), thiazolyl (e.g.,

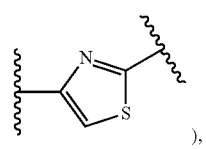), or

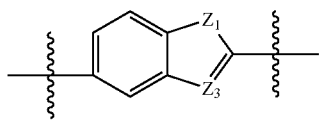

(e.g.,

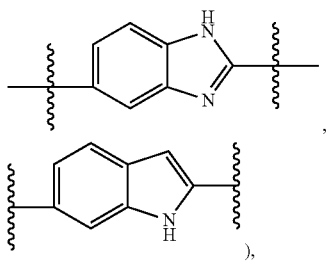

), and is optionally substituted with one or more $R_A$.

Highly preferably, both A and B are phenyl (e.g., both A and B are

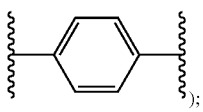);

or A is

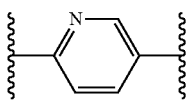

and B is

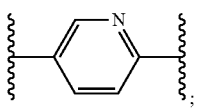;

or A is

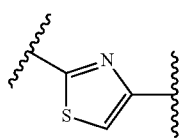 [SMILES: *c1csc(*)n1]

and B is

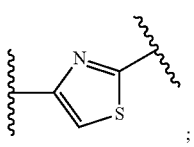 [SMILES: *c1csc(*)n1 ; ";"];

or A is

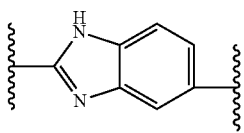 [SMILES: *c1ccc2[nH]c(*)nc2c1]

and B is

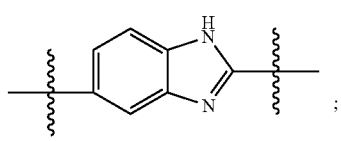 [SMILES: *c1ccc2[nH]c(*)nc2c1];

or A is

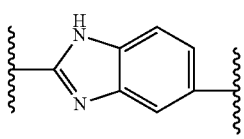 [SMILES: *c1ccc2[nH]c(*)nc2c1]

and B is

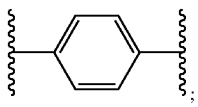;

or A is

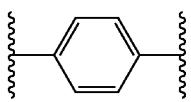

and B is

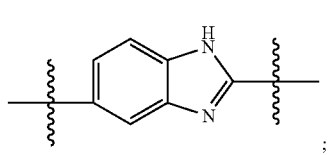;

wherein each A and B is independently optionally substituted with one or more $R_A$.

In certain embodiments of this aspect of the invention, A and B are substituted by one or more $R_A$, wherein each $R_A$ is independently selected from halogen (e.g., fluoro, chloro), $L_S$-$R_E$ (where $L_S$ is bond and $R_E$ is —$C_1$-$C_6$alkyl (e.g., methyl), —O—$R_S$ (e.g., —O—$C_1$-$C_6$alkyl, —$OCH_3$), or —$C_1$-$C_6$alkyl optionally substituted with one or more halogen (e.g., —$CF_3$)), or $L_S$-$R_E$ (where $L_S$ is $C_1$-$C_6$alkylene and $R_E$ is —O—$R_S$ (e.g., —$C_1$-$C_6$alkyl-O—$C_1$-$C_6$alkyl, —$CH_2OCH_3$)). For example, in certain embodiments A is

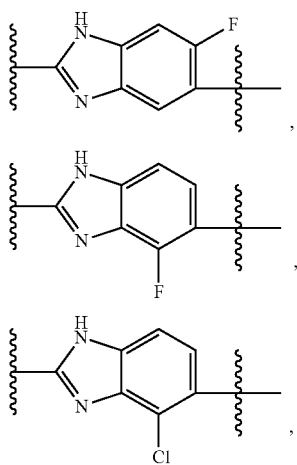
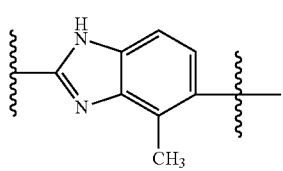
or
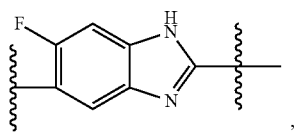
and B is as defined hereinabove. In certain other embodiments B is
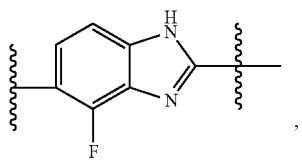
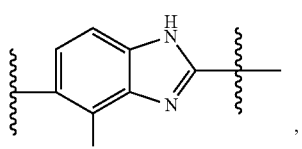
or
and A is as defined hereinabove. In still other embodiments A is
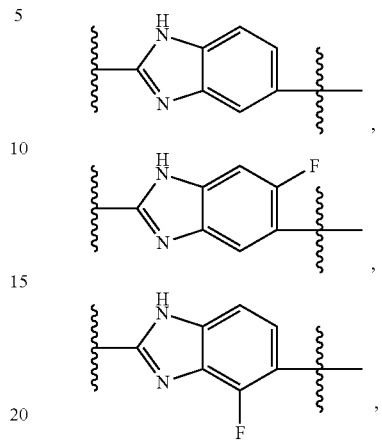
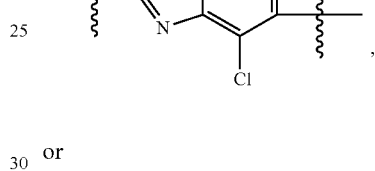
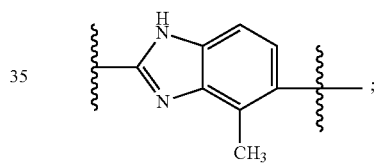
or
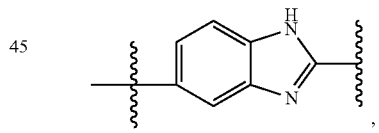
and B is
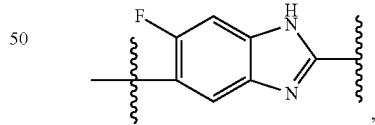
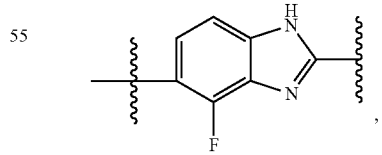
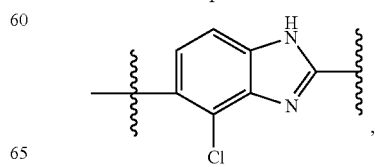

or

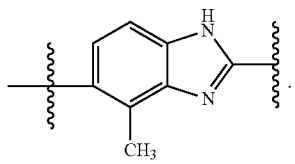

As described hereinabove for compounds of Formula $I_E$ D is $C_6$-$C_{10}$carbocycle or 3- to 12-membered heterocycle optionally substituted by one or more $R_M$. Preferably, D is $C_6$-$C_{10}$aryl (e.g., phenyl, naphthyl, indanyl), or 5- to 10-membered heteroaryl (pyridinyl, thiazolyl, 4,5,6,7-tetrahydrobenzo[d]thiazolyl, benzo[d]thiazolyl, indazolyl, benzo[d][1,3]dioxol-5-yl), and D is substituted with one or more $R_M$. For example, in certain embodiments D is preferably phenyl substituted by one or more $R_M$, wherein each $R_M$ is independently halogen (e.g., fluoro, chloro, bromo); $C_1$-$C_6$alkyl (e.g., tert-butyl); $C_1$-$C_6$alkyl substituted with one or more halogen (e.g., $CF_3$); —O—$R_S$ such as —O—$C_1$-$C_6$alkyl (e.g., —O—$CH_2CH_3$); or —O—$C_1$-$C_6$alkyl substituted at each occurrence with one or more halogen (e.g., —O—$CF_3$, —O—$CH_2CHF_2$) or —O—$C_1$-$C_6$alkyl (e.g., —O—$CH_2CH_2OCH_3$); —O—$R_S$ (e.g., —O—$C_1$-$C_6$alkyl, such as —O—$CH_2$) substituted with 3- to 12-membered heterocycle (e.g., 3-ethyloxetan-3-yl, 1,3-dioxolan-4-yl); —O—$R_S$ where $R_S$ is an optionally substituted 3- to 12-membered carbocycle or heterocycle (e.g., cyclopentyl, cyclohexyl, phenyl, 1,3-dioxan-5-yl); —N($R_S$)C(O)$R_S$' wherein $R_S$ and $R_S$' are each independently $C_1$-$C_6$alkyl (e.g., —N(t-Bu)C(O)Me); $SF_5$; —$SO_2R_S$ wherein $R_S$ is $C_1$-$C_6$alkyl (e.g., —$SO_2$Me); or $C_3$-$C_{12}$carbocycle (e.g., cyclopropyl, cyclohexyl, phenyl).

In certain embodiments of this aspect of the invention, D is preferably phenyl or pyridyl and is substituted by one or more $R_M$ where one $R_M$ is $G_2$. In certain embodiments where D is phenyl or pyridyl, D is substituted by $G_2$, $G_2$ is 3- to 12-membered heterocycle (e.g., pyridinyl, piperidinyl, pyrrolidinyl, azetidinyl, oxazolyl) and is optionally substituted with one or more halogen (e.g., fluoro, chloro), hydroxy, oxo, cyano, $C_1$-$C_6$alkyl (e.g., methyl), $C_2$-$C_6$alkenyl, $C_2$-$C_6$alkynyl, $C_1$-$C_6$haloalkyl (e.g., $CF_3$), $C_2$-$C_6$haloalkenyl, $C_2$-$C_6$haloalkynyl, —O—$C_1$-$C_6$alkyl (e.g., —O—$CH_3$), —C(O)O$R_S$(e.g., —C(O)O$CH_3$), —C(O)$R_S$ (e.g., —C(O)$CH_3$), or —N($R_SR_S$'); and D is further optionally substituted by one or more $R_M$ where $R_M$ is halogen (e.g., fluoro, chloro), $C_1$-$C_6$alkyl (e.g., methyl), $C_1$-$C_6$haloalkyl (e.g., $CF_3$), or —O—$C_1$-$C_6$alkyl (e.g., —O—$CH_3$). In certain other embodiments D is phenyl or pyridyl and $G_2$ is, for example, a monocyclic 3-8 membered carbocycle or monocyclic 4-8 membered heterocycle substituted with $L_4$-$G_3$ and optionally substituted with one or more $R_{G2}$ wherein $L_4$, $G_3$ and $R_{G2}$ are as defined herein. $L_4$, for example is a bond, a $C_1$-$C_6$alkylene (e.g., —$CH_2$—, —$CH_2CH_2$—, —$CH_2CH_2CH_2$—, etc.), —O—, or —S(O)$_2$—. $G_3$ is for example a $C_3$-$C_{12}$carbocycle optionally substituted with one or more $R_{G3}$. $R_{G2}$ and $R_{G3}$ are each independently at each occurrence halogen, —C(O)$C_1$-$C_6$alkyl, —$C_1$-$C_6$alkyl, —$C_1$-$C_6$haloalkyl, —O—$C_1$-$C_6$alkyl, or —O—$C_1$-$C_6$haloalkyl. In certain embodiments $G_2$ is

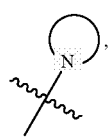

wherein

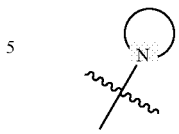

is a monocyclic 4-8 membered nitrogen-containing heterocycle (e.g., azetidinyl, pyrrolidinyl, piperidinyl, piperazinyl) attached to the parent molecular moiety through a nitrogen atom and substituted with one or two $L_4$-$G_3$ and optionally substituted with one or more $R_{G2}$. Thus, in certain embodiments where $L_4$ is a bond $G_2$ is

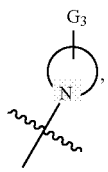

where

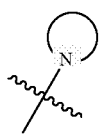

is optionally substituted with $R_{G2}$ and $G_3$ is optionally substituted with $R_{G3}$. Thus

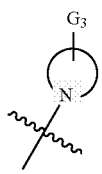

can be, for example, 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl, and wherein D can be further optionally substituted with one or more $R_M$ (e.g., fluoro, chloro, methyl, methoxy).

In certain other embodiments of this aspect of the invention, $L_4$ is a $C_1$-$C_6$alkylene, —O—, or —S(O)$_2$—, and $G_2$ is

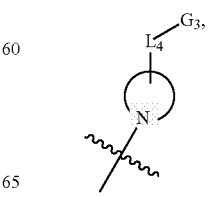

where

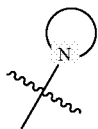

is as defined above and is optionally substituted with $R_{G2}$ and $G_3$ is as defined above and is optionally substituted with $R_{G3}$. Thus,

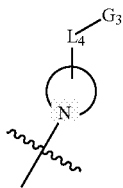

can be, for example, 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl.

In certain other embodiments of this aspect of the invention, D is phenyl or pyridyl, D is substituted by $G_2$ and $G_2$ is a spiro, bridged, or fused bicyclic carbocycle or heterocycle optionally substituted with $L_4$-$G_3$ and one or more $R_{G2}$, wherein D is optionally substituted with one or more $R_M$ and $R_M$, $L_4$, $G_3$, and $R_{G2}$ are as defined herein. In certain embodiments $G_2$ is

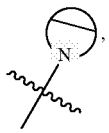

wherein

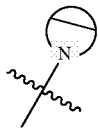

is a spiro, bridged, or fused bicyclic nitrogen-containing heterocycle (e.g., 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, 1,4-dioxa-8-azaspiro[4.5]dec-8-yl) attached to the parent molecular moiety through a nitrogen atom and optionally substituted with $G_3$ and one or more $R_{G2}$. Thus, $G_2$ is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl; $L_4$ is a bond and D is optionally substituted with one or more $R_M$ (e.g., fluoro, chloro, methyl, methoxy).

In certain embodiments of this aspect of the invention, D is

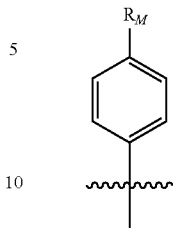

wherein $R_M$ is as defined above in connection with Formula $I_E$, and D is optionally substituted by one or more additional $R_M$.

For instance, where D is

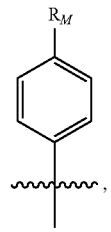

$R_M$ can be fluoro, chloro, tert-butyl, —O—CH$_2$CH$_3$, —O—CF$_3$, —O—CH$_2$CHF$_2$, —O—CH$_2$CH$_2$OCH$_3$, —O—CH$_2$-(3-ethyloxetan-3-yl), —O—CH$_2$-(1,3-dioxolan-4-yl), —O-cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D can be optionally substituted by one or more additional $R_M$ selected from the group consisting of halogen (e.g., fluoro, chloro) and $C_1$-$C_6$alkyl (e.g., methyl).

In certain embodiments, D is

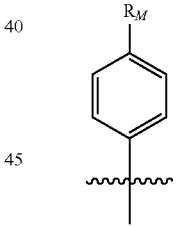

wherein $R_M$ is fluoro, chloro, tert-butyl, —O—CH$_2$CH$_3$, —O—CF$_3$, —O—CH$_2$CHF$_2$, —O—CH$_2$CH$_2$OCH$_3$, SF$_5$, —SO$_2$Me, or —N(t-Bu)C(O)Me and D is optionally substituted by one or more additional $R_M$ selected from the group consisting of halogen (e.g., fluoro, chloro) and $C_1$-$C_6$alkyl (e.g., methyl).

In certain embodiments, D is

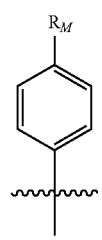

wherein $R_M$ is cyclopropyl, cyclohexyl, or phenyl and D is optionally substituted by one or more additional $R_M$ selected from the group consisting of halogen (e.g., fluoro, chloro) and $C_1$-$C_6$alkyl (e.g., methyl).

In certain embodiments, D is

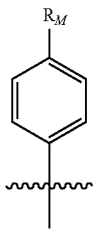

wherein $R_M$ is —O—CH$_2$-(3-ethyloxetan-3-yl), —O—CH$_2$-(1,3-dioxolan-4-yl), —O-cyclopentyl, —O-cyclohexyl, —O-phenyl, or —O-(1,3-dioxan-5-yl) and D is optionally substituted by one or more additional $R_M$ selected from the group consisting of halogen (e.g., fluoro, chloro) and $C_1$-$C_6$alkyl (e.g., methyl).

In certain embodiments, D is

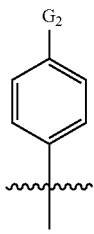

wherein $G_2$ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional $R_M$ selected from the group consisting of halogen (e.g., fluoro, chloro) and $C_1$-$C_6$alkyl (e.g., methyl).

In another embodiment of this aspect of the invention, D is

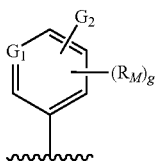

wherein $G_1$ is N, C—H, or C—$R_M$; $G_2$ is

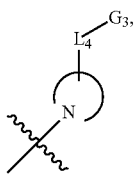

wherein

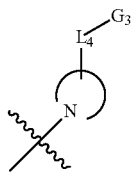

is a monocyclic 4-8 membered nitrogen-containing heterocycle (e.g., azetidinyl, pyrrolidinyl, piperidinyl) attached to the parent molecular moiety through a nitrogen atom and substituted by $L_4$-$G_3$ and optionally substituted with one or more $R_{G2}$; $L_4$ is a bond, $C_1$-$C_6$alkylene, —O—, or —S(O)$_2$—; $G_3$ is aryl (e.g., phenyl), cycloalkyl (e.g., cyclohexyl), or heterocycle (e.g., thienyl) wherein each $G_3$ is optionally substituted with one or more $R_{G3}$; $R_{G2}$ and $R_{G3}$ at each occurrence are each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; g is 0, 1, 2, or 3; and $R_M$ is as defined above in connection with Formula $I_E$. In one group of compounds according to this embodiment, D is

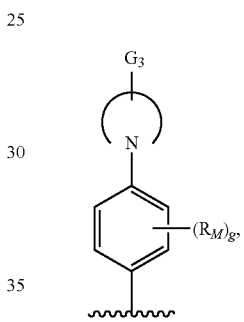

wherein $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

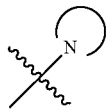 [SMILES: *N]

and $R_{G3}$ are as defined above. In a further subgroup of compounds of this embodiment, D is

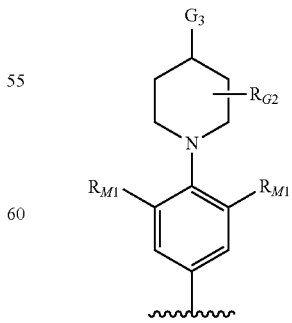

wherein $G_3$ is phenyl optionally substituted with one or two $R_{G3}$; $R_{M1}$ is each independently hydrogen, fluoro, chloro, or methyl; and $R_{G2}$ is an optional substituent as described herein. In another group of compounds according to this embodiment, D is

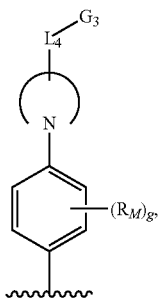

wherein $L_4$ is $C_1$-$C_6$alkylene, —O—, or —S(O)$_2$—; $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

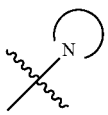 [SMILES: *N]

and $R_{G3}$ are as defined above.

In yet another embodiment of this aspect of the invention, D is

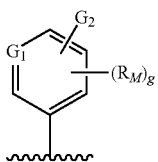

wherein $G_1$ is N, C—H, or C—$R_M$; $G_2$ is

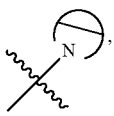 [SMILES: *N]

wherein

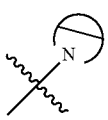

is a spiro, bridged, or fused bicyclic nitrogen-containing heterocycle (e.g., 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, 1,4-dioxa-8-azaspiro[4.5]dec-8-yl) attached to the parent molecular moiety through a nitrogen atom and optionally substituted with $L_4$-$G_3$ and one or more $R_{G2}$; $L_4$ is a bond, $C_1$-$C_6$ alkylene, —O—, or —S(O)$_2$—; $G_3$ is aryl (e.g., phenyl), cycloalkyl (e.g., cyclohexyl), or heterocycle (e.g., thienyl) wherein each $G_3$ is optionally substituted with one or more $R_{G3}$; $R_{G2}$ and $R_{G3}$ at each occurrence are each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; g is 0, 1, 2, or 3; and $R_M$ is as defined above in connection with Formula $I_E$. In one group of compounds according to this embodiment, D is

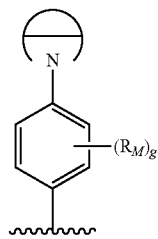

wherein g is 0, 1, or 2; $R_M$ is each independently fluoro, chloro, methyl, methoxy, trifluoromethyl, or trifluoromethoxy; and

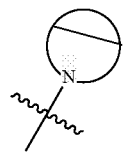

is as defined above. In a further subgroup of compounds D is

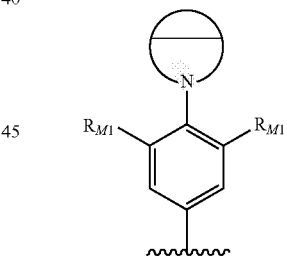

wherein $R_{M1}$ is each independently hydrogen, fluoro, chloro, or methyl, and

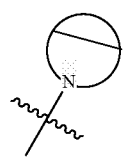

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In still another embodiment of this aspect of the invention, D is

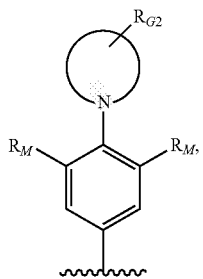

wherein

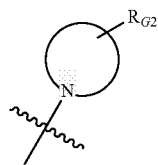

is a monocyclic 4-8 membered nitrogen-containing heterocycle (e.g., azetidinyl, pyrrolidinyl, piperidinyl) substituted with one or more $R_{G2}$, wherein $R_{G2}$ at each occurrence is each independently halogen, —C(O)$C_1$-$C_6$alkyl, —$C_1$-$C_6$alkyl, —$C_1$-$C_6$haloalkyl, —O—$C_1$-$C_6$alkyl, or —O—$C_1$-$C_6$haloalkyl; and $R_M$ is each independently halogen, —$C_1$-$C_6$alkyl, —$C_1$-$C_6$haloalkyl, —O—$C_1$-$C_6$alkyl, or —O—$C_1$-$C_6$haloalkyl. In one group of compounds according to this embodiment,

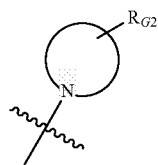

is azetidinyl, pyrrolidinyl, or piperidinyl substituted with one or two $R_{G2}$, wherein $R_{G2}$ at each occurrence is each independently methyl, ethyl, isopropyl, tert-butyl, fluoro, chloro, or trifluoromethyl; and $R_M$ is each independently fluoro, chloro, or methyl. For example

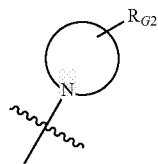

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

In certain preferred embodiments of this aspect of the invention, X is cyclopropyl, cyclopentyl or cyclopentenyl, and is optionally substituted with one or more $R_4$; and $L_1$, $L_2$, and $L_3$ are each a bond. In another embodiment, X is cyclopropyl, cyclopentyl or cyclopentenyl, and $L_1$ and $L_2$ are each methylene (i.e. —$CH_2$—), and $L_3$ is a bond.

In compounds of Formula $I_E$, Y is -T'-C($R_1R_2$)N($R_5$)-T-$R_D$ and Z is -T'-C($R_8R_9$)N($R_{12}$)-T-$R_D$; wherein T', $R_1$, $R_2$, $R_5$, $R_8$, $R_9$, $R_{12}$, T, and $R_D$ are as defined herein.

Preferably $R_1$, $R_2$, $R_5$, $R_8$, $R_9$, and $R_{12}$ are each independently hydrogen; $C_1$-$C_6$alkyl; or 3- to 6-membered carbocycle or heterocycle, wherein each 3- to 6-membered carbocycle or heterocycle is independently optionally substituted at each occurrence with one or more substituents selected from halogen or $C_1$-$C_6$alkyl; wherein $R_2$ and $R_5$, taken together with the atoms to which they are attached, optionally form a 3- to 12-membered heterocycle which is substituted with 0, 1, 2, 3, or 4 $R_4$, and $R_9$ and $R_{12}$ taken together with the atoms to which they are attached, optionally form a 3- to 12-membered heterocycle which is substituted with 0, 1, 2, 3, or 4 $R_4$ wherein $R_4$ is as defined herein.

In certain embodiments of this aspect of the invention, $R_1$ is hydrogen and $R_2$ and $R_5$, taken together with the atoms to which they are attached form a 3- to 12-membered heterocycle (e.g.,

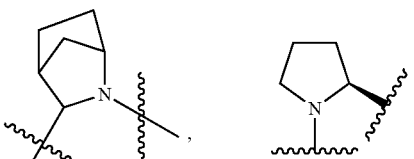

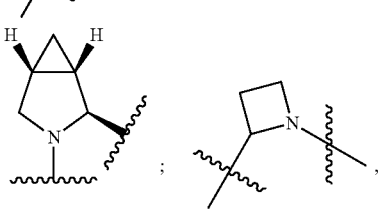

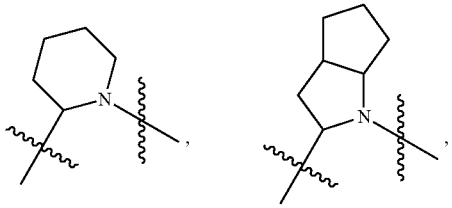

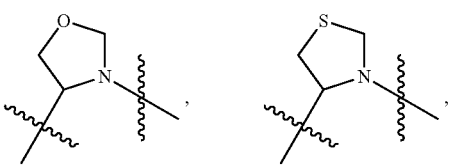

or

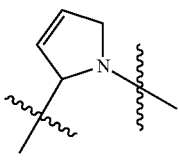
)

substituted with 0, 1, 2, 3, or 4 $R_A$ wherein $R_A$ is halogen (e.g., fluoro, chloro); cyano; $L_S$-$R_E$ where $L_S$ is a single bond and $R_E$ is $C_1$-$C_6$alkyl (e.g., methyl, ethyl), —O—$C_1$-$C_6$alkyl (e.g., methoxy), or —$C_1$-$C_6$haloalkyl (e.g., trifluoromethoxy); or $L_S$-$R_E$ where $L_S$ is a double bond and $R_E$ is =C($R_S R_S'$) (e.g.,

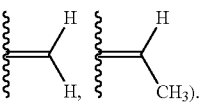

In a preferred embodiment $R_2$ and $R_5$, taken together with the atoms to which they are attached form a pyrrolidine ring (i.e.,

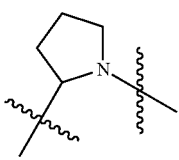 [SMILES: *C1CCCN1*]
)

substituted with 0 or 1 $R_A$ wherein $R_A$ is fluoro, methoxy, methyl, ethyl, or cyano. In another preferred embodiment $R_2$ and $R_5$, taken together with the atoms to which they are attached form a pyrrolidine ring (i.e.,

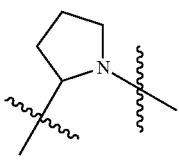
).

In certain other embodiments of this aspect of the invention, $R_8$ is hydrogen and $R_9$ and $R_{12}$, taken together with the atoms to which they are attached form a 3- to 12-membered heterocycle (e.g., or

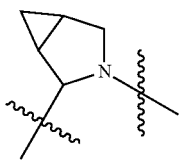
;

or

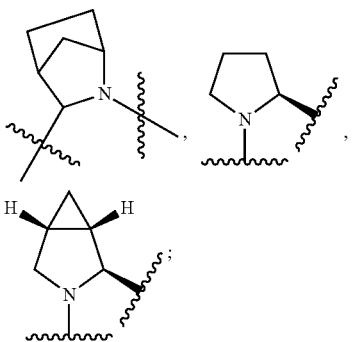

or

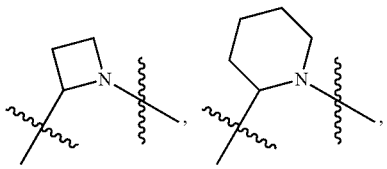

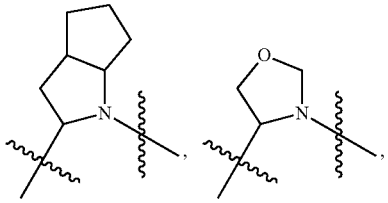

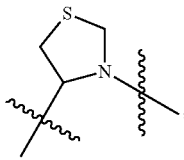
;

or

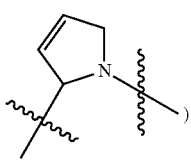
)

substituted with 0, 1, 2, 3, or 4 $R_A$ wherein $R_A$ is halogen (e.g., fluoro, chloro); cyano; $L_S$-$R_E$ where $L_S$ is a single bond and $R_E$ is $C_1$-$C_6$alkyl (e.g., methyl, ethyl), —O—$C_1$-$C_6$alkyl (e.g., methoxy), or —O—$C_1$-$C_6$haloalkyl (e.g., trifluoromethoxy); or $L_S$-$R_E$ where $L_S$ is a double bond and $R_E$ is =C($R_S R_S'$) (e.g.,

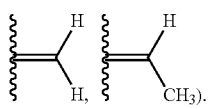

In a preferred embodiment, $R_9$ and $R_{12}$, taken together with the atoms to which they are attached form a pyrrolidine ring (i.e.,

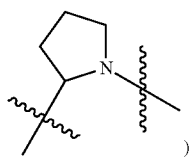 [SMILES: *C1CCCN1*]

)

substituted with 0 or 1 $R_A$ wherein $R_A$ is fluoro, methoxy, methyl, ethyl, or cyano. In another preferred embodiment $R_9$ and $R_{12}$, taken together with the atoms to which they are attached form a pyrrolidine ring (i.e.,

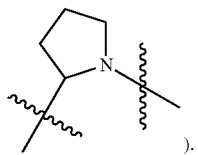 [SMILES: *C1CCCN1*]

).

As used herein, a chiral carbon in any rings formed by joining $R_2$ and $R_5$ or $R_9$ and $R_{12}$ may possess either (R) or (S) stereochemistry. A pyrrolidine ring (i.e.,

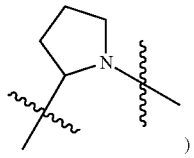 [SMILES: *C1CCCN1*]

)

formed from either $R_2$ and $R_5$ or $R_9$ and $R_{12}$ preferably possesses the (S) stereochemistry (i.e.,

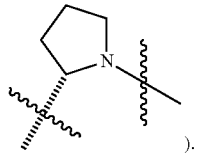 [SMILES: *N1CCC[C@H]1C]

).

In this aspect of the invention, T' is independently selected at each occurrence from a bond, —C(O)N($R_B$)—, —N($R_B$)C(O)—, or 3- to 12-membered heterocycle, and wherein said 3- to 12-membered heterocycle is each independently optionally substituted at each occurrence with one or more $R_A$, and $R_A$ and $R_B$ are as described herein. In particular, where T' is —C(O)N($R_B$)—, $R_B$ can be hydrogen (i.e., T' is —C(O)N(H)—). In certain embodiments, T' is imidazolyl (i.e.,

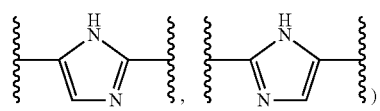

optionally substituted at each occurrence with one or more $R_A$ wherein $R_A$ is halogen (e.g., fluoro, chloro), $C_1$-$C_6$alkyl (e.g., methyl, ethyl), or $C_1$-$C_6$haloalkyl (e.g., trifluoromethyl). In certain embodiments, T' is imidazolyl (i.e.,

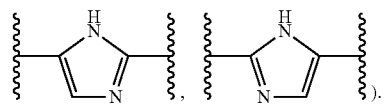

).

This aspect of the invention contemplates particular combinations of A with Y and B with Z. Non-limiting examples of preferred Y when A is $C_5$-$C_6$carbocycle (e.g., phenyl) or 5- to 6-membered heterocycle (e.g., pyridinyl or thiazolyl) and preferred Z when B is $C_5$-$C_6$carbocycle (e.g., phenyl) or 5- to 6-membered heterocycle (e.g., pyridinyl or thiazolyl) include:

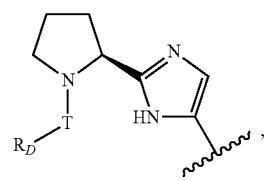

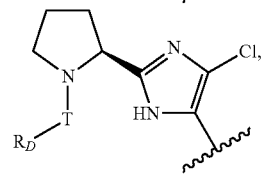

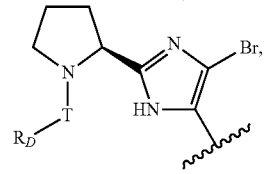

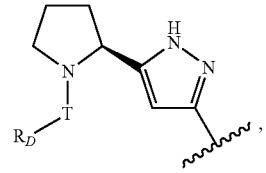

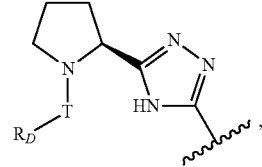

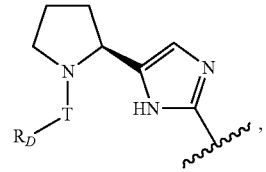

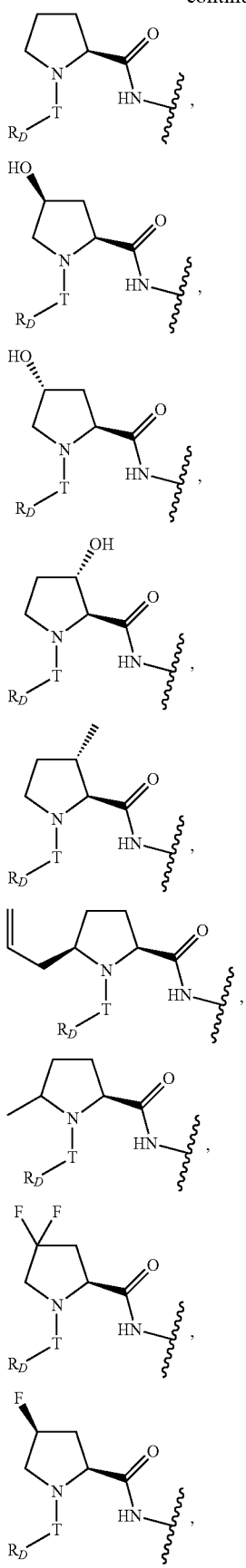
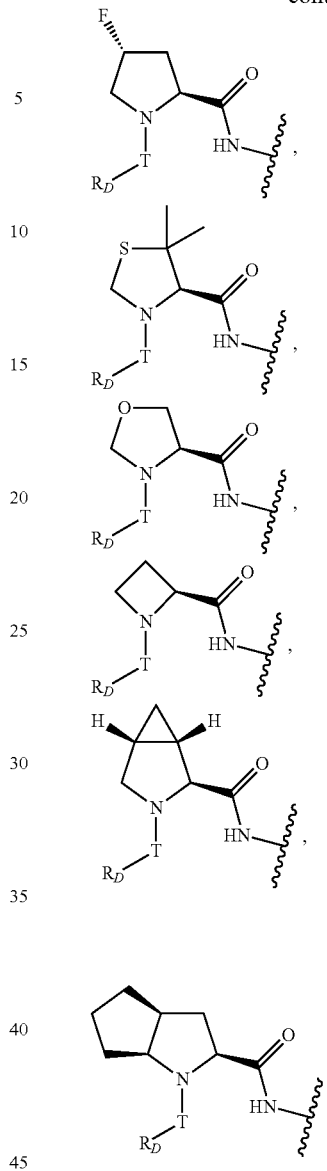
wherein T and $R_D$ are as defined herein.
In certain embodiments of this aspect of the invention, A is
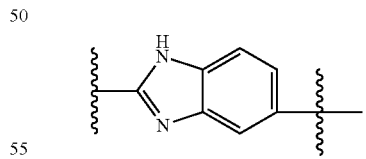
optionally substituted with one or more $R_A$ as described herein, or Y-A is
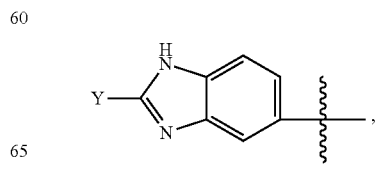

and non-limiting examples of preferred Y, where T' is a bond, include:

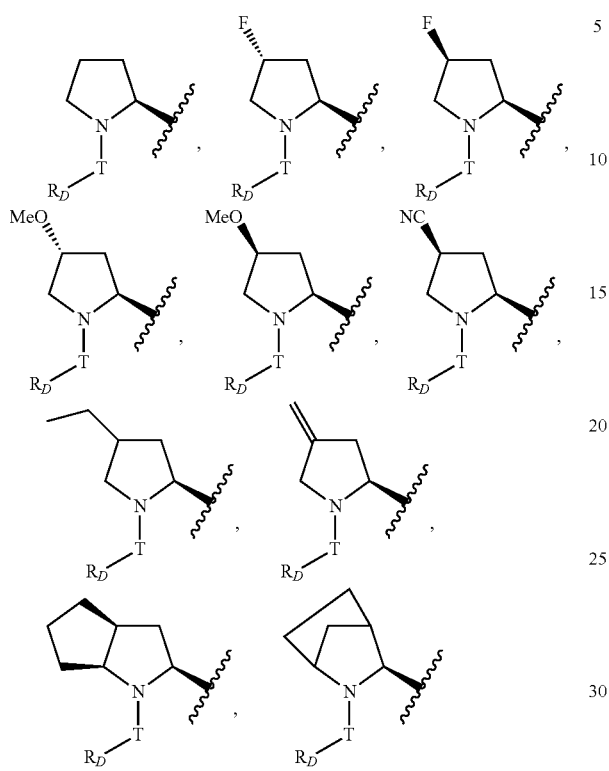

wherein T and $R_D$ are as defined herein.

In certain embodiments of this aspect of the invention, B is

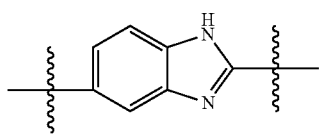 [SMILES: *c1ccc2[nH]c(*)nc2c1]

optionally substituted with one or more $R_A$ as described herein, or B—Z is

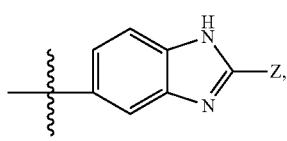

and non-limiting examples of preferred Z, where T' is a bond, include:

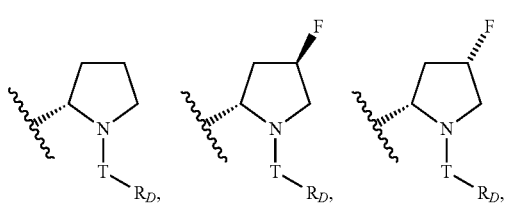

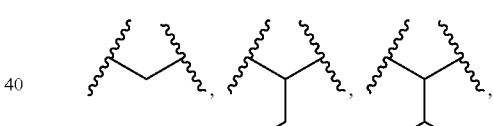

wherein T and $R_D$ are as defined herein.

T at each occurrence is independently a bond or —C(O)-$L_S'$-, wherein $L_S'$ is as defined herein. $L_S'$ includes, but is not limited to,

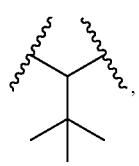

or

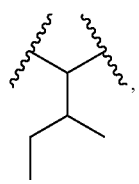

where $L_S'$ is optionally substituted with one or more $R_L$; and $R_L$ is a substituent such as, but not limited to carbocycle (e.g., cyclohexyl, cyclopentyl, cyclobutyl, cyclopropyl, phenyl), methoxy, or heterocycle (e.g., tetrahydrofuranyl, tetrahydropyranyl).

$R_D$ is hydrogen or $R_A$ wherein $R_A$ is as defined herein. Thus $R_D$ includes, but is not limited to, $R_A$ wherein $R_A$ is $L_S$-$R_E$, and $L_S$ and $R_E$ are as defined herein. Thus $R_D$ includes, but is not limited to, $L_S$-$R_E$ wherein $L_S$ is a bond and $R_E$ is —N($R_S R_S'$), —N($R_S$)C(O)$R_S'$, —N($R_S$)C(O)N($R_S'R_S''$), —N($R_S$)SO$_2R_S'$, —N($R_S$)SO$_2$N($R_S'R_S''$), —N($R_S$)S(O)N($R_S'R_S''$), —N($R_S$)C(O)OR$_S'$, or —N($R_S$)S(O)—$R_S'$; or $C_3$-$C_{12}$carbocycle or 3- to 12-membered heterocycle, each of which is independently optionally substituted at each occurrence with one or more substituents selected from halogen, hydroxy, cyano, $C_1$-$C_6$alkyl, $C_2$-$C_6$alkenyl, $C_2$-$C_6$alkynyl, or $C_1$-$C_6$haloalkyl.

In one embodiment of this aspect of the invention, $R_D$ is $L_S$-$R_E$ wherein $L_S$ is a bond and $R_E$ is —N($R_S$)C(O)OR$_S'$ or 3- to 12-membered heterocycle (e.g., pyrrolidine, piperidine, azepanyl) wherein $R_S$ and $R_S'$ are as defined herein. For example $R_D$ is preferably $L_S$-$R_E$ wherein $L_S$ is a bond and $R_E$ is —N(H)C(O)OMe.

Thus according to the foregoing description T-$R_D$ includes, but is not limited to:

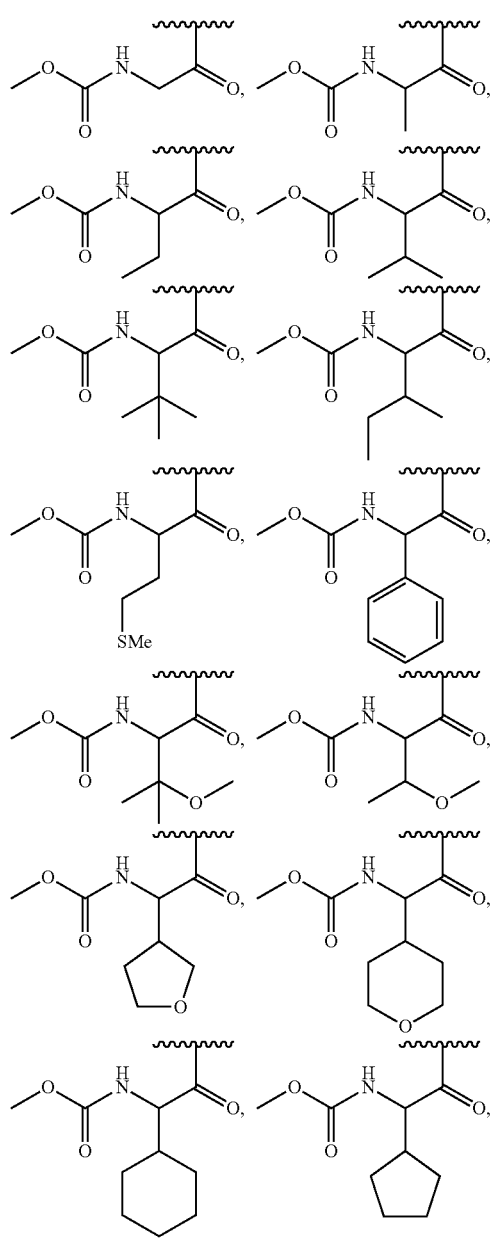

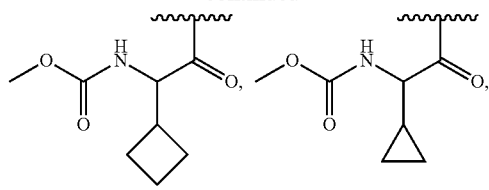

and

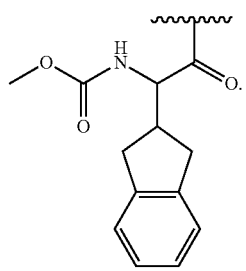 [SMILES: *C(=O)C(NC(=O)OC)C1Cc2ccccc2C1]

T-$R_D$ may also include particular stereochemical configurations; thus T-$R_D$ includes, but is not limited to:

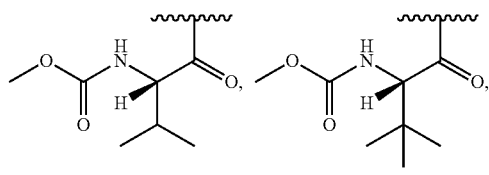

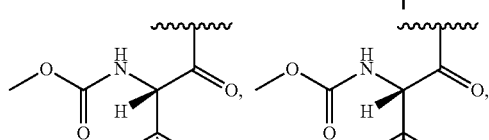

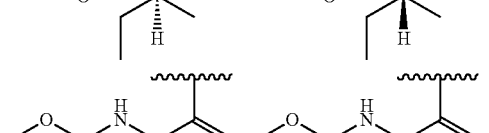

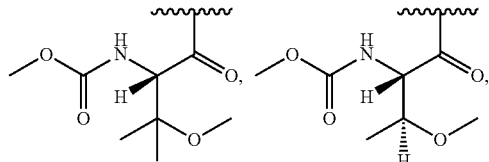

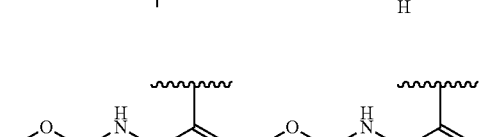

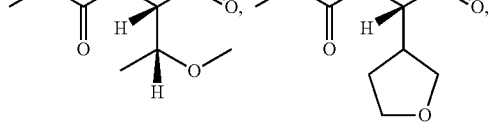

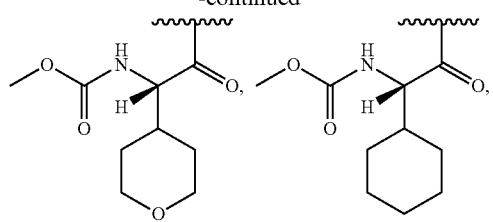
etc.
According to this aspect of the invention, non-limiting examples of preferred Y when A is $C_5$-$C_6$ carbocycle (e.g., phenyl) or 5- to 6-membered heterocycle (e.g., pyridinyl or thiazolyl) and preferred Z when B is $C_5$-$C_6$ carbocycle (e.g., phenyl) or 5- to 6-membered heterocycle (e.g., pyridinyl or thiazolyl) include:
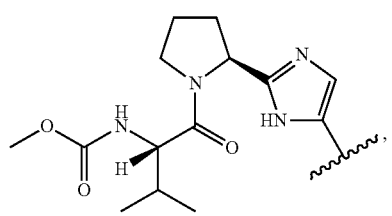
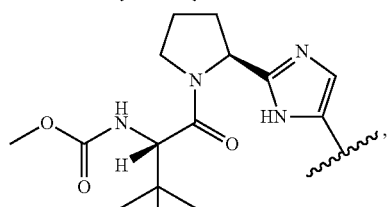
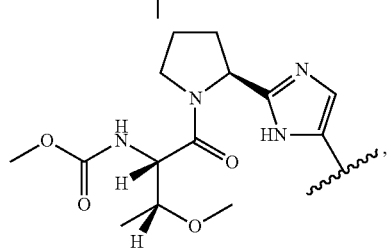
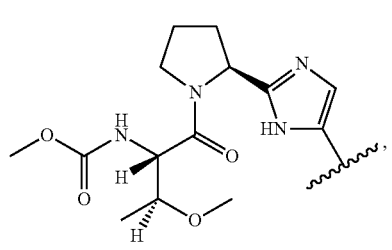
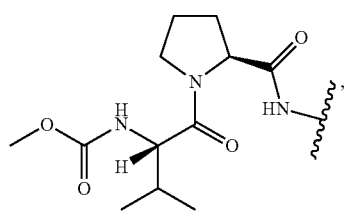
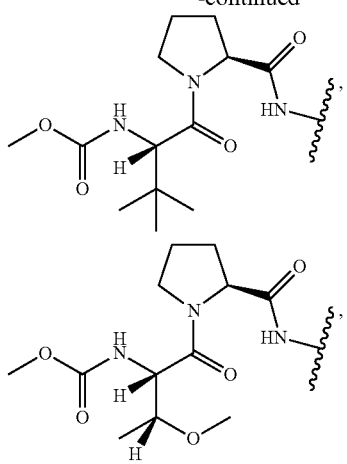
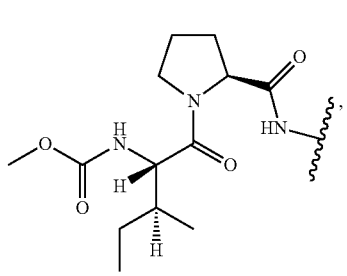
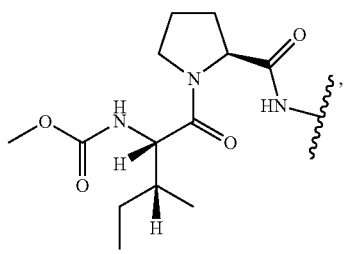
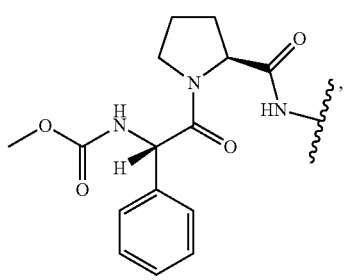

and
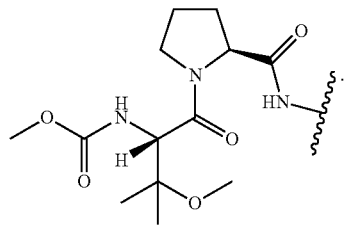 [SMILES: *NC(=O)[C@@H]1CCCN1C(=O)[C@@H](NC(=O)OC)C(C)(C)OC]
Non-limiting examples of preferred Y when A is
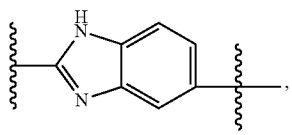 [SMILES: *c1ccc2[nH]c(*)nc2c1]
optionally substituted with one or more $R_A$ as described herein, and Y-A is
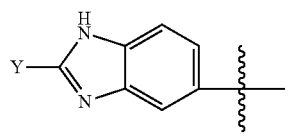
include:
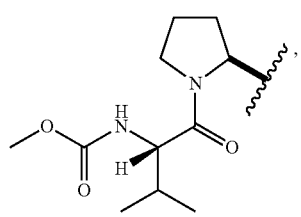
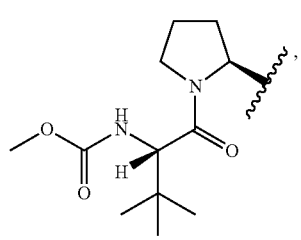
-continued
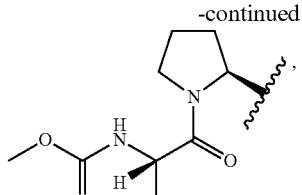
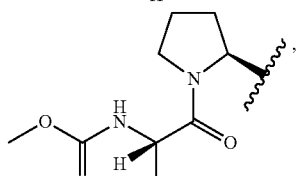
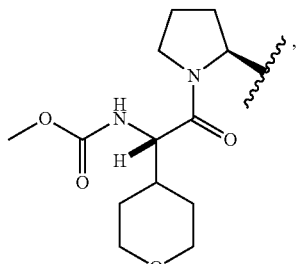
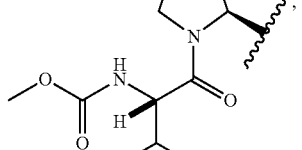
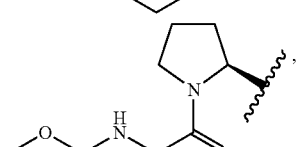
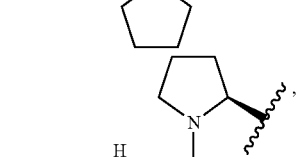
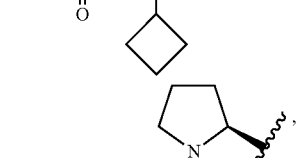
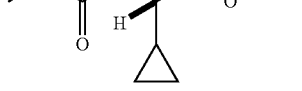

157
-continued
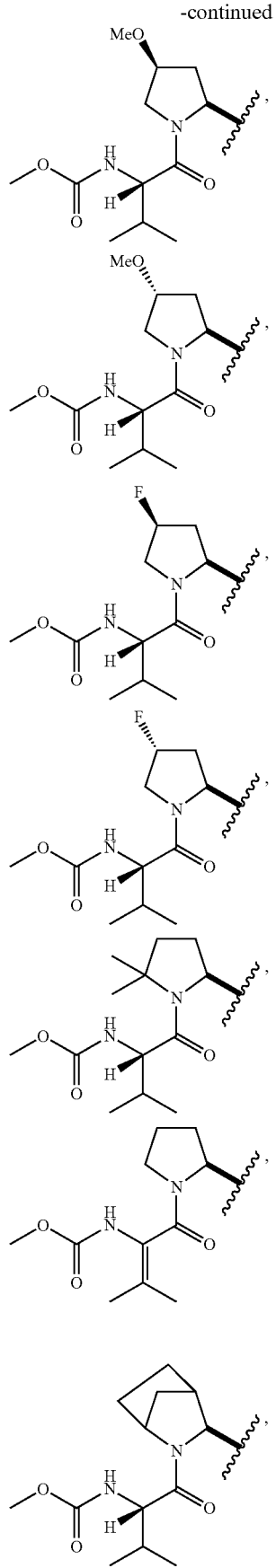
158
-continued
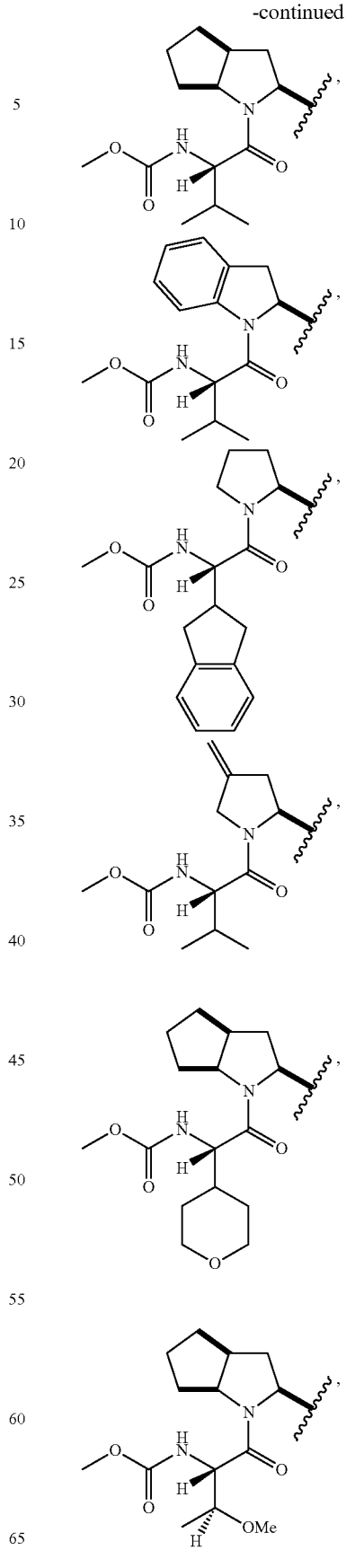

and
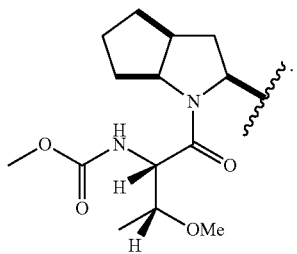
Non-limiting examples of preferred Z where B is
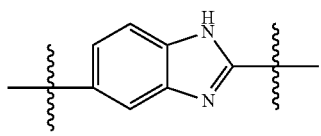 [SMILES: *c1ccc2[nH]c(*)nc2c1]
optionally substituted with one or more $R_A$ as described herein, and B—Z is
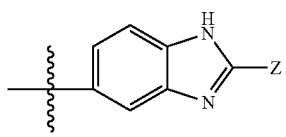
include:
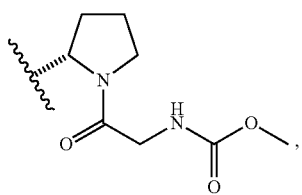
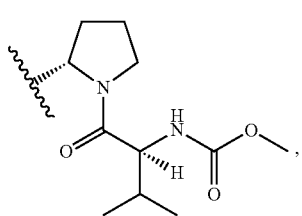
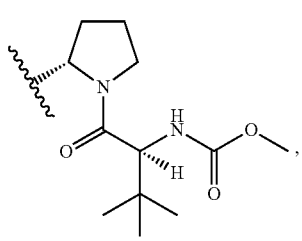
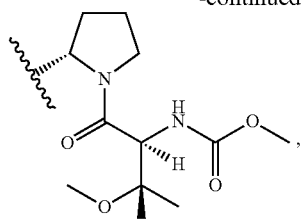
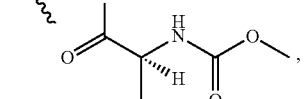
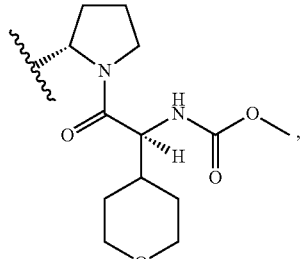
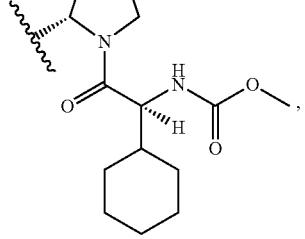
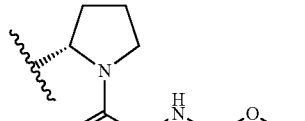
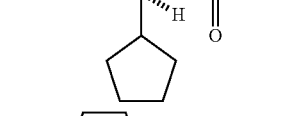
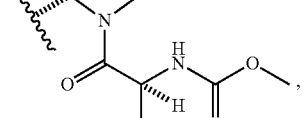
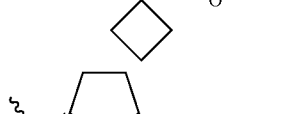
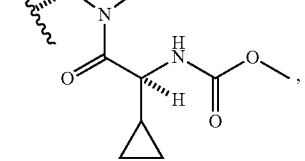

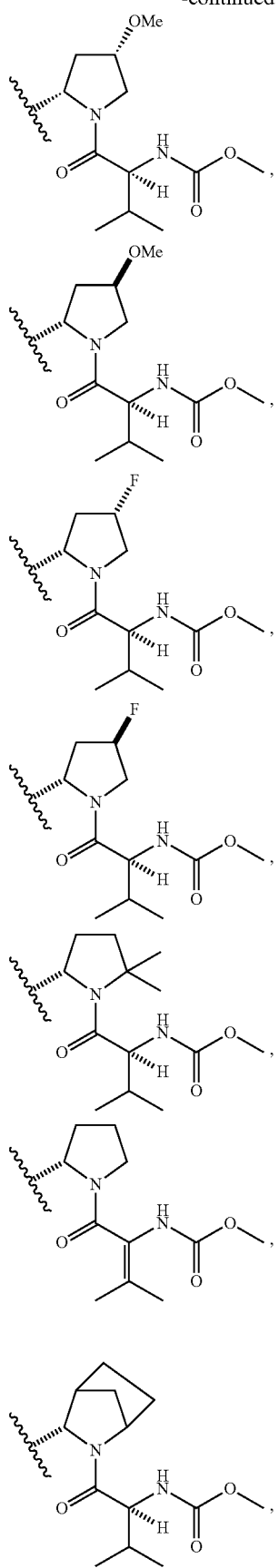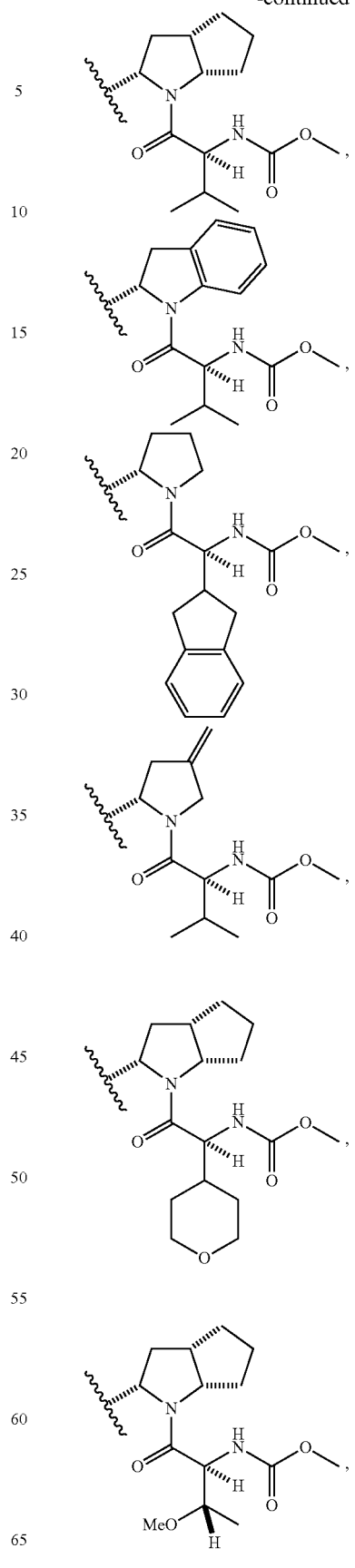

and

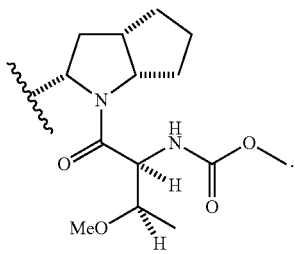

In still another aspect, the present invention features compounds of Formula I$_F$ and pharmaceutically acceptable salts thereof:

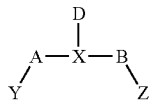

I$_F$ wherein:

X is cyclopropyl, cyclopentyl or cyclopentenyl, and is optionally substituted with one or more R$_A$ A is

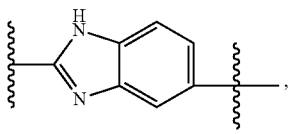

wherein A is optionally substituted with one or more R$_A$;

B is

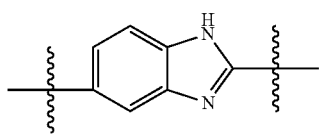 [SMILES: *c1ccc2[nH]c(*)nc2c1]

or

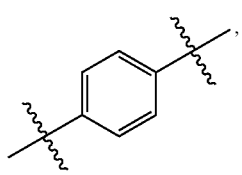

wherein B is optionally substituted with one or more R$_A$; and

Y, Z, R$_A$, and D are as described hereinabove (e.g., Y, Z, R$_A$, and D as described for Formula I, I$_A$, I$_B$, I$_C$, I$_D$, or I$_E$, preferably as described for Formula I$_E$).

In one embodiment of this aspect of the invention, A is

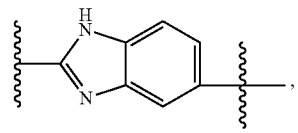

wherein A is optionally substituted with one or more R$_A$; B is

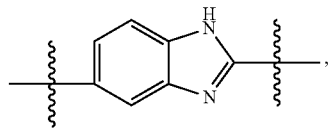

wherein B is optionally substituted with one or more R$_A$; Y is

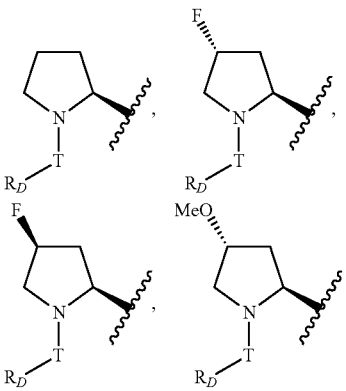

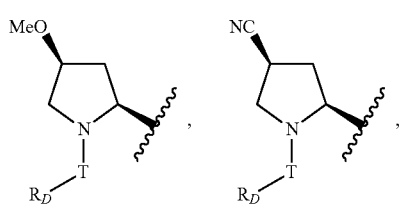

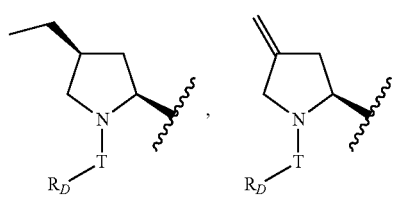

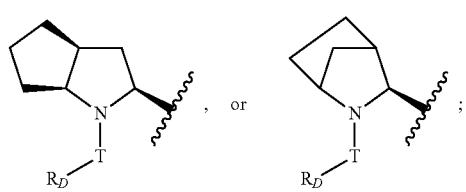

Z is

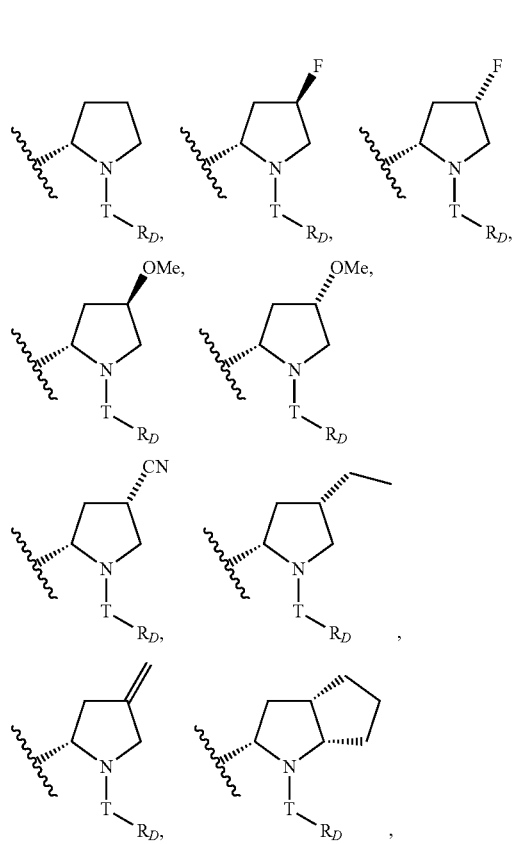

or

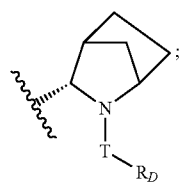

and D, $R_A$, T and $R_D$ are as defined hereinabove (e.g., as described for Formula I, $I_A$, $I_B$, $I_C$, $I_D$ or $I_E$, preferably as described for Formula $I_E$).

In another embodiment according to this aspect of the invention, A or B are optionally substituted with one or more substituents selected from: $R_A$ wherein $R_A$ is each independently halogen (e.g., fluoro, chloro); $L_S$-$R_E$ where $L_S$ is a single bond, and $R_E$ is —$C_1$-$C_6$alkyl (e.g., methyl), —O—$R_S$ (e.g., —O—$C_1$-$C_6$alkyl, —$OCH_3$), or —$C_1$-$C_6$alkyl optionally substituted with one or more halogen (e.g., —$CF_3$); or $L_S$-$R_E$ where $L_S$ is a $C_1$-$C_6$alkylene and $R_E$ is —O—$R_S$ (e.g., —$C_1$-$C_6$alkyl-O—$C_1$-$C_6$alkyl, —$CH_2OCH_3$). This embodiment includes compounds where A and B are both substituted by one $R_A$; compounds where A and B are both substituted by zero $R_A$; compounds where A is substituted by one $R_A$ and B is substituted by zero $R_A$; and compounds where A is substituted by zero $R_A$ and B is substituted by one $R_A$. Preferably, A is

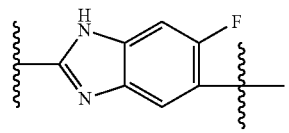 [SMILES: *c1nc2cc(*)c(F)cc2[nH]1]

and B is

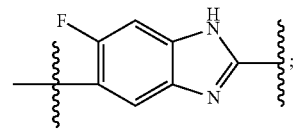

or A is

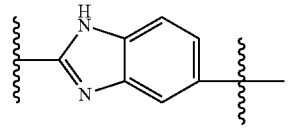

and B is

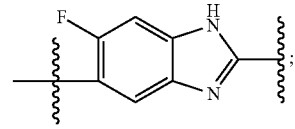 [SMILES: *c1nc2cc(*)c(F)cc2[nH]1]

or A is

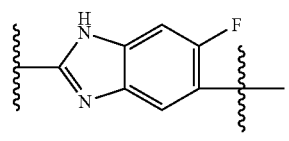

and B is

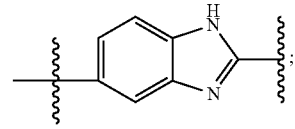 [SMILES: *c1ccc2[nH]c(*)nc2c1]

or A is

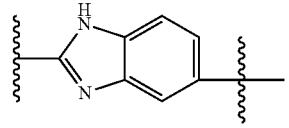 [SMILES: *c1ccc2[nH]c(*)nc2c1]

and B is
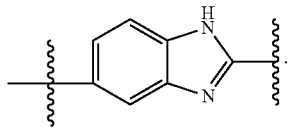 [SMILES: *c1ccc2[nH]c(*)nc2c1]
In a further embodiment of this aspect of the invention, T-R$_D$ is independently selected at each occurrence from the group consisting of
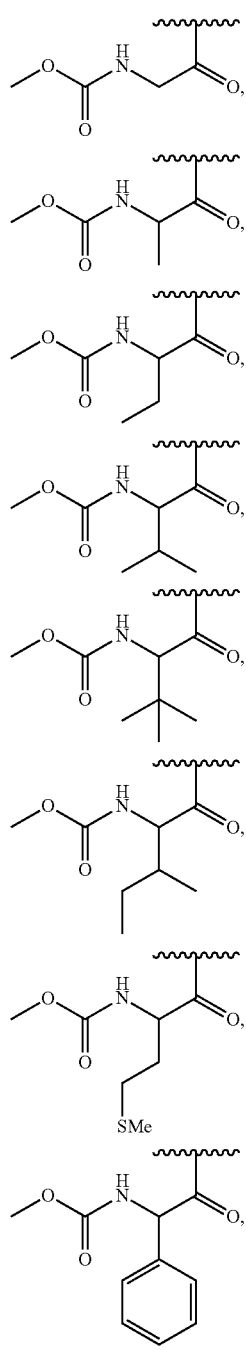
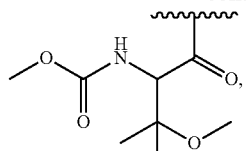
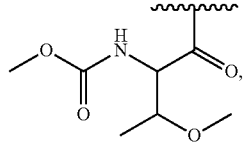
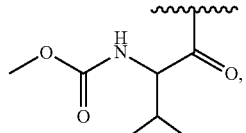
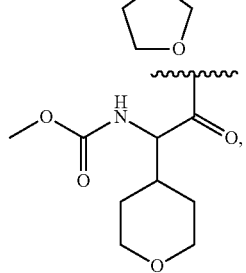
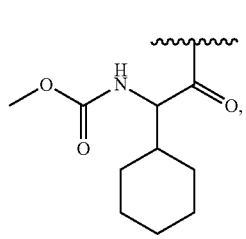
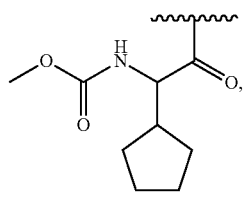
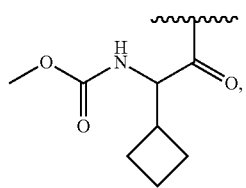
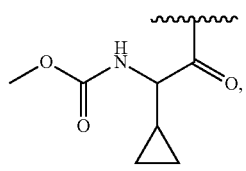

and

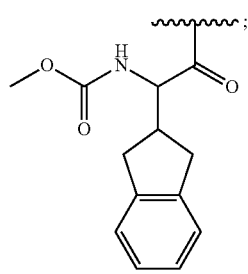 [SMILES: *C(=O)C(NC(=O)OC)C1Cc2ccccc2C1]

wherein compounds having (S) stereochemistry (e.g.,

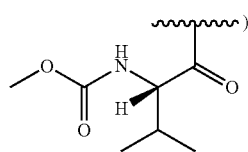)

are preferred and wherein D is as defined hereinabove.

In another embodiment, this aspect of the invention features compound of Formula $I_F$ and pharmaceutically acceptable salts thereof, wherein:

A is

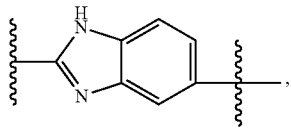

wherein A is optionally substituted with one or more $R_A$; B is

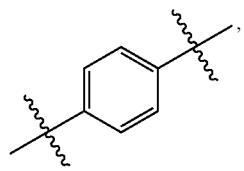

wherein B is optionally substituted with one or more $R_A$; Y is

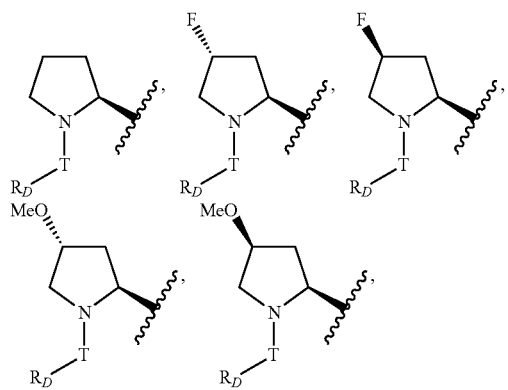

or

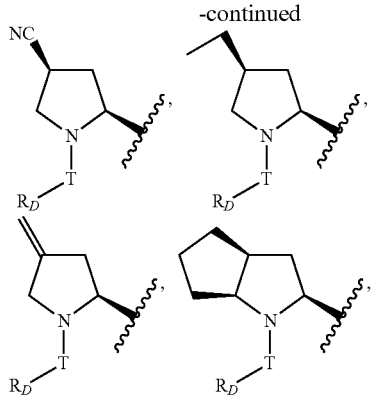

Z is

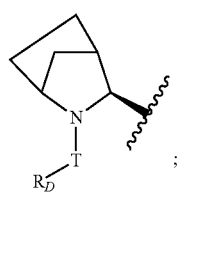

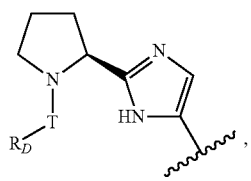

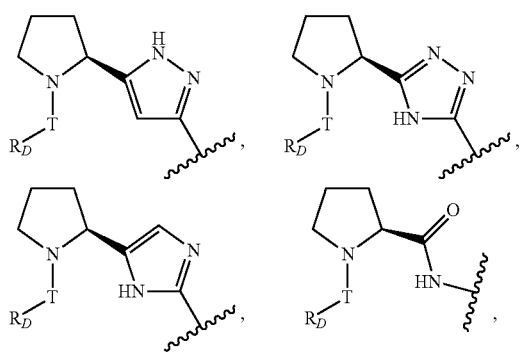

or

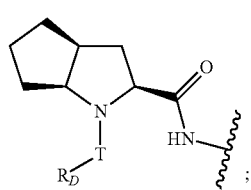

and D, $R_A$, T and $R_D$ are as defined hereinabove. A particular subgroup according to this embodiment includes compounds where A is

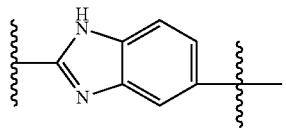 [SMILES: *c1ccc2[nH]c(*)nc2c1]

or

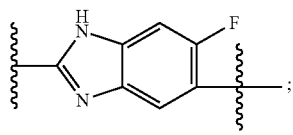 [SMILES: *c1nc2cc(*)c(F)cc2[nH]1]

B is

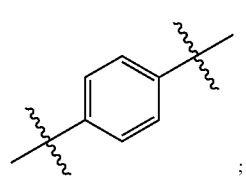 [SMILES: *c1ccc(*)cc1]

Y is

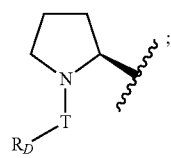

Z is

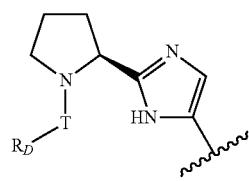

or

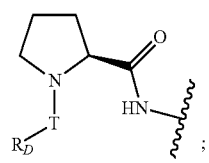

T-$R_D$ is each independently

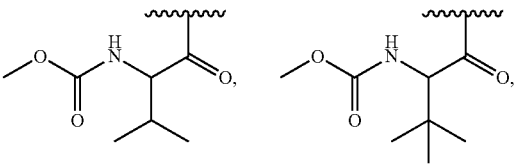

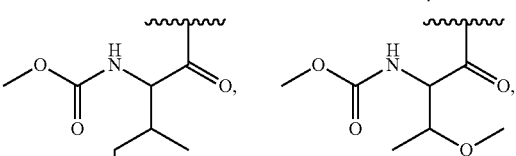

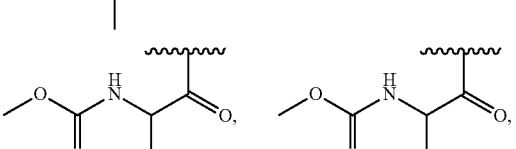

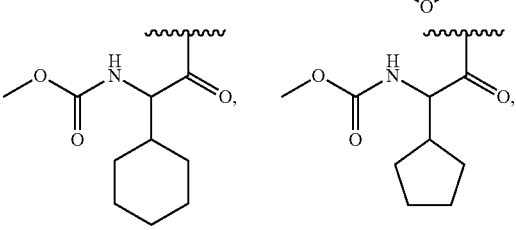

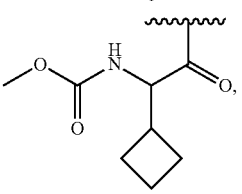

or

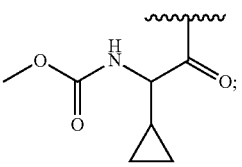 [SMILES: *C(=O)C(NC(=O)OC)C1CC1]

and D is as defined hereinabove.

In yet another embodiment, this aspect of the invention features compounds of Formula $I_F$ and pharmaceutically acceptable salts thereof, wherein: A and B are each

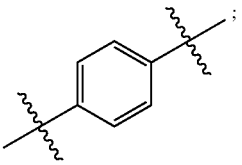 [SMILES: *c1ccc(*)cc1]

Y and Z are each independently

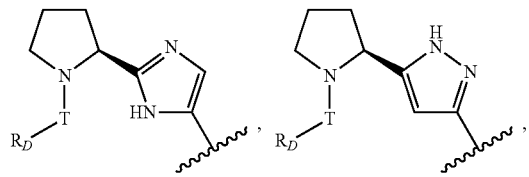

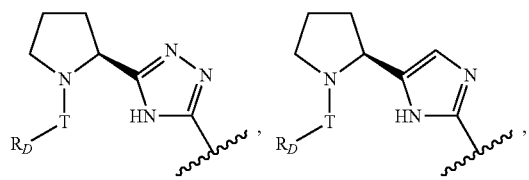

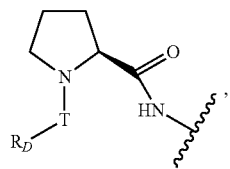

or

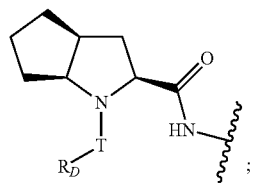

and D, T and $R_D$ are as defined hereinabove. A particular subgroup according to this embodiment includes compounds where T-$R_D$ is each independently selected from

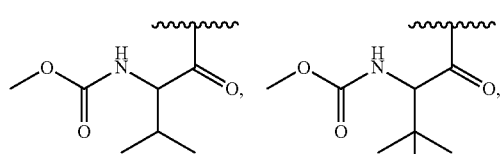

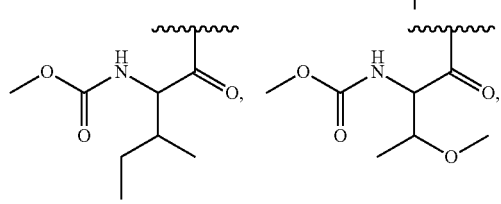

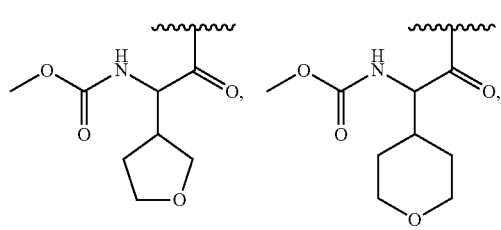

-continued

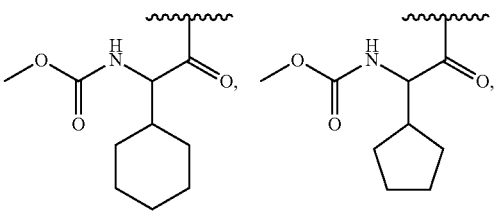

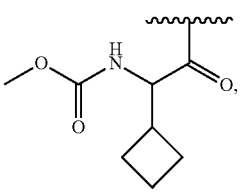

or

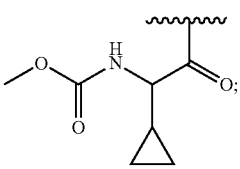 [SMILES: *C(=O)C(NC(=O)OC)C1CC1]

and D is as defined hereinabove.

According to each of the foregoing embodiments and description of this aspect of the invention of Formula $I_F$ are groups and subgroups of compounds having particular values for D. Included in each of the foregoing embodiments are groups and subgroups of compounds with the following particular values for D:

In certain groups of compounds according to Formula $I_F$ and the foregoing embodiments and description of this aspect of the invention, D is

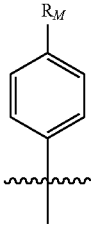

where $R_M$ is fluoro, chloro, tert-butyl, —O—CH$_2$CH$_3$, —O—CF$_3$, —O—CH$_2$CHF$_2$, —O—CH$_2$CH$_2$OCH$_3$, —O—CH$_2$-(3-ethyloxetan-3-yl), —O—CH$_2$-(1,3-dioxolan-4-yl), —O-cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D is optionally substituted by one or more additional $R_M$, selected from the group consisting of halogen (e.g., fluoro, chloro) or C$_1$-C$_6$alkyl (e.g., methyl).

In other groups of compounds according Formula $I_F$ and the foregoing embodiments and description of this aspect of the invention, D is

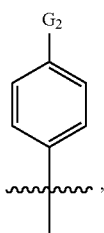

wherein G₂ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional $R_M$ selected from the group consisting of halogen (e.g., fluoro, chloro), or $C_1$-$C_6$alkyl (e.g., methyl). In particular according to these groups are compounds where D is

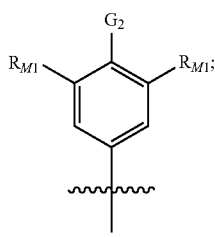

$G_2$ is piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl; and $R_{M1}$ is each independently hydrogen, fluoro, chloro, or methyl.

In other groups of compounds according Formula $I_F$ and the foregoing embodiments and description of this aspect of the invention, D is

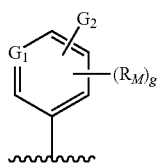

wherein $G_1$ is N, C—H, or C—$R_M$; $G_2$ is

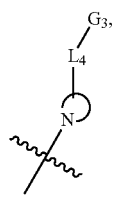

wherein

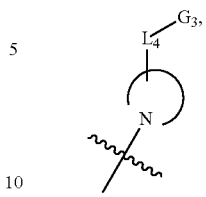

$R_M$, and g are as defined hereinabove. In particular according to these groups, $R_M$ is each independently fluoro, chloro, methyl, methoxy, trifluoromethyl, or trifluoromethoxy; g is 0, 1, or 2; and

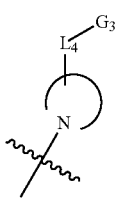

is as defined hereinabove. In further subgroups $L_4$ is a bond; $G_2$ is

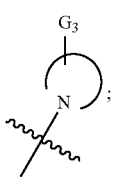

$R_M$ is each independently fluoro, chloro, methyl, methoxy, trifluoromethyl, or trifluoromethoxy; and g is 0, 1, or 2. In particular subgroups

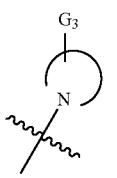

is 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl; $R_M$ is each independently fluoro, chloro, methyl, methoxy, trifluoromethyl, or trifluoromethoxy; and g is 0, 1, or 2. In other subgroups $L_4$ is $C_1$-$C_6$alkylene, —O—, or —S(O)₂—; $G_2$ is

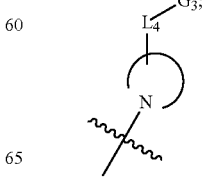

$R_M$ is each independently fluoro, chloro, methyl, methoxy, trifluoromethyl, or trifluoromethoxy; and g is 0, 1, or 2. In particular subgroups,

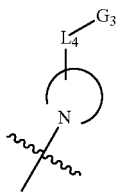

is 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl; $R_M$ is each independently fluoro, chloro, methyl, methoxy, trifluoromethyl, or trifluoromethoxy; and g is 0, 1, or 2. In further subgroups of compounds D is

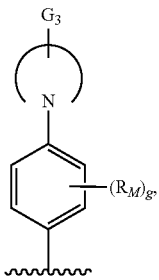

wherein $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

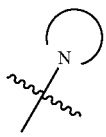 [SMILES: *N]

and $R_{G3}$ are as defined above. In other groups of compounds D is

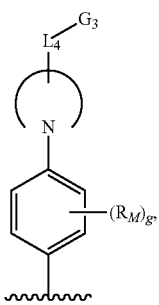

wherein $L_4$ is $C_1$-$C_6$alkylene, —O—, or —S(O)$_2$—; $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

and $R_{G3}$ are as defined above. In further subgroups of compounds D is

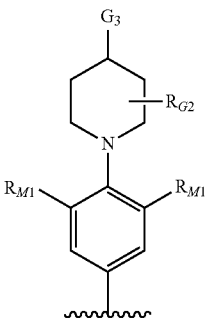

wherein $G_3$ is phenyl optionally substituted with one or two $R_{G3}$ as defined hereinabove; $R_{M1}$ is each independently hydrogen, fluoro, chloro, or methyl; and $R_{G2}$ is an optional substituent, as described above, selected from the group consisting of —C(O)C$_1$-C$_6$alkyl, —C$_1$-C$_6$alkyl, —C$_1$-C$_6$haloalkyl, —O—C$_1$-C$_6$alkyl, and —O—C$_1$-C$_6$haloalkyl.

In other groups of compounds according Formula I$_F$ and the foregoing embodiments and description of this aspect of the invention, D is

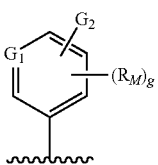

wherein $G_1$ is N, C—H, or C—$R_M$; $G_2$ is

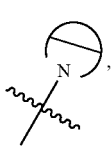

wherein

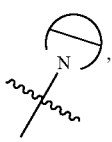 [SMILES: *N]

$R_M$, and g are as defined hereinabove. In particular according to these subgroups, $R_M$ is each independently fluoro, chloro, methyl, methoxy, trifluoromethyl, or trifluoromethoxy; g is 0, 1, or 2; and

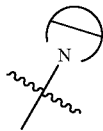 [SMILES: *N]

is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl. In further subgroups of compounds D is

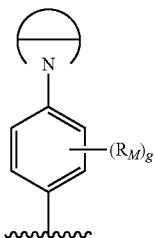

wherein g is 0, 1, or 2; $R_M$ is each independently fluoro, chloro, methyl, methoxy, trifluoromethyl, or trifluoromethoxy; and

is as defined above. In further subgroups of compounds D is

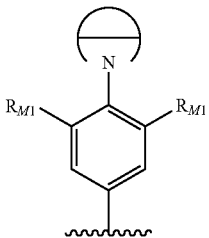

wherein $R_{M1}$ is each independently hydrogen, fluoro, chloro, or methyl and

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In other groups of compounds according Formula $I_F$ and the foregoing embodiments and description of this aspect of the invention, D is

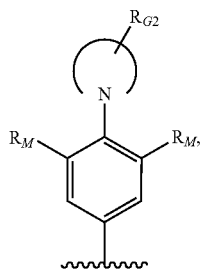

wherein

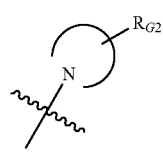

is a monocyclic 4-8 membered nitrogen-containing heterocycle (e.g., azetidinyl, pyrrolidinyl, piperidinyl) substituted with one or more $R_{G2}$, wherein $R_{G2}$ at each occurrence is each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; and $R_M$ is each independently halogen, —C$_1$-C$_6$alkyl, —C$_1$-C$_6$haloalkyl, —O—C$_1$-C$_6$alkyl, or —O—C$_1$-C$_6$haloalkyl. In each group of compounds according to the foregoing embodiments

is azetidinyl, pyrrolidinyl, or piperidinyl substituted with one or two $R_{G2}$, wherein $R_{G2}$ at each occurrence is each methyl, ethyl, isopropyl, tert-butyl, fluoro, chloro, or trifluoromethyl; and $R_M$ is each independently fluoro, chloro, or methyl. For example

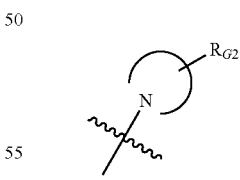

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

In still another aspect, the present invention features compounds of Formula $I_G$ and pharmaceutically acceptable salts thereof,

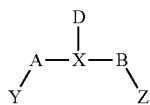

wherein:
X is cyclopropyl, cyclopentyl or cyclopentenyl, and is optionally substituted with one or more $R_A$
A is

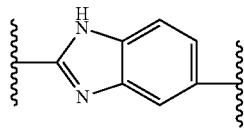

or

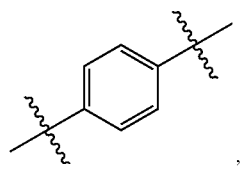

wherein A is optionally substituted with one or more $R_A$; B is

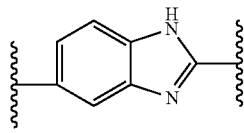 [SMILES: *c1ccc2[nH]c(*)nc2c1]

or

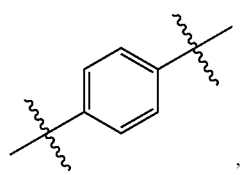

wherein B is optionally substituted with one or more $R_A$; and
Y, Z, $R_A$, and D are as described hereinabove (e.g., as described for Formula I, $I_A$, $I_B$, $I_C$, $I_D$, $I_E$ or $I_F$, preferably as described for Formula $I_E$).

In one embodiment, this aspect of the invention features compounds of Formula $I_G$ and pharmaceutically acceptable salts thereof, wherein: A is

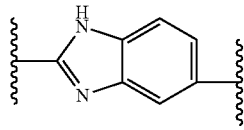

or $I_G$

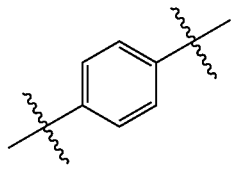

wherein A is optionally substituted with one $R_A$; B is

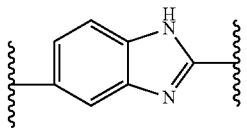 [SMILES: *c1ccc2[nH]c(*)nc2c1]

or

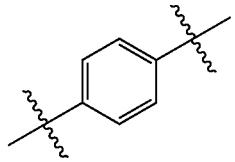

wherein B is optionally substituted with one $R_A$; $R_A$ is halogen (e.g., fluoro, chloro); $L_S$-$R_E$ where $L_S$ is a single bond and $R_E$ is —$C_1$-$C_6$alkyl (e.g., methyl), —O—$R_S$ (e.g., —O—$C_1$-$C_6$alkyl, —OCH$_3$), or —$C_1$-$C_6$alkyl optionally substituted with one or more halogen (e.g., —CF$_3$); or $L_S$-$R_E$ where $L_S$ is a $C_1$-$C_6$alkylene and $R_E$ is —O—$R_S$ (e.g., —$C_1$-$C_6$alkyl-O—$C_1$-$C_6$alkyl, —CH$_2$OCH$_3$); Y and Z are each independently

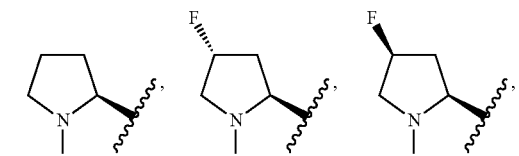

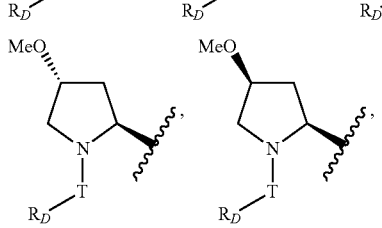

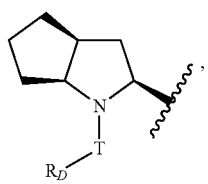
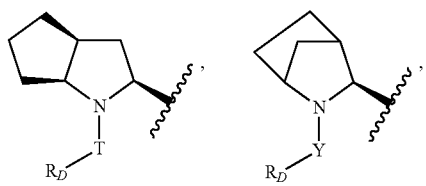

-continued
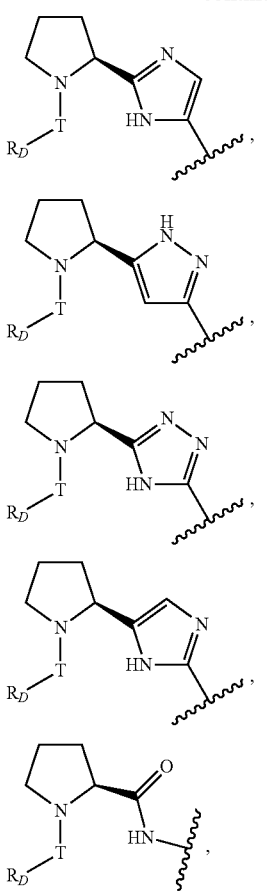
or
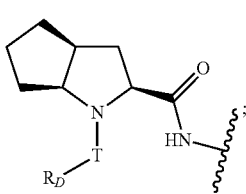
T-R_D is each independently
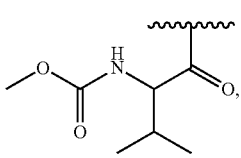
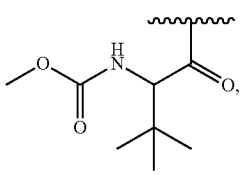
-continued
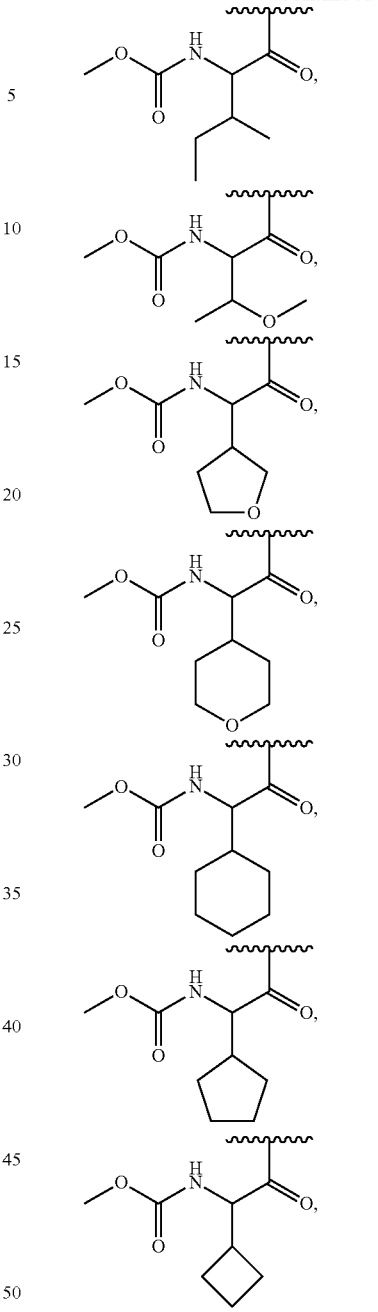
or
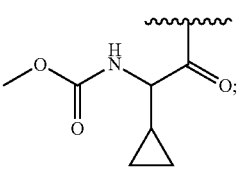 [SMILES: *C(=O)C(NC(=O)OC)C1CC1]
and D is as defined hereinabove.
In another embodiment, this aspect of the invention features compounds of Formula $I_G$ and pharmaceutically acceptable salts thereof, wherein A is

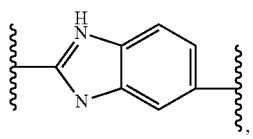

wherein A is optionally substituted with one R$_A$; B

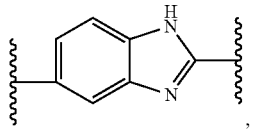

wherein B is optionally substituted with one R$_A$; R$_A$ is halogen (e.g., fluoro, chloro); L$_S$-R$_E$ where L$_S$ is a single bond and R$_E$ is —C$_1$-C$_6$alkyl (e.g., methyl), —O—R$_S$ (e.g., —O—C$_1$-C$_6$alkyl, —OCH$_3$), or —C$_1$-C$_6$alkyl optionally substituted with one or more halogen (e.g., —CF$_3$); or L$_S$-R$_E$ where L$_S$ is a C$_1$-C$_6$alkylene and R$_E$ is —O—R$_S$(e.g., —C$_1$-C$_6$alkyl-O—C$_1$-C$_6$alkyl, —CH$_2$OCH$_3$); Y and Z are each independently

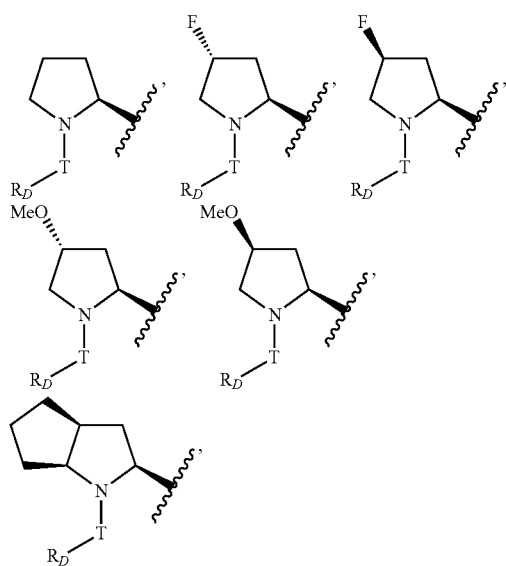

or

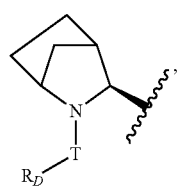

T-R$_D$ is each independently

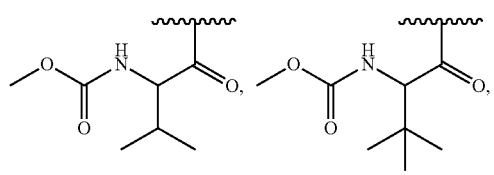

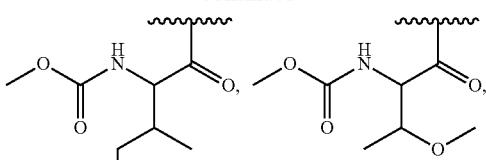

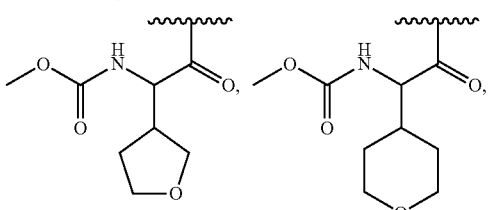

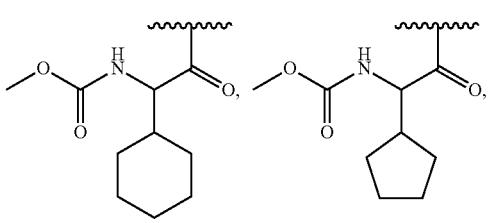

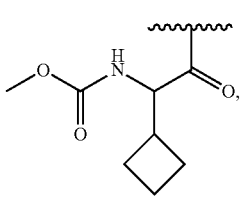

or

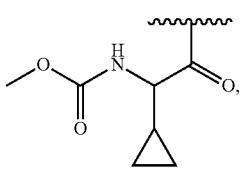 [SMILES: *C(=O)C(NC(=O)OC)C1CC1]

wherein compounds having (S) stereochemistry (e.g.,

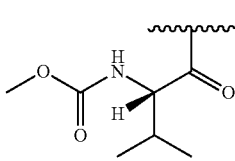

)

are particularly contemplated; and D is as defined hereinabove. This subgroup includes compounds where A and B are both substituted by one R$_A$; compounds where A and B are both substituted by zero R$_A$; compounds where A is substituted by one R$_A$ and B is substituted by zero R$_A$; and compounds where A is substituted by zero R$_A$ and B is substituted by one R$_A$. In particular, according to this subgroup are included compounds where A is

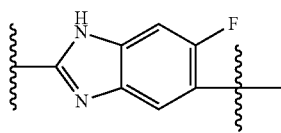 [SMILES: *c1nc2cc(*)c(F)cc2[nH]1]

and B is

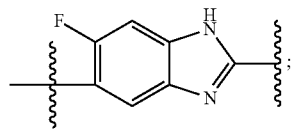

or A is

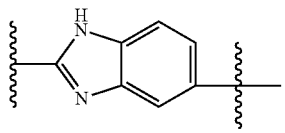 [SMILES: *c1ccc2[nH]c(*)nc2c1]

and B is

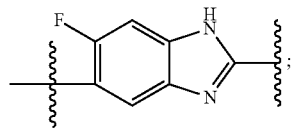 [SMILES: *c1nc2cc(*)c(F)cc2[nH]1]

or A is

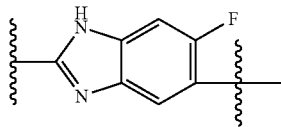 [SMILES: *c1nc2cc(*)c(F)cc2[nH]1]

and B is

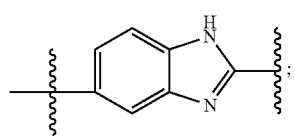

or A is

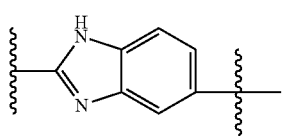 [SMILES: *c1ccc2[nH]c(*)nc2c1]

and B is

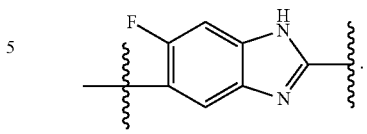

According to each of the foregoing embodiments and description of this aspect of the invention of Formula $I_G$ are groups and subgroups of compounds having particular values for D. Included in each of the foregoing embodiments are groups and subgroups of compounds with the following particular values for D:

Groups of compounds according to this aspect of the invention include compounds where D is $C_6$-$C_{10}$aryl (e.g., phenyl, naphthyl, indanyl), or 5- to 10-membered heteroaryl (pyridinyl, thiazolyl, 4,5,6,7-tetrahydrobenzo[d]thiazolyl, benzo[d]thiazolyl, indazolyl, benzo[d][1,3]dioxol-5-yl), and D is substituted with one or more $R_M$. Particular subgroups according to this aspect and these embodiments include compounds wherein $R_M$ is halogen (e.g., fluoro, chloro, bromo); $C_1$-$C_6$alkyl (e.g., tert-butyl); $C_1$-$C_6$alkyl substituted with one or more halogen (e.g., $CF_3$); —O—$C_1$-$C_6$alkyl (e.g., —O—$CH_2CH_3$); —O—$C_1$-$C_6$alkyl substituted at each occurrence with one or more halogen (e.g., —O—$CF_3$, —O—$CH_2CHF_2$) or —O—$C_1$-$C_6$alkyl (—O—$CH_2CH_2OCH_3$); —O—$C_1$-$C_6$alkyl (e.g., —O—$CH_2$) substituted with an optionally substituted 3- to 12-membered heterocycle (e.g., 3-ethyloxetan-3-yl, 1,3-dioxolan-4-yl); —O—$R_S$ where $R_S$ is an optionally substituted 3- to 12-membered carbocycle or heterocycle (e.g., cyclopentyl, cyclohexyl, phenyl, 1,3-dioxan-5-yl); —N($R_S$)C(O)$R_S'$ wherein $R_S$ and $R_S'$ are each independently $C_1$-$C_6$alkyl (e.g., —N(t-Bu)C(O)Me); $SF_5$; —$SO_2R_S$ wherein $R_S$ is $C_1$-$C_6$alkyl (e.g., —$SO_2$Me); or $C_3$-$C_{12}$carbocycle (e.g., cyclopropyl, cyclohexyl, phenyl). Other subgroups according to this embodiment include compounds wherein D is phenyl substituted by $G_2$ and optionally substituted by one or more $R_M$, wherein $G_2$ is a 3- to 12-membered heterocycle (e.g., pyridinyl, piperidinyl, pyrrolidinyl, azetidinyl, oxazolyl) wherein the heterocycle is optionally substituted with one or more substituents selected from halogen, hydroxy, oxo, cyano, $C_1$-$C_6$alkyl (e.g., methyl), $C_2$-$C_6$alkenyl, $C_2$-$C_6$alkynyl, $C_1$-$C_6$haloalkyl (e.g., $CF_3$), $C_2$-$C_6$haloalkenyl, $C_2$-$C_6$haloalkynyl, —O—$C_1$-$C_6$alkyl (e.g., —O—$CH_3$), —C(O)O$R_S$(e.g., —C(O)O$CH_3$), —C(O)$R_S$ (e.g., —C(O)$CH_3$), —N($R_SR_S'$), or $L_4$-$G_3$; $R_M$ is halogen (e.g., fluoro, chloro), alkyl (e.g., methyl), haloalkyl (e.g., $CF_3$), or —O—$C_1$-$C_6$alkyl (e.g., —O—$CH_3$); and $L_4$, $G_3$, $R_S$, and $R_S'$ are as defined hereinabove.

In certain groups of compounds according to Formula $I_G$ and the foregoing embodiments and description of this aspect of the invention, D is

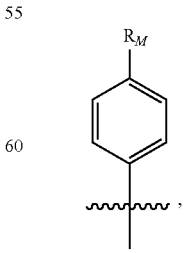

where $R_M$ is fluoro, chloro, tert-butyl, —O—$CH_2CH_3$, —O—$CF_3$, —O—$CH_2CHF_2$, —O—$CH_2CH_2OCH_3$, —O—CH$_2$-(3-ethyloxetan-3-yl), —O—CH$_2$-(1,3-dioxolan-4-yl), —O-cyclopentyl, —O-cyclohexyl, —O-phenyl, —O-(1,3-dioxan-5-yl), cyclopropyl, cyclohexyl, phenyl, SF$_5$, —SO$_2$Me, or —N(t-Bu)C(O)Me and D is optionally substituted by one or more additional R$_M$, selected from the group consisting of halogen (e.g., fluoro, chloro) or C$_1$-C$_6$alkyl (e.g., methyl).

In other groups of compounds according Formula I$_G$ and the foregoing embodiments and description of this aspect of the invention, D is

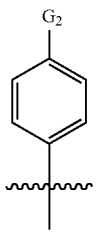

L wherein G$_2$ is pyridinyl (e.g., pyridin-2-yl), piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, 3,3-dimethylazetidin-1-yl, or oxazolyl (e.g., 1,3-oxazol-2-yl) and D is optionally substituted by one or more additional R$_M$ selected from the group consisting of halogen (e.g., fluoro, chloro), or C$_1$-C$_6$alkyl (e.g., methyl). In particular according to these groups are compounds where D is

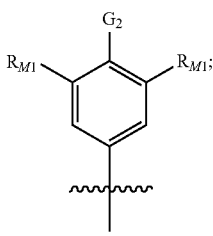

G$_2$ is piperidin-1-yl, 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl; and R$_{M1}$ is each independently hydrogen, fluoro, chloro, or methyl.

In other groups of compounds according Formula I$_G$ and the foregoing embodiments and description of this aspect of the invention, D is

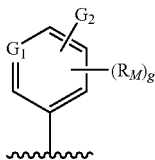

wherein G$_1$ is N, C—H, or C—R$_M$; G$_2$ is

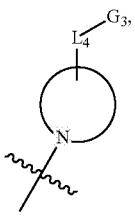

wherein

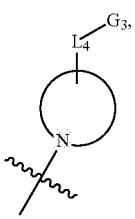

R$_M$, and g are as defined hereinabove. In particular according to these groups, R$_M$ is each independently fluoro, chloro, methyl, methoxy, trifluoromethyl, or trifluoromethoxy; g is 0, 1, or 2; and

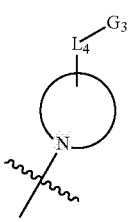

is as defined hereinabove. In further subgroups L$_4$ is a bond; G$_2$ is

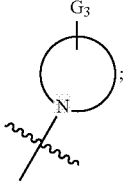

R$_M$ is each independently fluoro, chloro, methyl, methoxy, trifluoromethyl, or trifluoromethoxy; and g is 0, 1, or 2. In particular subgroups,

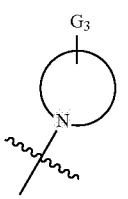

is 3-phenylazetidin-1-yl, 3-phenylpyrrolidin-1-yl, 4-phenylpiperazin-1-yl, 4-phenylpiperidin-1-yl, 4-phenyl-3,6-dihydropyridin-1(2H)-yl, 4,4-diphenylpiperidin-1-yl, 4-acetyl-4-phenylpiperidin-1-yl, 4-(4-methoxyphenyl)piperidin-1-yl, 4-(4-fluorophenyl)piperidin-1-yl, or 3-phenylpiperidin-1-yl; $R_M$ is each independently fluoro, chloro, methyl, methoxy, trifluoromethyl, or trifluoromethoxy; and g is 0, 1, or 2. In other subgroups $L_4$ is $C_1$-$C_6$alkylene, —O—, or —S(O)$_2$—; $G_2$ is

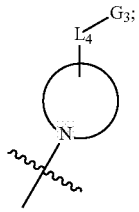

$R_M$ is each independently fluoro, chloro, methyl, methoxy, trifluoromethyl, or trifluoromethoxy; and g is 0, 1, or 2. In particular subgroups,

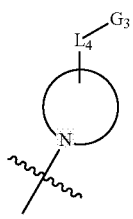

is 4-tosylpiperazin-1-yl, 4-phenoxypiperidin-1-yl, 3-phenoxypyrrolidin-1-yl, 4-benzylpiperidin-1-yl, 4-phenethylpiperidin-1-yl, or 3-phenylpropyl)piperidin-1-yl; $R_M$ is each independently fluoro, chloro, methyl, methoxy, trifluoromethyl, or trifluoromethoxy; and g is 0, 1, or 2. In further subgroups of compounds D is

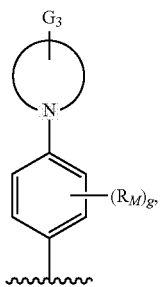

wherein $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

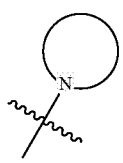

and $R_{G3}$ are as defined above. In other groups of compounds D is

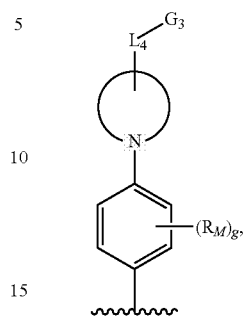

wherein $L_4$ is $C_1$-$C_6$alkylene, —O—, or —S(O)$_2$—; $G_3$ is phenyl optionally substituted with one or two $R_{G3}$; g is 0, 1, or 2; $R_M$ is each independently fluoro, chloro, methyl, methoxy, trifluoromethyl, or trifluoromethoxy; and

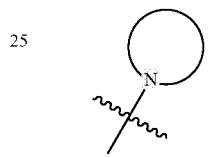

and $R_{G3}$ are as defined above. In further subgroups of compounds D is

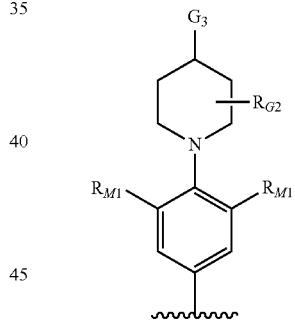

wherein $G_3$ is phenyl optionally substituted with one or two $R_{G3}$ as defined hereinabove; $R_{M1}$ is each independently hydrogen, fluoro, chloro, or methyl; and $R_{G2}$ is an optional substituent, as described above, selected from the group consisting of —C(O)C$_1$-C$_6$alkyl, —C$_1$-C$_6$alkyl, —C$_1$-C$_6$haloalkyl, —O—C$_1$-C$_6$alkyl, and —O—C$_1$-C$_6$haloalkyl.

In other groups of compounds according Formula $I_G$ and the foregoing embodiments and description of this aspect of the invention, D is

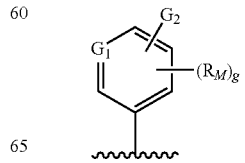

wherein G$_1$ is N, C—H, or C—R$_M$; G$_2$ is

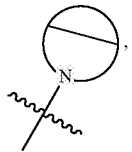

wherein

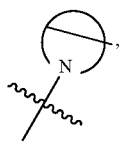

R$_M$, and g are as defined hereinabove. In particular according to these subgroups, R$_M$ is each independently fluoro, chloro, methyl, methoxy, trifluoromethyl, or trifluoromethoxy; g is 0, 1, or 2; and

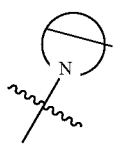 [SMILES: *N]

is 3-azabicyclo[3.2.0]hept-3-yl, 2-azabicyclo[2.2.2]oct-2-yl, 6-azaspiro[2.5]oct-6-yl, octahydro-2H-isoindol-2-yl, 3-azaspiro[5.5]undec-3-yl, 1,3-dihydro-2H-isoindol-2-yl, or 1,4-dioxa-8-azaspiro[4.5]dec-8-yl. In further subgroups of compounds D is

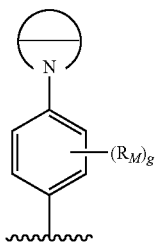

wherein g is 0, 1, or 2; R$_M$ is each independently fluoro, chloro, methyl, methoxy, trifluoromethyl, or trifluoromethoxy; and

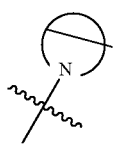

is as defined above. In further subgroups of compounds D is

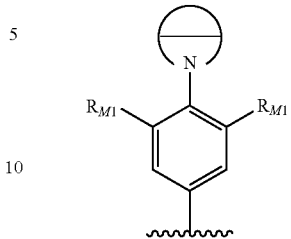

wherein R$_{M1}$ is each independently hydrogen, fluoro, chloro, or methyl and

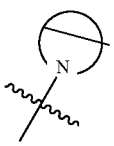

is as defined above (e.g., 3-azabicyclo[3.2.0]hept-3-yl, octahydro-2H-isoindol-2-yl, 2-azabicyclo[2.2.2]oct-2-yl, 6-azaspiro[2.5]oct-6-yl, 3-azaspiro[5.5]undec-3-yl, 1,3-dihydro-2H-isoindol-2-yl, 1,4-dioxa-8-azaspiro[4.5]dec-8-yl).

In other groups of compounds according Formula I$_G$ and the foregoing embodiments and description of this aspect of the invention, D is

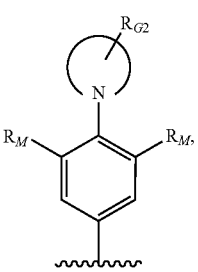

wherein

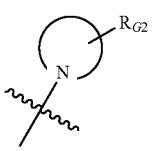

is a monocyclic 4-8 membered nitrogen-containing heterocycle (e.g., azetidinyl, pyrrolidinyl, piperidinyl) substituted with one or more R$_{G2}$, wherein R$_{G2}$ at each occurrence is each independently halogen, —C(O)C$_1$-C$_6$alkyl, —C$_1$-C$_6$alkyl, —C$_1$-C$_6$haloalkyl, —O—C$_1$-C$_6$alkyl, or —O—C$_1$-C$_6$haloalkyl; and R$_M$ is each independently halogen, —C$_1$-C$_6$alkyl, —C$_1$-C$_6$haloalkyl, —O—C$_1$-C$_6$alkyl, or —O—C$_1$-C$_6$haloalkyl. In each group of compounds according to the foregoing embodiments

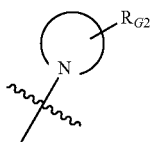

is azetidinyl, pyrrolidinyl, or piperidinyl substituted with one or two $R_{G2}$, wherein $R_{G2}$ at each occurrence is each methyl, ethyl, isopropyl, tert-butyl, fluoro, chloro, or trifluoromethyl; and $R_M$ is each independently fluoro, chloro, or methyl. For example

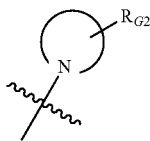

is 4,4-dimethylpiperidin-1-yl, 4,4-difluoropiperidin-1-yl, 2,6-dimethylpiperidin-1-yl, 4-(propan-2-yl)piperidin-1-yl, 4-fluoropiperidin-1-yl, 3,5-dimethylpiperidin-1-yl, 4-(trifluoromethyl)piperidin-1-yl, 4-methylpiperidin-1-yl, 4-tert-butylpiperidin-1-yl, 2-oxopiperidin-1-yl, or 3,3-dimethylazetidin-1-yl.

The present invention also features compounds of Formulae $I_E$, $I_F$ and $I_G$ as described herein (including each embodiment described hereunder) and pharmaceutically acceptable salts thereof, wherein:

$R_E$ is independently selected at each occurrence from —O—$R_S$, —S—$R_S$, —C(O)$R_S$, —OC(O)$R_S$, —C(O)O$R_S$, —N($R_S R_S'$), —S(O)$R_S$, —SO$_2 R_S$, —C(O)N($R_S R_S'$), —N($R_S$)C(O)$R_S'$, —N($R_S$)C(O)N($R_S' R_S''$), —N($R_S$)SO$_2 R_S'$, —SO$_2$N($R_S R_S'$), —N($R_S$)SO$_2$N($R_S' R_S''$), —N($R_S$)S(O)N($R_S' R_S''$), —OS(O)—$R_S$, —OS(O)$_2$—$R_S$, —S(O)$_2$O$R_S$, —S(O)O$R_S$, —OC(O)O$R_S$, —N($R_S$)C(O)O$R_S'$, —OC(O)N($R_S R_S'$), —N($R_S$)S(O)—$R_S'$, —S(O)N($R_S R_S'$), —P(O)(O$R_S$)$_2$, =C($R_S R_S'$), or —C(O)N($R_S$)C(O)—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_{12}$carbocycle or 3- to 12-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, trimethylsilyl, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, —O—$R_S$, —S—$R_S$, —C(O)$R_S$, —C(O)O$R_S$, or —N($R_S R_S'$).

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibutyl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer;

and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The invention encompasses each conformational isomer of these compounds and mixtures thereof.

Certain compounds of the invention may also exist in zwitterionic form and the invention encompasses each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., A, B, D, X, $L_1$, $L_2$, $L_3$, Y, Z, T, $R_A$ or $R_B$). Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties.

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$ cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$carbocyclyl$C_1$-$C_6$alkyl refers to a $C_3$-$C_6$carbocyclyl appended to the parent molecular moiety through a $C_1$-$C_6$alkyl group.

Unless otherwise specified, when a linking element links two other elements in a depicted chemical structure, the leftmost-described component of the linking element is bound to the left element in the depicted structure, and the rightmost-described component of the linking element is bound to the right element in the depicted structure. To illustrate, if the chemical structure is -$L_S$-M-$L_S$'- and M is —N($R_B$)S(O)—, then the chemical structure is -$L_S$-N($R_B$)S(O)-$L_S$'-.

If a linking element in a depicted structure is a bond, then the element left to the linking element is joined directly to the element right to the linking element via a covalent bond. For example, if a chemical structure is depicted as -$L_S$-M-$L_S$'- and M is selected as bond, then the chemical structure will be -$L_S$-$L_S$'-. If two or more adjacent linking elements in a depicted structure are bonds, then the element left to these linking elements is joined directly to the element right to these linking elements via a covalent bond. For instance, if a chemical structure is depicted as -$L_S$-M-$L_S$'-M'-$L_S$"-, and M and $L_S$' are selected as bonds, then the chemical structure will be -$L_S$-M'-$L_S$"-. Likewise, if a chemical structure is depicted as -$L_S$-M-$L_S$'-M'-$L_S$"-, and M, $L_S$' and M' are bonds, then the chemical structure will be -$L_S$-$L_S$"-.

When a chemical formula is used to describe a moiety, the dash(s) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)═C(H)—, —C(H)═C(H)—CH$_2$—, —C(H)═C(H)—CH$_2$—CH$_2$—, —CH$_2$—C(H)═C(H)—CH$_2$—, —C(H)═C(H)—CH(CH$_3$)—, and —CH$_2$—C(H)═C(H)—CH(CH$_2$CH$_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple bonds. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—CH(CH$_2$CH$_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom. Where a carbocycle group is a divalent moiety linking two other elements in a depicted chemical structure (such as A in Formula I), the carbocycle group can be attached to the two other elements through any two substitutable ring atoms. Likewise, where a carbocycle group is a trivalent moiety linking three other elements in a depicted chemical structure (such as X in Formula I), the carbocycle group can be attached to the three other elements through any three substitutable ring atoms, respectively.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group. Where a heterocycle group is a divalent moiety that links two other elements in a depicted chemical structure (such as A in Formula I), the heterocycle group can be attached to the two other elements through any two substitutable ring atoms. Likewise, where a heterocycle group is a trivalent moiety that links three other elements in a depicted chemical structure (such as X in Formula I), the heterocycle group can be attached to the three other elements through any three substitutable ring atoms, respectively.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl"), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, thiomorpholinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzopyrazolyl" or indazolyl), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, 4,5,6,7-tetrahydrobenzo[d]thiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may also be, without limitation, a spiro ring system, such as, for example, 1,4-dioxa-8-azaspiro[4.5]decanyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

═══ in a chemical formula refers to a single or double bond.

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, PROTECTIVE GROUPS IN ORGANIC SYNTHESIS ($3^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

Abbreviations which have been used in the descriptions of the Schemes, Intermediates and Examples that follow are: Ac for acetyl; aq or aq. for aqueous; Boc for t-butoxycarbonyl; Bu for butyl; n-Bu or n-butyl; t-Bu or tert-butyl or tertiary-butyl; Cbz for benzyloxycarbonyl; DCI for desorption chemical ionization; DEPBT for 3-(diethoxyphosphoryloxy)-1,2,3-benzotriazin-4(3H)-one; DME for 1,2-dimethoxyethane; DMF for N,N-dimethylformamide; DMSO for dimethyl sulfoxide; dppf for 1,1'-bis(diphenylphosphino)ferrocene; EDC, EDAC or EDCI for N-(3-dimethylaminopropyl)-N'-ethylcarbodiimide hydrochloride; ESI for electrospray ionization; Et for ethyl; EtOAc for ethyl acetate; EtOH for ethanol; Et$_2$O for diethyl ether; eq or equiv for equivalents; Fmoc for 9-fluorenylmethoxycarbonyl; HATU for O-(7-azabenzotriazol-1-yl)-N,N,N',N'-tetramethyluronium hexafluorophosphate; HMDS for hexamethyldisilazane; HOBt for 1-hydroxybenzotriazole; HPLC for high performance liquid chromatography; LCMS for liquid chromatography/mass spectrometry; Me for methyl; MeOH for methanol; NBS for N-bromosuccinimide; OAc for acetate; OTf for triflate or trifluoromethanesulfonate; PA-Ph for 1,3,5,7-tetramethyl-2,4,8-trioxa-6-phenyl-6-phosphaadamantane; Ph for phenyl; psi or psig for pounds per square inch (gas); PyBOP® for (benzotriazol-1-yloxy)tripyrrolidinophosphonium hexafluorophosphate; SEM for 2-(trimethylsilyl)ethoxymethyl; T3P for propane phosphonic acid anhydride; Tf for trifluorosulfonyl; TFA for trifluoroacetic acid; THF for tetrahydrofuran; Troc for 2,2,2-trichloroethoxycarbonyl; v/v for volume/volume; wt % for weight percent; and w/v for weight/volume.

As another non-limiting example, the compounds of the present invention can be prepared as shown in Scheme I. The diamine (I-1) may be reacted with a suitably protected proline acid [t-butoxycarbonyl (Boc) is shown, although benzyloxycarbonyl (Cbz), 2,2,2-trichloroethoxycarbonyl (Troc), or 9-fluorenylmethoxycarbonyl (Fmoc) may be substituted] in the presence of a peptide coupling reagent, such as N-(3-dimethylaminopropyl)-N'-ethylcarbodiimide hydrochloride/ 1-hydroxybenzotriazole [EDAC/HOBT], (benzotriazol-1-yloxy)tripyrrolidinophosphonium hexafluorophosphate [PyBOP®], O-(7-azabenzotriazol-1-yl)-N,N,N',N'-tetramethyluronium hexafluorophosphate [HATU], or 3-(diethoxyphosphoryloxy)-1,2,3-benzotriazin-4(3H)-one [DEPBT], in a solvent such as tetrahydrofuran, N,N-dimethylformamide, dichloromethane, or dimethyl sulfoxide, with or without the addition of an amine base such as Hunig's base, pyridine, 2,6-lutidine, 4-methylmorpholine, or triethylamine, to give (I-2). Reaction of an aldehydes of formula (I-3) with the anion of trialkyltin such as tri-n-butyltin, followed by reaction with a chloroformate such as methyl chloroformate, in organic solvents such as tetrahydrofuran, dioxane or dichloromethane wherein R$_P$ is non-electron-withdrawing substituent such as alkyl (methyl, ethyl, etc.), benzyl (e.g., benzyl, 4-methoxybenzyl, etc.), trialkylsilyl (e.g., triisopropylsilyl); R$^I$ is an alkyl group; R$_A$ is alkyl, alkoxy, halo, haloalkyl, or haloalkoxy, and n is 0, 1, 2, 3, or 4 can give compounds of formula (I-4). The alkene (I-2) may be reacted with 1 to 5 equivalents or more of compounds of formula (I-4) in the presence of a suitable acid such as toluene sulfonic acid or other reagents such as boron trifluoride etherate in organic solvents such as dichloromethane or toluene to give cyclopropane compounds of formula (I-5) [Sugawara, M.; et al. J. Am. Chem. Soc. 1997, 119, 11986]. Removal of the t-butoxycarbonyl (Boc) protecting groups to give (I-6) may be accomplished by treatment with an acid, such as trifluoroacetic acid, HCl, or formic acid. Compounds of the present invention I-7), wherein T and R$_D$ are as described above, may be prepared by coupling of (I-6) with an acid of choice using the standard peptide coupling reagents and conditions described above.

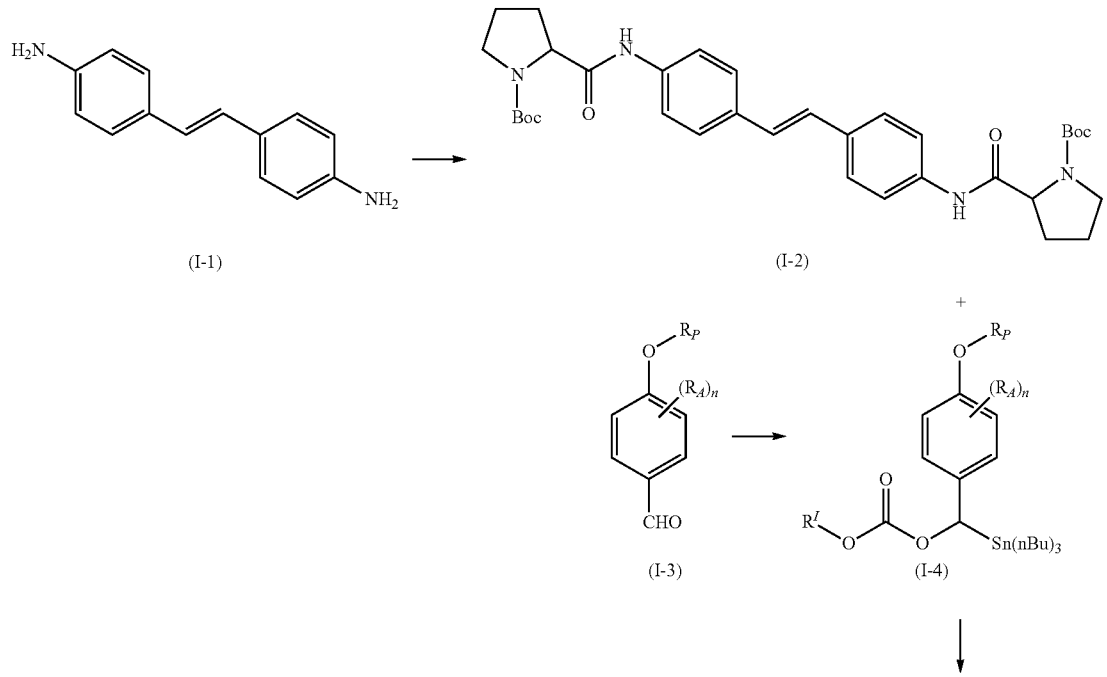

Scheme I 205 206
-continued
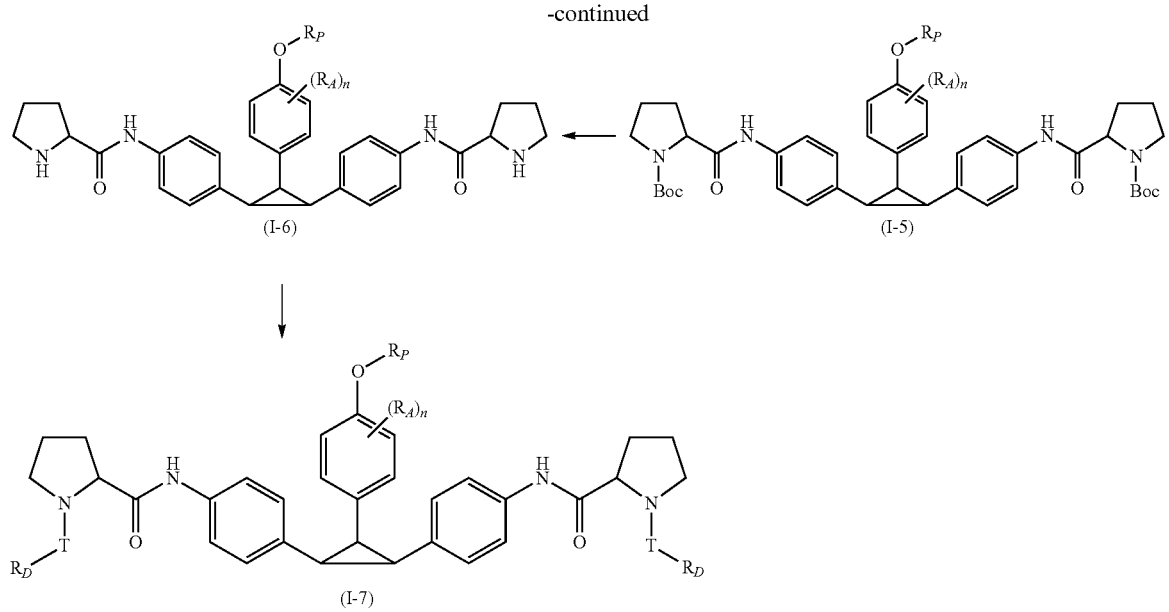
Certain compounds of the invention (II-7) optionally substituted with 1, 2, 3, or 4 groups $R_A$; where $R_A$ and $R_P$ are as defined in Scheme I: and $R_D$ and T are as described above, can be prepared according to the general method illustrated in Scheme II.
Scheme II
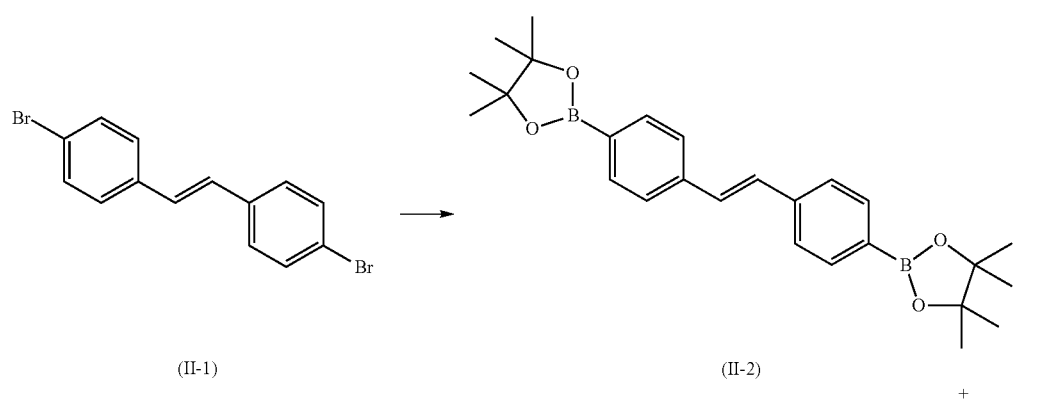
(II-1)   (II-2)
+
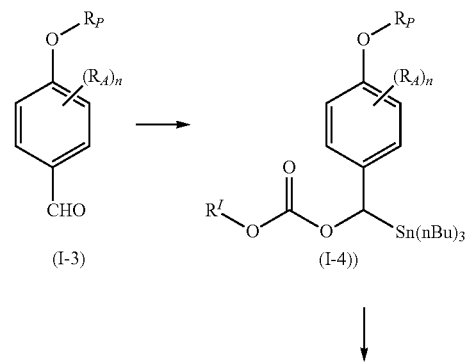
(I-3)   (I-4))

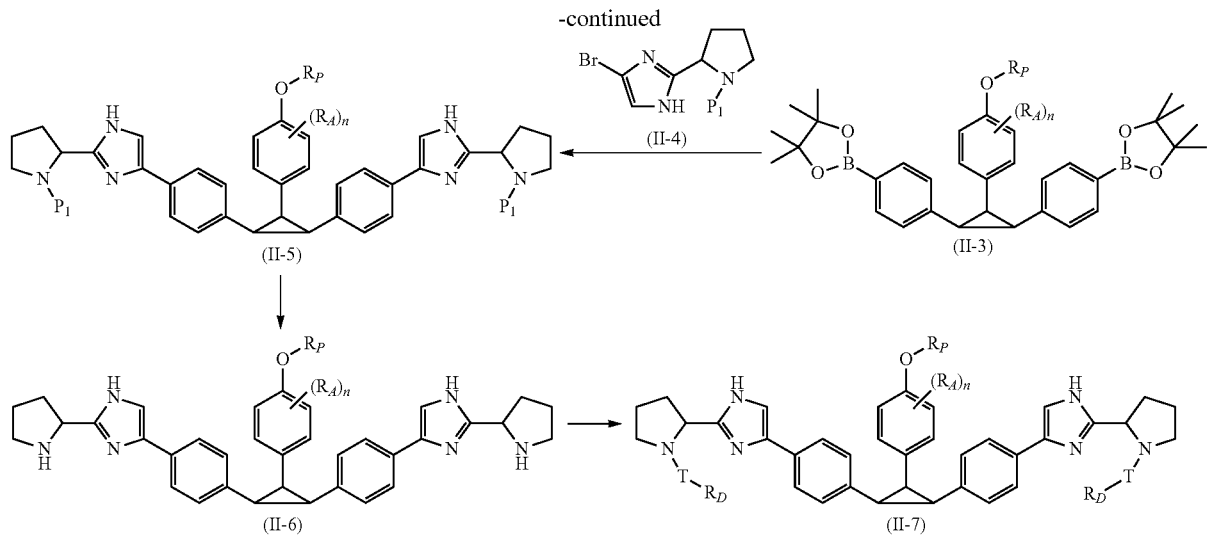

(II-5)   (II-3)

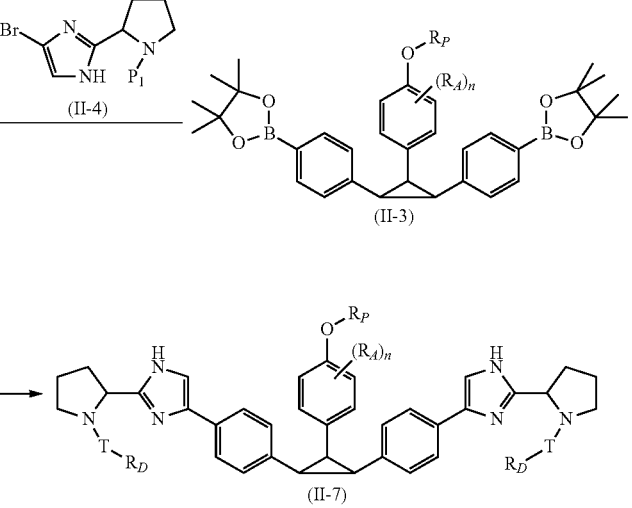

(II-6)   (II-7)

Dibromostilbene (II-1) can be reacted with bis(pinacolato) diboron with potassium acetate in solvents such as, but not limited to, toluene at temperatures from about 80° C. to about 120° C. to give alkene (II-2). The alkene (II-2) may be reacted with 1 to 5 equivalents or more of compounds of formula (I-4) in the presence of a suitable acid such as toluene sulfonic acid or other reagents such as boron trifluoride etherate in organic solvents such as dichloromethane or toluene to give cyclopropane compounds of formula (II-3). The cyclopropane compounds (II-3) can be reacted with bromoimidazoles (II-4), wherein $P_1$ is a nitrogen-protecting group, using Suzuki reaction conditions to give the phenylimidazole (II-5). A variety of reaction conditions are well known to those of skill in the art to be effective in mediating the Suzuki reaction. In particular, the reaction of (II-3) with (II-4) to produce (II-5) can be performed with [1,1'-bis(diphenylphosphino)ferrocene]dichloropalladium(II) [Pd(dppf)Cl$_2$] catalyst and potassium carbonate in a mixture of toluene and water and with heating to about 100° C. Removal of the protecting groups to give (II-6) may be accomplished using methodologies known to one skilled in the art and dependent upon the particular protecting group used. Compounds of the present invention (II-7), wherein T, and $R_D$ are as described above, may be prepared by coupling of (II-6) with an appropriately functionalized amino acid derivative using the standard peptide coupling reagents and conditions described above.

The intermediate of general formula (II-4), wherein $P_1$ is a nitrogen protecting group as described hereinabove, can be prepared using the general method in Scheme III.

Scheme III

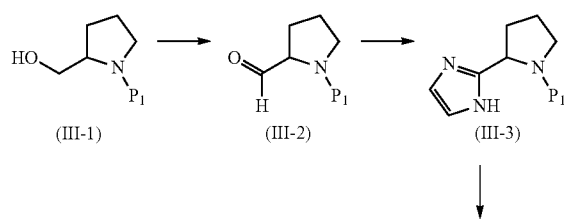

(III-1)   (III-2)   (III-3)

↓

-continued

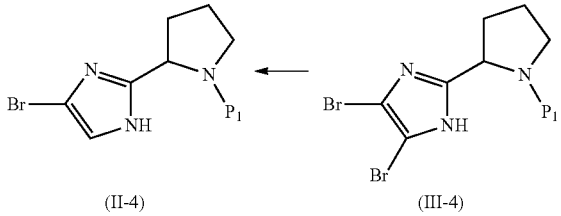

(II-4)   (III-4)

Alcohols (III-1) can be oxidized to aldehydes (III-2) using well-known methods such as, for example, reacting the alcohols (III-1) with Dess-Martin periodinane in the presence of sodium bicarbonate in a solvent such as, but not limited to, dichloromethane. Compounds (III-2) can be reacted with glyoxal and ammonium hydroxide in methanol/water to give (III-3). Compounds (III-3), in turn can be brominated using N-bromosuccinimide in solvents such as, but not limited to, dichloromethane at temperatures from 0° C. to room temperature to give (III-4). Compounds (III-4) can be monodebrominated by reaction with sodium sulfite (Na$_2$SO$_3$) in a mixture of dioxane and water with heating to reflux to give intermediates (II-4). Although no particular stereochemistry is designated for intermediate (II-4), the foregoing chemical methods can be used to prepare (II-4) as a racemate or a single enantiomer (R or S stereochemistry). The choice of (R) or (S) stereochemistry in the starting alcohol (III-1) will lead to compounds of the invention having a single absolute stereochemistry at the corresponding carbon of the final compound.

Benzimidazole derivatives of general structural formula (VI-2) can be prepared by synthetic sequences summarized in Schemes IV-VI. As shown in Scheme IV, the requisite stilbene derivative (IV-6) can be prepared starting by treatment of bromide (IV-1) with di-tert-butyl dicarbonate in the presence of a suitable base such as, but not limited to, aqueous sodium bicarbonate solution, to afford bis-t-butoxycarbonyl protected (IV-2). Bromide (IV-2) is reacted with an acetylene derivative such as trimethylsilylacetylene under Sonogashira conditions using a suitable palladium catalyst such as bis(triphenylphosphine)palladium (II) chloride in the presence of a copper salt, such as, but not limited to, copper (I) iodide, and a suitable amine base, such as triethylamine or diisopropyl amine. Acetylene (IV-3) so obtained is then deprotected by treatment with a suitable alcoholic base, such as potassium carbonate or potassium hydroxide, or by treatment with fluoride ion, in the form of tetrabutylammonium fluoride to afford acetylene derivative (IV-4). Boronate (IV-5) is prepared by hydroboration of (IV-4) with diisopinocampheylborane followed by reaction of the resulting trialkylborane with an aldehyde, such as acetaldehyde, and aqueous hydrolysis of the dialkyl borate to afford boronic acid (IV-5). Stilbene (IV-6) can then be obtained from the Suzuki-Miyaura coupling of boronic acid (IV-5) with bromide (IV-2), catalyzed by either a palladium (II) salt or a palladium (0) source, such as tris(dibenzylideneacetone)dipalladium (0) or the like in conjunction with a phosphine ligand, preferably with a Cytec® phenyl phosphaadamantyl ligand (PA-Ph) (Adjabeng, J., et al. Org. Lett. 2003, 5, 953; Adjabeng, J., et al. J. Org. Chem. 2004, 69, 5082) in the presence of an aqueous base, such as tribasic potassium phosphate, potassium carbonate, or the like, in a suitable solvent, such as tetrahydrofuran, dimethoxyethane, or the like.

As shown in Scheme V, stilbene (IV-6) can then be reacted with stannane (I-4) in the presence of a Lewis acid such as boron trifluoride etherate in solvents such as toluene or dichloromethane (or mixtures thereof) to afford cyclopropane (V-1). Cyclopropane derivative (V-1) can be transformed to the benzimidazole ring system by the sequence of transformations summarized in Schemes V and VI. Treatment of (V-1) with a number of acid conditions known to those skilled in the art affords the tetraamine (V-2). Tetraamine (V-2) can be coupled with two equivalents of a suitably protected proline acid (t-butoxycarbonyl (Boc) is shown, other protecting groups such as benzyloxycarbonyl or 9-fluorenylmethoxycarbonyl would also be useful) using preferably coupling agent O-(7-azabenzotriazol-1-yl)-N,N,N',N'-tetramethyluronium hexafluorophosphate (HATU) in the presence of an amine base such as diisopropylethylamine or N-methylmorpholine, or other coupling agents known to those skilled in the art, to afford the two regioisomeric anilides (V-3) and (V-4). The regioisomeric anilides are not separated, but directly cyclized to (V-6) by treatment with 5-10 equivalents of glacial acetic acid in toluene or tetrahydrofuran (or mixtures thereof) at a temperature in the range of 50-85° C.

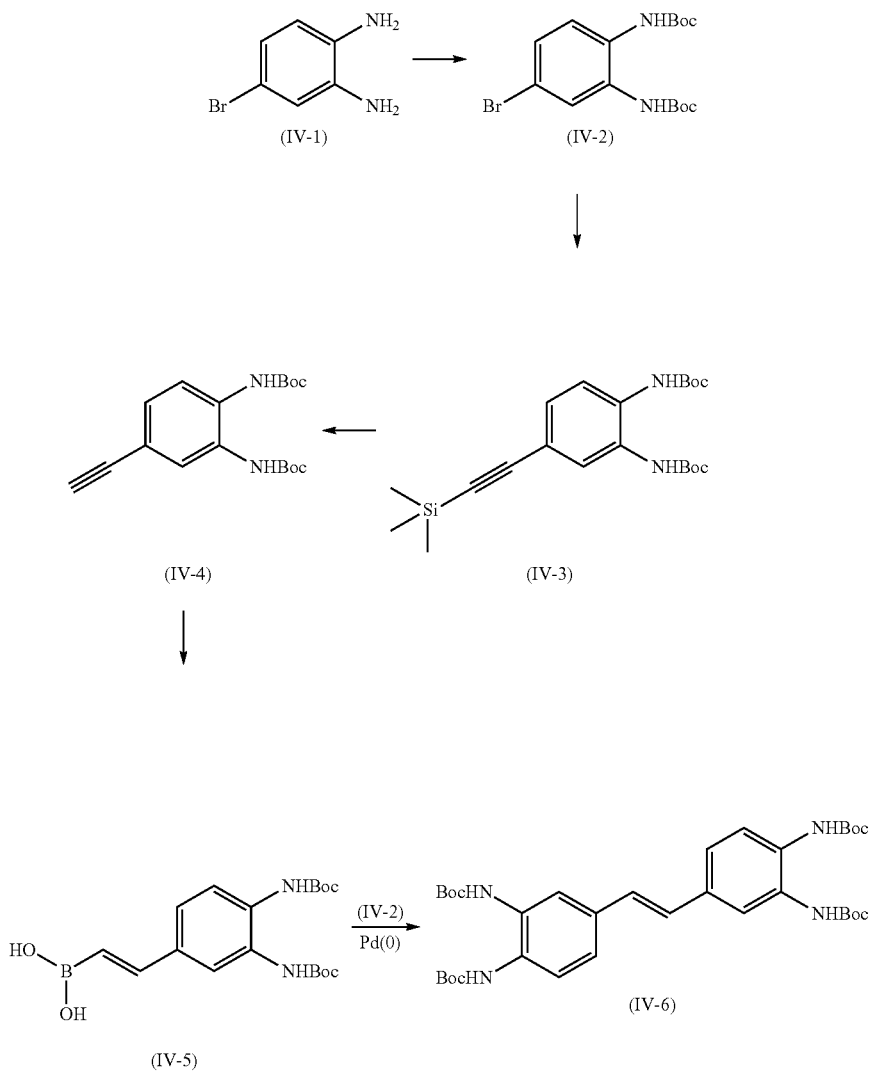

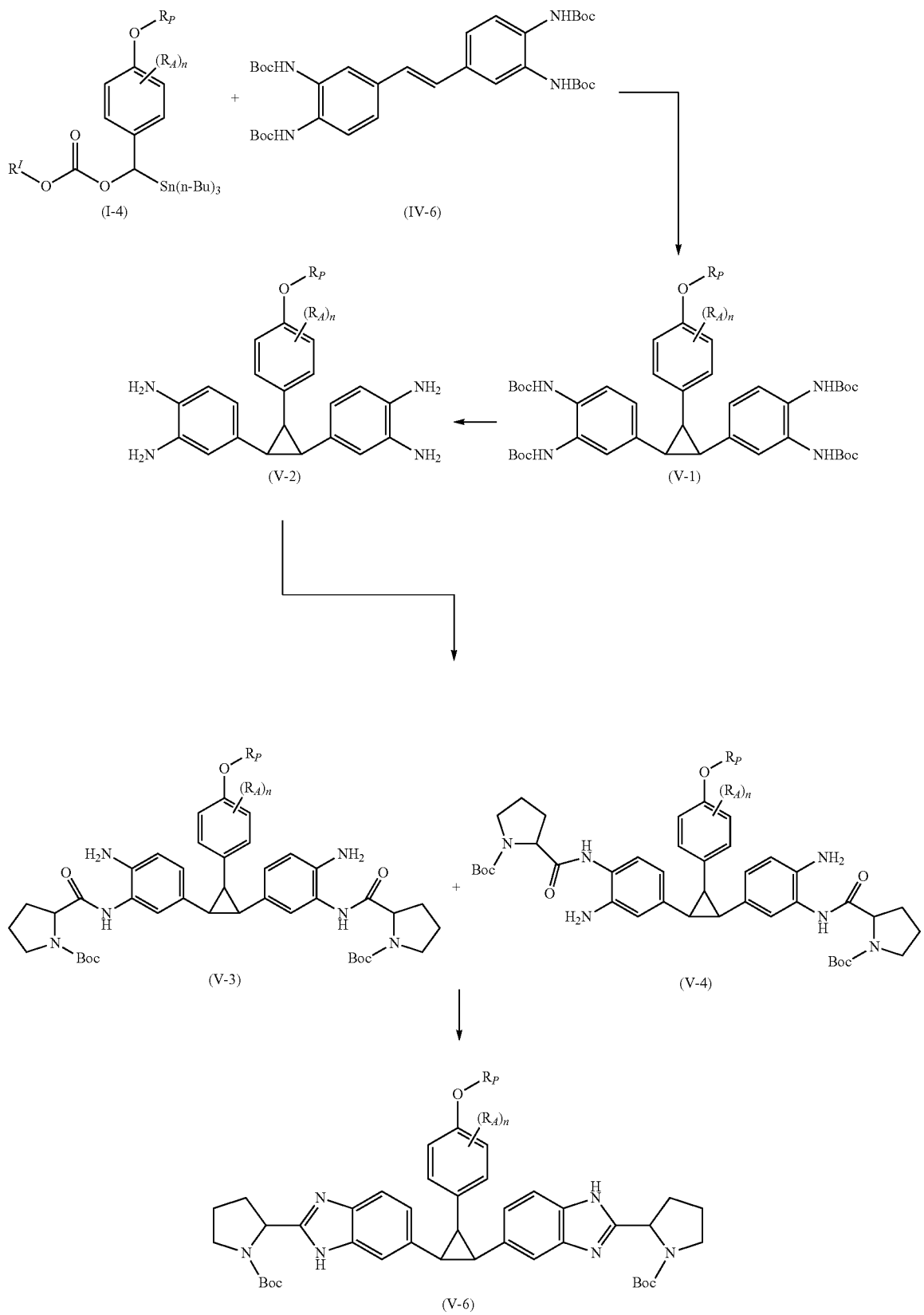

Benzimidazole (V-6) can be transformed to representative compounds of this invention by the sequence of transformations shown in Scheme VI. As shown, treatment of (V-6) with a suitable acid removes the two t-butoxycarbonyl (Boc) protecting groups to afford diamine (VI-1). Diamine (VI-1) can then be coupled with two equivalents of an appropriately functionalized amino acid derivative, by use of amino acid coupling methods known to those skilled in the art to afford final benzimidazole derivative (VI-2), wherein $R_A$ and $R_P$ are as defined in Scheme I and n, $R_D$ and T are as defined above.

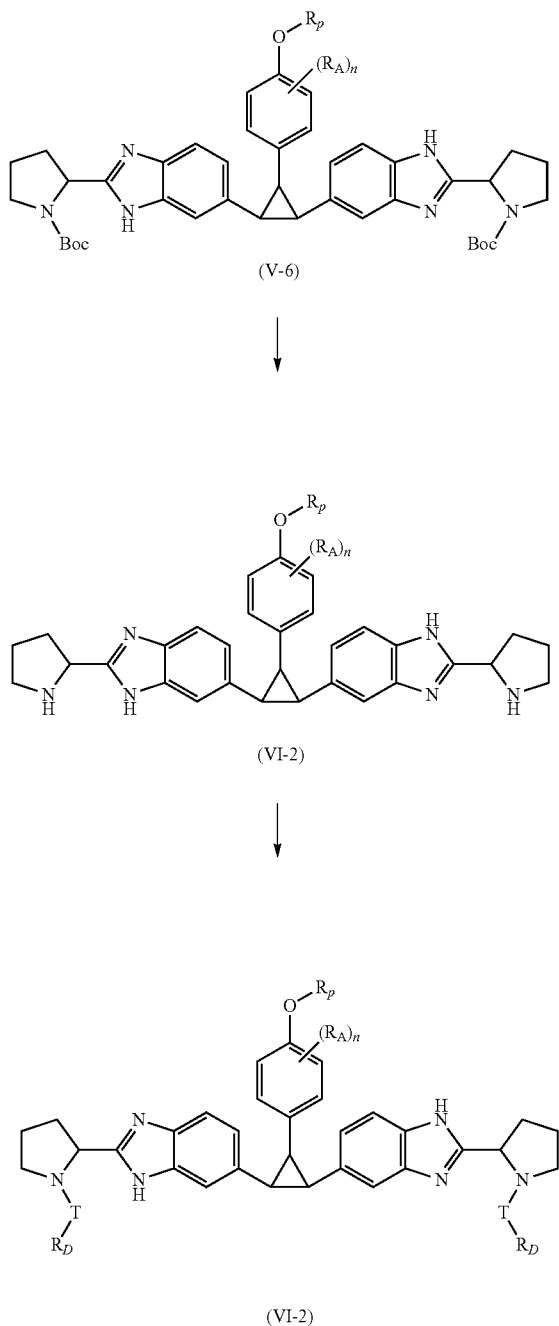

Scheme VI (V-6)

(VI-2)

(VI-2)

Further compounds of the invention may be prepared according to the methods outlined in Scheme VII. Compounds (VII-1), where R is a group such as benzyl, 4-methoxybenzyl, 3,4-dimethoxybenzyl, methyl, triisopropylsilyl, etc., may be converted to compounds (VII-2) using standard conditions known to remove these groups from a phenolic oxygen. For example, where R is benzyl or methyl, (VII-1) may be converted to (VII-2) by treatment with $BBr_3$. Where R is triisopropylsilyl, (VII-1) may be converted to (VII-2) by reaction with a fluoride source. Compounds (VII-2) can be converted to compounds (VII-3) by reaction with a triflating source such as triflic anhydride. Compounds (VII-3) may be converted to further compounds of the invention using well-known organic transformations of aromatic triflates such as Suzuki, Sonogashira, or Buchwald reactions. Using a Suzuki reaction, (VII-3) may be converted to compounds (VII-4), wherein $R_{100}$ is group such as alkenyl, aryl, heteroaryl, or cycloalkenyl, by reaction with a suitable boronic acid or ester $R_{100}B(OR')_2$, wherein R' is hydrogen, alkyl, or together with the oxygen atoms and adjacent boron atom to which they are attached form a dioxaborolane or a dioxaborinane, such as, but not limited to, 1-cyclohexen-yl-boronic acid pinacol ester or other boronic acids/esters, in the presence of a source of palladium and phosphine ligand (e.g., $PdCl_2[dppf]_2$) and base (e.g., triethylamine, sodium carbonate, potassium carbonate, potassium phosphate, sodium bicarbonate), in solvents such as, but not limited to, DME and water at temperatures from about 80° C. to about 100° C. The compounds (VII-4) derived from Suzuki reaction with an alkeneboronic acid/ester or cycloalkenylboronic acid/ester and having an alkene in the $R_{100}$ group may be further elaborated to compounds of the invention by reaction of the alkene present in $R_{100}$ (e.g. reduction by catalytic hydrogenation). A variety of reaction conditions are well known to those of skill in the art to be effective in mediating the Suzuki reaction. Other substrates utilized in the Suzuki reaction such as aromatic, heteroaromatic, or heterocyclic boronates or boronic acids may provide compounds (VII-4) having heteroaryl, heterocyclic, or aryl groups at $R_{100}$. Suitably substituted amines may combine with a triflate (VII-3) in a Buchwald-type reaction to provide compounds (VII-5), wherein $R_{101}$ and $R_{102}$ are each alkyl or taken together with the nitrogen atom to which they are attached form a heterocycloalkyl. Suitable conditions for effecting this transformation may be found in the following references: Wolfe and Buchwald, *J. Org. Chem.* 1997, 1264-1267; Louie et al, *J. Org. Chem.* 1997, 1268-1273; Peng, T.; Yang, D. *Organic Lett.* 2010, 12, 496-499; Hartwig, J. F. in *Handbook of Organopalladium Chemistry for Organic Synthesis*; Negishi, E., Ed. Wiley-Interscience: New York, 2002; pp 1051-1096; Muci, A. R.; Buchwald, S. L. *Top. Curr. Chem.* 2002, 219, 131-209; Jiang, L.; Buchwald, S. L. In *Metal-Catalyzed Cross-Coupling Reactions*; De Meijere, A., Diederich, F., Eds.; Wiley-VCH: New York, 2004; pp 699-760 and references cited therein. Additionally, substituted alkynes may couple in a Sonogashira reaction with (VII-3) to provide compounds (VII-6), wherein $R_{103}$ is aryl or heteroaryl.

Scheme VII

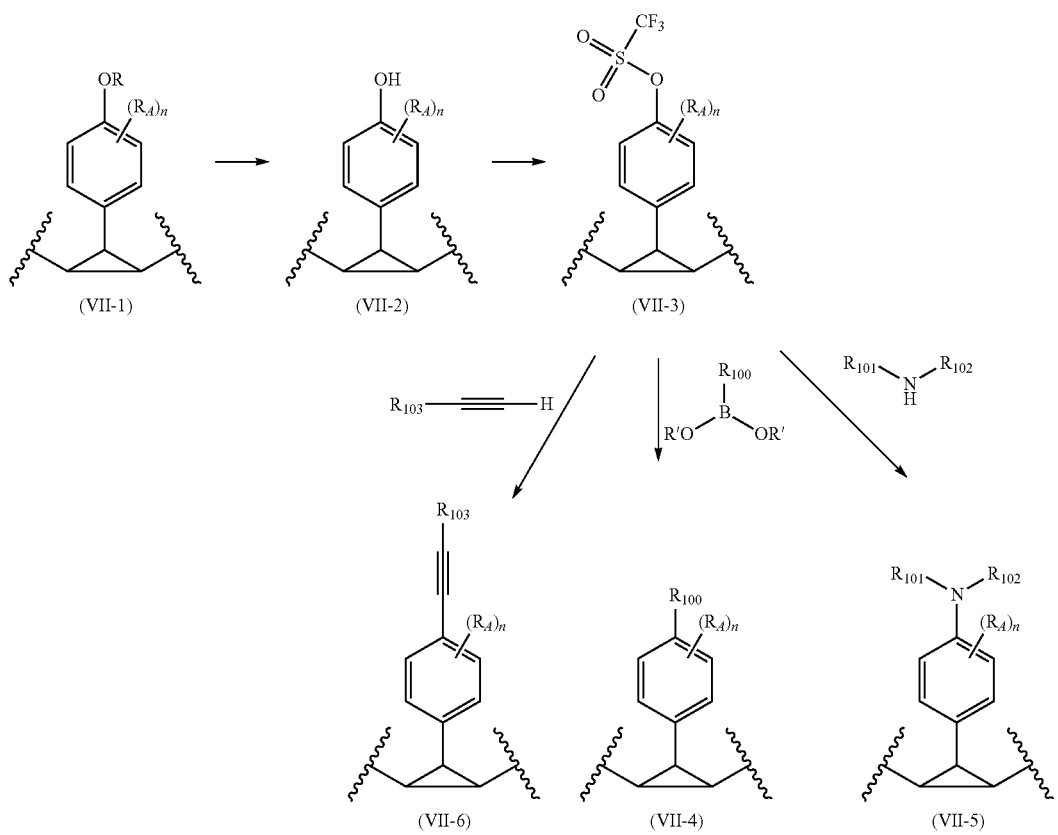

Further compounds of the invention may be prepared according to the methods outlined in Scheme VIII. Compound (VIII-1) can be converted to compound (VIII-2) as described in J. Org. Chem. 2002, 5993-6000. Compound (VIII-2) can be converted to compounds (VIII-3) by a Suzuki reaction with an appropriate boronic acid or ester using conditions such as those described in J. Org. Chem. 2002, 5993-6000 or as generally known in the art. Either an aryl or heteroaryl boronic acid or ester may be used (product of reaction with a phenyl boronic acid is shown in Scheme VIII). As further described in J. Org. Chem. 2002, 5993-6000, compounds (VIII-3) can be converted to compounds (VIII-4) by reaction with PBr$_3$. Compounds (VIII-4) may be converted to compounds (VIII-5) by reaction with 4-(tert-butoxycarbonylamino)phenylboronic acid or tert-butyl 4-(4,4,5,5-tetramethyl-1,3,2-dioxaborolan-2-yl)phenylcarbamate using Suzuki reaction conditions (see for example: J. Chem. Soc. Chem. Commun. (1994) 2305-2306; Org. Lett. (1999) 1839-1842). Compounds (VIII-5) may be converted to compounds (VIII-6) by catalytic hydrogenation using PtO$_2$ or Pd/C as described for enone reduction in Aust. J. Chem. (1997) 149-152; J. Med. Chem. (1976) 414-419 (see bottom of table III on page 417); and Org. Lett. (2009) 5450-5453 and supporting information. Compounds (VIII-6) may be converted to compounds (VIII-7) by treatment with base (e.g., NaH, LiHMDS, KHMDS) followed by reaction with (Tf)$_2$NPh as shown in the following references: Ang. Chem. Int. Ed. Eng. (2005) 403-406 and supporting information; J. Med. Chem. (2008) 8077-8087 (see Scheme 2 step iv) and supporting information. Alternatively, compounds (VIII-5) may be converted directly to compounds (VIII-7) by reduction with L-selectride or sodium selectride followed by trapping of the in-situ formed enolate with (Tf)$_2$NPh or Comins' reagent as described in the following references: see J. Org. Chem. (2007) 4616 and supporting information on page S33; also WO2007144174 on page 25; see also http://en.wikipedia.org/wiki/L-selectride. Compounds (VIII-7) may be converted to compounds (VIII-8) by a Suzuki reaction with an appropriate boronic acid or ester as described above or as generally known in the art. Compounds (VIII-8) may be converted to compounds (VIII-9) by Boc removal using standard conditions such as TFA/CH$_2$Cl$_2$ or HCl in dioxane. Compounds (VIII-9) may be converted to compounds (VIII-10) by reaction with (S)-1-(tert-butoxycarbonyl)pyrrolidine-2-carboxylic acid using standard amide bond forming techniques such as the use of a peptide coupling reagent (e.g., EDAC/HOBT, PyBOP®, HATU, T3P, or DEPBT), in a solvent such as THF, DMF, dichloromethane, or DMSO, with or without the addition of an amine base such as N-methylmorpholine, Hunig's base, pyridine, 2,6-lutidine, or triethylamine. Compounds (VIII-10) may be converted to compounds (VIII-11) using the Boc removal conditions referred to above. Compounds (VIII-11) may be converted to compounds (VIII-12) by reaction with an appropriate carboxylic acid such, but not limited to, 2-(methoxycarbonylamino)-3-methylbutanoic acid, 2-(methoxycarbonylamino)-3,3-dimethylbutanoic acid, 2-cyclohexyl-2-(methoxycarbonylamino)acetic acid, 2-(methoxycarbonylamino)-2-(tetrahydro-2H-pyran-4-yl) acetic acid, etc., using the standard amide bond forming conditions referred to above. Compounds (VIII-12) may be converted to compounds (VIII-13) by catalytic hydrogenation using catalysts such as PtO$_2$ or Pd/C under 1-4 atmospheres of hydrogen in typical organic solvents (e.g., ethyl acetate, methanol, etc).

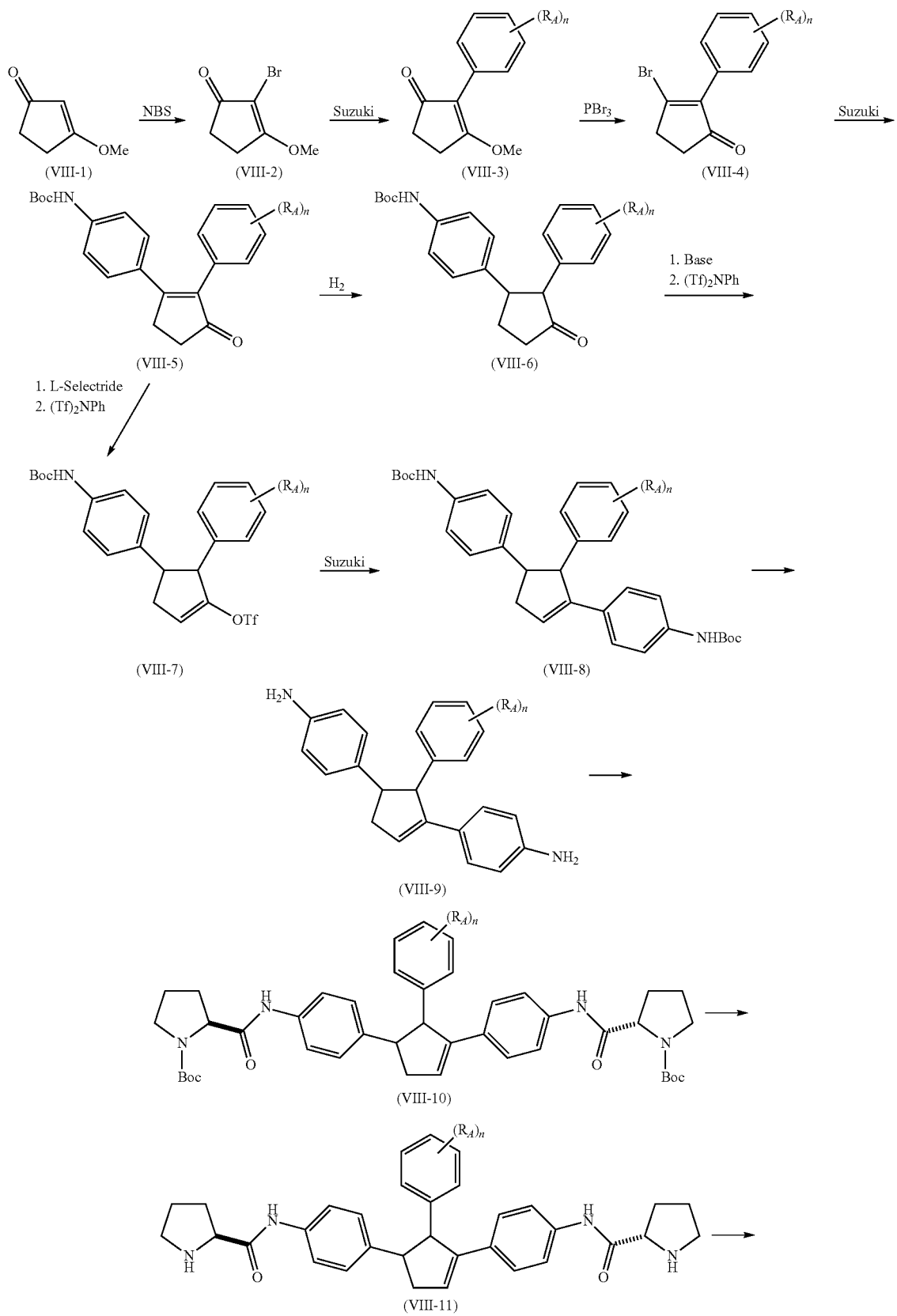

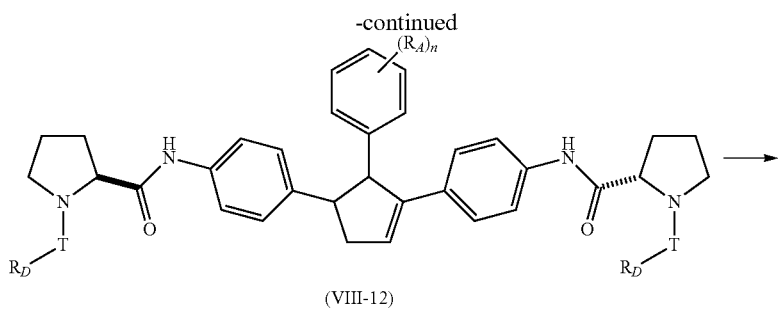

(VIII-12)

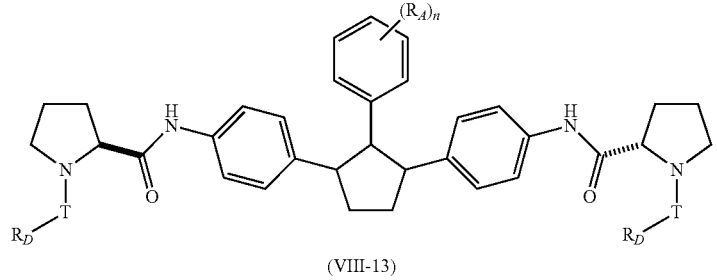

(VIII-13)

By analogy with the methods outlined in Scheme VIII, further compounds of the invention may be prepared according to the methods outlined in Scheme IX. Compounds (VIII-4) may be reacted with compound (IX-1) under standard Suzuki conditions to give compounds (IX-2). Compounds (IX-2) may be converted to compounds (IX-3) using conditions and steps analogous to those in Scheme VIII used to convert (VIII-5) to (VIII-8). Alternatively, the benzimidazole of (IX-1) and (IX-2) may be protected as a SEM derivative. Compounds (IX-3) may be converted to compounds (IX-4) by deprotection and reaction with an appropriate acid to give compounds in analogy with the methods of Scheme VIII converting (VIII-10) to (VIII-12). Analogously to the conversion of (VIII-12) to (VIII-13), compounds (IX-4) may be converted to (IX-5) by catalytic hydrogenation.

Scheme IX

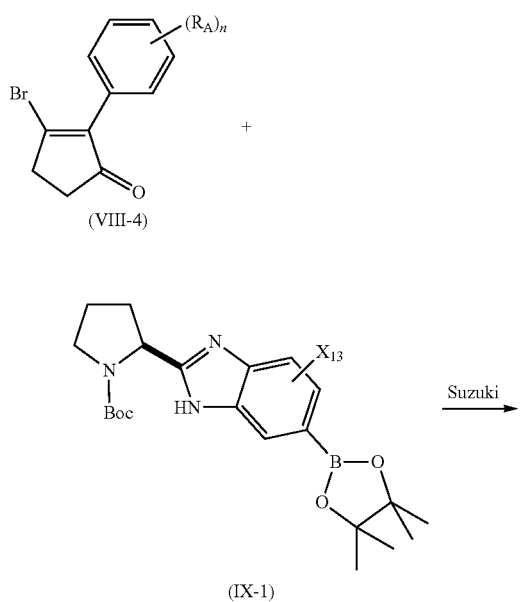

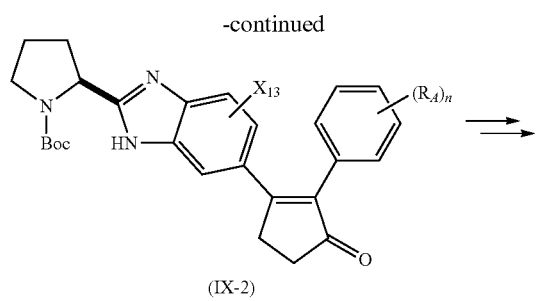

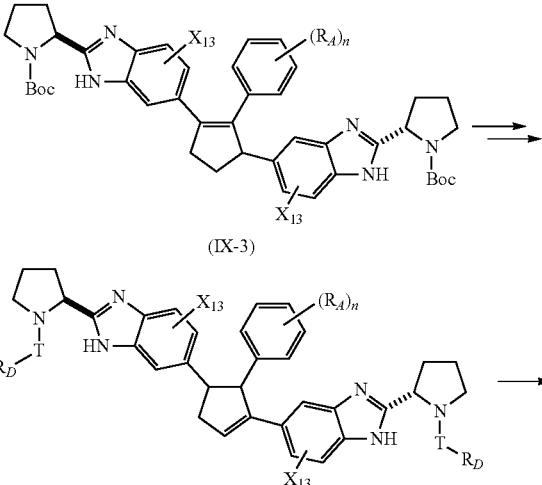

By analogy with the methods outlined in Schemes VIII and IX, further compounds of the invention may be prepared according to the methods outlined in Scheme X. Compounds (VIII-4) may be reacted with compound (X-1) under standard Suzuki conditions to give compounds (X-2). Compounds (X-2) may be converted to compounds (X-3) using conditions and steps analogous to those in Scheme VIII used to convert (VIII-5) to (VIII-8). Compounds (X-3) may be converted to compounds (X-4), having either a cyclopentene or cyclopentane core in analogy with the methods of Schemes VIII and IX.

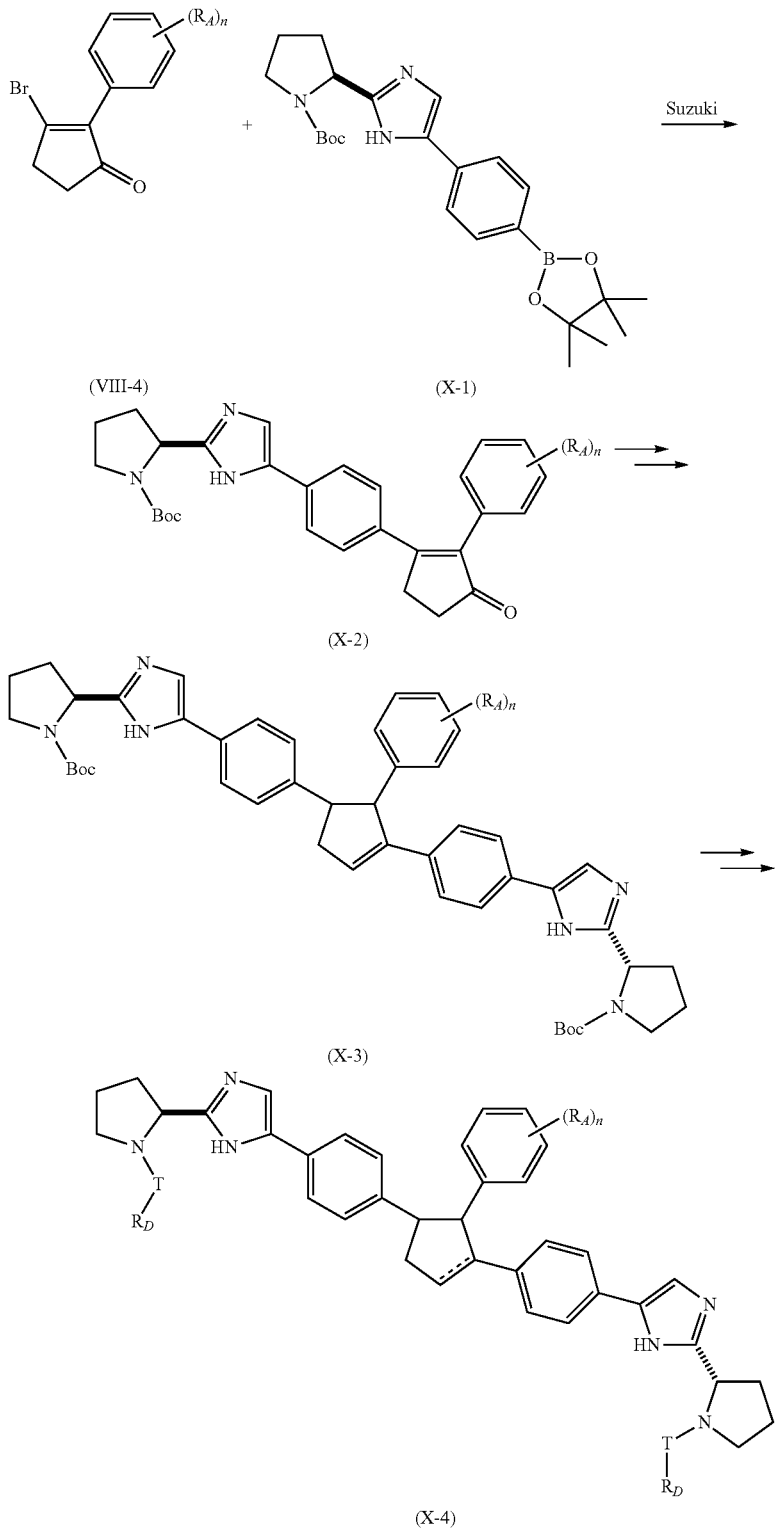

Scheme X

The foregoing Schemes VIII, IX, and X show, by way of example, the synthesis of compounds of the invention having a five-membered carbocyclic core. As is readily apparent to those skilled in the art, these methods may be modified to also prepare compounds having six- or seven-membered carbocyclic cores by selection of the appropriate starting materials such as, but not limited to, 2-bromo-3-ethoxycyclohex-2-enone (see J. Org. Chem. 1990, 4025-33) or 3-ethoxycyclohept-2-enone (see Helv. Chim. Acta 2010, 17-24, Synthesis 1995, 1432-4). The foregoing Schemes VIII-X may also be modified to produce compounds of the invention bearing different groups flanking the central core by appropriate choice of a distinct boronic acid or ester for each Suzuki reaction. For example, compounds may be prepared having a benzimidazole moiety on one side and a phenylimidazole on the other; or a benzimidazole on one side and a phenylamide on the other; or a phenylamide on one side and a phenylimidazole on the other.

Compounds (XI-1), where $X_{13}$ is alkyl, haloalkyl, alkoxy, haloalkoxy, alkoxycarbonyl, etc., can be coupled with an acid (e.g., (S)-1-(tert-butoxycarbonyl)pyrrolidine-2-carboxylic acid) using peptide coupling procedures described above to give an amide that can be heated in acetic acid to about 100° C. to give (XI-2). Compounds (XI-2) can be reacted with SEM-Cl and diisopropylethylamine in dichloromethane to give (XI-3). For convenient illustration, the SEM protecting groups on the benzimidazoles are shown attached to particular nitrogens of the benzimidazole. The actual substitution positions of the SEM groups may be at either nitrogen (i.e., (XI-3) may be a mixture of regioisomers). In subsequent compounds, the positional isomerism of the SEM group results in mixtures of SEM regioisomers that may or may not be separable. In practice the SEM regioisomers can be carried through as mixtures. Compounds (XI-2) and (XI-3) may each, respectively, be converted to the corresponding pinacol boronates by reaction with bis(pinacolato)diboron in the presence of a base such as potassium acetate, a catalyst such as $PdCl_2$ (dppf)-$CH_2Cl_2$, in a solvent such as DMSO, dimethoxyethane or dioxane with heating to between 60-100° C.

Compound (VIII-2) may react with a variety of boronic acids or esters as mentioned above. Certain boronic acids suitable for reaction with (VIII-2) may be prepared as outlined in Scheme XII, where q is 0, 1, or 2; $R_A$ is halo, alkyl, cycloalkyl, alkoxy, haloalkyl, haloalkoxy, etc.; and n is 0, 1, 2, 3, or 4. Bromoanilines may be reacted with a dihaloalkane (e.g., 1,5-dibromopentane) generally in solvents such as benzene, toluene, DMF, etc. with heating to around 50-100° C. to form azetidines, pyrrolidines, or piperidines, etc. (see J. Org. Chem. 1984, 269-276; J. Org. Chem. 1983, 4649-4658). These products may, in turn, be converted to the corresponding pinacol boronates by reaction with bis(pinacolato)diboron, a palladium catalyst such as $PdCl_2$ (dppf), a base such as KOAc with heating to around 50-100° C. in a solvent such as DMSO.

Scheme XII

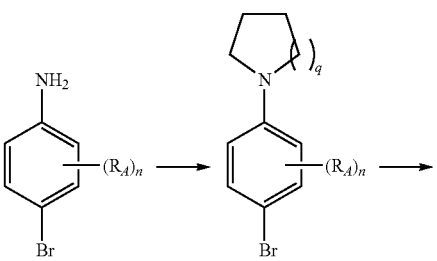

Scheme XI

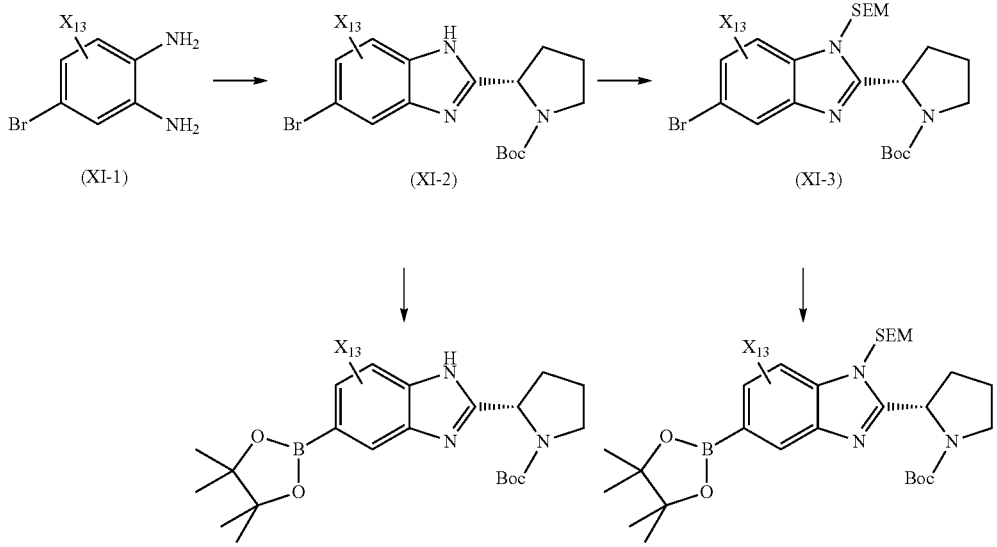

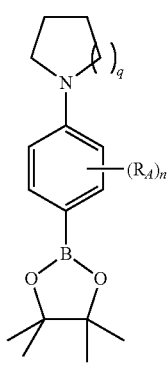

An alternative to the procedures in Scheme VIII wherein compounds of formula (VIII-5) are converted to compounds of formula (VIII-12) is described in Scheme XIII. Compounds of formula (VIII-5) can be hydrogenated in the presence of a palladium on charcoal catalyst in methanol to give compounds of formula (XIII-1). The cyclopentanol moiety can then be oxidized with a suitable oxidant such as but not limited to Dess-Martin periodinane. Subsequently, the tert-butoxycarbonyl group can be removed under acidic conditions to give compounds of formula (XIII-2). Compounds of formula (XIII-2) can then be reacted with hexane-2,5-dione in the presence of heat and acid to give a pyrrole protecting group. Then treatment with base (e.g., NaH, LiHMDS, KHMDS) followed by reaction with (Tf)$_2$NPh supplies compounds of formula (XIII-3). Compounds of formula (XIII-3) can be converted to compounds of formula (XIII-4) under Suzuki reaction conditions described for the conversion of compounds of formula (XIII-7) to compounds of formula (XIII-8) in Scheme VIII. The protecting groups of compounds of formula (XIII-4) can be removed in a two-step sequence. In the first step, compounds of formula (XIII-4) can be treated with hydroxylamine hydrochloride in the presence of potassium hydroxide in a heated mixture of ethanol and water to remove the 2,4-dimethylpyrrole. Then treatment with acid under conditions known to one skilled in the art removes the tert-butoxycarbonyl protecting group to deliver compounds of formula (VIII-9). Compounds of formula (VIII-9) can be coupled with compounds of formula (XIII-5) under standard amide bond coupling procedures to give compounds of formula (VIII-12). Compounds of formula (VIII-12) can be further transformed as described in Scheme VIII.

Scheme XIII

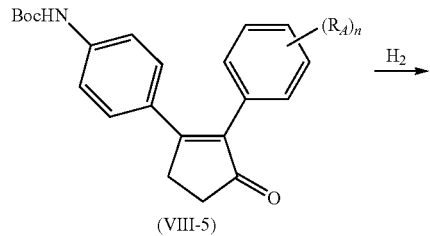

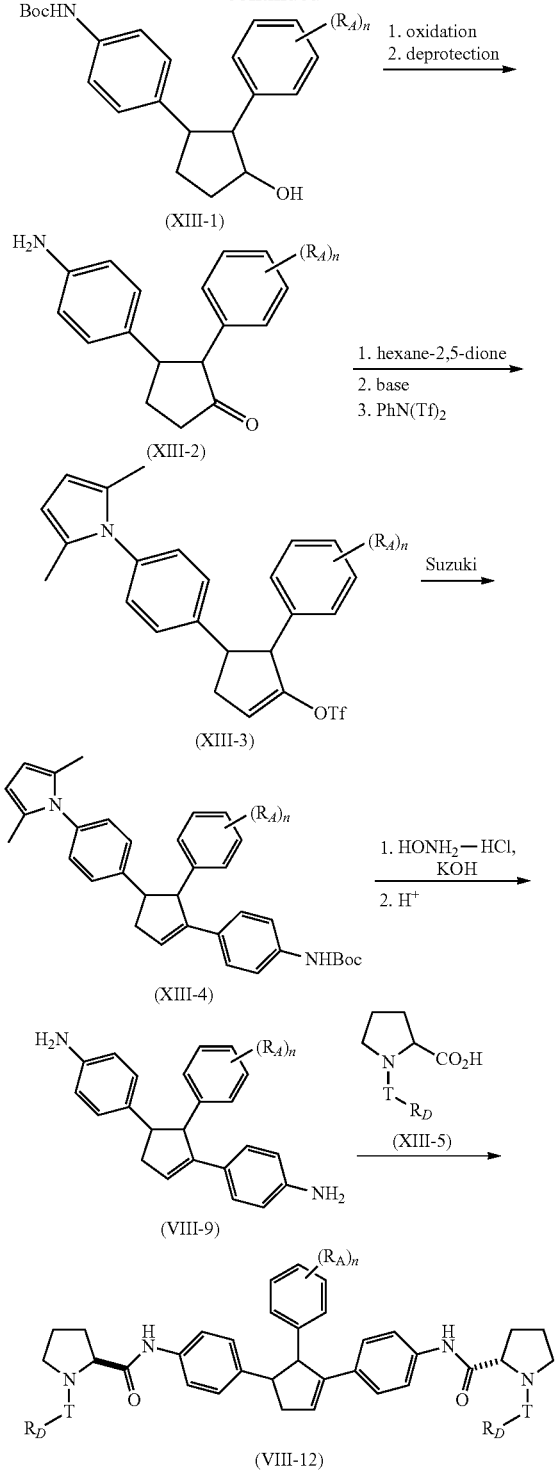

In the foregoing Schemes, compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemistry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —NH$_2$ or —OH) is not compatible with the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

Other compounds of the invention can be similarly prepared according to the above-described schemes as well as the procedures described in following examples, as appreciated by those skilled in the art. It should be understood that the above-described embodiments and schemes and the following examples are given by way of illustration, not limitation. Various changes and modifications within the scope of the present invention will become apparent to those skilled in the art from the present description.

Example compounds below were named using either ChemDraw version 9.0 or ACD/Name release 12.00 12 (ACD v12). Final compounds for Examples 1-8 were named using ChemDraw unless otherwise indicated as being named using ACD v12. Intermediates were named using ChemDraw, unless otherwise indicated as being named using ACD v12.

Example compounds below were named using ACD Name version 12 (ACD Name v12). Other compounds were named using ChemDraw version 9.0 (v9), unless otherwise indicated as being named using ACD Name v12. Both naming programs may provide a chemical name that depends on the tautomeric structure chosen for naming. Structures may be shown or named as any chemically distinct tautomer.

For example, the tautomeric structure:

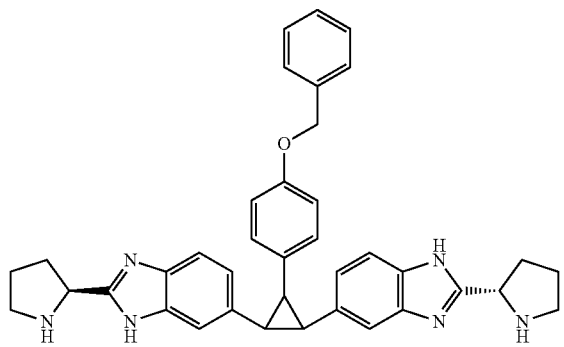 [SMILES: c1ccc(COc2ccc(C3C(c4ccc5[nH]c([C@@H]6CCCN6)nc5c4)C3c3ccc4nc([C@@H]5CCCN5)[nH]c4c3)cc2)cc1]

(S)-5,5'-(3-(4-(benzyloxy)phenyl)cyclopropane-1,2-diyl)bis (2-((S)-pyrrolidin-2-yl)-1H-benzo[d]imidazole)
is given the following names:
(S)-5,5'-(3-(4-(benzyloxy)phenyl)cyclopropane-1,2-diyl)bis (2-((S)-pyrrolidin-2-yl)-1H-benzo[d]imidazole) (Chemdraw v9);
5-(2-[4-(benzyloxy)phenyl]-3-{2-[(2S)-pyrrolidin-2-yl]-1H-benzimidazol-6-yl}cyclopropyl)-2-[(2S)-pyrrolidin-2-yl]-1H-benzimidazole (ACD Name v12).

The tautomeric structure:

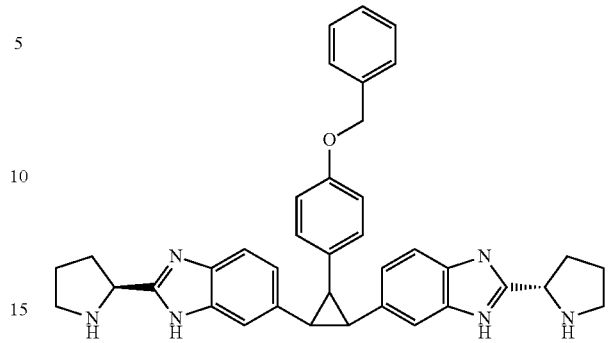

is given the following names:
(S)-6,6'-(3-(4-(benzyloxy)phenyl)cyclopropane-1,2-diyl)bis (2-((S)-pyrrolidin-2-yl)-1H-benzo[d]imidazole) (Chemdraw v9);
6,6'-{3-[4-(benzyloxy)phenyl]cyclopropane-1,2-diyl}bis{2-[(2S)-pyrrolidin-2-yl]-1H-benzimidazole} (ACD Name v12).

The tautomeric structure:

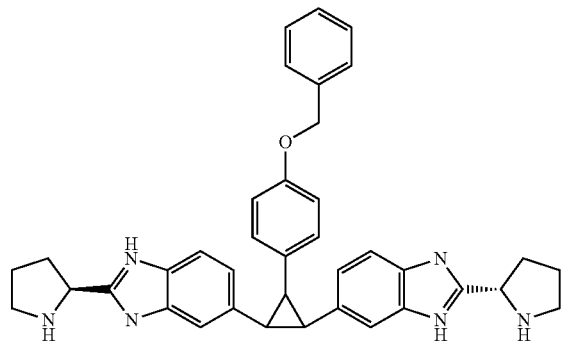

is given the following names:
(S)-6,6'-(3-(4-(benzyloxy)phenyl)cyclopropane-1,2-diyl)bis (2-((S)-pyrrolidin-2-yl)-1H-benzo[d]imidazole) (Chemdraw v9);
5-(2-[4-(benzyloxy)phenyl]-3-{2-[(2S)-pyrrolidin-2-yl]-1H-benzimidazol-6-yl}cyclopropyl)-2-[(2S)-pyrrolidin-2-yl]-1H-benzimidazole (ACD Name v12).

Certain compounds in the Examples below were purified using reverse-phase HPLC. Purification was conducted using either a C18 or C8 reverse-phase column. Compounds were eluted using a gradient of about 10-100% acetonitrile in 0.1% aqueous trifluoroacetic acid; about 60-100% methanol in 10 mM aqueous ammonium acetate; or about 10-95% methanol in 10 mM aqueous ammonium acetate. For purifications conducted with trifluoroacetic acid, the product thus obtained may be in the form of a trifluoroacetic acid salt. Compounds may be characterized as the trifluoroacetic acid salt or as the free base following neutralization, extraction and isolation.

Certain compounds in the Examples below can be purified using normal phase silica gel chromatography including traditional flash chromatography or an automated purification system (e.g., Isco CombiFlash®, Analogix Intelliflash) using pre-packed silica gel columns (55 or 35 μm silica gel, Isco gold columns). Compounds can also be purified by preparative thin-layer chromatography. Typical solvents for silica gel chromatography include: Ethyl acetate in hexanes, diethyl ether in hexanes, tetrahydrofuran in hexanes, ethyl acetate in methylene chloride, methanol in methylene chloride, methanol in methylene chloride with ammonium hydroxide, acetone in hexanes, and methylene chloride in hexanes.

Representative compounds contemplated as part of the invention:

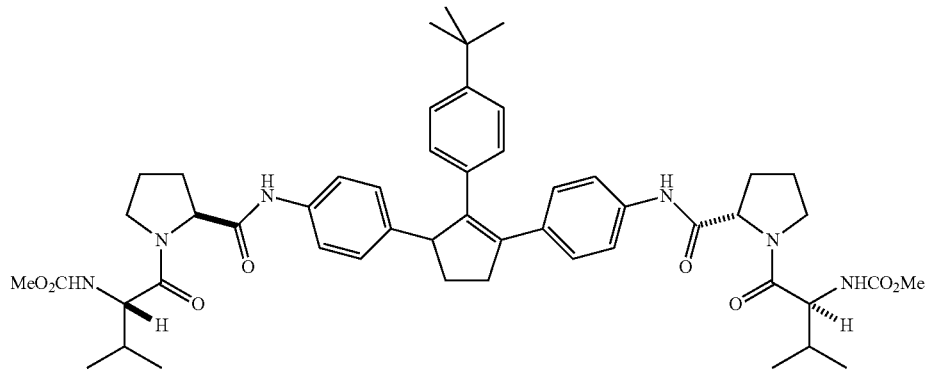

dimethyl ([2-(4-tert-butylphenyl)cyclopent-1-ene-1,3-diyl] bis{benzene-4,1-diylcarbamoyl(2S)pyrrolidine-2,1-diyl [(2S)-3-methyl-1-oxobutane-1,2-diyl]})biscarbamate;

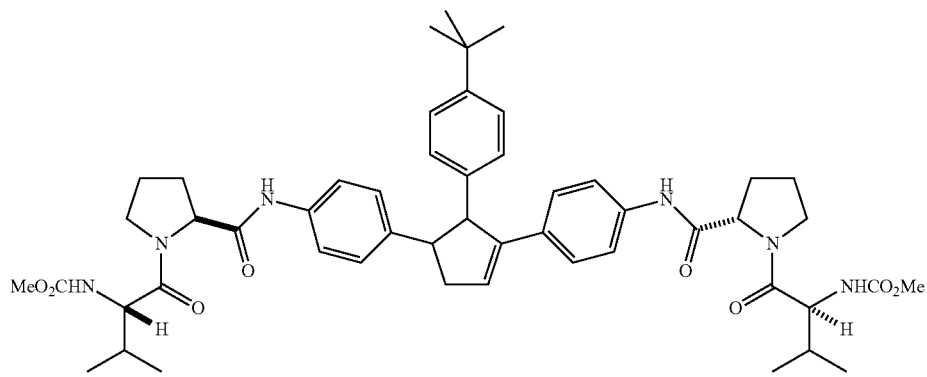

dimethyl (2S,2'S)-1,1'-((2S,2'S)-2,2'-(4,4'-(2-(4-tert-butylphenyl)cyclopent-3-ene-1,3-diyl)bis(4,1-phenylene)bis(azanediyl)bis(oxomethylene))bis(pyrrolidine-2,1-diyl)) bis(3-methyl-1-oxobutane-2,1-diyl)dicarbamate;

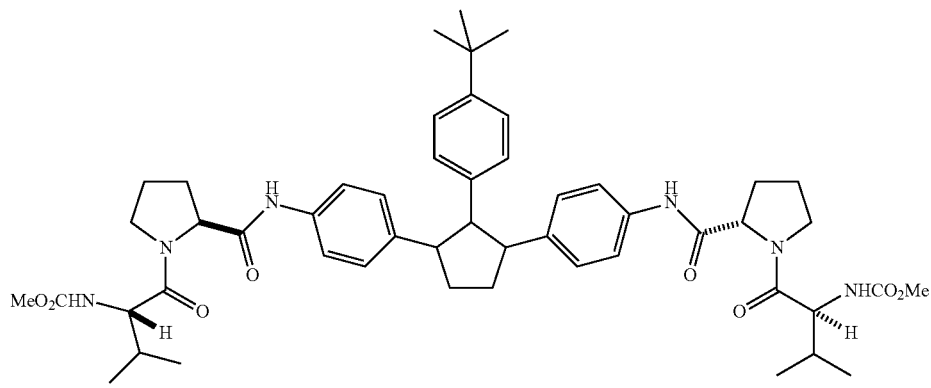

dimethyl ([2-(4-tert-butylphenyl)cyclopentane-1,3-diyl] bis{benzene-4,1-diylcarbamoyl(2S)pyrrolidine-2,1-diyl [(2S)-3-methyl-1-oxobutane-1,2-diyl]})biscarbamate;

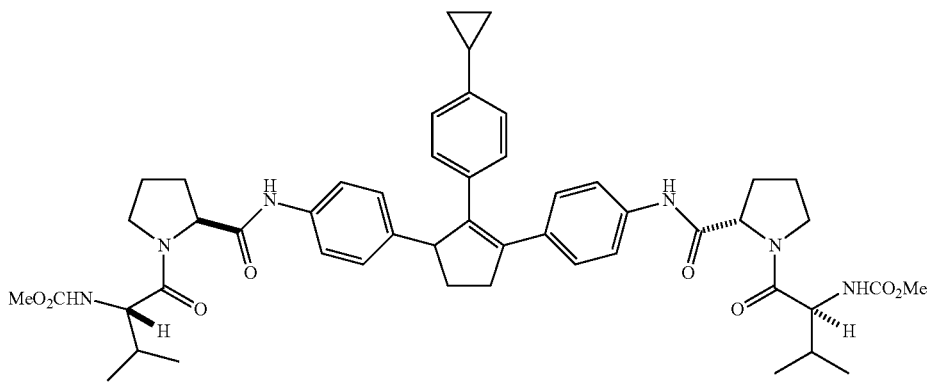

dimethyl ([2-(4-cyclopropylphenyl)cyclopent-1-ene-1,3-diyl]bis{benzene-4,1-diylcarbamoyl(2S)pyrrolidine-2,1-diyl[(2S)-3-methyl-1-oxobutane-1,2-diyl]})biscarbamate;

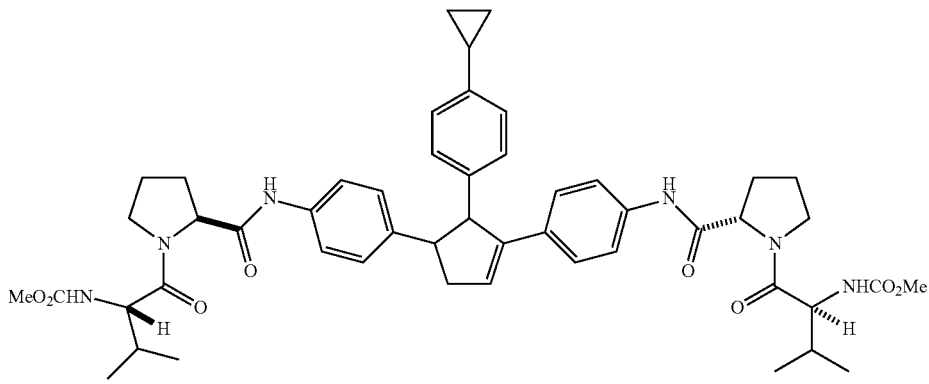

dimethyl (2S,2'S)-1,1'-((2S,2'S)-2,2'-(4,4'-(2-(4-cyclopropylphenyl)cyclopent-3-ene-1,3-diyl)bis(4,1-phenylene))bis(azanediyl)bis(oxomethylene)bis(pyrrolidine-2,1-diyl))bis(3-methyl-1-oxobutane-2,1-diyl)dicarbamate;

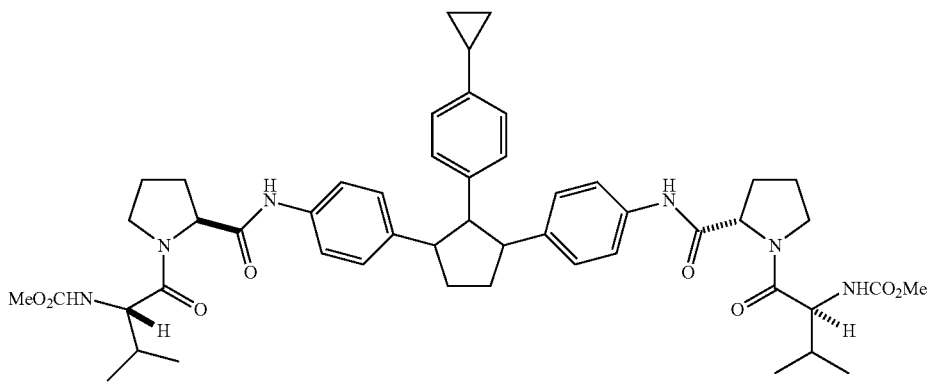

dimethyl ([2-(4-cyclopropylphenyl)cyclopentane-1,3-diyl]bis{benzene-4,1-diylcarbamoyl(2S)pyrrolidine-2,1-diyl[(2S)-3-methyl-1-oxobutane-1,2-diyl]})biscarbamate;

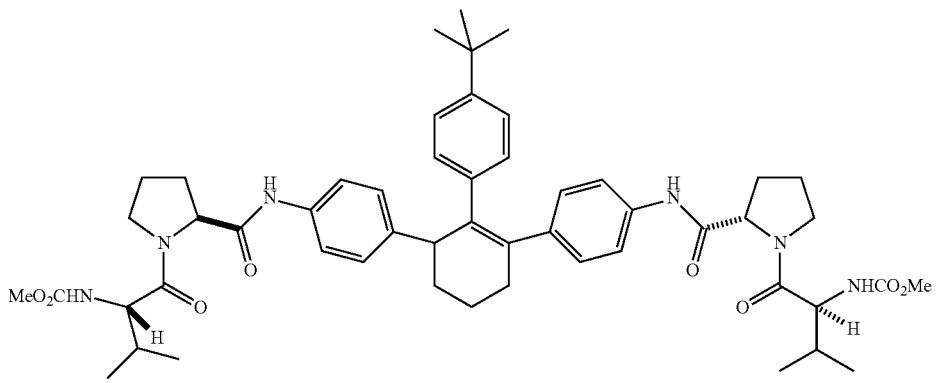

dimethyl ([2-(4-tert-butylphenyl)cyclohex-1-ene-1,3-diyl] bis{benzene-4,1-diylcarbamoyl(2S)pyrrolidine-2,1-diyl [(2S)-3-methyl-1-oxobutane-1,2-diyl]})biscarbamate;

dimethyl ([2-(4-tert-butylphenyl)cyclohexane-1,3-diyl] bis{benzene-4,1-diylcarbamoyl(2S)pyrrolidine-2,1-diyl [(2S)-3-methyl-1-oxobutane-1,2-diyl]})biscarbamate;

methyl {(2S)-1-[(2S)-2-{6-[2-(4-cyclopropylphenyl)-3-{2-[(2S)-1-{(2S)-2-[(methoxycarbonyl)amino]-3-methylbutanoyl}pyrrolidin-2-yl]-1H-benzimidazol-6-yl}cyclopentyl]-1H-benzimidazol-2-yl}pyrrolidin-1-yl]-3-methyl-1-oxobutan-2-yl}carbamate;

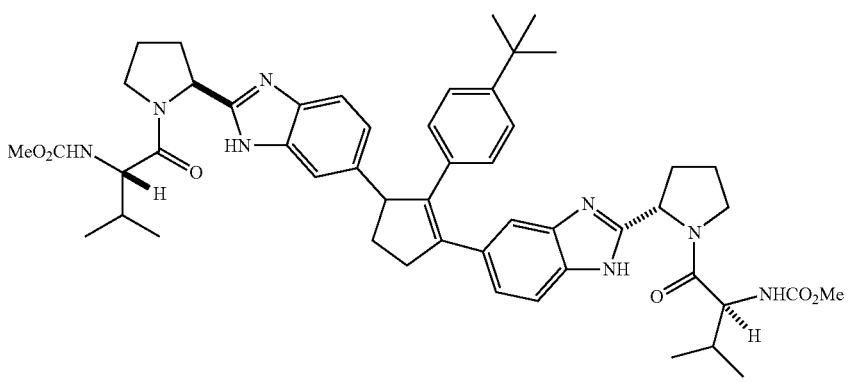

methyl {(2S)-1-[(2S)-2-{5-[2-(4-tert-butylphenyl)-3-{2-[(2S)-1-{(2S)-2-[(methoxycarbonyl)amino]-3-methylbutanoyl}pyrrolidin-2-yl]-1H-benzimidazol-6-yl}cyclopent-1-en-1-yl]-1H-benzimidazol-2-yl}pyrrolidin-1-yl]-3-methyl-1-oxobutan-2-yl}carbamate;

dimethyl (2S,2'S)-1,1'-((2S,2'S)-2,2'-(6,6'-(2-(4-tert-butylphenyl)cyclopent-3-ene-1,3-diyl)bis(1H-benzo[d]imidazole-6,2-diyl))bis(pyrrolidine-2,1-diyl))bis(3-methyl-1-oxobutane-2,1-diyl)dicarbamate;

methyl {(2S)-1-[(2S)-2-{5-[2-(4-tert-butylphenyl)-3-{2-[(2S)-1-{(2S)-2-[(methoxycarbonyl)amino]-3-methylbutanoyl}pyrrolidin-2-yl]-1H-benzimidazol-6-yl}cyclopent-1-en-1-yl]-1H-benzimidazol-2-yl}pyrrolidin-1-yl]-3-methyl-1-oxobutan-2-yl}carbamate;

methyl [(2S)-1-(2-{6-[5-(4-cyclopropylphenyl)-4-{2-[(2S)-1-{2-[(methoxycarbonyl)amino]-3-methylbutanoyl}pyrrolidin-2-yl]-1H-benzimidazol-6-yl}cyclopent-1-en-1-yl]-1H-benzimidazol-2-yl}pyrrolidin-1-yl)-3-methyl-1-oxobutan-2-yl]carbamate;

methyl {(2S)-1-[(2S)-2-{6-[2-(4-cyclopropylphenyl)-3-{2-[(2S)-1-{(2S)-2-[(methoxycarbonyl)amino]-3-methylbutanoyl}pyrrolidin-2-yl]-1H-benzimidazol-6-yl}cyclopentyl]-1H-benzimidazol-2-yl}pyrrolidin-1-yl]-3-methyl-1-oxobutan-2-yl}carbamate;

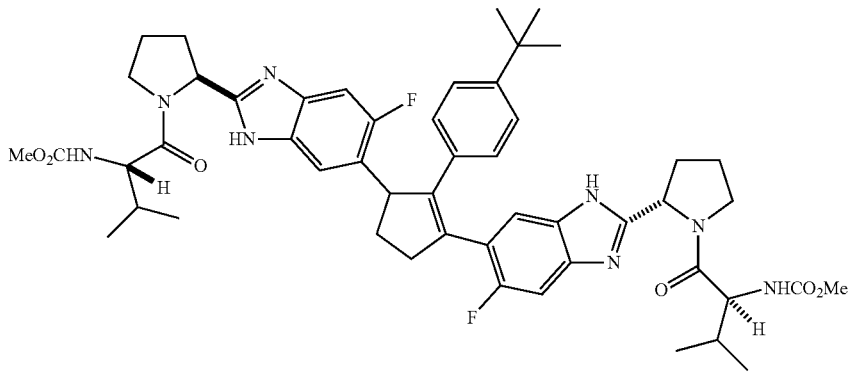

methyl {(2S)-1-[(2S)-2-{6-[2-(4-tert-butylphenyl)-3-{5-fluoro-2-[(2S)-1-{(2S)-2-[(methoxycarbonyl)amino]-3-methylbutanoyl}pyrrolidin-2-yl]-1H-benzimidazol-6-yl}cyclopent-1-en-1-yl]-5-fluoro-1H-benzimidazol-2-yl}pyrrolidin-1-yl]-3-methyl-1-oxobutan-2-yl}carbamate;

methyl [(2S)-1-(2-{6-[2-(4-tert-butylphenyl)-3-{5-fluoro-2-[(2S)-1-{2-[(methoxycarbonyl)amino]-3-methylbutanoyl}pyrrolidin-2-yl]-1H-benzimidazol-6-yl}cyclopent-3-en-1-yl]-5-fluoro-1H-benzimidazol-2-yl}pyrrolidin-1-yl)-3-methyl-1-oxobutan-2-yl]carbamate;

methyl {(2S)-1-[(2S)-2-{6-[2-(4-tert-butylphenyl)-3-{5-fluoro-2-[(2S)-{(2S)-2-[(methoxycarbonyl)amino]-3-methylbutanoyl}pyrrolidin-2-yl]-1H-benzimidazol-6-yl}cyclopentyl]-5-fluoro-1H-benzimidazol-2-yl}pyrrolidin-1-yl]-3-methyl-1-oxobutan-2-yl}carbamate;

methyl [(2S)-1-{(2S)-2-[6-(2-[3-fluoro-4-(piperidin-1-yl)phenyl]-3-{2-[(2S)-1-{(2S)-2-[(methoxycarbonyl)amino]-3-methylbutanoyl}pyrrolidin-2-yl]-1H-benzimidazol-6-yl}cyclopent-1-en-1-yl)-1H-benzimidazol-2-yl]pyrrolidin-1-yl}-3-methyl-1-oxobutan-2-yl]carbamate;

methyl [(2S)-1-{(2S)-2-[6-(5-[3-fluoro-4-(piperidin-1-yl)phenyl]-4-{2-[(2S)-1-{(2S)-2-[(methoxycarbonyl)amino]-3-methylbutanoyl}pyrrolidin-2-yl]-1H-benzimidazol-6-yl}cyclopent-1-en-1-yl)-1H-benzimidazol-2-yl]pyrrolidin-1-yl}-3-methyl-1-oxobutan-2-yl]carbamate;

methyl [(2S)-1-{(2S)-2-[6-(2-[3-fluoro-4-(piperidin-1-yl)phenyl]-3-{2-[(2S)-1-{(2S)-2-[(methoxycarbonyl)amino]-3-methylbutanoyl}pyrrolidin-2-yl]-1H-benzimidazol-6-yl}cyclopentyl)-1H-benzimidazol-2-yl]pyrrolidin-1-yl}-3-methyl-1-oxobutan-2-yl]carbamate;

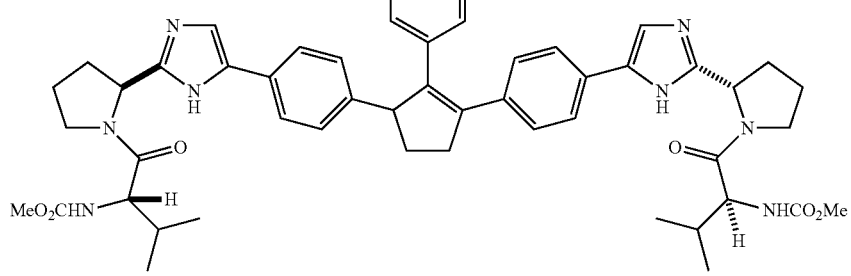

methyl {((2S)-1-[(2S)-2-(5-{4-[2-(4-tert-butylphenyl)-3-(4-{2-[(2S)-1-(2S)-2-[(methoxycarbonyl)amino]-3-methylbutanoyl}pyrrolidin-2-yl]-1H-imidazol-5-yl}phenyl)cyclopent-1-en-1-yl]phenyl}-1H-imidazol-2-yl)pyrrolidin-1-yl]-3-methyl-1-oxobutan-2-yl}carbamate; and methyl {((2S)-1-[(2S)-2-(5-{4-[5-(4-tert-butylphenyl)-4-(4-{2-[(2S)-{(2S)-2-[(methoxycarbonyl)amino]-3-methylbutanoyl}pyrrolidin-2-yl]-1H-imidazol-5-yl}phenyl)cyclopent-1-en-1-yl]phenyl}-1H-imidazol-2-yl)pyrrolidin-1-yl]-3-methyl-1-oxobutan-2-yl}carbamate;

methyl {(2S)-1-[(2S)-2-(5-{4-[2-(4-tert-butylphenyl)-3-(4-{2-[(2S)-{(2S)-2-[(methoxycarbonyl)amino]-3-methylbutanoyl}pyrrolidin-2-yl]-1H-imidazol-5-yl}phenyl)cyclopentyl]phenyl}-1H-imidazol-2-yl)pyrrolidin-1-yl]-3-methyl-1-oxobutan-2-yl}carbamate.

SYNTHESIS OF INTERMEDIATES

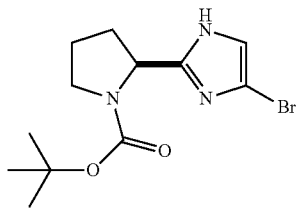 [SMILES: CC(C)(C)OC(=O)N1CCC[C@H]1c1nc(Br)c[nH]1]

Intermediate 1

(S)-tert-butyl 2-(4-bromo-1H-imidazol-2-yl)pyrrolidine-1-carboxylate

Intermediate 1A (S)-tert-butyl 2-formylpyrrolidine-1-carboxylate

To an oven-dried 500-mL 3-neck flask purged with nitrogen was added oxalyl chloride (5.32 mL, 60.8 mmol) and anhydrous dichloromethane (125 mL), and the solution was cooled to −78° C. A solution of anhydrous DMSO (7.30 mL, 103 mmol) in anhydrous dichloromethane (25 mL) was added dropwise from a constant-pressure addition funnel over a 20-minute period. A solution of (S)-tert-butyl 2-(hydroxymethyl)pyrrolidine-1-carboxylate (9.41 g, 46.8 mmol) in anhydrous dichloromethane (50 mL) was added dropwise from a constant-pressure addition funnel over a 20-minute period, and then the reaction mixture was stirred at −78° C. for 30 minutes. Triethylamine (32.6 mL, 234 mmol) was added dropwise via syringe over a 5-minute period and the thick white mixture was stirred in an ice-water bath for 30 minutes. The reaction was quenched with 10% (w/v) aq. citric acid (30 mL). The mixture was partitioned in a separatory funnel between $Et_2O$ (550 mL) and 10% (w/v) aq citric acid. The layers were separated, and the organic phase was washed with water and brine. The organic phase was dried over anhydrous $Na_2SO_4$, filtered, and concentrated to afford a yellow oil (9.4 g), which was used directly in the next reaction.

Intermediate 1B (S)-tert-butyl 2-(1H-imidazol-2-yl)pyrrolidine-1-carboxylate The product from Intermediate 1A (20 g, 100 mmol) was dissolved in methanol (50.2 mL) and ammonium hydroxide (50.2 mL) was added. To this solution, glyoxal (40% in water; 24.08 mL, 211 mmol) was added, dropwise, over 10 minutes. The reaction was stirred at room temperature overnight. The reaction was concentrated under reduced pressure, diluted with 50 mL of water, and then extracted with ethyl acetate. The organic layer was washed with brine, dried ($Na_2SO_4$) and concentrated to a tan solid. The solid was treated with ether and concentrated. The solid was then triturated with 2:1 diethyl ether:hexanes (150 mL) to afford 17 g of solid, which was used directly in the next reaction. $^1$HNMR (400 MHz, DMSO-$d_6$) δ ppm 1.14/1.40 (s, 9H), 1.81-2.12 (m, 4H), 3.32-3.33 (m, 1H), 3.35-3.50 (m, 1H), 4.72-4.81 (m, 1H), 6.84 (s, 1 H), 11.68 (s, 1 H).

Intermediate 1C (S)-tert-butyl 2-(4,5-dibromo-1H-imidazol-2-yl)pyrrolidine-1-carboxylate N-Bromosuccinimide (108 mmol) was added to a cold (0° C.) solution of the product from Intermediate 1B (12.05 g, 50.8 mmol) in dichloromethane (200 mL). The mixture was stirred in ice bath for 2 hours and then concentrated, dissolved in ethyl acetate (250 mL), washed with water (3×1150 mL) and brine (1×100 mL), dried (MgSO$_4$), and concentrated to very dark residue. The residue was mixed with and concentrated from dichloromethane/hexanes (1:1) to get brown solid (~19 g). The solid was triturated with ether (~100 mL) and filtered to isolate a tan solid (13.23 g, 65% yield). $^1$H NMR (400 MHz, CDCl$_3$) δ ppm 1.49 (s, 9 H), 1.86-2.17 (m, 3 H), 2.80-2.95 (m, 1 H), 3.30-3.44 (m, 2 H), 4.85 (dd, J=7.54, 2.55 Hz, 1 H), 10.82 (s, 1 H); MS (DCI+) m/z 394/396/398 $(M+H)^+$.

Intermediate 1D (S)-tert-butyl 2-(4-bromo-1H-imidazol-2-yl)pyrrolidine-1-carboxylate The product from Intermediate 1C (6.25 g, 15.82 mmol) was dissolved in dioxane (200 mL) and water (200 mL) in a 1 L round bottom flask equipped with a condenser and glass stopper. A solution of sodium sulfite (22.38 g, 174 mmol) in water (200 mL) was added, and the mixture was heated at reflux for 16 hours. The reaction mixture was cooled to room temperature, and dioxane and some water were removed by rotary evaporation. The residue was extracted with dichloromethane. The combined organic phases were washed with brine (50 mL), dried over anhydrous $Na_2SO_4$, filtered, and concentrated by rotary evaporation, co-evaporating with 2:1 hexanes/dichloromethane (100 mL) to give a beige foam (4.38 g). The foam was dissolved in dichloromethane (2 mL), hexanes (2 mL) were added, and the resultant solution was applied to a column, and purified by silica gel flash chromatography eluting with 30% to 80% ethyl acetate/hexanes to afford the title compound as a white solid (3.48 g). $^1$H NMR (400 MHz, CDCl$_3$) δ ppm 1.48 (s, 9 H), 1.83-2.33 (m, 3 H), 2.79-3.02 (m, 1 H), 3.37 (dd, J=7.10, 5.37 Hz, 2 H), 4.88 (dd, J=7.59, 2.49 Hz, 1 H), 6.92 (s, 1 H), 10.70 (br s, 1 H); MS (ESI+) m/z 316/318 $(M+H)^+$.

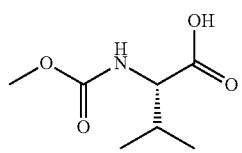

Intermediate 2

(S)-2-(methoxycarbonylamino)-3-methylbutanoic acid

To (S)-2-amino-3-methylbutanoic acid (57 g, 487 mmol) dissolved in dioxane (277 mL) was added a 2 N aqueous sodium hydroxide solution (803 mL, 1606 mmol) followed by the dropwise addition of methyl chloroformate (75 mL, 973 mmol) over 1 hour which caused warming of the solution to occur. After the addition, the mixture was heated at 60° C. for 22 hours, then cooled and extracted with dichloromethane (400 mL). The resultant aqueous layer was cooled in an ice bath, and then 12 N hydrochloric acid was added dropwise until the pH was 2. The resultant mixture was stirred at 0° C. for 2 hours, and then the resultant solid was collected by vacuum filtration, and dried in a vacuum oven to provide 80 g (94%) of the title compound as a colorless solid. $^1$H NMR (400 MHz, DMSO-$d_6$) δ ppm 12.50 (bs, 1H), 7.34 (d, J=8.6 Hz, 1H), 3.84 (dd, J=8.6, 6.0 Hz, 1H), 3.54 (s, 3H), 2.03 (m, 1H), 0.86 (t, J=7.0 Hz, 6H).

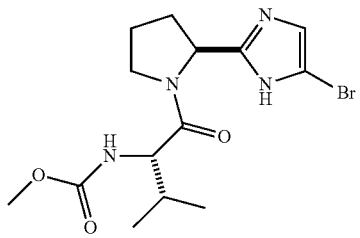 [SMILES: COC(=O)N[C@H](C(=O)N1CCC[C@H]1c1ncc(Br)[nH]1)C(C)C]

Intermediate 4 methyl (S)-1-((S)-2-(5-bromo-1H-imidazol-2-yl)pyrrolidin-1-yl)-3-methyl-1-oxobutan-2-ylcarbamate Intermediate 4A (S)-5-bromo-2-(pyrrolidin-2-yl)-1H-imidazole hydrochloride A mixture of Intermediate 1D (5.0 g, 15.8 mmol) in 4 M HCl/dioxane (40 mL) was allowed to stir for one hour. The mixture was concentrated to afford 3.99 g (100%) of the title compound. MS (ESI) m/z 217 (M+H)$^+$.

Intermediate 4B methyl (S)-1-((S)-2-(5-bromo-1H-imidazol-2-yl)pyrrolidin-1-yl)-3-methyl-1-oxobutan-2-ylcarbamate A mixture of Intermediate 4A (3.99 g, 15.8 mmol), Intermediate 2 (2.77 g, 15.8 mmol), N-(3-dimethylaminopropyl)-N'-ethylcarbodiimide hydrochloride (3.63 g, 19.0 mmol), 1-hydroxy-benzotriazole hydrate (2.90 g, 19.0 mmol) and N-methylmorpholine (12.2 mL, 111.0 mmol) in DMF (150 mL) were allowed to stir overnight. The mixture was diluted with H$_2$O and extracted with EtOAc (3×300 mL). The organic was washed with H$_2$O and brine. The organic phase was then dried (MgSO$_4$), filtered and concentrated. Purification by chromatography (silica gel, 75% EtOAc in hexanes) afforded 5.2 g (88%) of the title compound. $^1$H NMR (400 MHz, DMSO-$d_6$) δ ppm 0.79 (dd, J=6.67, 3.63 Hz, 6 H), 1.84-1.96 (m, 3 H), 2.02-2.14 (m, 2 H), 3.51 (s, 3 H), 3.66-3.80 (m, 2 H), 3.96-4.03 (m, 1 H), 4.91-4.99 (m, 1 H), 7.06 (d, J=1.52 Hz, 1 H), 7.26 (d, J=8.46 Hz, 1 H), 12.01 (s, 1 H); MS (ESI) m/z 373 (M+H)$^+$.

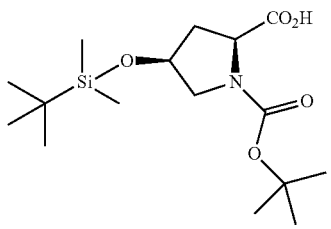 [SMILES: CC(C)(C)OC(=O)N1C[C@@H](O[Si](C)(C)C(C)(C)C)C[C@H]1C(=O)O]

Intermediate 8

(2S,4S)-1-(tert-butoxycarbonyl)-4-(tert-butyldimethylsilyloxy)pyrrolidine-2-carboxylic acid (2S,4S)-1-(tert-Butoxycarbonyl)-4-hydroxypyrrolidine-2-carboxylic acid (5.31 g, 22.96 mmol) and imidazole (7.82 g, 115 mmol) were combined in dichloromethane (106 mL) and dimethylformamide (22 mL) at ambient temperature and treated with portionwise addition of tert-butylchlorodimethylsilane (7.61 g, 50.5 mmol). The mixture was stirred for 18 hours then diluted with water and extracted into ethyl acetate and concentrated to provide the title compound.

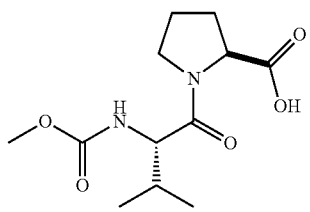 [SMILES: COC(=O)N[C@H](C(=O)N1CCC[C@H]1C(=O)O)C(C)C]

Intermediate 9

(S)-1-((S)-2-(methoxycarbonylamino)-3-methylbutanoyl)pyrrolidine-2-carboxylic acid Intermediate 2 (150 g, 856 mmol), HOBt hydrate (138 g, 899 mmol) and DMF (1500 mL) were charged to a flask. The mixture was stirred for 15 minutes to give a clear solution. EDC hydrochloride (172 g, 899 mmol) was charged and mixed for 20 minutes. The mixture was cooled to 13° C. and (L)-proline benzyl ester hydrochloride (207 g, 856 mmol) was charged. Triethylamine (109 g, 1079 mmol) was then charged in 30 minutes. The resulting suspension was mixed at room temperature for 1.5 hours. The reaction mixture was cooled to 15° C. and 1500 mL of 6.7% NaHCO$_3$ was charged in 1.5 hours, followed by the addition of 1200 mL of water over 60 minutes. The mixture was stirred at room temperature for 30 minutes, an then it was filtered and washed with water/DMF mixture (1:2, 250 mL) and then with water (1500 mL). The wetcake was dried at 55° C. for 24 hours to give 282 g of product (S)-benzyl 1-((S)-2-(methoxycarbonylamino)-3-methylbutanoyl)pyrrolidine-2-carboxylate as a white solid (90%).

(S)-Benzyl 1-((S)-2-(methoxycarbonylamino)-3-methylbutanoyl)pyrrolidine-2-carboxylate (40 g) and 5% Pd/alumina were charged to a Parr® reactor followed by THF (160 mL). The reactor was sealed and purged with nitrogen (6×20 psig) followed by a hydrogen purge (6×30 psig). The reactor was pressurized to 30 psig with hydrogen and agitated at room temperature for approximately 15 hours. The resulting slurry was filtered through a GF/F filter and concentrated to approximately 135 g solution. Heptane (120 mL) was added, and the solution was stirred until solids formed. After an addition 2-3 hours, additional heptane (240 mL) was added drop-wise, the slurry was stirred for approximately 1 hour, then filtered. The solids were dried to afford the title compound (S)-1-((S)-2-(methoxycarbonylamino)-3-methylbutanoyl)pyrrolidine-2-carboxylic acid.

Intermediate 11A

N-(4-bromo-5-fluoro-2-nitrophenyl)-2,2,2-trifluoroacetamide

To a flask containing trifluoroacetic anhydride (10.0 mL, 70.5 mmol) at 0° C. was added 4-bromo-3-fluoroaniline (2.0 μg, 10.5 mmol) and stirring was continued for 30 minutes (Charifson, P. S.; et al. J. Med. Chem. 2008, 51, 5243-5263). Potassium nitrate (1.3 g, 12.6 mmol) was added and the solution was allowed to warm to 25° C. The solution was concentrated, the residue dissolved in EtOAc and washed with 10% NaHCO$_3$, brine, dried (Na$_2$SO$_4$), and filtered. The filtrate was concentrated to give the title compound (3.5 g, 10.5 mmol, 100%).

Intermediate 11B

4-bromo-5-fluoro-2-nitroaniline

To N-(4-bromo-5-fluoro-2-nitrophenyl)-2,2,2-trifluoroacetamide (3.5 g, 10.5 mmol) was added CH$_3$OH (30 mL) followed by 1.0 M K$_2$CO$_3$ (10.5 mL, 10.5 mmol), and the solution was stirred for 30 minutes (Charifson, P. S.; et al. J. Med. Chem. 2008, 51, 5243-5263). The solution was diluted with H$_2$O and stirred for 1 hour. The resulting orange solid was collected by filtration and dried in a vacuum oven to give the title compound (2.1 g, 8.8 mmol, 84%).

Intermediate 11C

4-bromo-5-fluorobenzene-1,2-diamine

To a solution of 4-bromo-5-fluoro-2-nitroaniline (1.0 g, 4.3 mmol) in THF (9.0 mL), EtOH (9.0 mL) and H$_2$O (3 mL) was added iron powder (1.2 g, 21.3 mmol) and ammonium chloride (0.34 g, 6.4 mmol), and the mixture was heated at 95° C. for 4 hours. The cooled mixture was diluted with EtOH, filtered through diatomaceous earth until no further color came through the filter, and concentrated. The residue was dissolved in EtOAc, washed with H$_2$O, brine, dried (Na$_2$SO$_4$), filtered and concentrated. Hexane was added and the resulting solid collected by filtration to give the title compound (710 mg, 3.5 mmol, 81%).

Intermediate 12

4-bromo-3-chlorobenzene-1,2-diamine

Intermediate 12A

4-bromo-3-chloro-2-nitroaniline

3-Chloro-2-nitroaniline (5.00 g, 29.0 mmol) was dissolved in glacial acetic acid (258 mL). N-Bromosuccinimide (5.06 g, 28.4 mmol) was added and the resulting mixture was refluxed for 1 hour. The reaction was cooled to room temperature and poured into water to give a precipitate that was filtered, rinsed with water and dried to constant weight to give the title compound (4.78 g, 67%). $^1$H NMR (400 MHz, CDCL$_3$) δ ppm 7.46 (d, J=9.0, 1H), 6.64 (d, J=9.0, 1H), 4.74 (s, 2H).

Intermediate 12B

4-bromo-3-chlorobenzene-1,2-diamine

4-Bromo-3-chloro-2-nitroaniline (4.78 g, 19.01 mmol) was dissolved in ethanol (112 mL). Tin (II) chloride (14.42 g, 76 mmol) was added, and the resulting mixture was stirred at reflux for 12 hours. The mixture was cooled to room temperature, poured into water, and adjusted to pH 5 with saturated sodium bicarbonate solution. The resulting solid was filtered and rinsed well with ethyl acetate. The filtrate was washed with water and brine, dried over Na$_2$SO$_4$, filtered and concentrated in vacuo. The crude product was purified by column chromatography on silica gel using a solvent gradient of 0-50% EtOAc in hexane to give the title compound (3.32 g, 79%). $^1$H NMR (400 MHz, CDCl$_3$) δ ppm 6.94 (d, 1H), 6.51 (d, J=7.0, 1H), 3.87 (br s, 2H), 3.46 (br s, 2H).

Intermediate 13

4-bromo-3-methylbenzene-1,2-diamine

Intermediate 13A

N-(3-bromo-2-methyl-6-nitrophenyl)-2,2,2-trifluoroacetamide

To a solution of 3-bromo-2-methylaniline (1.0 g, 5.37 mmol) in CH$_2$Cl$_2$ (4.0 mL) at 0° C. was added trifluoroacetic anhydride (2.0 mL, 14.2 mmol). The mixture was stirred at 0° C. for 30 minutes, and solid potassium nitrate (0.679 g, 6.72 mmol) was added. The cooling bath was removed, and the mixture was stirred at room temperature overnight. LCMS showed a single product formed. The mixture was concentrated in vacuo, and the residue was partitioned between water and CH$_2$Cl$_2$ (2×). The organic layers were combined and dried over Na$_2$SO$_4$. The drying agent was filtered off and the crude product was purified by crystallization from aq EtOH to give the title compound (1.3 g, 74%).

Intermediate 13B

3-bromo-2-methyl-6-nitroaniline

A solution of N-(3-bromo-2-methyl-6-nitrophenyl)-2,2,2-trifluoroacetamide (1.3 g, 3.97 mmol) in CH$_3$OH (30 mL) was treated with potassium carbonate (1.099 g, 7.95 mmol), and the mixture was stirred at 50° C. overnight. The mixture was cooled to room temperature and poured into water, 1 N HCl was added to adjust to pH 6, and the mixture was extracted with CH$_2$Cl$_2$ (3×). The combined extracts were dried over Na$_2$SO$_4$, and the drying agent was filtered off and solvent was removed in vacuo to give the title compound as a yellow solid (0.57 g, 62%).

Intermediate 13C

4-bromo-3-methylbenzene-1,2-diamine

To a solution of 3-bromo-2-methyl-6-nitroaniline (0.45 g, 1.95 mmol) in EtOH (6 mL) was added tin(II) chloride (1.48 g, 7.8 mmol), and the resulting solution was stirred at 70° C. for 4 hours. The mixture was cooled to room temperature and poured into water, and 1 N aq. NaOH was added to adjust to pH>7. The resulting mixture was extracted with CH$_2$Cl$_2$ (2×), and the combined extracts were dried over Na$_2$SO$_4$. The drying agent was filtered off and solvent was removed in vacuo to give the title compound as an oil (0.34 g, 88%).

Intermediate 14

5-bromo-3-fluorobenzene-1,2-diamine

To a solution of 4-bromo-2-fluoro-6-nitroaniline (0.5 g, 2.1 mmol) in THF (4.6 mL), EtOH (4.6 mL) and H$_2$O (1.5 mL)

was added iron powder (0.6 g, 10.6 mmol) and ammonium chloride (0.17 g, 3.2 mmol). The resulting mixture was stirred at 95° C. for 22 hours. The mixture was cooled to room temperature and filtered through diatomaceous earth. The solid was washed with EtOH until no further color came through the filter. The filtrate was concentrated and the residue was dissolved in EtOAc, washed with $H_2O$ and brine, dried over $Na_2SO_4$, filtered and concentrated to give the title compound (0.43 g, 99%) as a brown, waxy solid.

Intermediate 15

4-bromo-3-fluorobenzene-1,2-diamine

Intermediate 15A 3-fluoro-2-nitroaniline

To a pressure tube was added 1,3-difluoro-2-nitrobenzene (2.8 mL, 26.4 mmol) and 7 N $NH_3$ in $CH_3OH$ (10 mL, 70 mmol). The tube was sealed and the mixture was stirred at room temperature for 5 days. The solution was diluted with $H_2O$, extracted with $CH_2Cl_2$, and the combined extracts were washed with brine, dried over $Na_2SO_4$, filtered and concentrated to give an oil. The oil was triturated with hexane and the resulting orange solid was collected by filtration to give the title compound (2.1 g, 51%).

Intermediate 15B 4-bromo-3-fluoro-2-nitroaniline

To a solution of 3-fluoro-2-nitroaniline (2.1 g, 13.4 mmol) in DMF (30 mL) at 0° C. was added a solution of N-bromosuccinimide (2.4 g, 13.4 mmol) in DMF (20 mL). The resulting solution was stirred at 0° C. for 30 minutes and then warmed to room temperature over 1 hour. The solution was diluted with EtOAc, washed with $H_2O$ and brine, dried over $MgSO_4$, filtered and concentrated to give the title compound (3.1 g, 97%).

Intermediate 15C 4-bromo-3-fluorobenzene-1,2-diamine

To a solution of 4-bromo-3-fluoro-2-nitroaniline (3.0 g, 12.8 mmol) in THF (30 mL) was added EtOH (30 mL) and $H_2O$ (10 mL) followed by iron powder (3.6 g, 63.8 mmol) and ammonium chloride (1.0 g, 19.2 mmol). The resulting mixture was stirred at 80° C. for 16 hours. The mixture was cooled to room temperature and filtered through diatomaceous earth. The solid was washed with EtOH until no further color came through the filter. The filtrate was concentrated in vacuo and the crude product was purified by column chromatography on silica gel using a solvent gradient of 0-40% EtOAc in hexane to give the title compound (2.2 g, 84%).

General Procedure 20

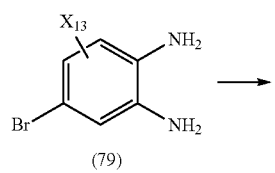
(79)

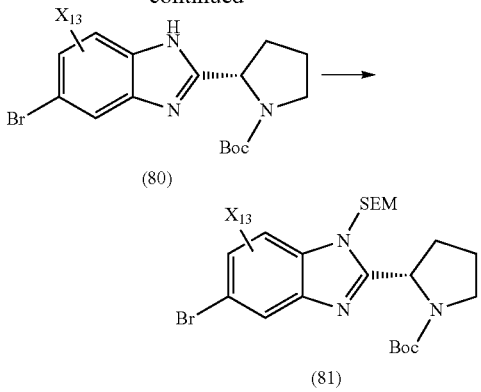
(80)

(81)

As described above generally in Scheme XI, diamines (XI-1) can be converted to benzimidazoles (XI-3) in two steps.

Illustration of General Procedure 20. General Procedure 20A (S)-tert-butyl 2-(6-bromo-5-fluoro-1H-benzo[d]imidazol-2-yl)pyrrolidine-1-carboxylate To a solution of 4-bromo-5-fluorobenzene-1,2-diamine (1.7 g, 8.4 mmol) in DMSO (42 mL) was added (S)-1-(tert-butoxycarbonyl)pyrrolidine-2-carboxylic acid (1.8 g, 8.4 mmol) followed by HATU (3.5 g, 9.3 mmol) and N,N-diisopropyl-N-ethylamine (3.7 mL, 21.1 mmol), and the solution was stirred for 16 hours. The reaction mixture was diluted with EtOAc, washed with $H_2O$ and brine, dried ($Na_2SO_4$), filtered and concentrated. Acetic acid (40 mL) was added, and the mixture was stirred at 60° C. for 4 hours. Then, the reaction mixture was cooled and concentrated. The residue was azeotroped 2 times with toluene to give crude product which was purified by flash chromatography (0-50% EtOAc/hexane) to give the title compound (2.5 g, 6.4 mmol, 77%).

(S)-tert-butyl 2-(5-bromo-6-fluoro-1-((2-(trimethylsilyl)ethoxy)methyl)-1H-benzo[d]imidazol-2-yl)pyrrolidine-1-carboxylate To a solution of (S)-tert-butyl 2-(6-bromo-5-fluoro-1H-benzo[d]imidazol-2-yl)pyrrolidine-1-carboxylate (2.5 g, 6.4 mol) in THF (32 mL) was added sodium hydride (0.27 g, 6.8 mmol) and stirring was continued for 30 minutes. 2-(Trimethylsilyl)-ethoxymethyl chloride (1.2 mL, 6.8 mmol) was added and stirring was continued for 30 minutes. Water was added to quench the reaction. The mixture was diluted with EtOAc, washed with 1N HCl, $H_2O$, and brine, dried ($Na_2SO_4$), filtered and concentrated to an oil. The oil was purified by flash chromatography (0-30% EtOAc/hexane) to give the title compound (2.9 g, 5.7 mmol, 89%).

The following compounds of general formula (XI-3) can be made following General Procedure 20 starting from the appropriate diamine:

(S)-tert-butyl 2-(5-bromo-1-((2-(trimethylsilyl)ethoxy)methyl)-1H-benzo[d]imidazol-2-yl)pyrrolidine-1-carboxylate;

(S)-tert-butyl 2-(5-bromo-4-methyl-1-((2-(trimethylsilyl)ethoxy)methyl)-1H-benzo[d]imidazol-2-yl)pyrrolidine-1-carboxylate;

(S)-tert-butyl 2-(5-bromo-4-chloro-1-((2-(trimethylsilyl)ethoxy)methyl)-1H-benzo[d]imidazol-2-yl)pyrrolidine-1-carboxylate;

(S)-tert-butyl 2-(5-bromo-4-fluoro-1-((2-(trimethylsilyl)ethoxy)methyl)-1H-benzo[d]imidazol-2-yl)pyrrolidine-1-carboxylate;
(S)-tert-butyl 2-(6-bromo-3-((2-(trimethylsilyl)ethoxy)methyl)-3H-imidazo[4,5-b]pyridin-2-yl)pyrrolidine-1-carboxylate;
(S)-tert-butyl 2-(5-bromo-7-methyl-1-((2-(trimethylsilyl)ethoxy)methyl)-1H-benzo[d]imidazol-2-yl)pyrrolidine-1-carboxylate;
(S)-tert-butyl 2-(5-bromo-6-methyl-1-((2-(trimethylsilyl)ethoxy)methyl)-1H-benzo[d]imidazol-2-yl)pyrrolidine-1-carboxylate;
(S)-tert-butyl 2-(5-bromo-6-(trifluoromethyl)-1-((2-(trimethylsilyl)ethoxy)methyl)-1H-benzo[d]imidazol-2-yl)pyrrolidine-1-carboxylate;
(S)-tert-butyl 2-(5-bromo-7-(trifluoromethyl)-1-((2-(trimethylsilyl)ethoxy)methyl)-1H-benzo[d]imidazol-2-yl)pyrrolidine-1-carboxylate;
(S)-tert-butyl 2-(5-bromo-6-methoxy-1-((2-(trimethylsilyl)ethoxy)methyl)-1H-benzo[d]imidazol-2-yl)pyrrolidine-1-carboxylate;
(S)-tert-butyl 2-(5-bromo-7-methoxy-1-((2-(trimethylsilyl)ethoxy)methyl)-1H-benzo[d]imidazol-2-yl)pyrrolidine-1-carboxylate; and
(S)-methyl 5-bromo-2-(1-(tert-butoxycarbonyl)pyrrolidin-2-yl)-1-((2-(trimethylsilyl)ethoxy)methyl)-1H-benzo[d]imidazole-7-carboxylate.

EXAMPLE 1A (2R,2'S)-tert-butyl 2,2'-(4,4'-((E)-ethene-1,2-diyl)bis(4,1-phenylene))bis(azanediyl)bis(oxomethylene)dipyrrolidine-1-carboxylate To a solution of 4,4'-diaminostilbene dihydrochloride (0.5 g, 2.38 mmol) in dimethyl sulfoxide (10 mL) was added (S)-1-(tert-butoxycarbonyl)pyrrolidine-2-carboxylic acid (1.024 g, 4.76 mmol), O-(7-azabenzotriazol-1-yl)-N,N,N',N'-tetramethyluronium hexafluorophosphate (HATU) (1.808 g, 4.76 mmol) and Hunig's base (1.66 mL, 9.51 mmol), and the mixture was stirred at room temperature for 3 hours. Then 1 N aqueous hydrochloric acid (20 mL) was added to the reaction mixture followed by extraction with dichloromethane (2×20 mL). The organic extract was dried, filtered and concentrated. The residue was purified by chromatography (silica gel, methanol in dichloromethane) which afforded 1.09 g, (76%) of the title compound. MS (ESI) m/z 604 (M+H)$^+$.

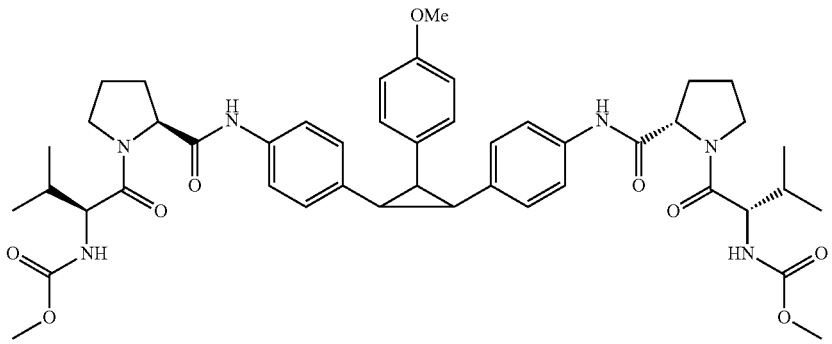 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(OC)cc2)cc1)C(C)C]

EXAMPLE 1 dimethyl (2S,2'S)-1,1'-((2S,2'S)-2,2'-(4,4'-(3-(4-methoxyphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl)dicarbamate

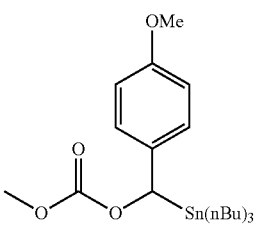

EXAMPLE 1B (4-methoxyphenyl)(tributylstannyl)methyl methyl carbonate

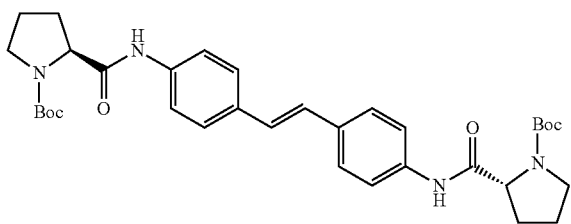 [SMILES: CC(C)(C)OC(=O)N1CCC[C@@H]1C(=O)Nc1ccc(/C=C/c2ccc(NC(=O)[C@@H]3CCCN3C(=O)OC(C)(C)C)cc2)cc1]

To dry tetrahydrofuran (80 mL) cooled to −78° C. was added a solution of lithium diisopropylamide (2.0 M in heptane/tetrahydrofuran/ethylbenzene, 18.36 mL, 37.5 mmol) followed by tri-n-butyltin hydride (9.81 mL, 37.5 mmol) dropwise. After 5 minutes, the mixture was placed in an ice water bath for 0.5 hours, then recooled to −78° C. 4-Methoxybenzaldehyde (4.45 mL, 37.5 mmol) was added dropwise, and the reaction mixture was stirred at this temperature for 1.5 hours. Afterwards, methyl chloroformate (3.41 mL, 44.1 mmol) was added dropwise, the cooling bath was removed, and the mixture was allowed to stir overnight at room temperature. Then a solution of saturated aqueous ammonium chloride (100 mL) was added followed by extraction with ethyl acetate. The organic extract was dried, filtered and concentrated. The residue was purified by chromatography (silica gel, ethyl acetate in hexanes) which afforded 6.7 g, (38%) of the title compound.

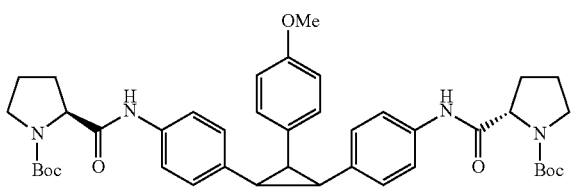 [SMILES: COc1ccc(C2C(c3ccc(NC(=O)[C@@H]4CCCN4C(=O)OC(C)(C)C)cc3)C2c2ccc(NC(=O)[C@@H]3CCCN3C(=O)OC(C)(C)C)cc2)cc1]

EXAMPLE 1C (2S,2'S)-tert-butyl 2,2'-(4,4'-(3-(4-methoxyphenyl) cyclopropane-1,2-diyl)bis(4,1-phenylene))bis (azanediyl)bis(oxomethylene)dipyrrolidine-1-carboxylate The product of Example 1A (100 mg, 0.165 mmol) and the product from Example 1B (241 mg, 0.496 mmol) were partially dissolved in dichloromethane (5 mL), and then the mixture was cooled to −25° C. Boron trifluoride etherate (0.063 mL, 0.496 mmol) was added, and the resultant mixture stirred for 1 hour. The solution was then warmed to room temperature, 0.5 N aqueous hydrochloric acid (10 mL) was added followed by extraction with dichloromethane (2×10 mL). The organic extract was dried, filtered and concentrated. The residue was purified by chromatography (silica gel, methanol in dichloromethane) which afforded 0.115 g, (96%) of the title compound. MS (ESI) m/z 725 (M+H)+.

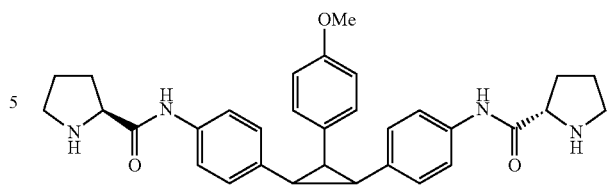

EXAMPLE 1D (2S,2'S)—N,N'-(4,4'-(3-(4-methoxyphenyl)cyclopropane-1,2-diyl)bis(4,1-phenylene))dipyrrolidine-2-carboxamide The product of Example 1C (115 mg, 0.159 mmol) was dissolved in dioxane (1.5 mL) and hydrochloric acid in dioxane (4.0 N, 0.6 mL, 2.38 mmol), and the mixture was stirred at room temperature for 4 hours. Afterwards, the mixture was concentrated to afford the title compound as a hydrochloride salt. MS (ESI) m/z 548 (M+H)+.

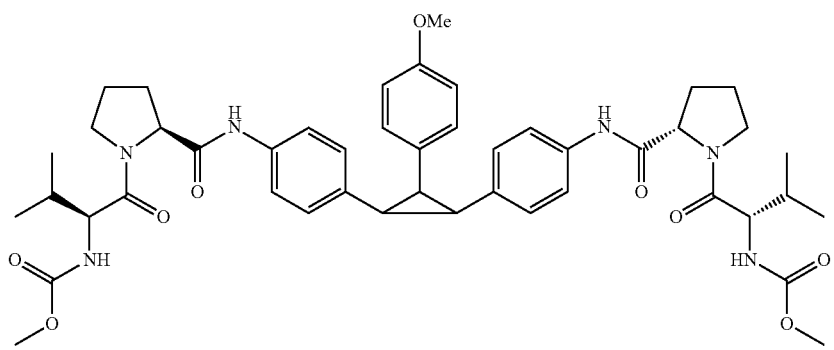 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(OC)cc2)cc1)C(C)C]

EXAMPLE 1E dimethyl (2S,2'S)-1,1'-((2S,2'S)-2,2'-(4,4'-(3-(4-methoxyphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate The product from Example 1D (83 mg, 0.158 mmol), (S)-2-(methoxycarbonylamino)-3-methylbutanoic acid (55 mg, 0.316 mmol), N-(3-dimethylaminopropyl)-N'-ethylcarbodiimide hydrochloride (67 mg, 0.348 mmol), 1-hydroxybenzotriazole hydrate (53 mg, 0.348 mmol) and 4-methylmorpholine (1.38 mL, 1.27 mmol) were dissolved in N,N-dimethylformamide (3 mL), and the mixture stirred at room temperature for 3 hours. Afterwards, 1 N aqueous hydrochloric acid (10 mL) was added followed by extraction with dichloromethane (2×10 mL). The combined organic extracts were dried, filtered and concentrated. The residue was purified by chromatography (silica gel, methanol in dichloromethane) which afforded 60 mg, (45%) of the title compound. $^1$H NMR (400 MHz, DMSO-$d_6$) δ ppm 9.96 (s, 1H), 9.87 (s, 1H), 7.96 (d, J=8.1 Hz, 1H), 7.70 (d, J=8.5 Hz, 1H), 7.55 (m, 2H), 7.32 (m, 4H), 6.98 (m, 4H), 6.72 (d, J=8.6 Hz, 2H), 4.43 (m, 1H), 4.39 (m, 1H), 4.02 (m, 2H), 3.65 (s, 3H), 3.62 (m, 2H), 3.53 (s, 3H), 3.52 (s, 3H), 2.87 (m, 1H), 2.70 (m, 2H), 2.15 (m, 2H), 1.90 (m, 8H), 0.90 (m, 12H); MS (ESI) m/z 839 (M+H)+.

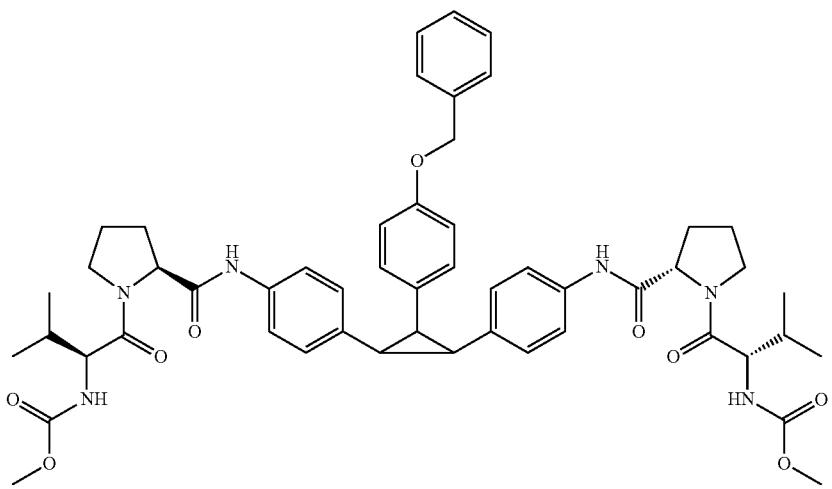 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(OCc3ccccc3)cc2)cc1)C(C)C]

EXAMPLE 2 dimethyl (2S,2'S)-1,1'-((2S,2'S)-2,2'-(4,4'-(3-(4-(benzyloxy)phenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate

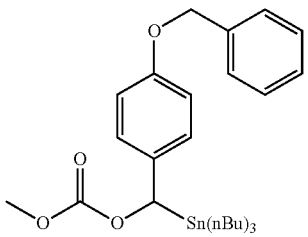

EXAMPLE 2A (4-(benzyloxy)phenyl)(tributylstannyl)methyl methyl carbonate

A solution of lithium diisopropylamide (2.0 M in heptane/tetrahydrofuran/ethylbenzene, 10.5 mL, 21 mmol), tri-n-butyltin hydride (5.55 mL, 21 mmol), 4-benzyloxybenzaldehyde (4.24 g, 20 mmol), and methyl chloroformate (1.86 mL, 24 mmol) were processed using the method described in Example 1B to afford 4.6 g (41%) of the title compound.

EXAMPLE 2B (2S,2'S)-tert-butyl 2,2'-(4,4'-(3-(4-(benzyloxy)phenyl)cyclopropane-1,2-diyl)bis(4,1-phenylene))bis(azanediyl)bis(oxomethylene)dipyrrolidine-1-carboxylate The product from Example 2A (0.34 g, 0.6 mmol), the product from Example 1A (0.12 g, 0.2 mmol), and boron trifluoride etherate (0.076 mL, 0.6 mmol) were processed using the method described in Example 1C to afford 108 mg (67%) of the title compound.

EXAMPLE 2C (2S,2'S)—N,N'-(4,4'-(3-(4-(benzyloxy)phenyl)cyclopropane-1,2-diyl)bis(4,1-phenylene))dipyrrolidine-2-carboxamide The product from Example 2B (100 mg, 0.125 mmol) was processed using the method described in Example 1D to afford 75 mg (100%) of the title compound.

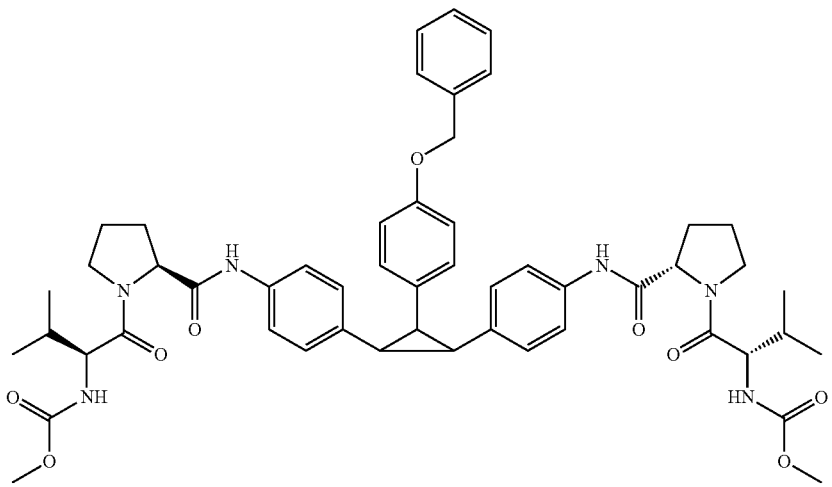 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(OCc3ccccc3)cc2)cc1)C(C)C]

EXAMPLE 2D dimethyl (2S,2'S)-1,1'-((2S,2'S)-2,2'-(4,4'-(3-(4-(benzyloxy)phenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl)dicarbamate The product from Example 2C (75 mg, 0.125 mmol), and (S)-2-(methoxycarbonylamino)-3-methylbutanoic acid (46 mg, 0.263 mmol), were processed using the method described in Example 1E to afford 70 mg (59%) of the title compound. $^1$H NMR (400 MHz, DMSO-d$_6$) d ppm 0.88 (t, J=6.07 Hz, 6 H) 0.93 (t, J=7.26 Hz, 6 H) 1.77-2.20 (m, 10 H) 2.70 (d, J=5.86 Hz, 2 H) 2.90 (t, J=5.75 Hz, 1 H) 3.52 (s, 3 H) 3.53 (s, 3 H) 3.57-3.67 (m, 2 H) 3.75-3.85 (m, 2 H) 4.03 (q, J=8.35 Hz, 2 H) 4.39 (dd, J=7.92, 4.88 Hz, 1 H) 4.44 (dd, J=8.13, 4.77 Hz, 1 H) 4.99 (s, 2 H) 6.80 (d, J=8.57 Hz, 2 H) 6.98 (dd, J=8.78, 2.28 Hz, 4 H) 7.26-7.42 (m, 11 H) 7.53 (d, J=8.57 Hz, 2 H) 9.87 (s, 1 H) 9.96 (s, 1 H); MS (ESI) m/z 915 (M+H)$^+$.

EXAMPLE 3 dimethyl (2S,2'S)-1,1'-((2S,2'S)-2,2'-(4,4'-(4,4'-(3-(4-methoxyphenyl)cyclopropane-1,2-diyl)bis(4,1-phenylene))bis(1H-imidazole-4,2-diyl))bis(pyrrolidine-2,1-diyl))bis(3-methyl-1-oxobutane-2,1-diyl)dicarbamate

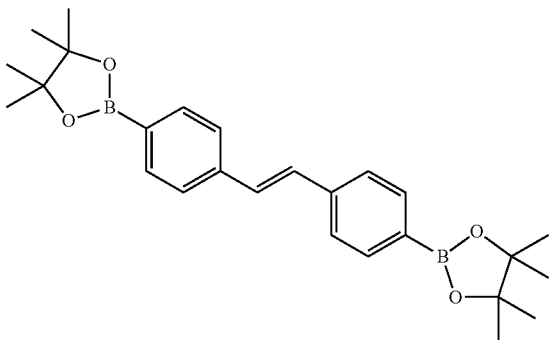

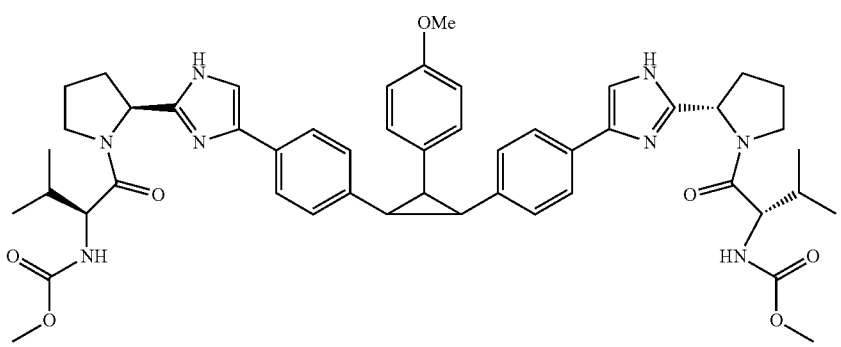 [SMILES: COC(=O)N[C@H](C(=O)N1CCC[C@H]1c1nc(-c2ccc(C3C(c4ccc(OC)cc4)C3c3ccc(-c4c[nH]c([C@@H]5CCCN5C(=O)[C@@H](NC(=O)OC)C(C)C)n4)cc3)cc2)c[nH]1)C(C)C]

EXAMPLE 3A (E)-1,2-bis(4-(4,4,5,5-tetramethyl-1,3,2-dioxaborolan-2-yl)phenyl)ethane A solution of (E)-1,2-bis(4-bromophenyl)ethene (10 g, 29.6 mmol), 4,4,4',4',5,5,5',5'-octamethyl-2,2'-bi(1,3,2-dioxaborolane) (16.53 g, 65.1 mmol), potassium acetate (8.71 g, 89 mmol) and [1,1'-bis(diphenylphosphino)ferrocene] dichloropalladium(II), complex with dichloromethane (2.42 g, 2.96 mmol) in dioxane (550 mL) was heated at 100° C. for 18 hours. The mixture was then filtered through diatomaceous earth, the filtrate was concentrated, and the residue was dissolved in ethyl acetate and extracted with brine. The organic extract was concentrated to a small volume, passed through a short pad of silica gel, and then concentrated which afforded 9.6 g, (75%) of the title compound. MS (ESI) m/z 433 (M+H)+.

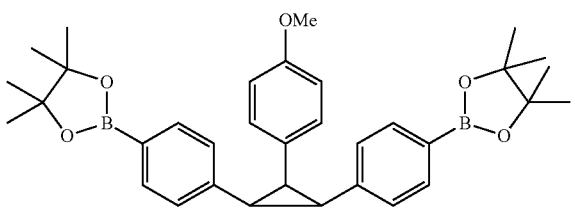

EXAMPLE 3B 2,2'-(4,4'-(3-(4-methoxyphenyl)cyclopropane-1,2-diyl)bis(4,1-phenylene))bis(4,4,5,5-tetramethyl-1,3,2-dioxaborolane)

The product from Example 3A (1.0 g, 2.31 mmol), the product from Example 1B (1.18 g, 2.43 mmol), and boron trifluoride etherate (0.308 mL, 2.43 mmol) were processed using the method described in Example 1C to afford 100 mg (8%) of the title compound.

EXAMPLE 3C (S)-tert-butyl 2-formylpyrrolidine-1-carboxylate

Oxalyl chloride (5.32 mL, 60.8 mmol) and anhydrous dichloromethane (125 mL) were combined under nitrogen, and the solution was cooled to −78° C. A solution of anhydrous dimethyl sulfoxide (7.30 mL, 103 mmol) in anhydrous dichloromethane (25 mL) was added dropwise over 20 minutes. A solution of (S)-tert-butyl 2-(hydroxymethyl)pyrrolidine-1-carboxylate (9.41 g, 46.8 mmol) in anhydrous dichloromethane (50 mL) was added dropwise over 20 minutes, and then the reaction mixture was stirred at −78° C. for 30 minutes. Triethylamine (32.6 mL, 234 mmol) was then added dropwise over a 5 minutes, and the reaction mixture was stirred in an ice-water bath for 30 minutes. The reaction was quenched with 10% (w/v) aqueous citric acid (30 mL), and the resultant mixture was partitioned between diethyl ether (550 mL) and 10% (w/v) aqueous citric acid. The organic phase was subsequently washed with water and brine. The organic phase was dried over anhydrous $Na_2SO_4$, filtered, and concentrated to afford the title compound (9.4 g), which was used directly in the next reaction.

EXAMPLE 3D (S)-tert-butyl 2-(1H-imidazol-2-yl)pyrrolidine-1-carboxylate

The product from Example 3C (20 g, 100 mmol) was dissolved in methanol (50.2 mL) and ammonium hydroxide (50.2 mL) was added. To this solution glyoxal (40% in water; 24.08 mL, 211 mmol) was added, dropwise, over 10 minutes. The reaction was stirred at room temperature overnight. The reaction was concentrated under reduced pressure, diluted with 50 mL of water, and then extracted with ethyl acetate. The organic layer was washed with brine, dried ($Na_2SO_4$), and concentrated. The residue was treated with ether and concentrated. The solid was then triturated with 2:1 diethyl ether:hexanes (150 mL) to afford 17 g of solid which was used directly in the next reaction.

EXAMPLE 3E (S)-tert-butyl 2-(4,5-dibromo-1H-imidazol-2-yl)pyrrolidine-1-carboxylate N-Bromosuccinimide (108 mmol) was added to a cold (0° C.) solution of the product from Example 3D (12.05 g, 50.8 mmol) in dichloromethane (200 mL). The reaction mixture was stirred in an ice bath for 2 hours and then concentrated. The residue was dissolved in ethyl acetate (250 mL), and the resultant solution was extracted with water (3×150 mL) and brine (1×100 mL). The organic phase was dried ($MgSO_4$) and concentrated. The residue was treated with dichloromethane/hexanes (1:1) to get brown solid (~19 g). The solid was triturated with diethyl ether (~100 mL), and the title compound was collected by filtration (13.23 g, 65% yield).

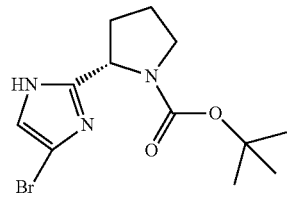 [SMILES: CC(C)(C)OC(=O)N1CCC[C@H]1c1nc(Br)c[nH]1]

EXAMPLE 3F (S)-tert-butyl 2-(5-bromo-1H-imidazol-2-yl)pyrrolidine-1-carboxylate or (S)-tert-butyl 2-(4-bromo-1H-imidazol-2-yl)pyrrolidine-1-carboxylate The product from Example 3E (6.25 g, 15.82 mmol) was dissolved in dioxane (200 mL) and water (200 mL). A solution of sodium sulfite (22.38 g, 174 mmol) in water (200 mL) was added, and the reaction mixture was heated at reflux for 16 hours. The reaction mixture was cooled to room temperature, concentrated under reduced pressure, and extracted with dichloromethane. The combined organic extracts were washed with brine (50 mL), dried over anhydrous $Na_2SO_4$, filtered, and concentrated under reduced pressure, co-evaporating with 2:1 hexanes/dichloromethane (100 mL) to give the crude title compound (4.38 g). The crude product was dissolved in dichloromethane (2 mL) and hexanes (2 mL) were added. The solution was purified by silica gel flash chromatography eluting with 30% to 80% ethyl acetate/hexanes to afford the title compound (3.48 g, 70% yield).

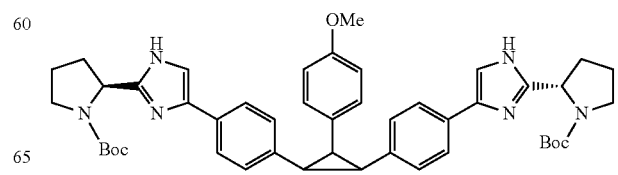

EXAMPLE 3G (2S,2'S)-tert-butyl 2,2'-(4,4'-(4,4'-(3-(4-methoxyphenyl)cyclopropane-1,2-diyl)bis(4,1-phenylene))bis(1H-imidazole-4,2-diyl))dipyrrolidine-1-carboxylate The product from Example 3B (100 mg, 0.181 mmol), the product from Example 3F (172 mg, 0.543 mmol), [1,1'-bis(diphenylphosphino)ferrocene]dichloropalladium(II), complex with dichloromethane (14.8 mg, 0.018 mmol), and a solution of sodium carbonate (1.0 M in water, 0.543 mL, 0.543 mmol) was heated in a solution of ethanol (1.5 mL) and toluene (1.5 mL) at 85° C. for 18 hours. Water (10 mL) was added followed by extraction with ethyl acetate (2×110 mL). The combined organic washes were dried, filtered and concentrated. The residue was purified by chromatography (silica gel, methanol in dichloromethane) which afforded 70 mg, (50%) of the title compound. MS (ESI) m/z 771 (M+H)$^+$.

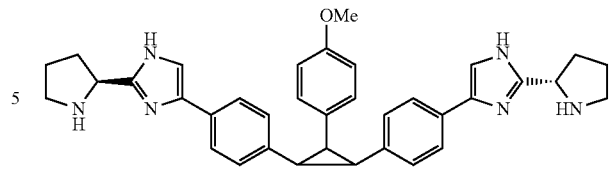

EXAMPLE 3H (S)-4,4'-(4,4'-(3-(4-methoxyphenyl)cyclopropane-1,2-diyl)bis(4,1-phenylene))bis(2-((S)-pyrrolidin-2-yl)-1H-imidazole)

The product from Example 3G (70 mg, 0.091 mmol) was processed using the method described in Example 1D to afford 52 mg (100%) of the title compound.

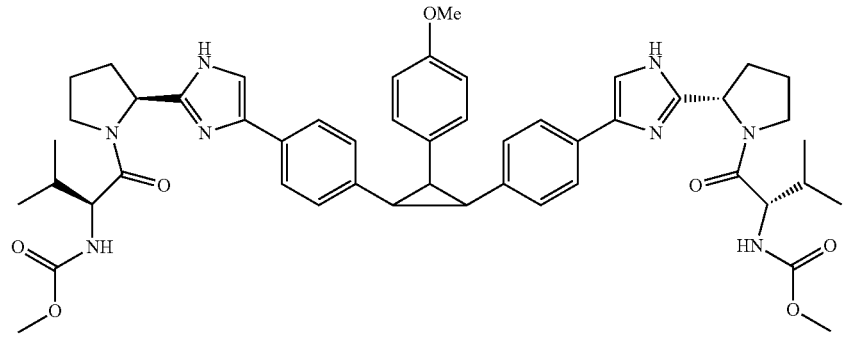 [SMILES: COC(=O)N[C@H](C(=O)N1CCC[C@H]1c1nc(-c2ccc(C3C(c4ccc(OC)cc4)C3c3ccc(-c4c[nH]c([C@@H]5CCCN5C(=O)[C@@H](NC(=O)OC)C(C)C)n4)cc3)cc2)c[nH]1)C(C)C]

EXAMPLE 3I dimethyl (2S,2'S)-1,1'-((2S,2'S)-2,2'-(4,4'-(4,4'-(3-(4-methoxyphenyl)cyclopropane-1,2-diyl)bis(4,1-phenylene))bis(1H-imidazole-4,2-diyl))bis(pyrrolidine-2,1-diyl))bis(3-methyl-1-oxobutane-2,1-diyl) dicarbamate The product from Example 3H (50 mg, 0.088 mmol), and (S)-2-(methoxycarbonylamino)-3-methylbutanoic acid (30 mg, 0.171 mmol) were processed using the method described in Example 1E to afford 31 mg (40%) of the title compound. $^1$H NMR (400 MHz, DMSO-$d_6$) δ ppm 14.5 (bs, 2H), 7.98 (bs, 1H), 7.90 (bs, 1H), 7.78 (m, 2H), 7.64 (m, 4H), 7.29 (t, J=7.8 Hz, 2H), 7.18 (m, 2H), 7.05 (m, 2H), 6.72 (m, 2H), 5.09 (m, 2H), 4.07 (m, 2H), 3.83 (m, 4H), 3.54 (s, 3H), 3.53 (s, 6H), 3.18 (m, 1H), 2.92 (m, 2H), 2.35 (m, 2H), 2.01 (m, 8H), 0.88 (m, 12H); MS (ESI) m/z 885 (M+H)$^+$.

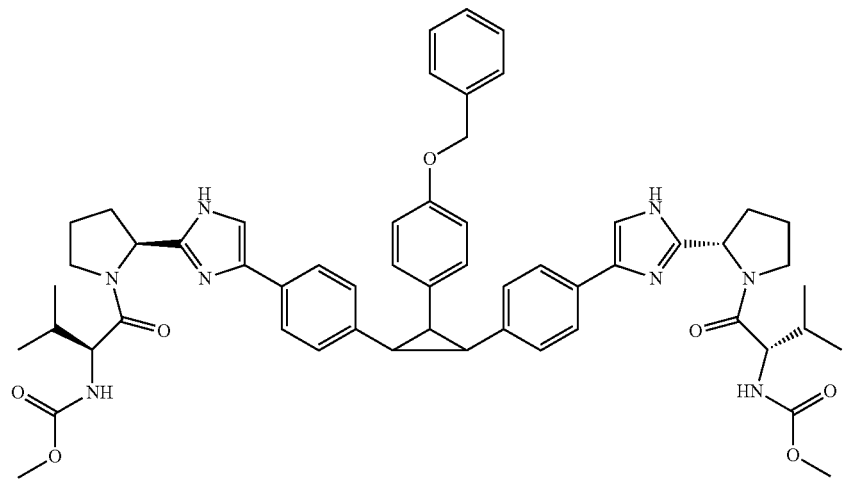 [SMILES: COC(=O)N[C@H](C(=O)N1CCC[C@H]1c1nc(-c2ccc(C3C(c4ccc(OCc5ccccc5)cc4)C3c3ccc(-c4c[nH]c([C@@H]5CCCN5C(=O)[C@@H](NC(=O)OC)C(C)C)n4)cc3)cc2)c[nH]1)C(C)C]

EXAMPLE 4 dimethyl (2S,2'S)-1,1'-(((2S,2'S)-2,2'-(4,4'-(4,4'-(3-(4-(benzyloxy)phenyl)cyclopropane-1,2-diyl)bis(4,1-phenylene))bis(1H-imidazole-4,2-diyl)))bis(pyrrolidine-2,1-diyl))bis(3-methyl-1-oxobutane-2,1-diyl) dicarbamate

EXAMPLE 4A 2,2'-(4,4'-(3-(4-(benzyloxy)phenyl)cyclopropane-1,2-diyl)bis(4,1-phenylene))bis(4,4,5,5-tetramethyl-1,3,2-dioxaborolane)

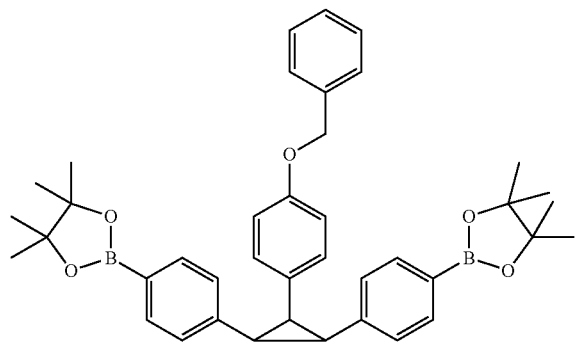

The product from Example 3A (0.25 g, 0.578 mmol), the product from Example 2A (1.62 g, 2.89 mmol), and boron trifluoride etherate (0.367 mL, 2.89 mmol) were processed using the method described in Example 1C to afford 150 mg (41%) of the title compound. MS (ESI) m/z 629 (M+H)⁺.

EXAMPLE 4B (2S,2'S)-tert-butyl 2,2'-(4,4'-(4,4'-(3-(4-(benzyloxy)phenyl)cyclopropane-1,2-diyl)bis(4,1-phenylene))bis(1H-imidazole-4,2-diyl))dipyrrolidine-1-carboxylate The product from Example 4A (150 mg, 0.239 mmol), the product from Example 3F (303 mg, 0.955 mmol), and [1,1'-bis(diphenylphosphino)ferrocene]dichloropalladium(II), complex with dichloromethane (24.4 mg, 0.03 mmol) were processed using the method described in Example 3G to afford 130 mg (64%) of the title compound. MS (ESI) m/z 847 (M+H)⁺.

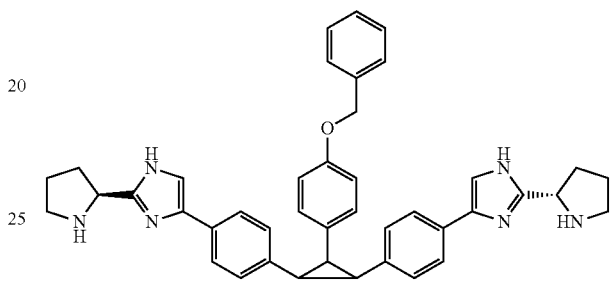

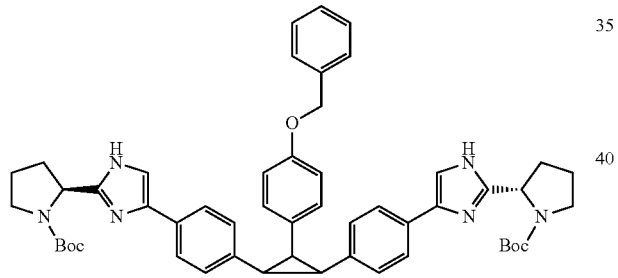

EXAMPLE 4C (S)-4,4'-(4,4'-(3-(4-(benzyloxy)phenyl)cyclopropane-1,2-diyl)bis(4,1-phenylene))bis(2-((S)-pyrrolidin-2-yl)-1H-imidazole)

The product from Example 4B (125 mg, 0.148 mmol) was processed using the method described in Example 1D to afford 95 mg (100%) of the title compound.

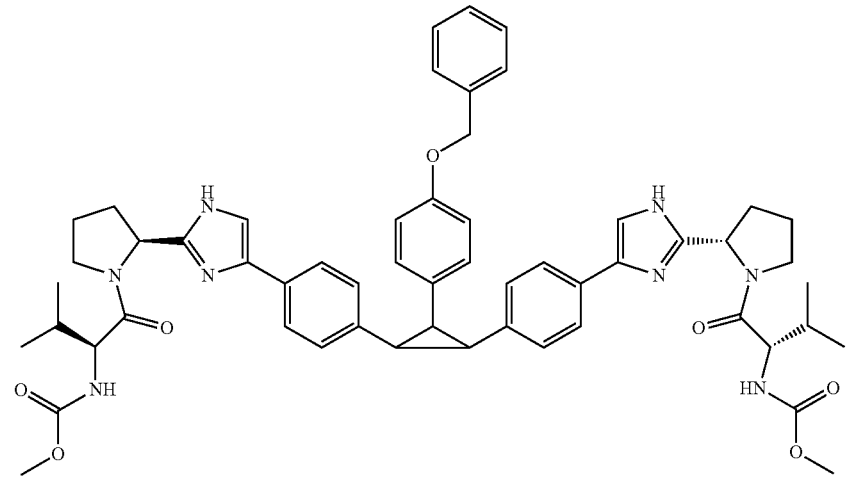 [SMILES: COC(=O)N[C@H](C(=O)N1CCC[C@H]1c1nc(-c2ccc(C3C(c4ccc(OCc5ccccc5)cc4)C3c3ccc(-c4c[nH]c([C@@H]5CCCN5C(=O)[C@@H](NC(=O)OC)C(C)C)n4)cc3)cc2)c[nH]1)C(C)C]

EXAMPLE 4D dimethyl (2S,2'S)-1,1'-((2S,2'S)-2,2'-(4,4'-(4,4'-(3-(4-(benzyloxy)phenyl)cyclopropane-1,2-diyl)bis(4,1-phenylene))bis(1H-imidazole-4,2-diyl))bis(pyrrolidine-2,1-diyl))bis(3-methyl-1-oxobutane-2,1-diyl) dicarbamate The product from Example 4C (95 mg, 0.148 mmol) and (S)-2-(methoxycarbonylamino)-3-methylbutanoic acid (52 mg, 0.296 mmol) were processed using the method described in Example 1E to afford 57 mg (40%) of the title compound. $^1$H NMR (400 MHz, DMSO-d$_6$) δ ppm 14.6 (bs, 2H), 7.99 (bs, 1H), 7.93 (bs, 1H), 7.79 (d, J=7.9 Hz, 2H), 7.59 (d, J=7.9 Hz, 2H), 7.56 (m, 2H), 7.31 (m, 7H), 7.20 (m, 2H), 7.04 (m, 2H), 6.81 (m, 2H), 5.14 (m, 2H), 4.99 (s, 2H), 4.10 (m, 2H), 3.83 (m, 4H), 3.54 (s, 3H), 3.53 (s, 6H), 3.20 (m, 1H), 2.95 (m, 2H), 2.35 (m, 2H), 2.05 (m, 8H), 0.91 (m, 12H); MS (ESI) m/z 961 (M+H)$^+$.

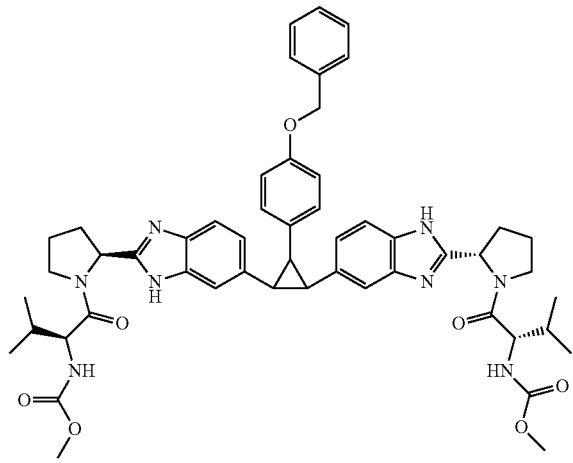 [SMILES: COC(=O)N[C@H](C(=O)N1CCC[C@H]1c1nc2cc(C3C(c4ccc(OCc5ccccc5)cc4)C3c3ccc4nc([C@@H]5CCCN5C(=O)[C@@H](NC(=O)OC)C(C)C)[nH]c4c3)ccc2[nH]1)C(C)C]

EXAMPLE 5 dimethyl (2S,2'S)-1,1'-((2S,2'S)-2,2'-(5,5'-(3-(4-(benzyloxy)phenyl)cyclopropane-1,2-diyl)bis(1H-benzo[d]imidazole-5,2-diyl))bis(pyrrolidine-2,1-diyl))bis(3-methyl-1-oxobutane-2,1-diyl)dicarbamate

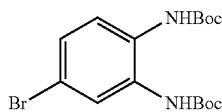

EXAMPLE 5A tert-butyl 4-bromo-1,2-phenylenedicarbamate

A suspension of 4-bromo-1,2-diaminobenzene (5.61 g, 30 mmol) and saturated sodium bicarbonate solution (100 mL) in tetrahydrofuran (150 mL) was treated with di-tert-butyl dicarbonate (17.5 g, 80 mmol) followed by stirring under nitrogen for 3 days. The mixture was diluted with ethyl acetate and extracted with water (2×) and saturated sodium chloride solution. Drying (Na$_2$SO$_4$) and concentration in vacuo afforded the crude product as a brown oil. This material was dissolved in ethyl acetate and treated with Darco G-60. The mixture was filtered through diatomaceous earth and the red filtrate was treated again with Darco G-60 and filtered through diatomaceous earth. The filtrate was concentrated in vacuo to afford a peach-colored solid, which was triturated with hexanes and collected by filtration. After drying in a vacuum oven at 50° C. for 18 hours, these procedures afforded the title compound (10.23 g, 88%) as a very light peach-colored solid. $^1$H NMR (400 MHz, CDCl$_3$) δ ppm 7.76 (s, 1 H), 7.32 (s, 1 H), 7.24 (m, 1 H), 6.73 (s, 1 H), 6.54 (s, 1 H), 1.52 (s, 9H), 1.51 (s, 9 H); MS (ESI–) m/z (relative abundance) 385 (100, M–H), 387 (92).

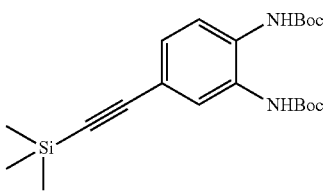 [SMILES: CC(C)(C)OC(=O)Nc1ccc(C#C[Si](C)(C)C)cc1NC(=O)OC(C)(C)C]

EXAMPLE 5B tert-butyl 4-((trimethylsilyl)ethynyl)-1,2-phenylenedicarbamate

In a microwave tube, a solution of the compound of Example 5A (2.0 g, 5.16 mmol) in triethylamine (17 mL) was degassed by nitrogen sparge for 20 minutes. The solution was then treated with bis(triphenylphosphine)palladium (II) chloride (181 mg, 0.26 mmol) and copper (I) iodide (98 mg, 0.52 mmol) followed by sparging with nitrogen for another 10 minutes. The mixture was treated with trimethylsilylacetylene (1.09 mL, 761 mg, 7.75 mmol). The microwave tube was sealed and the mixture was warmed at 70° C. for 18 hours. The mixture was cooled and diluted with ethyl acetate and extracted with water and saturated sodium chloride solution. The solution was dried (Na$_2$SO$_4$) and stirred with 3-(mercaptopropyl) silica gel for 1 hour. Filtration and concentration in vacuo afforded an oil, which was chromatographed over a 120 g silica gel cartridge, eluting with 0-20% ethyl acetate in hexanes. These procedures afforded the title compound (1.65 g, 79%) as a white solid. $^1$H NMR (400 MHz, CDCl$_3$) δ ppm 7.56 (m, 2 H), 7.27 (s, 1 H), 6.77 (s, 1 H), 6.56 (s, 1 H), 1.52 (s, 18 H), 0.23 (m, 9 H); MS (ESI+) m/z (relative abundance) 405 (8, M+H)$^+$, 421 (36, M+NH$_4$)+$^+$, 826 (100, 2M+NH$_4$)$^+$.

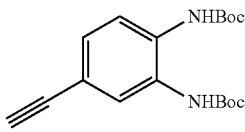 [SMILES: C#Cc1ccc(NC(=O)OC(C)(C)C)c(NC(=O)OC(C)(C)C)c1]

EXAMPLE 5C tert-butyl 4-ethynyl-1,2-phenylenedicarbamate

A solution of the compound of Example 5B (1.68 g, 4.16 mmol) in 2:1 methanol-tetrahydrofuran was treated with potassium carbonate (402 mg, 2.91 mmol) followed by stirring at room temperature for 3 hours. The solution was diluted with ethyl acetate and extracted with water and saturated sodium chloride solution. Drying (Na₂SO₄) and concentration in vacuo afforded an oil which was chromatographed over a 120 g silica gel cartridge eluting with 5-40% ethyl acetate in hexanes. These procedures afforded the title compound (1.21 g, 88%) as a white solid. ¹H NMR (400 MHz, CDCl₃) δ ppm 7.58 (s, 2 H), 7.26 (m, 1 H), 6.80 (s, 1 H), 6.56 (s, 1 H), 3.02 (s, 1 H), 1.51 (s, 18H). MS+ESI m/z (relative abundance) 333 (16, M+H)⁺, 350 (100, M+NH₄)⁺, 682 (38, 2M+NH₄)⁺.

6.00 (d, J=18.4 Hz, 1 H), 1.47 (s, 18 H); MS (ESI−) m/z (relative abundance) 377 (100, M−H)⁻.

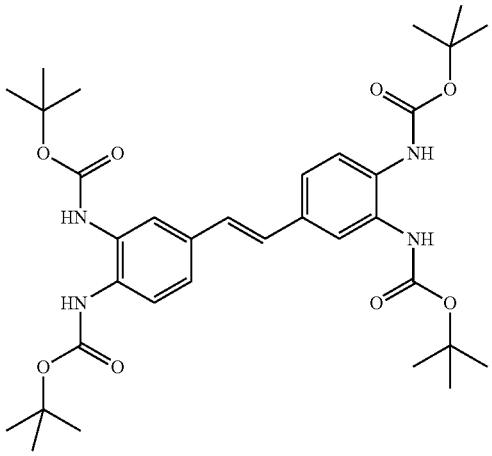

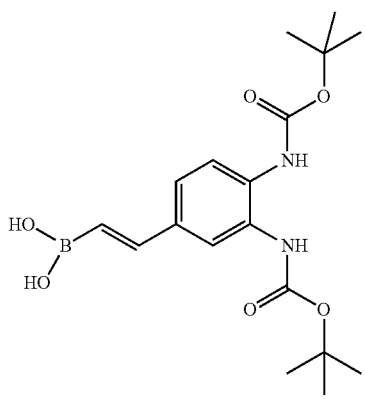 [SMILES: CC(C)(C)OC(=O)Nc1ccc(/C=C/B(O)O)cc1NC(=O)OC(C)(C)C]

EXAMPLE 5D (E)-3,4-bis(tert-butoxycarbonylamino)styrylboronic acid

A solution of borane methyl sulfide complex (384 µL, 307 mg, 4.04 mmol) in dry tetrahydrofuran (0.67 mL) at 0° C. was treated with (1R)-(+)-α-pinene (1.28 mL, 1.10 g. 8.09 mmol) followed by warming to room temperature for 3 hours. The milky white solution was cooled to −40° C. and treated dropwise over 10 minutes with a solution of the compound of Example 5C (1.12 g, 3.37 mmol) in dry tetrahydrofuran (7 mL; 2 mL was used to rinse addition funnel) followed by warming to room temperature for 2 hours. The mixture was cooled to 0° C. and treated with acetaldehyde (2.66 mL, 2.08 g, 47.2 mmoL) followed by warming to room temperature and then warming at reflux for 18 hours. The mixture was cooled to room temperature and concentrated in vacuo to afford an oil. This material was treated with water (5.0 mL, 280 mmol) and tetrahydrofuran (2 mL) followed by stirring at ambient temperature for 3 hours. The mixture was diluted with ethyl acetate and extracted with water and saturated sodium chloride solution. Drying (Na₂SO₄) and concentration in vacuo afforded an oil, which smelled like α-pinene. This material was triturated with hexanes and collected by filtration. After drying in a vacuum oven at 50° C. for 2 hours, these procedures afforded the title compound (699 mg, 55%) as a buff-colored powder. ¹H NMR (400 MHz, DMSO-d₆) δ ppm 8.52 (m, 3 H), 7.75 (s, 2 H), 7.47 (m, 2 H), 7.18 (m, 3 H),

EXAMPLE 5E (E)-tert-butyl 4,4'-(ethene-1,2-diyl)bis(benzene-4,2,1-triyl)tetracarbamate In a microwave tube, a suspension of the compound of Example 5D (866 mg, 2.29 mmol), the compound of Example 5A (739 mg, 1.91 mmol), tribasic potassium phosphate (810 mg, 3.82 mmol), and Cytec® PA-Ph (G. Adjabeng, et al. Org. Lett. 2003, 5, 953; G. Adjabeng, et al. J. Org. Chem. 2004, 69, 5082) (56 mg, 0.19 mmol) in 4:1 tetrahydrofuran-water (9.5 mL) was degassed by nitrogen sparge for 30 minutes. The mixture was treated with tris(dibenzylideneacetone) dipalladium (0) (35 mg, 0.038 mmol) followed by degassing for another 5 minutes. The microwave tube was sealed and the mixture warmed at 80° C. for 18 hours. The mixture was cooled and diluted with ethyl acetate and extracted with water, 1 N tribasic potassium phosphate solution, and saturated sodium chloride solution. The solution was dried (Na₂SO₄) and stirred with 3-(mercaptopropyl) silica gel for 1 hour. After filtration and concentration in vacuo, the residue was chromatographed over a 120 g silica gel cartridge, eluting with 10-70% ethyl acetate in hexanes. These procedures afforded an oil, which was crystallized from dichloromethane-hexanes to afford the title compound (794 mg, 65%) as a white solid after drying in a vacuum oven at 50° C. for 18 hours. ¹H NMR (400 MHz, CDCl₃) δ ppm 7.62 (s, 2 H), 7.47 (s, 2 H), 7.25 (dd, J=10.2, 1.4 Hz, 2 H), 6.96 (s, 1 H), 6.71 (s, 4 H), 1.53 (s, 18 H), 1.52 (s, 18 H); MS (ESI−) m/z (relative abundance) 639 (100, M−H)⁻.

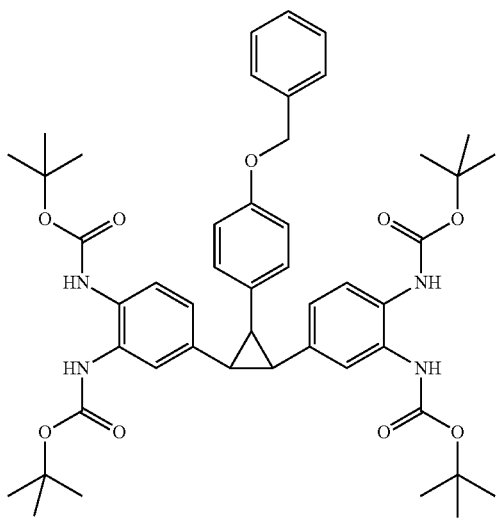 [SMILES: CC(C)(C)OC(=O)Nc1ccc(C2C(c3ccc(OCc4ccccc4)cc3)C2c2ccc(NC(=O)OC(C)(C)C)c(NC(=O)OC(C)(C)C)c2)cc1NC(=O)OC(C)(C)C]

EXAMPLE 5F tert-butyl 4,4'-(3-(4-(benzyloxy)phenyl)cyclopropane-1,2-diyl)bis(benzene-4,2,1-triyl)tetracarbamate A solution of the compound of Example 5E (794 mg, 1.24 mmol) and the compound of Example 2A (3.48 g, 6.20 mmol) in 3:1 (dry) dichloromethane-toluene (20 mL) at −25° C. was treated with boron trifluoride etherate (785 μL, 879 mg, 6.20 mmol) followed by stirring at −25° C. for 1 hour. The mixture was quenched by addition of 5 mL saturated sodium bicarbonate solution followed by warming to ambient temperature. The mixture was diluted with ethyl acetate and extracted with saturated sodium bicarbonate solution. Drying (Na$_2$SO$_4$) and concentration in vacuo afforded an amber oil, which was chromatographed over a 320 g silica gel cartridge, eluting with 10-60% ethyl acetate in hexanes. These procedures afforded the title compound (520 mg, 50%) as an off-white rigid foam. $^1$H NMR (400 MHz, CDCl$_3$) δ ppm 7.33 (m, 15 H), 6.98 (m, 4 H), 6.76 (m, 4 H), 6.63 (m, 4 H), 4.98 (s, 2 H), 2.72 (d, J=7.5 Hz, 1 H), 2.68 (t, J=9.8 Hz, 2 H), 1.50 (m, 9 H), 1.49 (s, 9 H), 1.48 (s, 18 H); MS (ESI+) m/z (relative abundance) 854 (100, M+NH$_4$)$^+$.

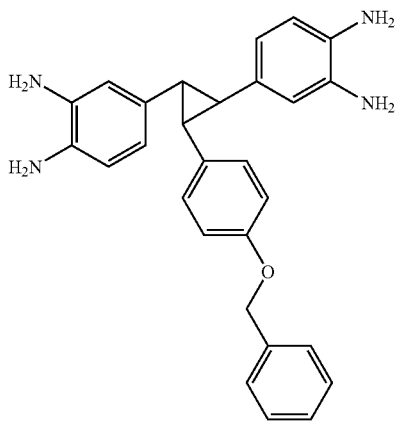 [SMILES: Nc1ccc(C2C(c3ccc(OCc4ccccc4)cc3)C2c2ccc(N)c(N)c2)cc1N]

EXAMPLE 5G 4,4'-(3-(4-(benzyloxy)phenyl)cyclopropane-1,2-diyl)dibenzene-1,2-diamine The compound of Example 5F (520 mg, 0.62 mmol) was dissolved in a solution of hydrogen chloride in dioxane (4 N, 15 mL) followed by stirring at room temperature for 2 hours. The mixture was diluted with ether and the solids collected by filtration, followed by washing with ether. After air drying, the solid was dried in a vacuum oven at 50° C. for 18 hours. These procedures afforded the title compound (283 mg, 78%) as a light brown solid. $^1$H NMR (400 MHz, DMSO-d$_6$) δ ppm 7.39 (m, 11 H), 6.98 (m, 8 H), 6.81 (m, 9 H), 6.51 (m, 2 H), 5.00 (s, 2 H), 2.76 (m, 1 H), 2.61 (m, 2 H); MS (ESI+) m/z (relative abundance) 437 (100, M+H)$^+$, 873 (50, 2M+H)$^+$.

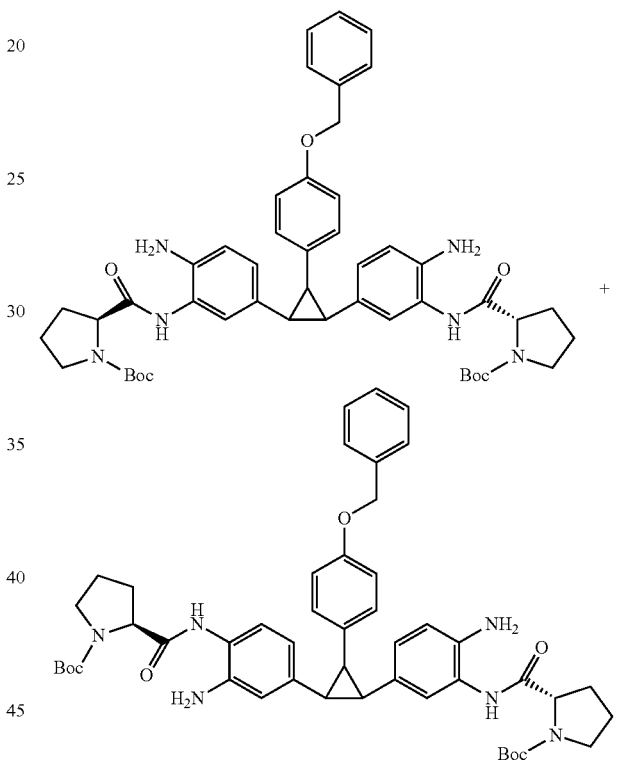

EXAMPLE 5H (2S,2'S)-tert-butyl 2,2'-(5,5'-(3-(4-(benzyloxy)phenyl)cyclopropane-1,2-diyl)bis(2-amino-5,1-phenylene))bis(azanediyl)bis(oxomethylene)dipyrrolidine-1-carboxylate And (2S)-tert-butyl 2-(2-amino-4-(2-(4-amino-3-((S)-1-(tert-butoxycarbonyl)pyrrolidine-2-carboxamido)phenyl)-3-(4-(benzyloxy)phenyl)cyclopropyl)phenylcarbamoyl)pyrrolidine-1-carboxylate A solution of the compound of Example 5G (209 mg, 0.36 mmol), 1-(tert-butoxycarbonyl)-L-proline (158 mg, 0.74 mmol), and O-(7-azabenzotriazol-1-yl)-N,N,N',N'-tetramethyluronium hexafluorophosphate (HATU, 280 mg, 0.74 mmol) in dry dimethyl sulfoxide (1.8 mL) was treated with diisopropylethylamine (627 μL, 464 mg, 3.59 mmol) followed by stirring at room temperature for 2 hours. The mixture was diluted with ethyl acetate and extracted with water (3×) and saturated sodium chloride solution. Drying (Na₂SO₄) and concentration in vacuo afforded a brown solid, which was used directly in the next step.

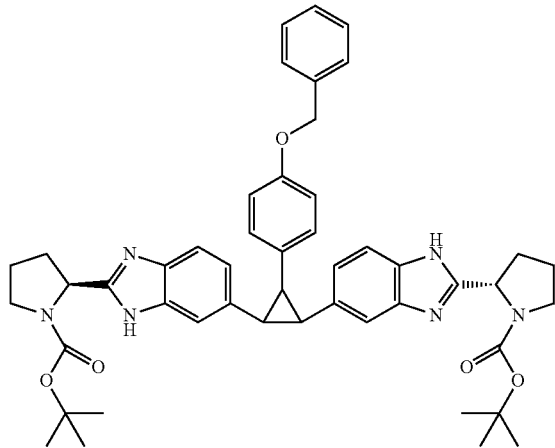 [SMILES: CC(C)(C)OC(=O)N1CCC[C@H]1c1nc2cc(C3C(c4ccc(OCc5ccccc5)cc4)C3c3ccc4nc([C@@H]5CCCN5C(=O)OC(C)(C)C)[nH]c4c3)ccc2[nH]1]

EXAMPLE 5I (2S,2'S)-tert-butyl 2,2'-(5,5'-(3-(4-(benzyloxy)phenyl)cyclopropane-1,2-diyl)bis(1H-benzo[d]imidazole-5,2-diyl))dipyrrolidine-1-carboxylate A suspension of the compound of Example 5H in toluene (2 mL) and tetrahydrofuran (0.5 mL) was treated with glacial acetic acid (150 μL) followed by warming at 70° C. for 1 hour. The mixture was cooled and concentrated in vacuo (3×) with toluene to remove acetic acid. The solid obtained was chromatographed over an 80 g silica gel cartridge, eluting with 3-12% methanol in dichloromethane. These procedures afforded an oil, which solidified upon trituration with ether-hexanes. The solids were collected by filtration and washed with hexanes. After drying in a vacuum oven at 50° C. for 24 hours, these procedures afforded the title compound (59 mg, 21% from Example 5G) as a buff-colored solid. ¹H NMR (400 MHz, CDCl₃) δ ppm 7.33 (m, 5 H), 6.92 (m, 2 H), 6.72 (d, J=8.5, 1 H), 5.09 (m, 1 H), 4.94 (s, 1 H), 3.40 (s, 2 H), 3.04 (s, 1 H), 2.92 (d, J=8.4, 1 H), 2.78 (m, 0.5 H), 2.17 (s, 2 H), 2.00 (s, 1 H), 1.62 (s, 4 H), 1.51 (s, 9 H), 1.50 (s, 9 H), 1.30 (m, 2 H); MS (ESI+) m/z (relative abundance) 795 (100, M+H)⁺, 796 (44), 1589 (52, 2M+H)⁺.

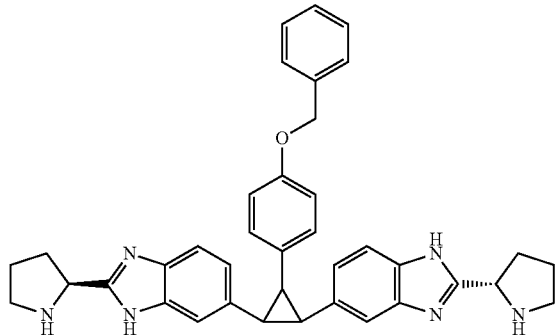 [SMILES: c1ccc(COc2ccc(C3C(c4ccc5[nH]c([C@@H]6CCCN6)nc5c4)C3c3ccc4nc([C@@H]5CCCN5)[nH]c4c3)cc2)cc1]

EXAMPLE 5J (S)-5,5'-(3-(4-(benzyloxy)phenyl)cyclopropane-1,2-diyl)bis(2-((S)-pyrrolidin-2-yl)-1H-benzo[d]imidazole)

The compound of Example 5I (59 mg, 0.074 mmol) was dissolved in a solution of hydrogen chloride in dioxane (4 N, 6 mL) with methanol (4 mL) followed by stirring at room temperature for 1 hour. The mixture was concentrated in vacuo followed by drying under high vacuum. The product was used directly in the next step.

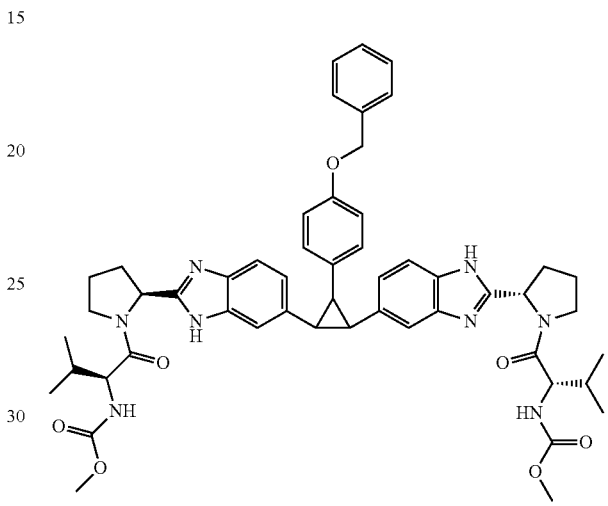

EXAMPLE 5K dimethyl (2S,2'S)-1,1'-((2S,2'S)-2,2'-(5,5'-(3-(4-(benzyloxy)phenyl)cyclopropane-1,2-diyl)bis(1H-benzo[d]imidazole-5,2-diyl))bis(pyrrolidine-2,1-diyl))bis(3-methyl-1-oxobutane-2,1-diyl)dicarbamate A solution of the compound of Example 5J (55 mg, 0.074 mmol), N-(methoxycarbonyl)-L-valine (33 mg, 0.19 mmol), N-(3-dimethylaminopropyl)-N'-ethylcarbodiimide hydrochloride (36 mg, 0.19 mmol), and 1-hydroxybenzotriazole (28 mg, 0.19 mmol) in dry N,N-dimethylformamide (400 μL) at 0° C. was treated with N-methylmorpholine (163 μL, 150 mg, 1.49 mmol). The solution was stirred at 0° C. for 30 minutes and was allowed to warm to room temperature for 2 hours. The solution was then diluted with ethyl acetate and extracted with water (3×) and saturated sodium chloride solution. Drying (Na₂SO₄) and concentration in vacuo afforded an oil, which was chromatographed over a 10 g silica gel cartridge, eluting with 1-12% methanol in dichloromethane. These procedures afforded the title compound (35 mg, 52%) as an off-white solid, after being concentrated with chloroform-hexanes. ¹H NMR (400 MHz, CDCl₃) δ ppm 10.44 (s, 1 H), 10.26 (s, 1 H), 7.68 (s, 1 H), 7.53 (m, 1 H), 7.30 (m, 10 H), 6.93 (m, 4 H), 6.70 (d, J=6.7, 2 H), 5.41 (m, 5 H), 4.93 (s, 2 H), 4.33 (m, 2 H), 3.85 (m, 2 H), 3.70 (s, 6 H), 3.63 (s, 4 H), 3.08 (s, 2 H), 2.83 (m, 3 H), 2.37 (s, 2 H), 2.18 (m, 4 H), 1.94 (m, 3 H), 1.24 (m, 2 H), 1.05 (m, 2 H), 0.86 (m, 12 H); MS (ESI+) m/z (relative abundance) 909 (100, M+H)⁺.

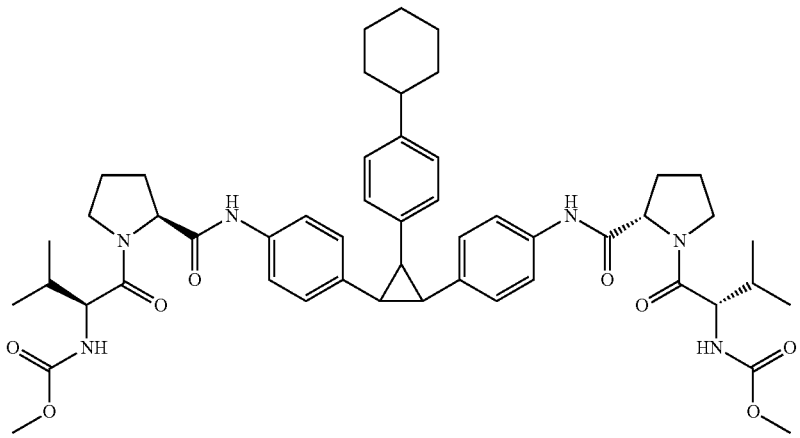 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(C3CCCCC3)cc2)cc1)C(C)C]

EXAMPLE 6 dimethyl (2S,2'S)-1,1'-((2S,2'S)-2,2'-(4,4'-(3-(4-cyclohexylphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate

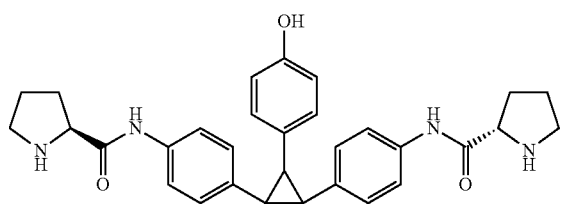 [SMILES: O=C(Nc1ccc(C2C(c3ccc(O)cc3)C2c2ccc(NC(=O)[C@@H]3CCCN3)cc2)cc1)[C@@H]1CCCN1]

EXAMPLE 6A (2S,2'S)—N,N'-(4,4'-(3-(4-hydroxyphenyl)cyclopropane-1,2-diyl)bis(4,1-phenylene))dipyrrolidine-2-carboxamide To the product from Example 2B (850 mg, 1.06 mmol) was added a solution of boron tribromide (1.0 M in dichloromethane, 2.34 mL, 2.34 mmol) in dichloromethane (25 mL) at room temperature for 0.25 hours. Then methanol (25 mL) was added to the solution and the mixture concentrated to afford 540 mg (76%) of the title compound as a bis-hydrobromide salt. MS (ESI) m/z 511 (M+H)$^+$.

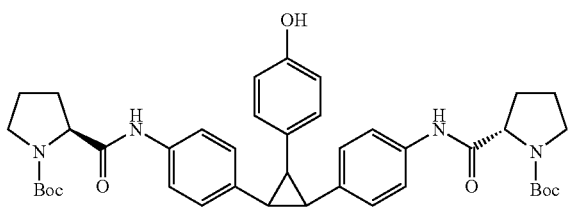 [SMILES: CC(C)(C)OC(=O)N1CCC[C@H]1C(=O)Nc1ccc(C2C(c3ccc(O)cc3)C2c2ccc(NC(=O)[C@@H]3CCCN3C(=O)OC(C)(C)C)cc2)cc1]

EXAMPLE 6B (2S,2'S)-tert-butyl 2,2'-(4,4'-(3-(4-hydroxyphenyl)cyclopropane-1,2-diyl)bis(4,1-phenylene))bis(azanediyl)bis(oxomethylene)dipyrrolidine-1-carboxylate To the bis-hydrobromide salt of the product from Example 6A (600 mg, 0.893 mmol) was added di-tert-butyl dicarbonate (487 mg, 2.23 mmol) and triethylamine (2.49 mL, 17.86 mmol) in dioxane (25 mL) and methanol (3 mL) and the mixture stirred at room temperature for 1 hour. The mixture was then concentrated. A solution of 1 N HCl (10 mL) was added to the residue followed by extraction with dichloromethane (2×10 mL). The organic extract was dried, filtered and concentrated. Then the residue was purified by chromatography (silica gel, methanol in dichloromethane) which afforded 425 mg, (67%) of the title compound. MS (ESI) m/z 711 (M+H)$^+$. Alternatively, the benzyl group in the product of Example 2B can be removed to provide Example 6B (without removal of the tert-butoxycarbonyl groups) by employing Raney® nickel and hydrogen under a high pressure environment.

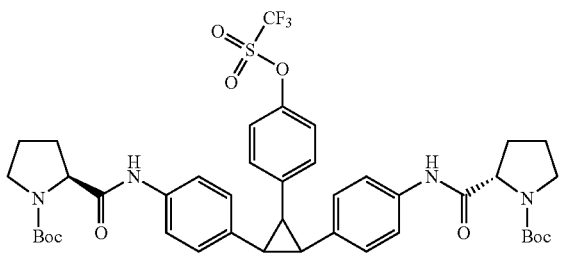 [SMILES: CC(C)(C)OC(=O)N1CCC[C@H]1C(=O)Nc1ccc(C2C(c3ccc(NC(=O)[C@@H]4CCCN4C(=O)OC(C)(C)C)cc3)C2c2ccc(OS(=O)(=O)C(F)(F)F)cc2)cc1]

EXAMPLE 6C (2S,2'S)-tert-butyl 2,2'-(4,4'-(3-(4-(trifluoromethylsulfonyloxy)phenyl)cyclopropane-1,2-diyl)bis(4,1-phenylene))bis(azanediyl)bis(oxomethylene)dipyrrolidine-1-carboxylate To the product from Example 6B (50 mg, 0.07 mmol) dissolved in dichloromethane (3 mL) was added triethylamine (0.098 mL, 0.702 mmol). Then a solution of trifluoromethanesulfonic anhydride (0.059 mL, 0.352 mmol) in dichloromethane (2 mL) was added dropwise at room temperature. After 1 hour, a solution of 1 N HCl (5 mL) was added followed by extraction with dichloromethane (10 mL). The organic extract was dried, filtered and concentrated which afforded 60 mg, (100%) of the title compound. MS (ESI) m/z 843 (M+H)+.

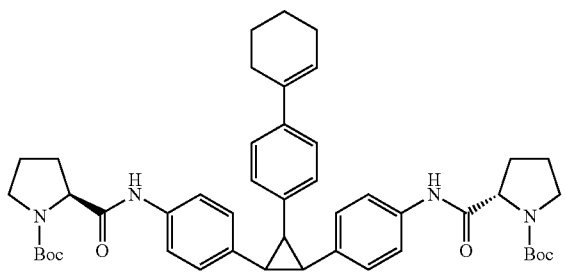 [SMILES: CC(C)(C)OC(=O)N1CCC[C@H]1C(=O)Nc1ccc(C2C(c3ccc(NC(=O)[C@@H]4CCCN4C(=O)OC(C)(C)C)cc3)C2c2ccc(C3=CCCCC3)cc2)cc1]

EXAMPLE 6D (2S,2'S)-tert-butyl 2,2'-(4,4'-(3-(4-cyclohexenylphenyl)cyclopropane-1,2-diyl)bis(4,1-phenylene))bis(azanediyl)bis(oxomethylene)dipyrrolidine-1-carboxylate To the product from Example 6C (60 mg, 0.070 mmol), 1-cyclohexen-yl-boronic acid pinacol ester (16.3 mg, 0.078 mmol), sodium bicarbonate (29.9 mg, 0.356 mmol) and [1,1'-bis(diphenylphosphino)ferrocene]dichloropalladium(II) (13 mg, 0.018 mmol) in dimethoxyethane (3 mL) and water (1 mL) was heated at 80° C. for 17 hours. Water (5 mL) was then added to the mixture followed by extraction with ethyl acetate (2×5 mL). The organic extract was dried, filtered and concentrated. Then the residue was purified by chromatography (silica gel, ethyl acetate in hexanes) which afforded 20 mg, (36%) of the title compound. MS (ESI) m/z 776 (M+H)+.

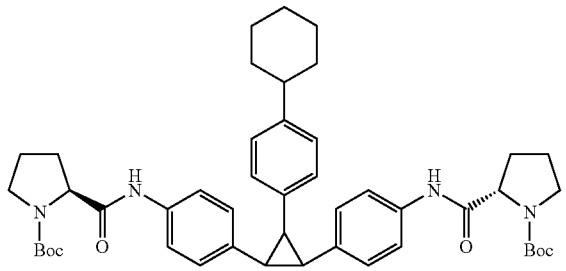 [SMILES: CC(C)(C)OC(=O)N1CCC[C@H]1C(=O)Nc1ccc(C2C(c3ccc(NC(=O)[C@@H]4CCCN4C(=O)OC(C)(C)C)cc3)C2c2ccc(C3CCCCC3)cc2)cc1]

EXAMPLE 6E (2S,2'S)-tert-butyl 2,2'-(4,4'-(3-(4-cyclohexylphenyl)cyclopropane-1,2-diyl)bis(4,1-phenylene))bis(azanediyl)bis(oxomethylene)dipyrrolidine-1-carboxylate To the product from Example 6D (20 mg, 0.026 mmol) in methanol (3 mL) was added 10% palladium on carbon (11 mg, 0.103 mmol), and the mixture was placed under an atmosphere of hydrogen (balloon). After hydrogenation at room temperature for 24 hours, the mixture was filtered through diatomaceous earth, and the filter cake was washed with methanol. The filtrate was concentrated to afford 20 mg (100%) of the title compound. MS (ESI) m/z 778 (M+H)+.

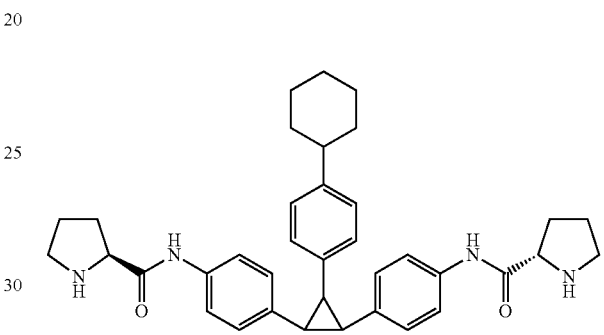

EXAMPLE 6F (2S,2'S)—N,N'-(4,4'-(3-(4-cyclohexylphenyl)cyclopropane-1,2-diyl)bis(4,1-phenylene))dipyrrolidine-2-carboxamide The product from Example 6F (20 mg, 0.026 mmol) was processed using the method described in Example 1D to afford 15 mg (100%) of the title compound.

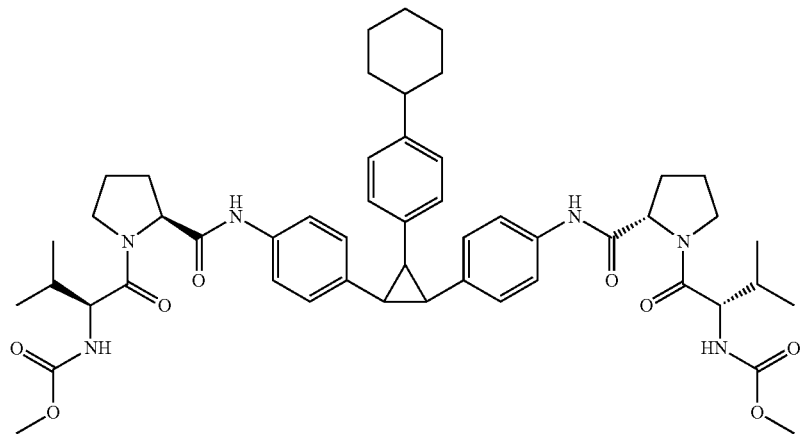 [SMILES: COC(=O)N[C@H](C(=O)N1CCC[C@H]1C(=O)Nc1ccc(C2C(c3ccc(NC(=O)[C@@H]4CCCN4C(=O)[C@@H](NC(=O)OC)C(C)C)cc3)C2c2ccc(C3CCCCC3)cc2)cc1)C(C)C]

EXAMPLE 6G dimethyl (2S,2'S)-1,1'-((2S,2'S)-2,2'-(4,4'-(3-(4-cyclohexylphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate The product from Example 6F (15 mg, 0.026 mmol), and (S)-2-(methoxycarbonylamino)-3-methylbutanoic acid (9 mg, 0.052 mmol), were processed using the method described in Example 1E to afford 9 mg (40%) of the title compound. $^1$H NMR (400 MHz, DMSO-d$_6$) δ ppm 9.96 (s, 1H), 9.87 (s, 1H), 7.53 (d, J=8.6 Hz, 2H), 7.33 (m, 5H), 6.98 (m, 5H), 4.43 (m, 1H), 4.39 (m, 1H), 4.02 (m, 2H), 3.80 (m, 4H), 3.61 (m, 2H), 3.54 (m, 6H), 2.90 (m, 1H), 2.74 (m, 1H), 2.68 (m, 1H), 2.12 (m, 2H), 1.80 (m, 14H), 1.26 (m, 5H), 0.88 (m, 12H); MS (ESI) m/z 891 (M+H)$^+$.

EXAMPLE 7 dimethyl (2S,2'S)-1,1'-((2S,2'S)-2,2'-(4,4'-(2-(4-tert-butylphenyl)cyclopent-3-ene-1,3-diyl)bis(4,1-phenylene)bis(azanediyl)bis(oxomethylene))bis(pyrrolidine-2,1-diyl))bis(3-methyl-1-oxobutane-2,1-diyl) dicarbamate

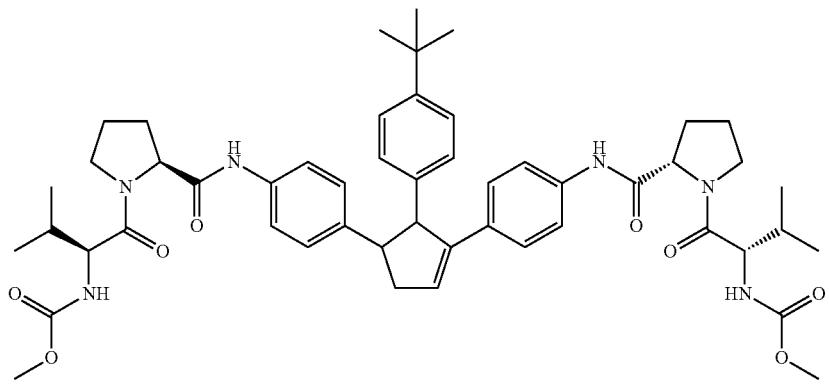

EXAMPLE 7A 3-methoxycyclopent-2-enone

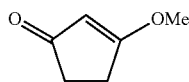

A mixture of 1,3-cyclopentanedione (15.0 g, 153 mmol) and I$_2$ (1.164 g, 4.59 mmol) in methanol (150 mL) was stirred at 25° C. for 16 hours. The solvent was removed under reduced pressure. The residue was dissolved in ethyl acetate (200 mL) and washed with aqueous Na$_2$S$_2$O$_3$ solution (100 mL), water (100 mL) and brine (100 mL) successively. The organic layer was dried over Na$_2$SO$_4$, filtered and concentrated in vacuo. The residue was used in the next step without further purification. LC/MS (ESI) m/z 113 (M+H)$^+$.

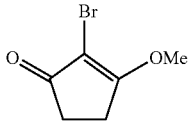

EXAMPLE 7B 2-bromo-3-methoxycyclopent-2-enone

A mixture of Example 7A (500 mg, 4.46 mmol) and N-bromosuccinimide (794 mg, 4.46 mmol) in dichloromethane (5 mL) was stirred at 25° C. for 16 hours. The mixture was concentrated in vacuo. The residue was purified on a silica column (dichloromethane/methanol=200:1, v/v) to afford the title compound (650 mg, 3.40 mmol, 76% yield) as a solid. $^1$H NMR (400 MHz, CDCl$_3$) δ ppm 4.12 (s, 3H), 2.79-2.82 (m, 2H), 2.62-2.65 (m, 2H); LC/MS (ESI) m/z 191 (M+H)$^+$.

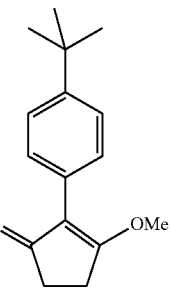

EXAMPLE 7C 2-(4-tert-butylphenyl)-3-methoxycyclopent-2-enone

A mixture of Example 7B (440 mg, 2.303 mmol), 4-tert-butylphenylboronic acid (492 mg, 2.76 mmol), [1,1'-bis(diphenylphosphino)ferrocene]dichloropalladium(II), complex with dichloromethane (188 mg, 0.230 mmol) and K$_2$CO$_3$ (637 mg, 4.61 mmol) in 1,4-dioxane (2 mL) and water (0.5 mL) was stirred at 100° C. for 16 hours. The mixture was diluted with ethyl acetate (100 mL) and washed with brine (30 mL×4). The organic layer was dried over Na$_2$SO$_4$, filtered and concentrated in vacuo. The residue was purified by column chromatography (on silica gel, eluted with petroleum ether/ ethyl acetate=5:1, v/v) to afford the title compound (445 mg, 1.821 mmol, 79% yield) as a white solid. LC/MS (ESI) m/z 245 (M+H)⁺.

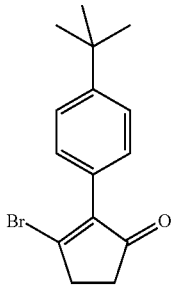

EXAMPLE 7D 3-bromo-2-(4-tert-butylphenyl)cyclopent-2-enone

To a solution of Example 7C (245 mg, 1.003 mmol) in 1,2-dichloroethane (5 mL) was added PBr₃ (0.142 mL, 1.504 mmol). The resulting mixture was heated to reflux for 1 hour, then cooled to ambient temperature, and poured over cracked ice. The organic layer was separated, washed with saturated aqueous NaHCO₃ (5 mL), and dried over MgSO₄. The solvent was removed under reduced pressure, and the residue was purified by column chromatography (on silica gel, eluted with dichloromethane/methanol=200:1, v/v) to afford the title compound (200 mg, 0.682 mmol, 68.0% yield) as a light yellow solid. ¹H NMR (400 MHz, CDCl₃) δ ppm 7.38 (s, 4H), 3.00-3.03 (m, 2H), 2.62-2.65 (m, 2H), 1.26 (s, 9H); LC/MS (ESI) m/z 293 (M+H)⁺.

EXAMPLE 7E tert-butyl 4-(2-(4-tert-butylphenyl)-3-oxocyclopent-1-enyl)phenylcarbamate A mixture of Example 7D (88 mg, 0.300 mmol), tert-butyl 4-(4,4,5,5-tetramethyl-1,3,2-dioxaborolan-2-yl)phenylcarbamate (105 mg, 0.330 mmol), [1,1'-bis(diphenylphosphino) ferrocene]dichloropalladium(II), complex with dichloromethane (24.51 mg, 0.030 mmol) and K₂CO₃ (83 mg, 0.600 mmol) in 1,4-dioxane (2 mL) and water (0.5 mL) was stirred at 100° C. for 16 hours. The mixture was diluted with ethyl acetate (30 mL) and washed with brine (10 mL×4). The organic layers were dried over Na₂SO₄, filtered and concentrated in vacuo. The residue was purified by preparative thin layer chromatography (eluted with petroleum ether/ethyl acetate=2:1, v/v) to afford the title compound (60 mg, 0.148 mmol, 49.3% yield) as a white solid. ¹H NMR (400 MHz, CDCl₃) δ ppm 7.28-7.36 (m, 6H), 7.14 (d, J=8.0 Hz, 2H), 6.52 (s, 1H), 3.00-3.03 (m, 2H), 2.66-2.69 (m, 2H), 1.51 (s, 9H), 1.32 (s, 9H); LC/MS (ESI) m/z 406 (M+H)⁺.

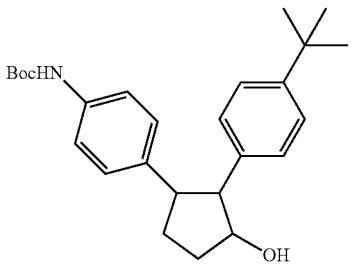 [SMILES: CC(C)(C)OC(=O)Nc1ccc(C2CCC(O)C2c2ccc(C(C)(C)C)cc2)cc1]

EXAMPLE 7F tert-butyl 4-(2-(4-tert-butylphenyl)-3-hydroxycyclopentyl)phenylcarbamate A mixture of Example 7E (20 mg, 0.049 mmol) and 10% palladium on carbon (5.25 mg, 0.049 mmol) in methanol (4 mL) was stirred at 25° C. under a hydrogen atmosphere (balloon) for 16 hours. The mixture was filtered, and the filtrate was concentrated in vacuo. The residue was directly used in the next step without further purification. ¹H NMR (400 MHz, CDCl₃) δ ppm 6.67-7.25 (m, 8H), 6.26 (s, 1H), 4.53 (brs, 1H), 3.52 (brs, 1H), 3.29 (br, 1H), 1.82-2.24 (m, 4H), 1.45 (s, 9H), 1.20 (s, 9H); LC/MS (ESI) m/z 408 (M−H)⁻.

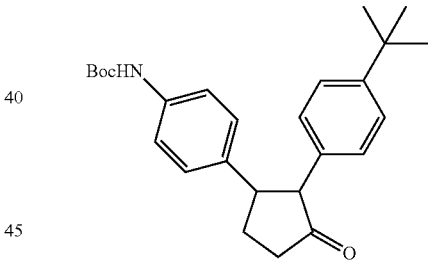

EXAMPLE 7G tert-butyl 4-(2-(4-tert-butylphenyl)-3-oxocyclopentyl)phenylcarbamate A mixture of crude Example 7F (263 mg, 0.641 mmol) and Dess-Martin periodinane (299 mg, 0.705 mmol) in dichloromethane (4 mL) was stirred at 25° C. for 30 minutes. The mixture was diluted with ethyl acetate (30 mL) and washed with saturated NaHCO₃ solution (10 mL×4) and then saturated Na₂S₂O₄ solution (10 mL×4). The organic layer was dried over Na₂SO₄, filtered and concentrated in vacuo. The residue was purified by preparative thin layer chromatography (eluted with dichloromethane/methanol=200:1, v/v) to afford the title compound (60 mg, 0.147 mmol, 22.97% yield) as a light yellow oil. ¹H NMR (400 MHz, CDCl₃) δ ppm 7.18-7.20 (m, 4H), 7.05 (d, J=8.8 Hz, 2H), 6.89 (d, J=8.4 Hz, 2H), 6.33 (s, 1H), 3.32-3.42 (m, 2H), 2.57-2.63 (m, 1H), 2.33-2.41 (m, 2H), 1.95-1.98 (m, 1H), 1.44 (s, 9H), 1.18 (s, 9H); LC/MS (ESI) m/z 406 (M−H)⁻.

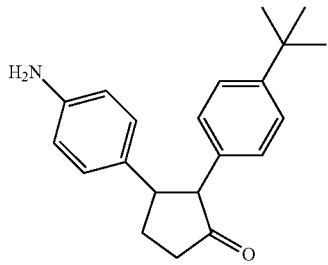 [SMILES: CC(C)(C)c1ccc(C2C(=O)CCC2c2ccc(N)cc2)cc1]

EXAMPLE 7H 3-(4-aminophenyl)-2-(4-tert-butylphenyl)cyclopentanone

A mixture of Example 7G (1.3 g, 3.19 mmol) in dichloromethane (12 mL) and trifluoroacetic acid (4 mL) was stirred at ambient temperature for 1 hour. The mixture was diluted with ethyl acetate (100 mL) and washed with saturated NaHCO₃ solution (30 mL×3) and brine (30 mL). The organic layer was dried over Na₂SO₄, filtered and concentrated in vacuo. The residue was purified by preparative thin layer chromatography (petroleum ether/ethyl acetate=2:1, v/v) to afford the title compound (586 mg, 1.906 mmol, 59.8% yield) as a solid. LC/MS (ESI) m/z 308 (M+H)⁺.

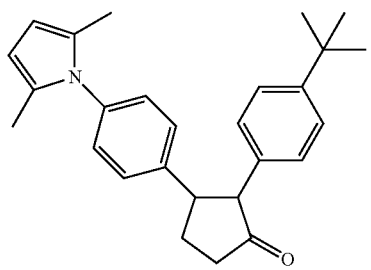 [SMILES: Cc1ccc(C)n1-c1ccc(C2CCC(=O)C2c2ccc(C(C)(C)C)cc2)cc1]

EXAMPLE 7I 2-(4-tert-butylphenyl)-3-(4-(2,5-dimethyl-1H-pyrrol-1-yl)phenyl)cyclopentanone A mixture of Example 7H (300 mg, 0.976 mmol), hexane-2,5-dione (134 mg, 1.171 mmol) and p-toluenesulfonic acid (1.856 mg, 9.76 mol) in toluene (2 mL) was stirred at 110° C. for 1 hour. The mixture was concentrated in vacuo. The residue was directly used in the next step without further purification. LC/MS (ESI) m/z 386 (M+H)⁺.

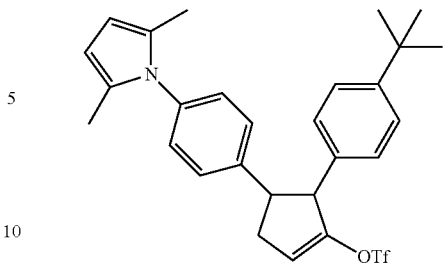

EXAMPLE 7J 5-(4-tert-butylphenyl)-4-(4-(2,5-dimethyl-1H-pyrrol-1-yl)phenyl)cyclopent-1-enyl trifluoromethanesulfonate To a solution of crude Example 7I (376 mg, 0.976 mmol) in tetrahydrofuran (10 mL) was added lithium bis(trimethylsilyl)amide (1.171 mL, 1.171 mmol, tetrahydrofuran) dropwise at −78° C. After stirring at ambient temperature for 30 minutes, 1,1,1-trifluoro-N-phenyl-N-[(trifluoromethyl)sulfonyl] methanesulfonamide (418 mg, 1.171 mmol) was added to the reaction mixture at −78° C. in one portion. The mixture was then allowed to warm to room temperature and stirred overnight. The reaction was quenched with saturated NH₄Cl solution. The organic layer was separated and concentrated in vacuo. The residue was purified by preparative thin layer chromatography (eluted with petroleum ether/ethyl acetate=20:1, v/v) to afford the title compound (300 mg, 0.580 mmol, 59.4% yield) as an oil. LC/MS (ESI) m/z 518 (M+H)⁺.

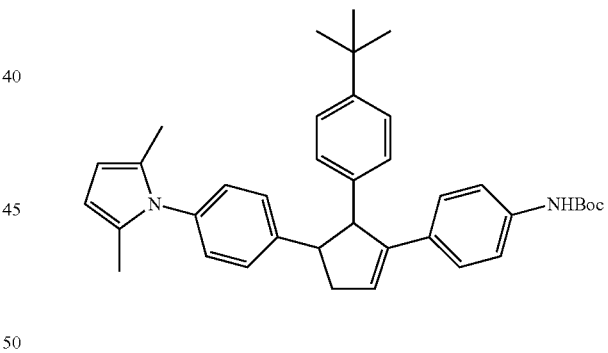

EXAMPLE 7K tert-butyl 4-(5-(4-tert-butylphenyl)-4-(4-(2,5-dimethyl-1H-pyrrol-1-yl)phenyl)cyclopent-1-enyl)phenylcarbamate A mixture of Example 7J (373 mg, 0.721 mmol), tert-butyl 4-(4,4,5,5-tetramethyl-1,3,2-dioxaborolan-2-yl)phenylcarbamate (253 mg, 0.793 mmol), K₂CO₃ (299 mg, 2.162 mmol) and [1,1'-bis(diphenylphosphino)ferrocene]dichloropalladium(II), complex with dichloromethane (58.8 mg, 0.072 mmol) in 1,4-dioxane (4 mL) and water (1 mL) was heated at 100° C. for 16 hours. The mixture was concentrated in vacuo, the residue was purified by column chromatography (on silica gel, eluted with dichloromethane/petroleum ether=2:1, v/v) to afford the title compound (386 mg, 0.688 mmol, 95% yield) as a solid. LC/MS (ESI) m/z 561 (M+H)⁺.

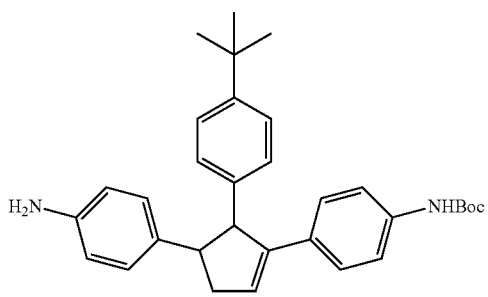 [SMILES: CC(C)(C)OC(=O)Nc1ccc(C2=CCC(c3ccc(N)cc3)C2c2ccc(C(C)(C)C)cc2)cc1]

EXAMPLE 7L tert-butyl 4-(4-(4-aminophenyl)-5-(4-tert-butylphenyl)cyclopent-1-enyl)phenylcarbamate A mixture of Example 7K (475 mg, 0.847 mmol), hydroxylamine hydrochloride (353 mg, 5.08 mmol) and KOH (143 mg, 2.54 mmol) in ethanol (6 mL) and water (2 mL) was stirred at 65° C. for 48 hours. The mixture was concentrated in vacuo. The residue was diluted with ethyl acetate (20 mL) and washed with brine (6 mL×2). The organic layer was dried over $Na_2SO_4$, filtered and concentrated. The residue was used directly in the next step without further purification. LC/MS (ESI) m/z 483 $(M+H)^+$.

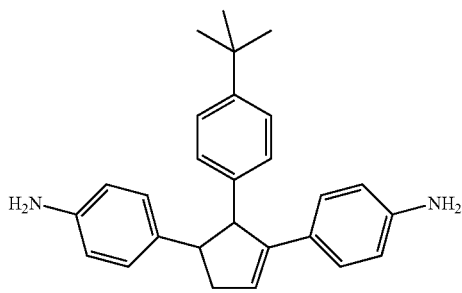 [SMILES: CC(C)(C)c1ccc(C2C(c3ccc(N)cc3)=CCC2c2ccc(N)cc2)cc1]

EXAMPLE 7M 4,4'-(2-(4-tert-butylphenyl)cyclopent-3-ene-1,3-diyl)dianiline

A mixture of crude Example 7L (372 mg, 0.771 mmol) in dichloromethane (3 mL) and trifluoroacetic acid (1 mL) was stirred at room temperature for 16 hours. The mixture was neutralized with aqueous $NaHCO_3$ solution and extracted with dichloromethane (10 mL×2). The organic layer was dried over $Na_2SO_4$, filtered and concentrated. The residue was purified by column chromatography (on silica gel, eluted with dichloromethane/methanol=50:1, v/v) to afford the title compound (240 mg, 0.627 mmol, 81% yield) as a brown solid. $^1$H NMR (400 MHz, methanol-$d_4$) δ ppm 7.12 (d, J=8.8 Hz, 2H), 6.98 (d, J=8.8 Hz, 2H), 6.89 (d, J=8.4 Hz, 2H), 6.86 (d, J=8.4 Hz, 2H), 6.57 (d, J=8.4 Hz, 2 H), 6.43 (d, J=8.4 Hz, 2H), 6.12 (s, 1H), 4.49 (s, 1H), 3.02-3.05 (m, 1H), 2.87-2.93 (m, 1H), 2.41-2.45 (m, 1H), 1.16 (s, 9H); LC/MS (ESI) m/z 383 $(M+H)^+$.

EXAMPLE 7N dimethyl (2S,2'S)-1,1'-((2S,2'S)-2,2'-(4,4'-(2-(4-tert-butylphenyl)cyclopent-3-ene-1,3-diyl)bis(4,1-phenylene))bis(azanediyl)bis(oxomethylene))bis(pyrrolidine-2,1-diyl))bis(3-methyl-1-oxobutane-2,1-diyl) dicarbamate A mixture of Intermediate 9 (103 mg, 0.376 mmol), Example 7M (80 mg, 0.188 mmol), (benzotriazol-1-yloxy)tripyrrolidinophosphonium hexafluorophosphate (PyBOP®, 215 mg, 0.414 mmol) and diisopropylethylamine (0.197 mL, 1.129 mmol) in N,N-dimethylformamide (2 mL) was stirred at ambient temperature for 16 hours. The mixture was then purified by preparative HPLC (Instrument Gilson 281 (PHG008); Column Waters Xbridge™ OBD™ C18 19*250 mm, 10 μm; Mobile Phase A water (10 ppm $NH_4HCO_3$) B acetonitrile Gradient 32-80% B in 8 minutes, stop at 15 minutes; Flow Rate (mL/minute) 30.00; Detective Wavelength (nm) 214\254 Retention Time (minutes) 7.6; Number of Injections 2.00; Purity of crude sample (%) 17.82) to afford the title compound (30 mg, 0.034 mmol, 8.94% yield) as a white solid. $^1$H NMR (400 MHz, methanol-$d_4$) δ ppm 7.02-7.47 (m, 12H), 6.43 (s, 1H), 4.49-4.57 (m, 2H), 4.20-4.27 (m, 3H), 3.93-3.98 (m, 2H), 3.65-3.75 (m, 8H), 3.06-3.15 (m, 1H), 2.63-2.67 (m, 2H), 2.03-2.31 (m, 10H), 1.27 (s, 9H), 0.95-1.06 (m, 12H); LC/MS (ESI) m/z 891 $(M+H)^+$.

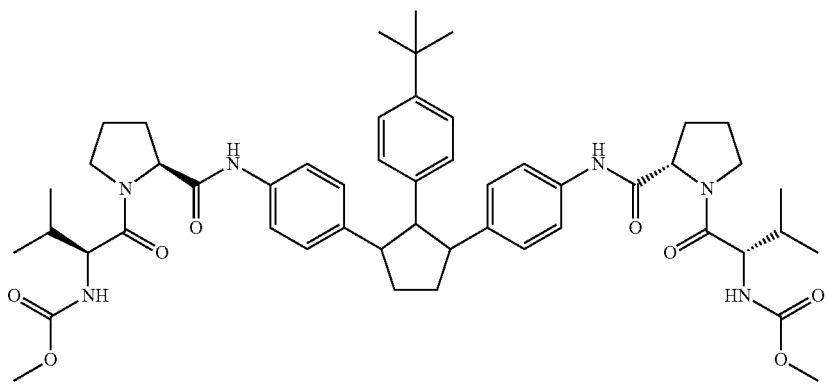 [SMILES: COC(=O)N[C@H](C(=O)N1CCC[C@H]1C(=O)Nc1ccc(C2CCC(c3ccc(NC(=O)[C@@H]4CCCN4C(=O)[C@@H](NC(=O)OC)C(C)C)cc3)C2c2ccc(C(C)(C)C)cc2)cc1)C(C)C]

EXAMPLE 8 dimethyl (2S,2'S)-1,1'-((2S,2'S)-2,2'-(4,4'-(2-(4-tert-butylphenyl)cyclopentane-1,3-diyl)bis(4,1-phenylene)bis(azanediyl)bis(oxomethylene))bis(pyrrolidine-2,1-diyl))bis(3-methyl-1-oxobutane-2,1-diyl) dicarbamate A mixture of Example 7N (50 mg, 0.056 mmol) and 10% palladium on carbon (5.97 mg, 0.056 mmol) in methanol (1 mL) was stirred under hydrogen (balloon) for 16 hours at 30° C. The mixture was filtered, and the filtrate was concentrated in vacuo. The residue was purified by preparative HPLC: Instrument Waters 2767 PHW003; Column Boston C18 10 μm 21*250 mm; Mobile Phase A: water (0.05% $NH_4HCO_3$); B: acetonitrile Gradient 55-85% B in 8 minutes, stop at 14 minutes; Flow Rate (mL/minute) 30.00; Detective Wavelength (nm) 214\254; Retention Time (minutes) 8.18; Number of Injections 2.00; Purity of Crude Sample (%) 70, to afford the title compound (31 mg, 0.035 mmol, 61.9% yield) as a white solid. $^1$H NMR (400 MHz, methanol-$d_4$) δ ppm 6.70-7.37 (m, 12H), 4.51-4.53 (m, 2H), 4.20-4.23 (m, 2H), 3.95-3.98 (m, 2H), 3.49-3.73 (m, 10H), 3.15-3.18 (m, 1H), 2.01-2.55 (m, 14H), 1.18-1.22 (m, 9H), 0.96-1.05 (m, 12H); LC/MS (ESI) m/z 893 (M+H)$^+$.

The title compounds of Examples 2, 3, 4, and 6 showed an $EC_{50}$ value of less than about 0.1 nM in HCV 1b-Con1 replicon assays in the presence of 5% FBS. The title compounds of Examples 1, 5 and 8 showed an $EC_{50}$ value of from about 0.1 to about 1 nM in HCV 1b-Con1 replicon assays in the presence of 5% FBS. The title compound of Examples 7 showed an $EC_{50}$ value of from about 1 to about 5 nM in HCV 1b-Con1 replicon assays in the presence of 5% FBS.

The present invention also contemplates pharmaceutically acceptable salts of each compound in Examples 1-8, as well as pharmaceutically acceptable salts of each compound described hereinbelow.

Likewise, the following compounds of Formula I or pharmaceutically acceptable salts thereof can be similarly prepared according to the schemes and procedures described above,

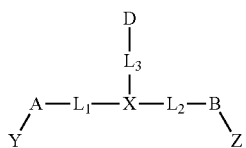

I wherein A is selected from Table 1a, B is selected from Table 1b, D is selected from Table 2, Y and Z are each independently selected from Table 3, and

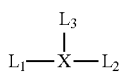

is selected from Table 4, and A, B, D and X are each independently optionally substituted with one or more $R_A$, and D is optionally substituted with J, and wherein J, $L_1$, $L_2$, $L_3$ and $R_A$ are as described above. Preferably, $L_1$, $L_2$ and $L_3$ are bond.

TABLE 1a

A

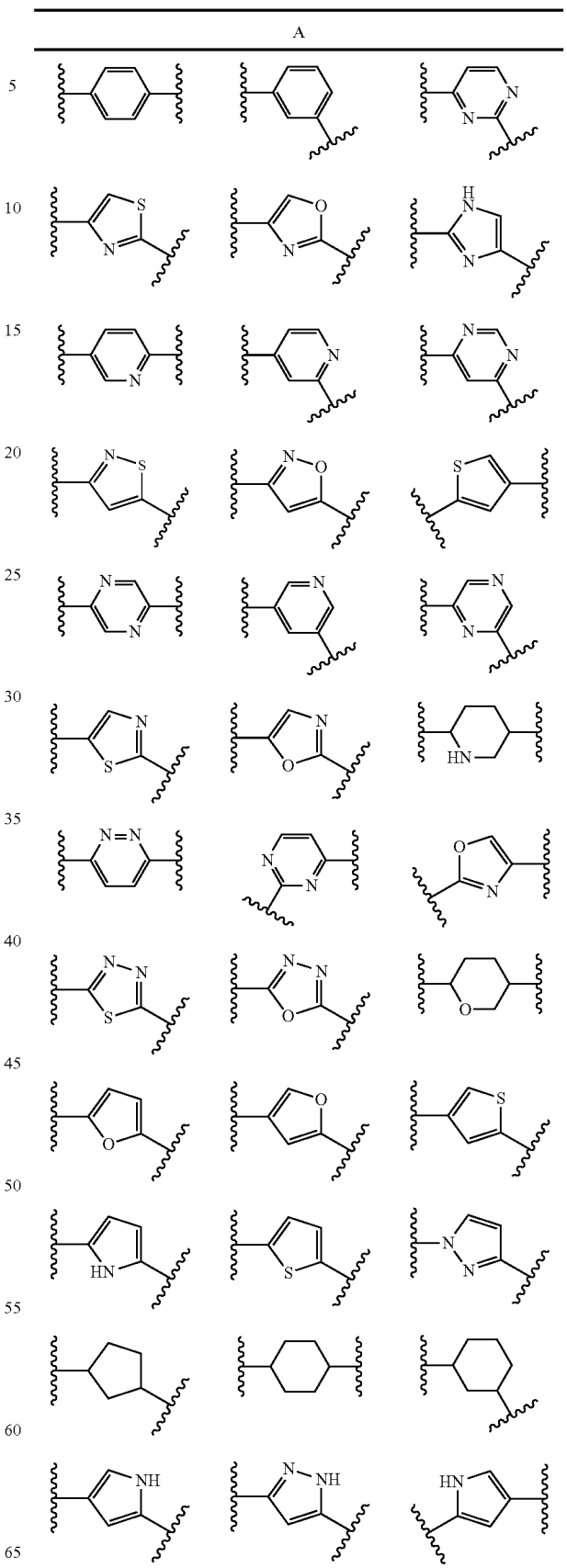

TABLE 1a-continued
A
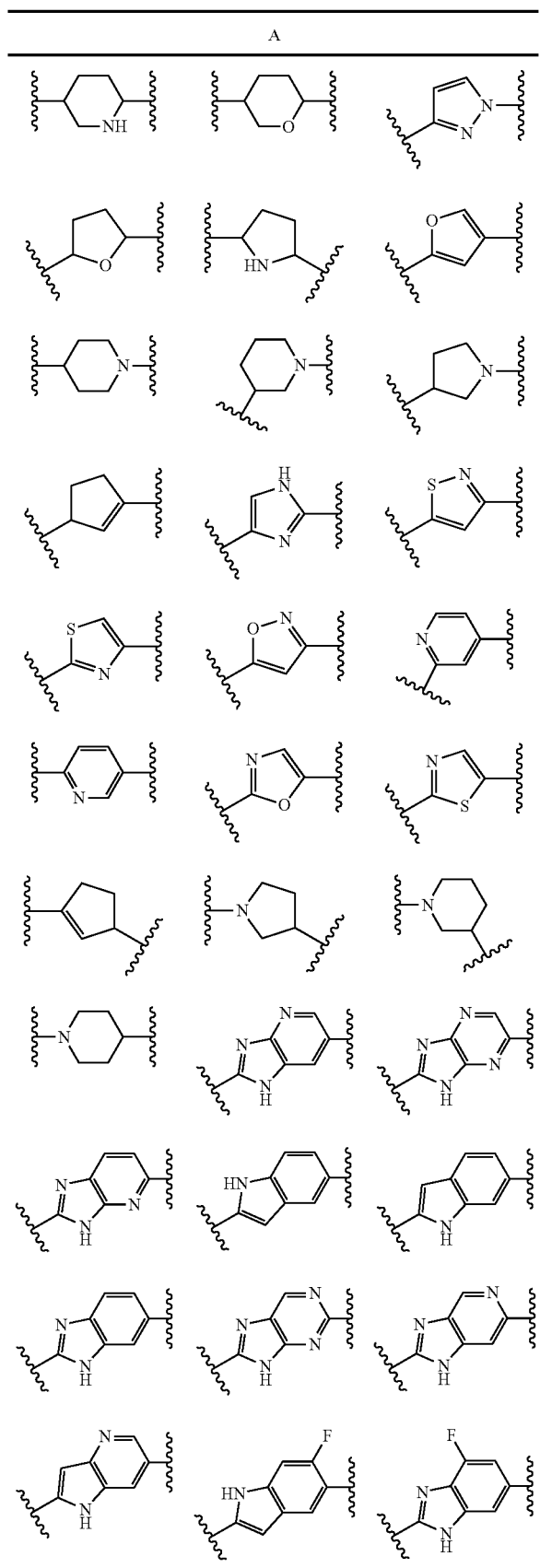
TABLE 1a-continued
A
TABLE 1b
B
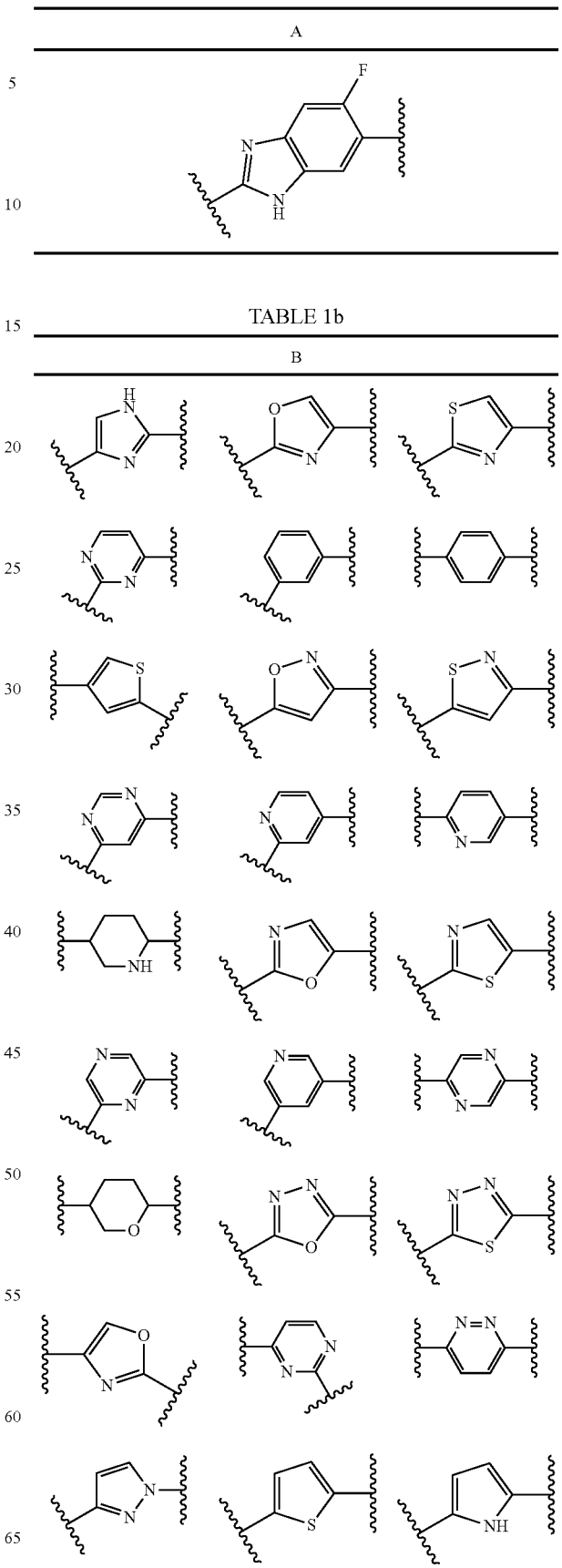

TABLE 1b-continued
B
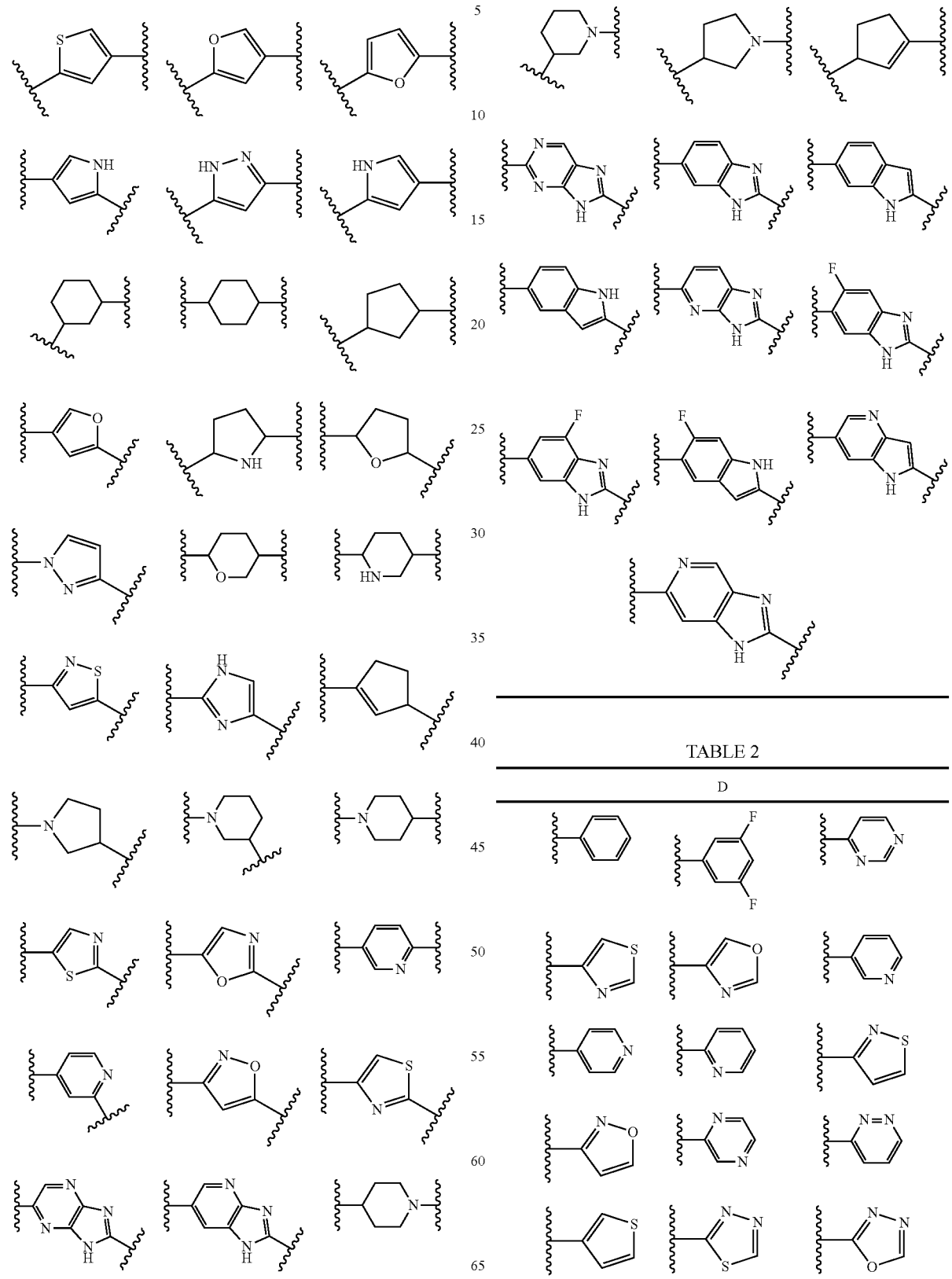
TABLE 2
D
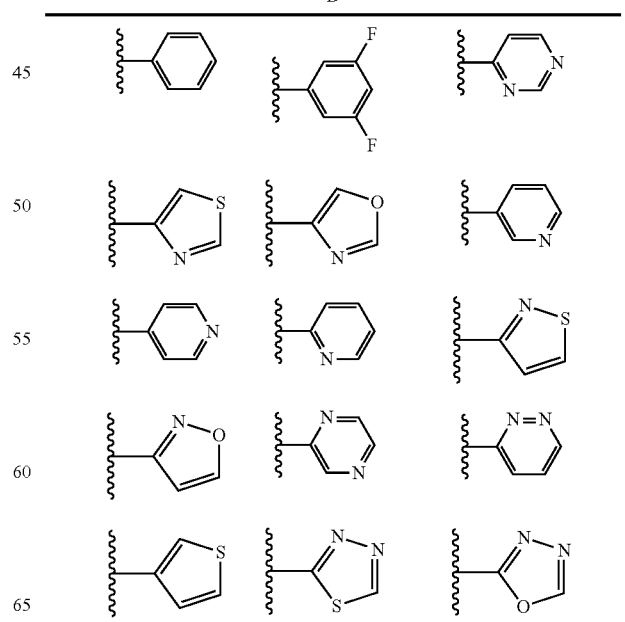

TABLE 2-continued

D

TABLE 3

Y and Z

TABLE 3-continued
Y and Z
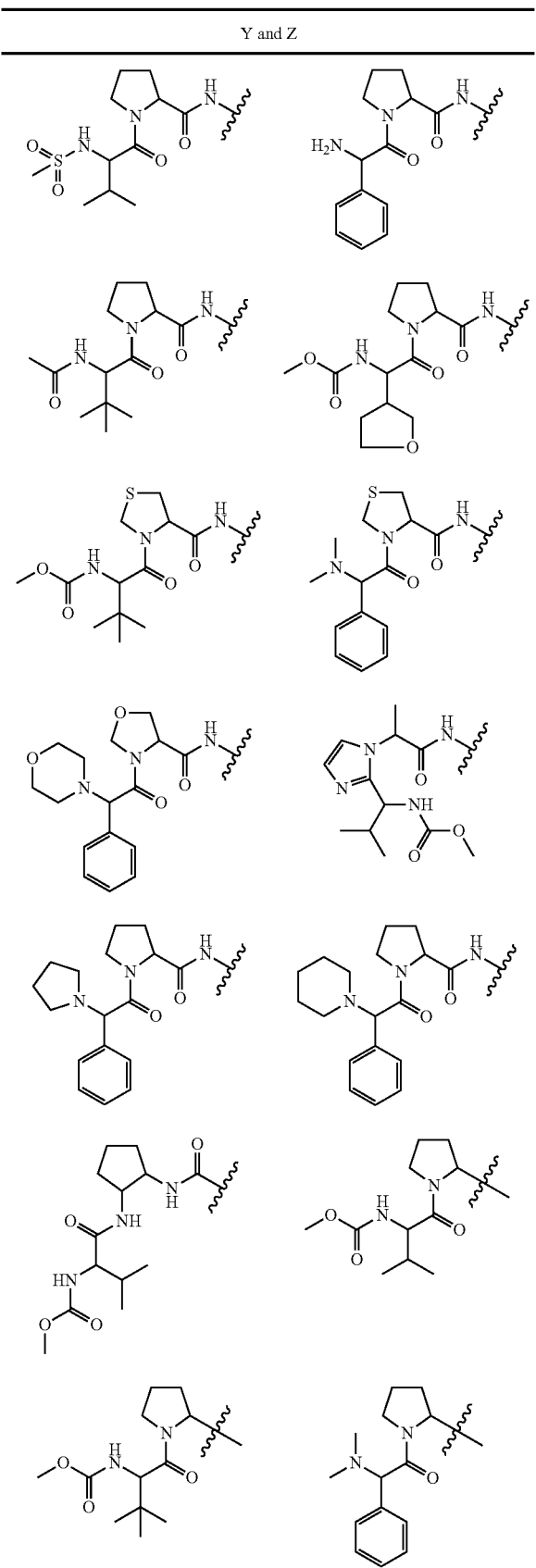
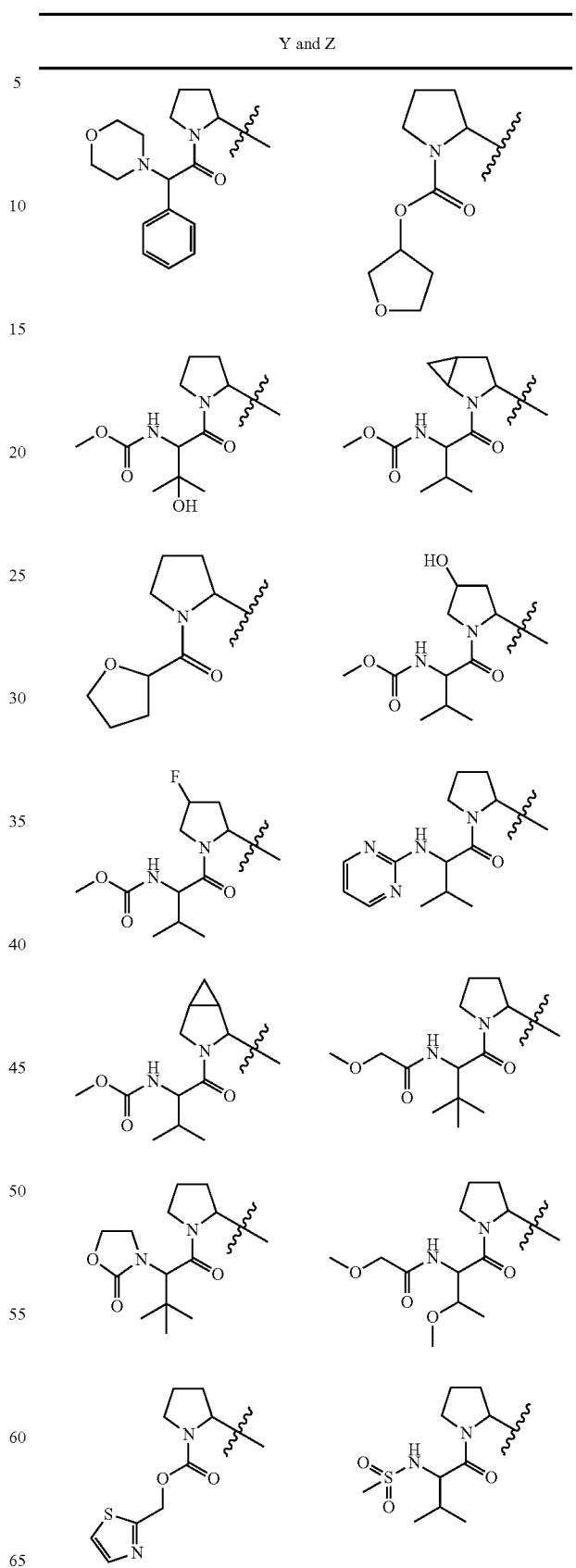

TABLE 3-continued
Y and Z
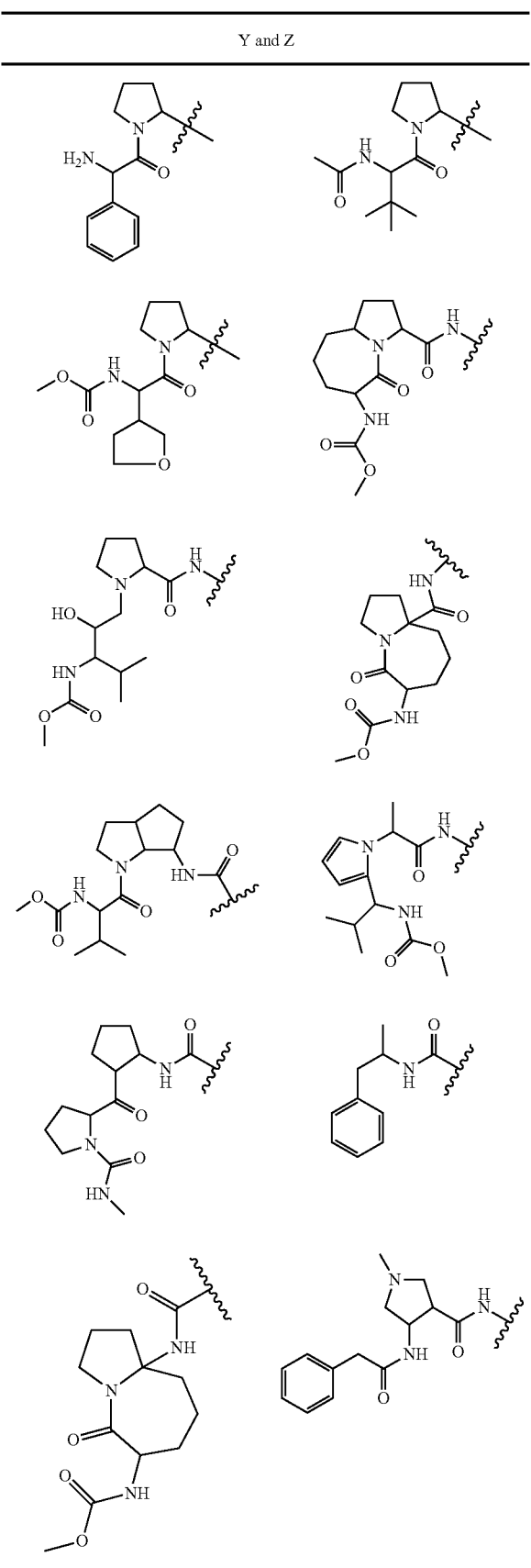
TABLE 3-continued
Y and Z
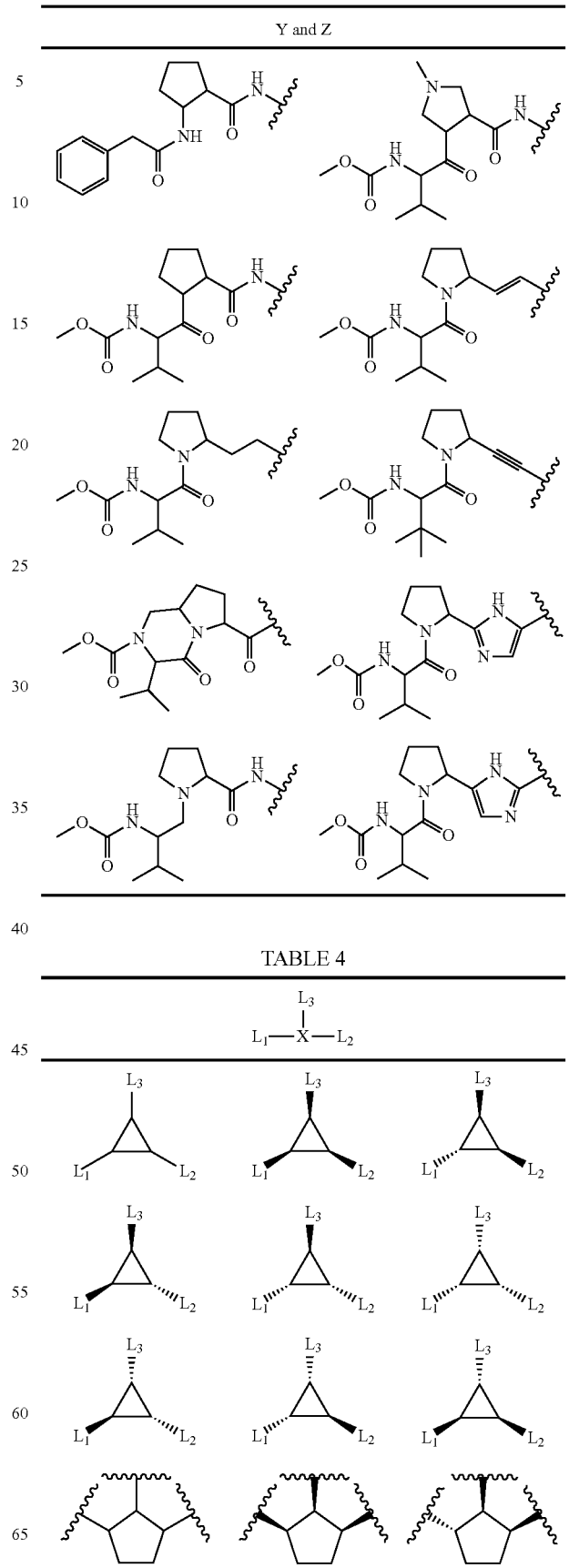
TABLE 4

TABLE 4-continued

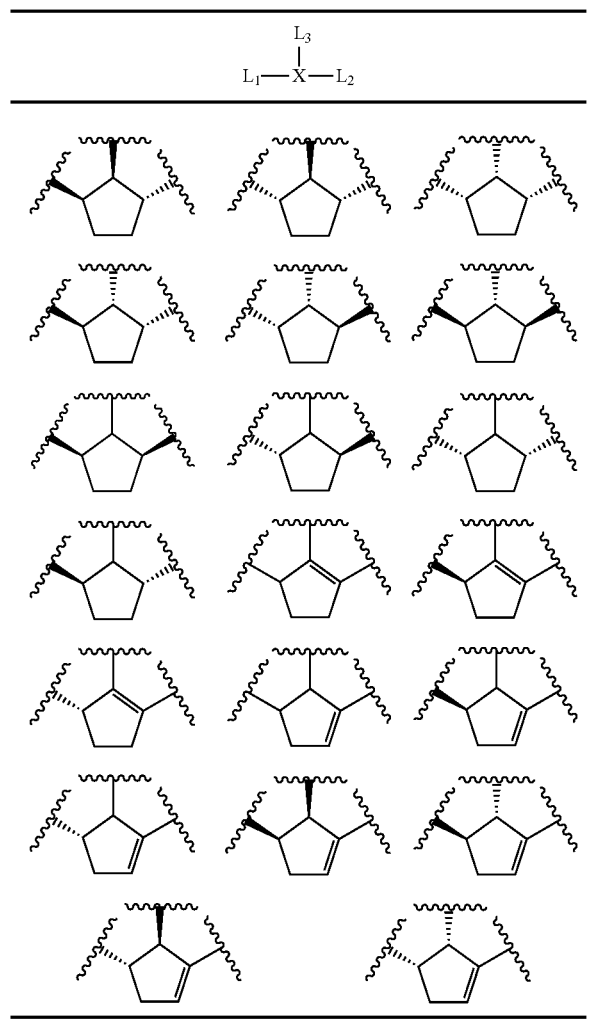

Each compound's anti-HCV activity can be determined by measuring the activity of the luciferase reporter gene in the replicon in the presence of 5% FBS. The luciferase reporter gene is placed under the translational control of the poliovirus IRES instead of the HCV IRES, and HuH-7 cells are used to support the replication of the replicon.

The inhibitory activities of the compounds of the present invention can be evaluated using a variety of assays known in the art. For instance, two stable subgenomic replicon cell lines can be used for compound characterization in cell culture: one derived from genotype 1a-H77 and the other derived from genotype 1b-Con1, obtained from University of Texas Medical Branch, Galveston, Tex. or Apath, LLC, St. Louis, Mo., respectively. The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the HCV 5' UTR, 3' UTR, and NS3-NS5B coding region are derived from the 1b-Con1 strain, and the adaptive mutations are K1609E, K1846T and Y3005C. In addition, the 1b-Con1 replicon construct contains a poliovirus IRES between the HCV IRES and the luciferase gene. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 μl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 μl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators after which time 30 μl of Passive Lysis buffer (Promega) can be added to each well, and then the plates are incubated for 15 minutes with rocking to lyse the cells. Luciferin solution (100 μl, Promega) can be added to each well, and luciferase activity can be measured with a Victor II luminometer (Perkin-Elmer). The percent inhibition of HCV RNA replication can be calculated for each compound concentration and the $EC_{50}$ value can be calculated using nonlinear regression curve fitting to the 4-parameter logistic equation and GraphPad Prism 4 software. Using the above-described assays or similar cell-based replicon assays, representative compounds of the present invention showed significantly inhibitory activities against HCV replication.

The present invention also features pharmaceutical compositions comprising the compounds of the invention. A pharmaceutical composition of the present invention can comprise one or more compounds of the invention, each of which has Formula I (or $I_A$, $I_B$, $I_C$, $I_D$, $I_E$, $I_F$ or $I_G$).

In addition, the present invention features pharmaceutical compositions comprising pharmaceutically acceptable salts, solvates, or prodrugs of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt, solvate or prodrug thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immunomodulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio- 025, NIM-811, R7128, R1626, R4048, T-1106, PSI-7851 (Pharmasset) (nucleoside polymerase inhibitor), PSI-938 (Pharmasset) (nucleoside polymerase inhibitor), PF-00868554, ANA-598, IDX184 (nucleoside polymerase inhibitor), IDX102, IDX375 (non-nucleoside polymerase inhibitor), GS-9190 (non-nucleoside polymerase inhibitor), VCH-759, VCH-916, MK-3281, BCX-4678, MK-3281, VBY708, ANA598, GL59728, GL60667, BMS-790052 (NS5A inhibitor), BMS-791325 (protease Inhibitor), BMS-650032, BMS-824393, GS-9132, ACH-1095 (protease inhibitor), AP-H005, A-831 (Arrow Therapeutics) (NS5A inhibitor), A-689 (Arrow Therapeutics) (NS5A inhibitor), INX08189 (Inhibitex) (polymerase inhibitor), AZD2836, telaprevir (protease Inhibitor), boceprevir (protease Inhibitor), ITMN-191 (Intermune/Roche), BI-201335 (protease Inhibitor), VBY-376, VX-500 (Vertex) (protease Inhibitor), PHX-B, ACH-1625, IDX136, IDX316, VX-813 (Vertex) (protease Inhibitor), SCH 900518 (Schering-Plough), TMC-435 (Tibotec) (protease Inhibitor), ITMN-191 (Intermune, Roche) (protease Inhibitor), MK-7009 (Merck) (protease Inhibitor), IDX-PI (Novartis), BI-201335 (Boehringer Ingelheim), R7128 (Roche) (nucleoside polymerase inhibitor), MK-3281 (Merck), MK-0608 (Merck) (nucleoside polymerase inhibitor), PF-868554 (Pfizer) (non-nucleoside polymerase inhibitor), PF-4878691 (Pfizer), IDX-184 (Novartis), IDX-375 (Pharmasset), PPI-461 (Presidio) (NS5A inhibitor), BILB-1941 (Boehringer Ingelheim), GS-9190 (Gilead), BMS-790052 (BMS), Albuferon (Novartis), ABT-450 (Abbott/Enanta) (protease Inhibitor), ABT-333 (Abbott) (non-nucleoside polymerase inhibitor), ABT-072 (Abbott) (non-nucleoside polymerase inhibitor), ritonavir, another cytochrome P450 monooxygenase inhibitor, or any combination thereof.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. For example, a pharmaceutical composition of the present invention can comprise a compound(s) of the present invention having Formula I, $I_A$, $I_B$, $I_C$, $I_D$, $I_E$, $I_F$ or $I_G$ (or a salt, solvate or prodrug thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NS5A inhibitors.

In yet another embodiment, a pharmaceutical composition of the present invention comprises one or more compounds of the present invention (or salts, solvates or prodrugs thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art.

In a preferred embodiment, a pharmaceutical composition of the invention comprises a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), and a HCV protease inhibitor. In another preferred embodiment, a pharmaceutical composition of the invention comprises a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), and a HCV polymerase inhibitor (e.g., a non-nucleoside polymerase inhibitor, or preferably a nucleoside polymerase inhibitor). In yet another preferred embodiment, a pharmaceutical composition of the present invention comprises (1) a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), (2) a HCV protease inhibitor, and (3) a HCV polymerase inhibitor (e.g., a non-nucleoside polymerase inhibitor, or preferably a nucleoside polymerase inhibitor). Non-limiting examples of protease and polymerase inhibitors are described above.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHAR- MACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

In a preferred embodiment, a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof) is formulated in a solid dispersion, where the compound of the invention can be molecularly dispersed in an amorphous matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt-extrusion, spray-drying, co-precipitation, freeze drying, or other solvent evaporation techniques, with melt-extrusion and spray-drying being preferred. In one example, a compound of the invention is formulated in a solid dispersion comprising copovidone and vitamin E TPGS. In another example, a compound of the invention is formulated in a solid dispersion comprising copovidone and Span 20.

A solid dispersion described herein may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion described herein may also contain at least 1% by weight of a pharmaceutically acceptable surfactant or a combination of such surfactants. Preferably, the solid dispersion contains at least 2% by weight of a pharmaceutically acceptable surfactant or a combination of such surfactants. More preferably, the solid dispersion contains from 4% to 20% by weight of the surfactant(s), such as from 5% to 10% by weight of the surfactant(s). In addition, a solid dispersion described herein may contain at least 1% by weight of a compound of the invention, preferably at least 5%, including, e.g., at least 10%. In one example, the solid dispersion comprises 5% of a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), which is molecularly dispersed in a an amorphous matrix comprising 7% Vitamin E-TPGS and 88% copovidone; the solid dispersion can also be mixed with other excipients such as mannitol/aerosil (99:1), and the weight ratio of the solid dispersion over the other excipients can range from 5:1 to 1:5 with 1:1 being preferred. In another example, the solid dispersion comprises 5% of a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), which is molecularly dispersed in a an amorphous matrix comprising 5% Span 20 and 90% copovidone; the solid dispersion can also be mixed with other excipients such as mannitol/aerosil (99:1), the solid dispersion can also be mixed with other excipients such as mannitol/aerosil (99:1), and the weight ratio of the solid dispersion over the other excipients can range from 5:1 to 1:5 with 1:1 being preferred.

Various additives can also be included in or mixed with the solid dispersion. For instance, at least one additive selected from flow regulators, binders, lubricants, fillers, disintegrants, plasticizers, colorants, or stabilizers may be used in compressing the solid dispersion to tablets. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like. Non-limiting examples of stabilizers include antioxidants, light stabilizers, radical scavengers, or stabilizers against microbial attack.

The present invention further features methods of using the compounds of the present invention (or salts, solvates or prodrugs thereof) to inhibit HCV replication. The methods comprise contacting cells infected with HCV virus with an effective amount of a compound of the present invention (or a salt, solvate or prodrug thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may inhibit one or more HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c, 3a or 4a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. The methods typically comprise administering a therapeutic effective amount of a compound of the present invention (or a salt, solvate or prodrug thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof), or a pharmaceutical composition comprising the same, to an HCV patient, thereby reducing the HCV viral level in the blood or liver of the patient.

A compound of the present invention (or a salt, solvate or prodrug thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention. In one embodiment, the present invention features methods of treating HCV infection, wherein said methods comprise administering a compound of the invention (e.g., a compound of Formula I, $I_A$, $I_B$, $I_C$, $I_D$, $I_E$, $I_F$ or $I_G$, or preferably a compound selected from Examples 1-8, or a salt, solvate or prodrug thereof), interferon and ribavirin to an HCV patient. The interferon preferably is α-interferon, and more preferably, pegylated interferon-α such as PEGASYS (peginterferon alfa-2a).

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The present invention further features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

The compounds of the present invention can also be isotopically substituted. Preferred isotopic substitution include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 5 mol % (e.g., at least 10 mol %) of hydrogen in a compound of the present invention is substituted with deuterium. In another example, at least 25 mole % of hydrogen in a compound of the present invention is substituted with deuterium. In a further example, at least 50, 60, 70, 80 or 90 mole % of hydrogen in a compound of the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound of Formula I, or a pharmaceutically acceptable salt thereof, $$Y-A-L_1-\overset{\overset{D}{\underset{L_3}{|}}}{X}-L_2-B-Z \qquad I$$

wherein:
X is cyclopropyl, and is optionally substituted with one or more $R_4$;
$L_1$, $L_2$ and $L_3$ are each a bond;
A is selected from

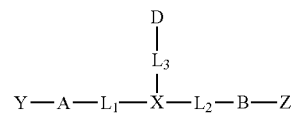

or

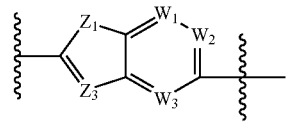

B is selected from

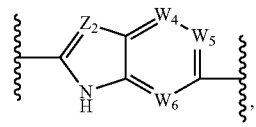

or

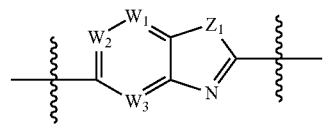

$Z_1$ is independently selected at each occurrence from O, S, NH or $CH_2$, $Z_2$ is independently selected at each occurrence from N or CH, and $W_1$, $W_2$, $W_3$, $W_4$, $W_5$ and $W_6$ are each independently selected at each occurrence from CH or N, wherein A and B are each independently optionally substituted with one or more $R_A$;

D is $C_3$-$C_{12}$carbocycle or 3- to 12-membered heterocycle, and is optionally substituted with one or more $R_A$; or D is $C_3$-$C_{12}$carbocycle or 3- to 12-membered heterocycle, and is substituted with J and optionally substituted with one or more $R_A$, wherein J is $C_3$-$C_{12}$carbocycle or 3- to 12-membered heterocycle and is optionally substituted with one or more $R_A$;

Y is —$C(R_1R_2)N(R_5)$-T-$R_D$, or —$C(R_3R_4)C(R_6R_7)$-T-$R_D$;

Z is —$C(R_8R_9)N(R_{12})$-T-$R_D$, or —$C(R_{10}R_{11})C(R_{13}R_{14})$-T-$R_D$;

$R_1$ is $R_C$, and $R_2$ and $R_5$, taken together with the atoms to which they are attached, form a 3- to 12-membered heterocycle which is optionally substituted with one or more $R_A$;

$R_3$ and $R_6$ are each independently $R_C$, and $R_4$ and $R_7$, taken together with the atoms to which they are attached, form a 3- to 12-membered carbocycle or heterocycle which is optionally substituted with one or more $R_A$;

$R_8$ is $R_C$, and $R_9$ and $R_{12}$, taken together with the atoms to which they are attached, form a 3- to 12-membered heterocycle which is optionally substituted with one or more $R_A$;

$R_{10}$ and $R_{13}$ are each independently $R_C$, and $R_{11}$ and $R_{14}$, taken together with the atoms to which they are attached, form a 3- to 12-membered carbocycle or heterocycle which is optionally substituted with one or more $R_A$;

T is each independently selected at each occurrence from bond, -$L_S$-, -$L_S$-M-$L_S'$-, or -$L_S$-M-$L_S'$-M'-$L_S''$-, wherein M and M' are each independently selected at each occurrence from bond, —O—, —S—, —$N(R_B)$—, —C(O)—, —$S(O)_2$—, —S(O)—, —OS(O)—, —OS$(O)_2$—, —$S(O)_2$O—, —S(O)O—, —C(O)O—, —OC(O)—, —OC(O)O—, —$C(O)N(R_B)$—, —$N(R_B)C(O)$—, —$N(R_B)C(O)O$—, —$OC(O)N(R_B)$—, —$N(R_B)S(O)$—, —$N(R_B)S(O)_2$—, —$S(O)N(R_B)$—, —$S(O)_2N(R_B)$—, —$C(O)N(R_B)C(O)$—, —$N(R_B)C(O)N(R_B')$—, —$N(R_B)SO_2N(R_B')$—, —$N(R_B)S(O)N(R_B')$—, $C_3$-$C_{12}$carbocycle or 3- to 12-membered heterocycle, and wherein said $C_3$-$C_{12}$carbocycle and 3- to 12-membered heterocycle are each independently optionally substituted at each occurrence with one or more $R_A$;

$R_D$ is each independently selected at each occurrence from hydrogen or $R_A$;

$R_A$ is independently selected at each occurrence from halogen, nitro, oxo, phosphonoxy, phosphono, thioxo, cyano, or -$L_S$-$R_E$;

$R_B$ and $R_B'$ are each independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_B$ or $R_B'$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_C$ is independently selected at each occurrence from hydrogen, halogen, hydroxy, mercapto, amino, carboxy, nitro, oxo, phosphonoxy, phosphono, thioxo, formyl or cyano; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle; wherein each 3- to 6-membered carbocycle or heterocycle in $R_C$ is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$R_E$ is independently selected at each occurrence from —O—$R_S$, —S—$R_S$, —$C(O)R_S$, —$OC(O)R_S$, —$C(O)OR_S$, —$N(R_SR_S')$, —$S(O)R_S$, —$SO_2R_S$, —$C(O)N(R_SR_S')$, —$N(R_S)C(O)R_S'$, —$N(R_S)C(O)N(R_S'R_S'')$, —$N(R_S)SO_2R_S'$, —$SO_2N(R_SR_S')$, —$N(R_S)SO_2N(R_S'R_S'')$, —$N(R_S)S(O)N(R_S'R_S'')$, —OS(O)—$R_S$, —OS$(O)_2$—$R_S$, —$S(O)_2OR_S$, —$S(O)OR_S$, —OC(O)$OR_S$, —$N(R_S)C(O)OR_S'$, —$OC(O)N(R_SR_S')$, —$N(R_S)S(O)$—$R_S'$, —$S(O)N(R_SR_S')$, $P(O)(OR_S)_2$ or —$C(O)N(R_S)C(O)$—$R_S'$; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl or cyano; or $C_3$-$C_6$carbocycle or 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C(O)OR_S$ or —$N(R_SR_S')$;

$R_L$ is independently selected at each occurrence from halogen, nitro, oxo, phosphonoxy, phosphono, thioxo, cyano, —O—$R_S$, —S—$R_S$, —$C(O)R_S$, —$OC(O)R_S$, —$C(O)OR_S$, —$N(R_SR_S')$, —$S(O)R_S$, —$SO_2R_S$, —$C(O)N(R_SR_S')$ or —$N(R_S)C(O)R_S'$; or $C_3$-$C_6$carbocycle 3- to 6-membered heterocycle, each of which is independently optionally substituted at each occurrence with one or more substituents selected from halogen, hydroxy, mercapto, amino, carboxy, nitro, oxo, phosphonoxy, phosphono, thioxo, formyl, cyano, $C_1$-$C_6$alkyl, $C_2$-$C_6$alkenyl, $C_2$-$C_6$alkynyl, $C_1$-$C_6$haloalkyl, $C_2$-$C_6$haloalkenyl or $C_2$-$C_6$haloalkynyl;

$L_S$, $L_S'$ and $L_S''$ are each independently selected at each occurrence from bond; or $C_1$-$C_6$alkylene, $C_2$-$C_6$alkenylene or $C_2$-$C_6$alkynylene, each of which is independently optionally substituted at each occurrence with one or more $R_L$; and $R_S$, $R_S'$ and $R_S''$ are each independently selected at each occurrence from hydrogen; or $C_1$-$C_6$alkyl, $C_2$-$C_6$alkenyl or $C_2$-$C_6$alkynyl, each of which is independently optionally substituted at each occurrence with one or more substituents selected from halogen, hydroxy, mercapto, amino, carboxy, nitro, oxo, phosphonoxy, phosphono, thioxo, formyl, cyano or 3- to 6-membered carbocycle or heterocycle; or —(R$_G$—R$_H$)$_n$—(R$_G$—R$_H$'), wherein each n is independently 0, 1, 2, 3 or 4; each R$_G$ is independently O, S or N(R$_B$); each R$_H$ is independently C$_1$-C$_6$alkylene, C$_2$-C$_6$alkenylene or C$_2$-C$_6$alkynylene, each of which is optionally substituted with one or more substituents selected from halogen, hydroxy, mercapto, amino, carboxy, nitro, oxo, phosphonoxy, phosphono, thioxo, formyl, cyano or 3- to 6-membered carbocycle or heterocycle; and each R$_H$' is independently C$_1$-C$_6$alkyl, C$_2$-C$_6$alkenyl or C$_2$-C$_6$alkynyl, each of which is optionally substituted with one or more substituents selected from halogen, hydroxy, mercapto, amino, carboxy, nitro, oxo, phosphonoxy, phosphono, thioxo, formyl, cyano or 3- to 6-membered carbocycle or heterocycle; or 3- to 6-membered carbocycle or heterocycle;

wherein each 3- to 6-membered carbocycle or heterocycle in R$_S$, R$_{S'}$ or R$_{S''}$ is independently optionally substituted at each occurrence with one or more substituents selected from halogen, hydroxy, mercapto, amino, carboxy, nitro, oxo, phosphonoxy, phosphono, thioxo, formyl, cyano, C$_1$-C$_6$alkyl, C$_2$-C$_6$alkenyl, C$_2$-C$_6$alkynyl, C$_1$-C$_6$haloalkyl, C$_2$-C$_6$haloalkenyl or C$_2$-C$_6$haloalkynyl.

2. The compound or salt of claim 1, wherein:

T is independently selected at each occurrence from —C(O)-L$_S$'-M'-L$_S$"- or —N(R$_B$)C(O)-L$_S$'-M'-L$_S$"-; and L$_S$' is each independently C$_1$-C$_6$alkylene, and is independently optionally substituted at each occurrence with one or more R$_L$.

3. The compound or salt of claim 1, wherein:

Y is —C(R$_1$R$_2$)N(R$_5$)-T-R$_D$;

Z is —C(R$_8$R$_9$)N(R$_{12}$)-T-R$_D$;

T is independently selected at each occurrence from —C(O)-L$_S$'-M'-L$_S$"-; and D is C$_5$-C$_6$carbocycle, 5- to 6-membered heterocycle, or 6- to 10-membered bicycles, and is substituted with one or more R$_A$; or D is C$_5$-C$_6$carbocycle or 5- to 6-membered heterocycle, and is substituted with J and optionally substituted with one or more R$_A$, wherein J is C$_3$-C$_6$carbocycle or 3- to 6-membered heterocycle and is optionally substituted with one or more R$_A$.

4. The compound or salt of claim 3, wherein T is independently selected at each occurrence from —C(O)-L$_S$'-N(R$_B$)C(O)-L$_S$"- or —C(O)-L$_S$'-N(R$_B$)C(O)O-L$_S$"-; and R$_2$ and R$_5$, taken together with the atoms to which they are attached, form

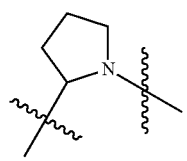 [SMILES: *C1CCCN1*]

which is optionally substituted with one or more R$_A$; and R$_9$ and R$_{12}$, taken together with the atoms to which they are attached, form

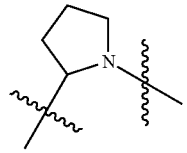 [SMILES: *C1CCCN1*]

which is optionally substituted with one or more R$_A$.

5. The compound of claim 4, wherein A is

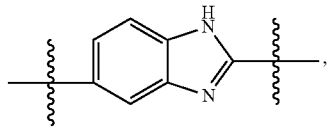 [SMILES: *c1ccc2[nH]c(*)nc2c1]

B is

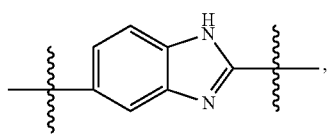 [SMILES: *c1ccc2[nH]c(*)nc2c1]

and A and B are each independently optionally substituted with one or more R$_A$.

6. The compound of claim 1, wherein the compound is selected from the group consisting of:

dimethyl (2S,2'S)-1,1'-((2S,2'S)-2,2'-(4,4'-(3-(4-methoxyphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl)dicarbamate;

dimethyl (2S,2'S)-1,1'-((2S,2'S)-2,2'-(4,4'-(3-(4-(benzyloxy)phenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate;

dimethyl (2S,2'S)-1,1'-((2S,2'S)-2,2'-(4,4'-(4,4'-(3-(4-methoxyphenyl)cyclopropane-1,2-diyl)bis(4,1-phenylene))bis(1H-imidazole-4,2-diyl))bis(pyrrolidine-2,1-diyl))bis(3-methyl-1-oxobutane-2,1-diyl) dicarbamate;

dimethyl (2S,2'S)-1,1'-((2S,2'S)-2,2'-(4,4'-(4,4'-(3-(4-(benzyloxy)phenyl)cyclopropane-1,2-diyl)bis(4,1-phenylene))bis(1H-imidazole-4,2-diyl))bis(pyrrolidine-2,1-diyl))bis(3-methyl-1-oxobutane-2,1-diyl) dicarbamate;

dimethyl (2S,2'S)-1,1'-((2S,2'S)-2,2'-(5,5'-(3-(4-(benzyloxy)phenyl)cyclopropane-1,2-diyl)bis(1H-benzo[d]imidazole-5,2-diyl))bis(pyrrolidine-2,1-diyl))bis(3-methyl-1-oxobutane-2,1-diyl)dicarbamate;

dimethyl (2S,2'S)-1,1'-((2S,2'S)-2,2'-(4,4'-(3-(4-cyclohexylphenyl)cyclopropane-1,2-diyl)bis(4,1-phenylene))bis(azanediyl)bis(oxomethylene)bis(pyrrolidine-2,1-diyl))bis(3-methyl-1-oxobutane-2,1-diyl) dicarbamate;

dimethyl (2S,2'S)-1,1'-((2S,2'S)-2,2'-(4,4'-(2-(4-tert-butylphenyl)cyclopent-3-ene-1,3-diyl)bis(4,1-phenylene)bis(azanediyl)bis(oxomethylene))bis(pyrrolidine-2,1-diyl))bis(3-methyl-1-oxobutane-2,1-diyl)dicarbamate; and dimethyl (2S,2'S)-1,1'-((2S,2'S)-2,2'-(4,4'-(2-(4-tert-butylphenyl)cyclopentane-1,3-diyl)bis(4,1-phenylene)bis (azanediyl)bis(oxomethylene))bis(pyrrolidine-2,1-diyl))bis(3-methyl-1-oxobutane-2,1-diyl)dicarbamate.

7. A pharmaceutical composition comprising a compound or salt according to claim 1 and another anti-HCV agent.

* * * * *